US012415994B2

(12) United States Patent
Qi et al.

(10) Patent No.: US 12,415,994 B2
(45) Date of Patent: Sep. 16, 2025

(54) SYNTHETIC MINIATURE CRISPR-CAS (CASMINI) SYSTEM FOR EUKARYOTIC GENOME ENGINEERING

(71) Applicant: The Board of Trustees of the Leland Stanford Junior University, Stanford, CA (US)

(72) Inventors: Lei S. Qi, Stanford, CA (US); Xiaoshu Xu, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 18/174,552

(22) Filed: Feb. 24, 2023

(65) Prior Publication Data

US 2023/0340439 A1 Oct. 26, 2023

Related U.S. Application Data

(63) Continuation of application No. PCT/US2021/048362, filed on Aug. 31, 2021.

(60) Provisional application No. 63/191,611, filed on May 21, 2021, provisional application No. 63/073,377, filed on Sep. 1, 2020.

(51) Int. Cl.
*C12N 9/22* (2006.01)
*C07K 14/31* (2006.01)
*C12N 15/86* (2006.01)

(52) U.S. Cl.
CPC .............. *C12N 9/22* (2013.01); *C07K 14/31* (2013.01); *C12N 15/86* (2013.01); *C12N 2310/20* (2017.05)

(58) Field of Classification Search
CPC ...................................................... C12N 9/22
See application file for complete search history.

(56) References Cited

U.S. PATENT DOCUMENTS

| | | | |
|---|---|---|---|
| 9,790,490 B2 | 10/2017 | Zhang et al. | |
| 10,648,020 B2 | 5/2020 | Zhang et al. | |
| 10,669,540 B2 | 6/2020 | Zhang et al. | |
| 10,934,536 B2 | 3/2021 | Hou et al. | |
| 11,091,798 B2 | 8/2021 | Zhang et al. | |
| 11,180,743 B2 | 11/2021 | Doudna et al. | |
| 11,180,751 B2 | 11/2021 | Koonin et al. | |
| 11,371,031 B2 | 6/2022 | Doudna et al. | |
| 11,441,137 B2 | 9/2022 | Doudna et al. | |
| 11,453,866 B2 | 9/2022 | Doudna et al. | |
| 2016/0355795 A1 | 12/2016 | Ran et al. | |
| 2019/0256900 A1 | 8/2019 | Zhang et al. | |
| 2020/0087640 A1 | 3/2020 | Doudna et al. | |
| 2020/0172886 A1 | 6/2020 | Doudna et al. | |
| 2020/0199555 A1 | 6/2020 | Zhang | |
| 2020/0308583 A1 | 10/2020 | Kim et al. | |
| 2020/0318172 A1 | 10/2020 | Zhang et al. | |
| 2020/0318173 A1 | 10/2020 | Zhang et al. | |
| 2021/0040546 A1 | 2/2021 | Zhang et al. | |
| 2021/0139276 A1 | 5/2021 | Hou et al. | |
| 2021/0163908 A1 | 6/2021 | Hou et al. | |
| 2021/0348156 A1 | 11/2021 | Koonin et al. | |
| 2021/0348157 A1 | 11/2021 | Koonin et al. | |
| 2022/0049241 A1 | 2/2022 | Harrington et al. | |
| 2022/0073890 A1 | 3/2022 | Hou et al. | |
| 2022/0195503 A1 | 6/2022 | Zhang et al. | |
| 2022/0307018 A1 | 9/2022 | Kim et al. | |
| 2023/0074840 A1 | 3/2023 | Zhang et al. | |

FOREIGN PATENT DOCUMENTS

| | | | |
|---|---|---|---|
| EP | 3436575 A1 | 2/2019 | |
| EP | 3604532 A1 | 2/2020 | |
| EP | 3704239 A1 | 9/2020 | |
| KR | 20230007218 A | 1/2023 | |
| WO | 2015/089277 A1 | 6/2015 | |
| WO | 2018/089664 A1 | 5/2018 | |
| WO | WO-2019089808 A1 | 5/2019 | |
| WO | WO-2019089820 A1 | 5/2019 | |
| WO | 2020088450 A1 | 5/2020 | |
| WO | WO-2020123887 A2 | 6/2020 | |
| WO | WO-2021084533 A1 | 5/2021 | |
| WO | WO-2021086083 A2 | 5/2021 | |
| WO | WO-2022051250 A1 | 3/2022 | |
| WO | 2022075813 A1 | 4/2022 | |
| WO | 2022075816 A1 | 4/2022 | |
| WO | 2022/092317 A1 | 5/2022 | |
| WO | 2022140572 A1 | 6/2022 | |
| WO | WO-2022150372 A1 | 7/2022 | |

(Continued)

OTHER PUBLICATIONS

Chen et al., "Dynamic Imaging of Genomic Loci in Living Human Cells by an Optimized CRISPR/Cas System," Cell, vol. 155, No. 7, Dec. 19, 2013, pp. 1479-1491.

Dang et al., "Optimizing sgRNA Structure to Improve CRISPR-Cas9 Knockout Efficiency," Genome Biology, vol. 16, No. 280, Dec. 15, 2015, pp. 1-10.

Karvelis et al., "PAM Recognition by Miniature CRISPR-Cas12f Nucleases Triggers Programmable Double-Stranded DNA Target Cleavage," Nucleic Acids Research, vol. 48, No. 9, Apr. 4, 2020, pp. 5016-5023.

Application No. PCT/US2021/048362, International Preliminary Report on Patentability, Mailed On Mar. 16, 2023, 7 pages.

Application No. PCT/US2021/048362, International Search Report and Written Opinion, Mailed On Jan. 10, 2022, 10 pages.

(Continued)

*Primary Examiner* — Suzanne M Noakes
(74) *Attorney, Agent, or Firm* — Kilpatrick Townsend & Stockton LLP

(57) ABSTRACT

Provided herein are Cas proteins and guide RNA molecules engineered to exhibit increased activity in eukaryotic cells. The provided Cas proteins and RNA molecules are particularly useful for applications where modulation of eukaryotic nucleic acids with relatively small molecules is advantageous. Also provided are nucleic acids and vectors encoding the disclosed Cas proteins and guide RNA molecules, pharmaceutical compositions including the Cas proteins and guide RNA molecules, and methods for using the disclosed materials.

31 Claims, 32 Drawing Sheets

Specification includes a Sequence Listing.

(56) References Cited

FOREIGN PATENT DOCUMENTS

| WO | 2022220503 | A1 | 10/2022 |
|---|---|---|---|
| WO | 2022/253185 | A1 | 12/2022 |
| WO | WO-2022266324 | A1 | 12/2022 |
| WO | WO-2023010135 | A1 | 2/2023 |
| WO | WO-2023168242 | A1 | 9/2023 |

OTHER PUBLICATIONS

Xu et al., "Engineered Miniature CRISPR-Cas System for Mammalian Genome Regulation and Editing," Molecular Cell, vol. 81, No. 20, Oct. 21, 2021, pp. 4333-4345.

Chavez, Alejandro et al. Comparison of Cas9 activators in multiple species. Nature methods vol. 13,7 (2016): 563-567. doi:10.1038/nmeth.3871.

Cong, Le et al. Multiplex genome engineering using CRISPR/Cas systems. Science (New York, N.Y.) vol. 339,6121 (2013): 819-23. doi:10.1126/science.1231143.

Fellmann, Christof et al. Cornerstones of CRISPR-Cas in drug discovery and therapy. Nature reviews. Drug discovery vol. 16,2 (2017): 89-100. doi:10.1038/nrd.2016.238.

Harrington, Lucas B et al. Programmed DNA destruction by miniature CRISPR-Cas14 enzymes. Science (New York, N.Y.) vol. 362,6416 (2018): 839-842. doi:10.1126/science.aav4294.

Harrow, Jennifer et al. GENCODE: the reference human genome annotation for The ENCODE Project. Genome research vol. 22,9 (2012): 1760-74. doi:10.1101/gr.135350.111.

Hilton, Isaac B et al. Epigenome editing by a CRISPR-Cas9-based acetyltransferase activates genes from promoters and enhancers. Nature biotechnology vol. 33,5 (2015): 510-7. doi:10.1038/nbt.3199.

Huang, Tony P et al. Precision genome editing using cytosine and adenine base editors in mammalian cells. Nature protocols vol. 16,2 (2021): 1089-1128. doi:10.1038/s41596-020- 00450-9.

Jinek, Martin et al. A programmable dual-RNA-guided DNA endonuclease in adaptive bacterial immunity. Science (New York, N.Y.) vol. 337,6096 (2012): 816-21. doi:10.1126/science.1225829.

Kempton, et al. Multiple Input Sensing and Signal Integration Using a Split Cas12a System. Mol. Cell 78,1 (2020): 184-191.

Kim et al. Genome-wide analysis reveals specificities of Cpf1 endonucleases in human cells. Nature Biotechnology Advance Online Publication. Published online Jun. 6, 2016. 7 pages. DOI: 10.1038/nbt.3609.

Klann, Tyler S et al. CRISPR-Cas9 epigenome editing enables high-throughput screening for functional regulatory elements in the human genome. Nature biotechnology vol. 35,6 (2017): 561-568. doi:10.1038/nbt.3853.

Kleinstiver, Benjamin P et al. Engineered CRISPR-Cas12a variants with increased activities and improved targeting ranges for gene, epigenetic and base editing. Nature biotechnology vol. 37,3 (2019): 276-282. doi:10.1038/s41587-018-0011-0.

Konermann, Silvana et al. Genome-scale transcriptional activation by an engineered CRISPR-Cas9 complex. Nature vol. 517,7536 (2015): 583-8. doi:10.1038/nature14136.

Li et al. Base editing with a Cpf1-cytidine deaminase fusion. Nature Biotechnology Advance Online Publication. Published online Mar. 19, 2018. 8 pages. DOI: 10.1038/nbt.4102.

Pausch, Patrick et al. CRISPR-Casϕ from huge phages is a hypercompact genome editor. Science (New York, N.Y.) vol. 369,6501 (2020): 333-337. doi:10.1126/science.abb1400.

Qi, Lei S et al. Repurposing CRISPR as an RNA-guided platform for sequence-specific control of gene expression. Cell vol. 152,5 (2013): 1173-83. doi:10.1016/j.cell.2013.02.022.

Qu et al. The Crucial Role of Methodology Development in Directed Evolution of Selective Enzymes. Accepted Article. Angew. Chem. Int. Ed. 10.1002/anie.201901491. First published Jul. 2, 2019.

Reetz, Manfred T, and Jose Daniel Carballeira. Iterative saturation mutagenesis (ISM) for rapid directed evolution of functional enzymes. Nature protocols vol. 2,4 (2007): 891-903. doi:10.1038/nprot.2007.72.

Richter, Michelle F et al. Phage-assisted evolution of an adenine base editor with improved Cas domain compatibility and activity. Nature biotechnology vol. 38,7 (2020): 883-891. doi:10.1038/s41587-020-0453-z.

Swarts, Daan C et al. Structural Basis for Guide RNA Processing and Seed-Dependent DNA Targeting by CRISPR-Cas12a. Molecular cell vol. 66,2 (2017): 221-233.e4. doi:10.1016/j.molcel.2017.03.016.

Tak, Y Esther et al. Inducible and multiplex gene regulation using CRISPR-Cpf1-based transcription factors. Nature methods vol. 14,12 (2017): 1163-1166. doi:10.1038/nmeth.4483.

Takeda, Satoru N et al. Structure of the miniature type V-F CRISPR-Cas effector enzyme. Molecular cell vol. 81,3 (2021): 558-570.e3. doi:10.1016/j.molcel.2020.11.035.

Xu, Xiaoshu, and Lei S Qi. A CRISPR-dCas Toolbox for Genetic Engineering and Synthetic Biology. Journal of molecular biology vol. 431,1 (2019): 34-47. doi:10.1016/j.jmb.2018.06.037.

Xu, Xiaoshu et al. Mutagenesis of Key Residues in the Binding Center of I-Aspartate-b-Semialdehyde Dehydrogenase from *Escherichia coli* Enhances Utilization of the Cofactor NAD(H). Chembiochem : a European journal of chemical biology vol. 17,1 (2016): 56-64. doi:10.1002/cbic.201500534.

Zetsche, Bernd et al. Cpf1 is a single RNA-guided endonuclease of a class 2 CRISPR-Cas system. Cell vol. 163,3 (2015): 759-71. doi:10.1016/j.cell.2015.09.038.

Zhang F., et al., "Development of CRISPR-Cas systems for genome editing and beyond", Quarterly Reviews of Biophysics., vol. 52, pp. 1-31 (Jan. 1, 2019).

Database Geneseq [Online], "CRISPR-associated protein Cas14, SEQ ID 55.", pp. 1-2, (Apr. 2, 2020).

Supplementary European Search Report dated Sep. 27, 2024 in related European application No. 21864970.5 (eight pages).

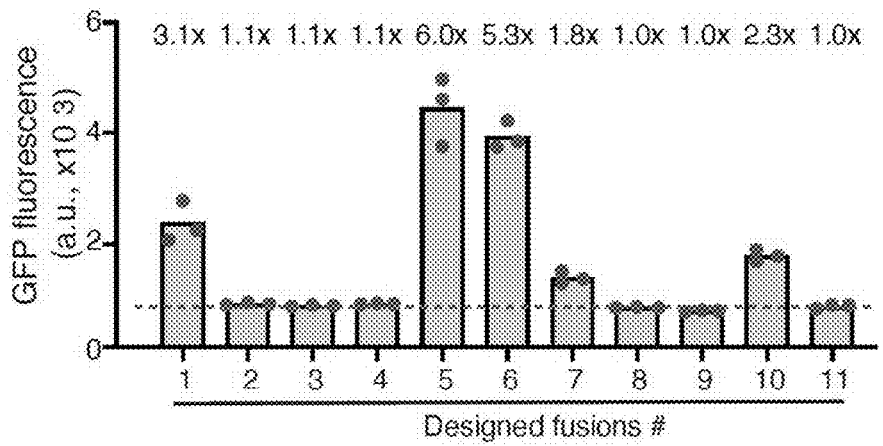

FIG. 14

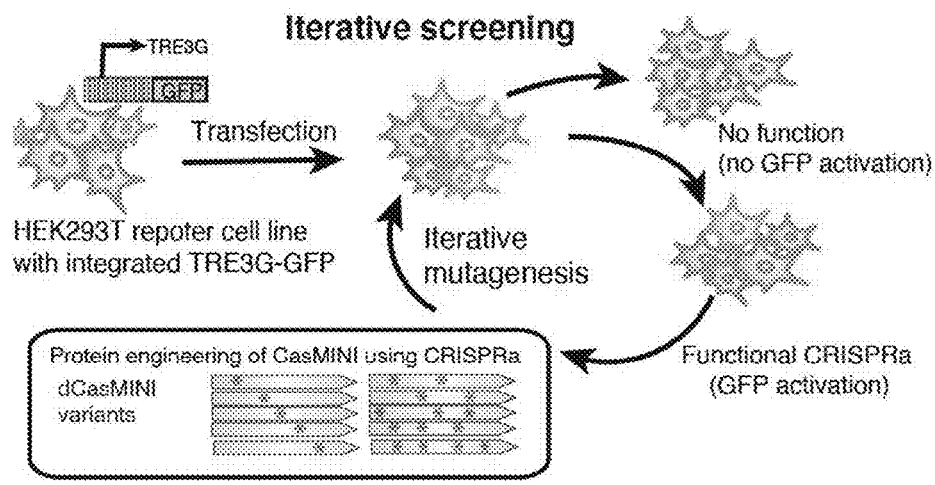

FIG. 15

```
              RuvC-I                    RuvC-II                   RuvC-III
         D326A                                                D510A
          *  K330                       E425                    *
Cas14    GIDVEVKSPLVCAI..........TVQMENLESMKRK..........NADYNAALNISNPKLKST
AsCas12a GIDRGERNLIYITV..........VVVLENLNPGFKS..........DADANGAYHIALKQLLL
LbCas12a GIDRGERNLLYIVV..........VIALEDLNSGFKN..........NADANGAYNIARKVLWAI
FnCas12a SIDRGERHLAYYTL..........IVVFEDLNFGFKR..........DADANGAYHIGLKGLMLL
MbCas12a GIDRGERHLLYLTV..........IVVLEDLNFGFKR..........NADANGAYHIALKGLWLL
DiTnpB   GVDLGLRNLAVVST..........VIVLEKLKGIRKR..........NADLMASRNIVKNYLASL
```

FIG. 16

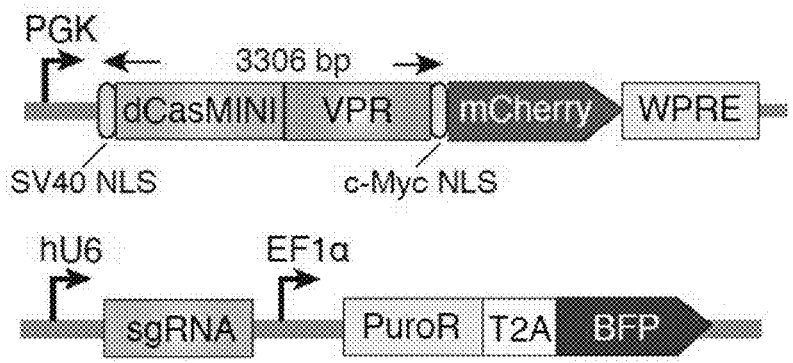
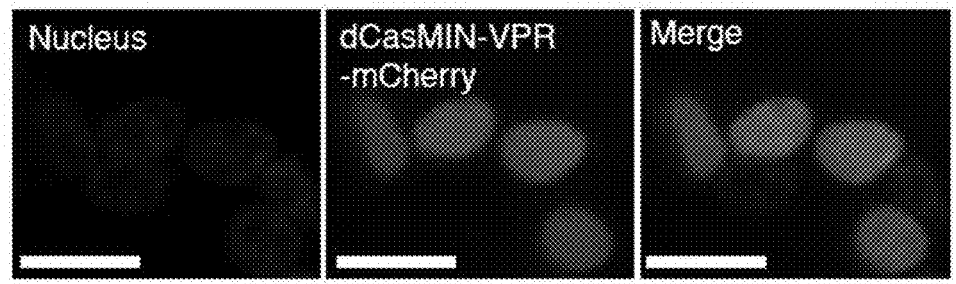
FIG. 30
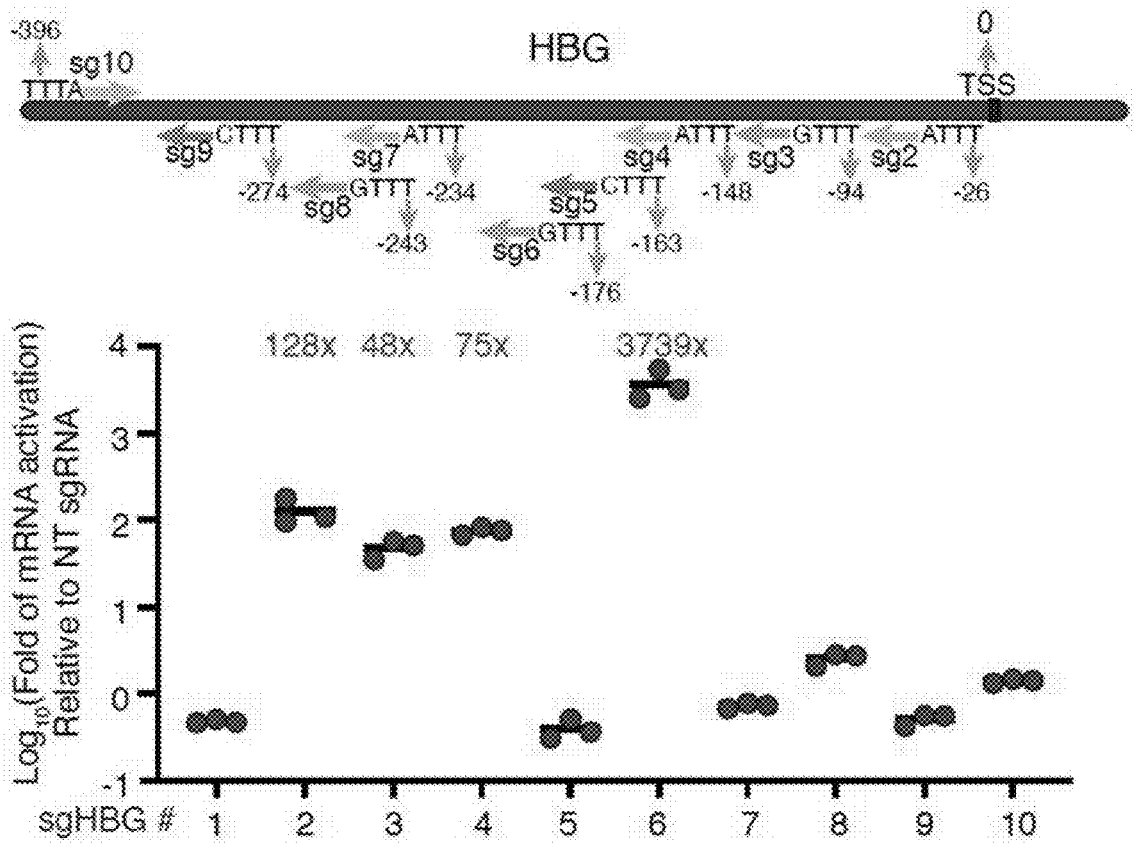
FIG. 31

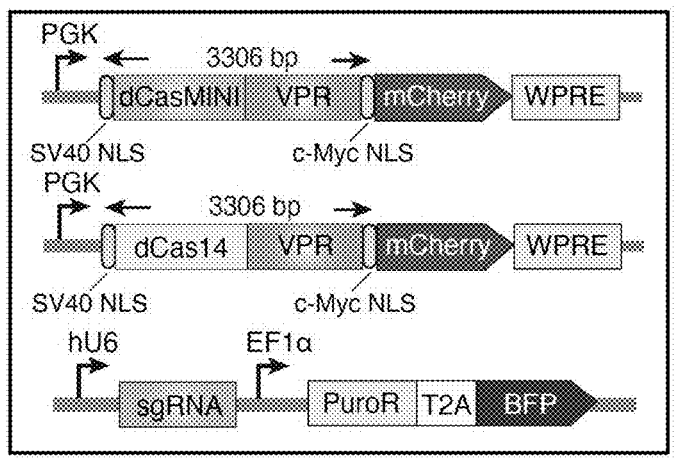
FIG. 38
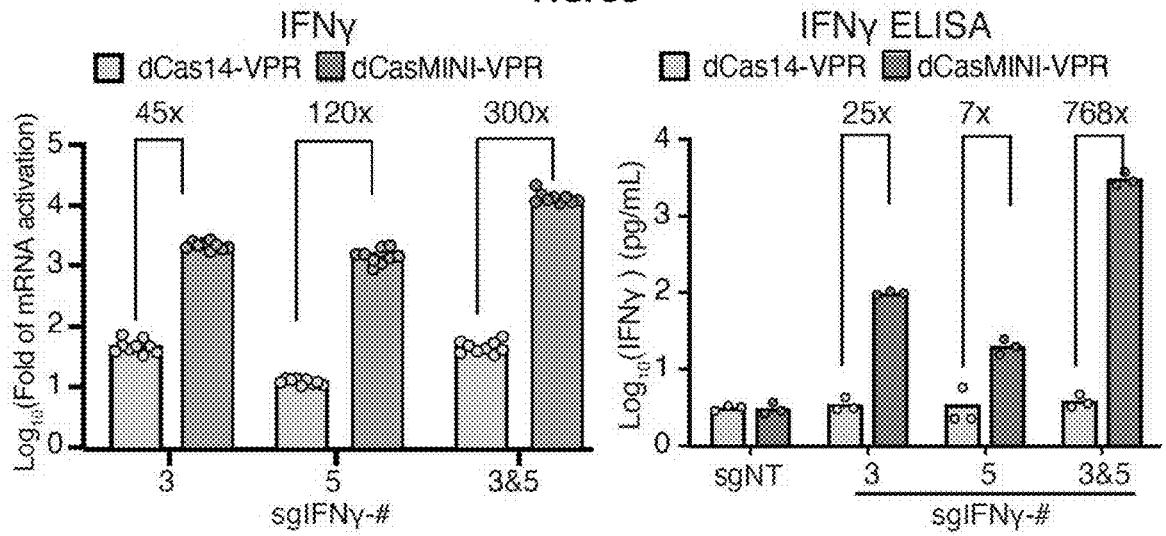
FIG. 39
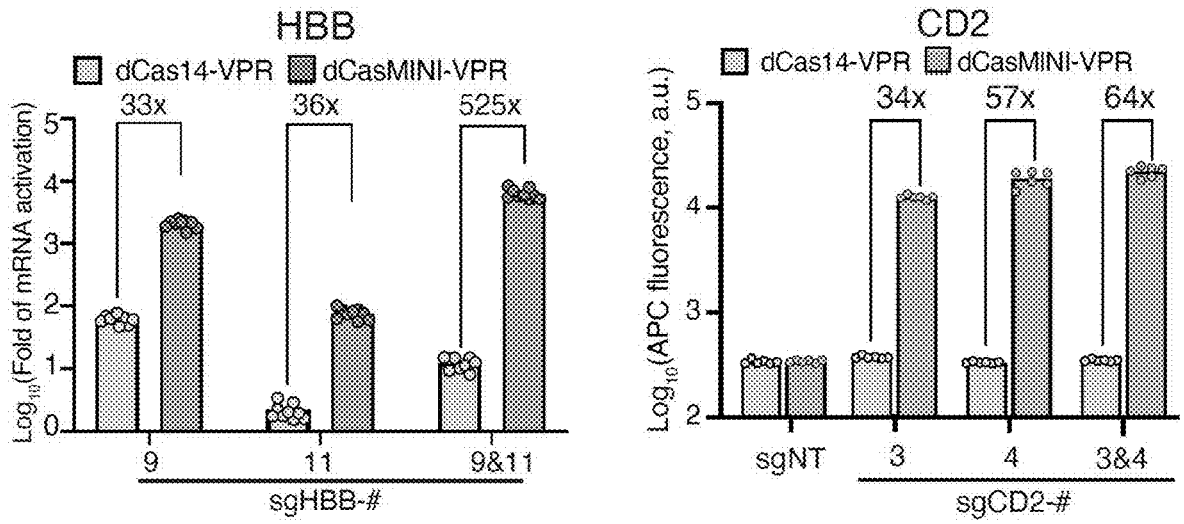
FIG. 40  FIG. 41

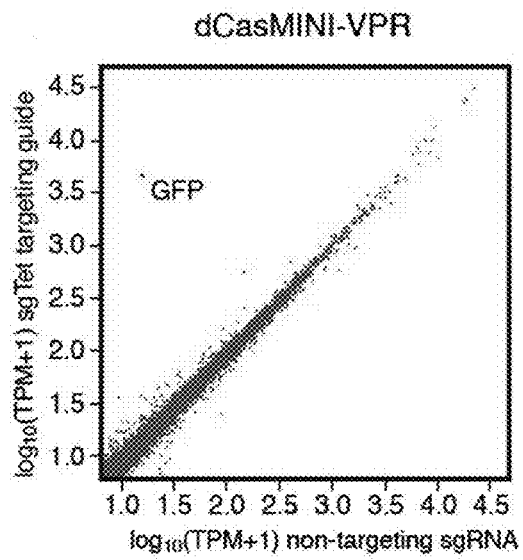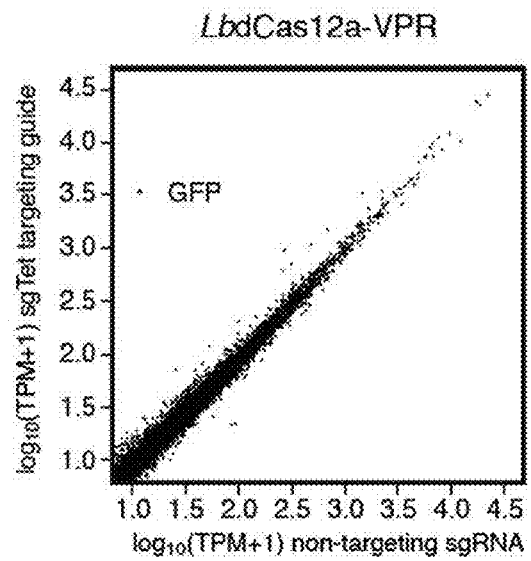
FIG. 46
FIG. 47
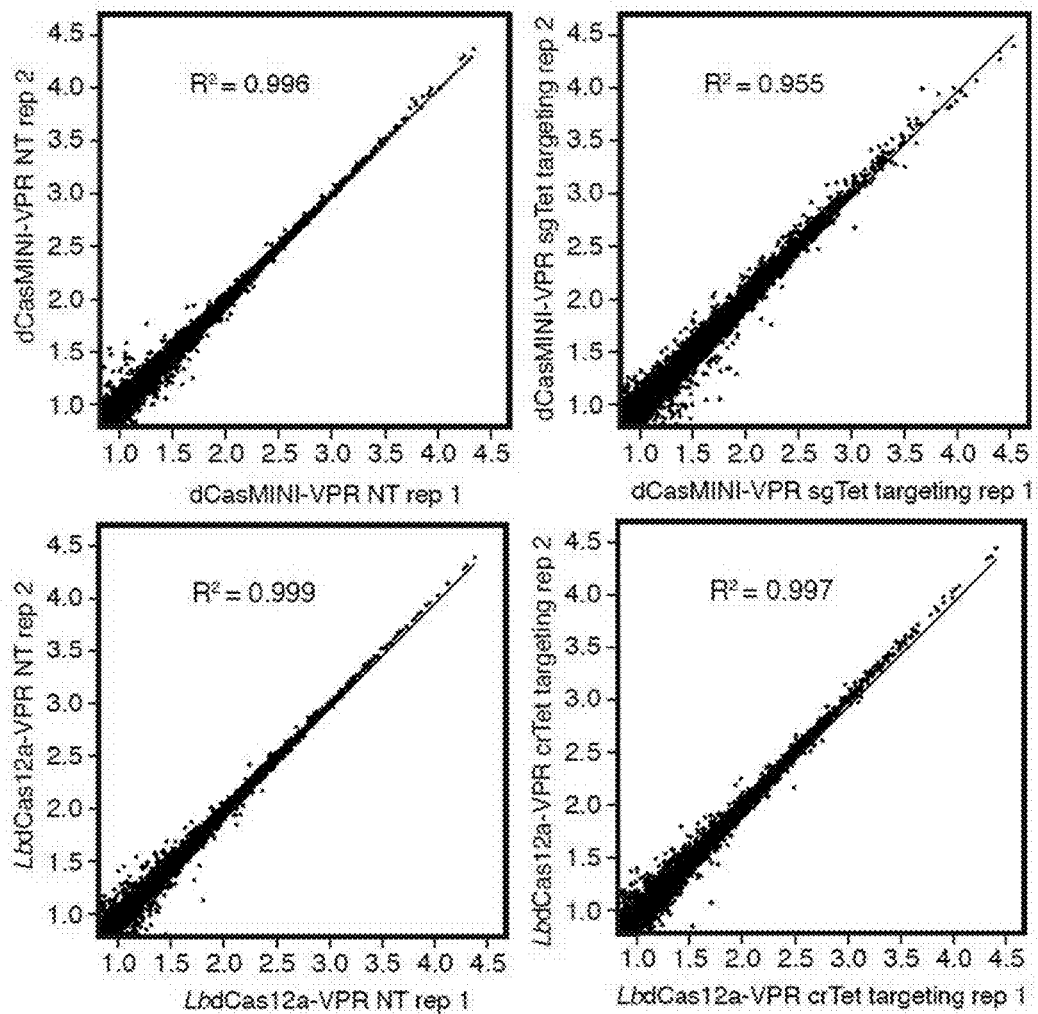
FIG. 48

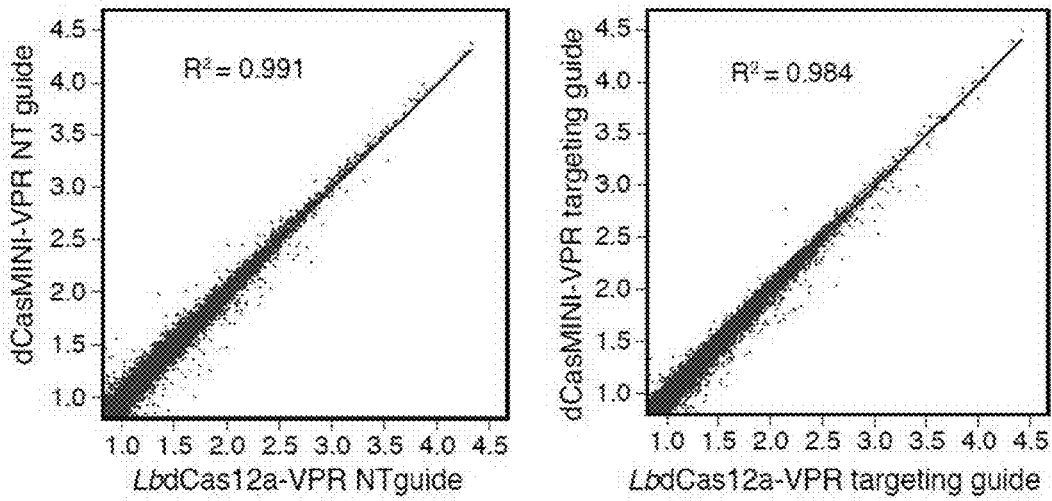
FIG. 49
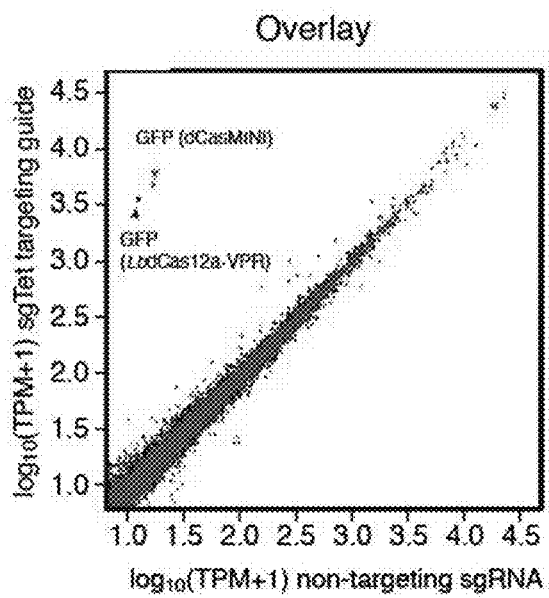
FIG. 50
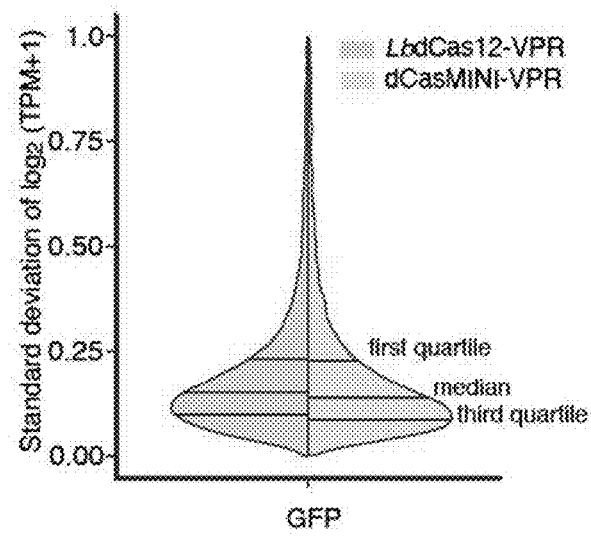
FIG. 51
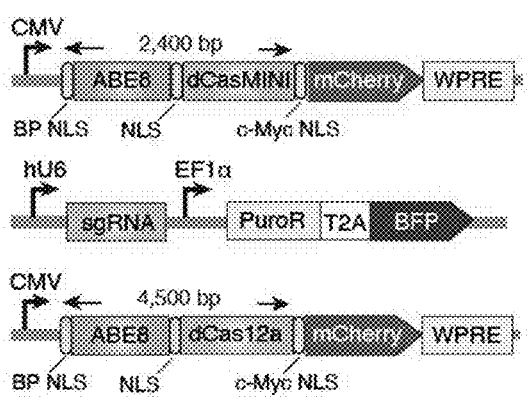
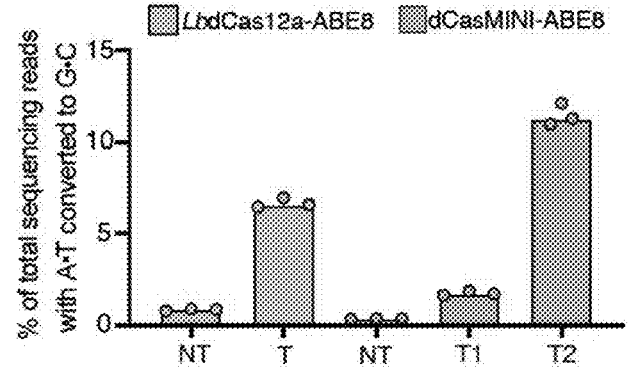
FIG. 52

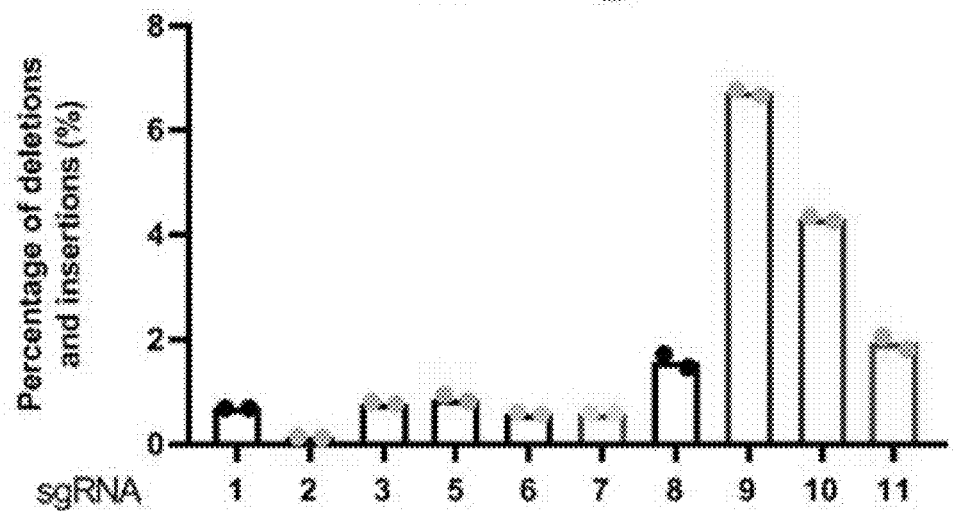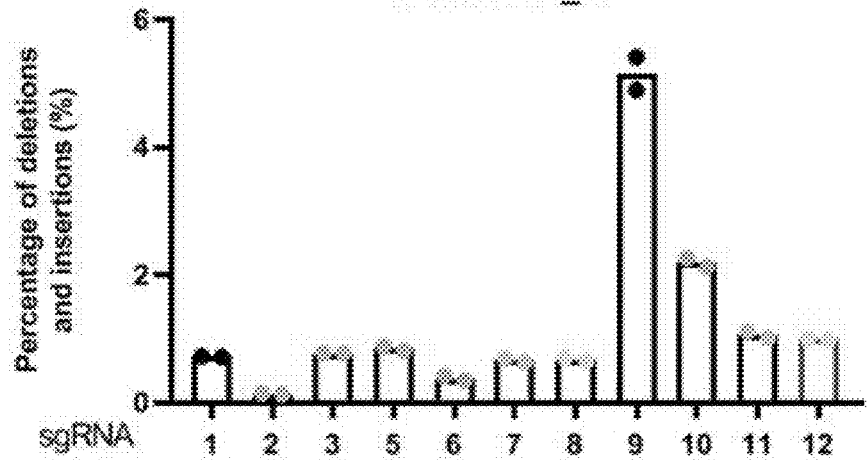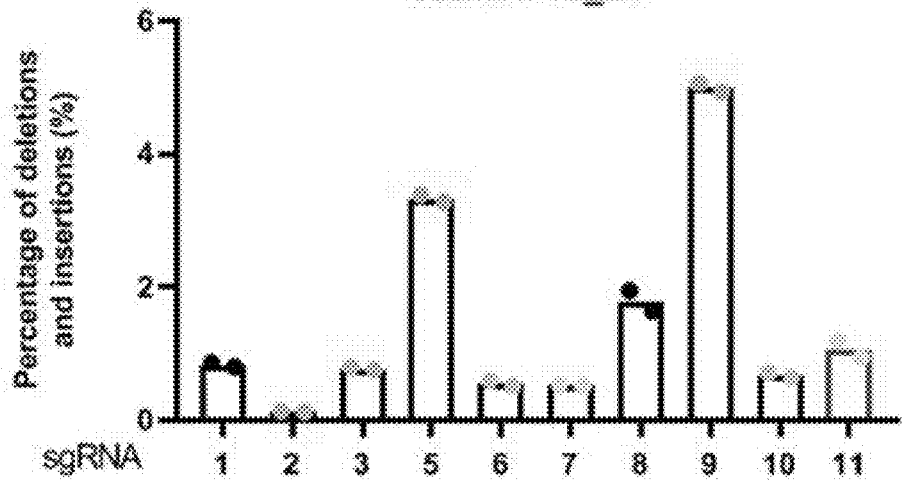
FIG. 54

FIG. 55

| CasMINI-V2 | D143R/T147R |
| CasMINI-V3.1 | D143R/T147R/E151A |
| CasMINI-V4 | D143R/T147R/K330R/E528R |

SYNTHETIC MINIATURE CRISPR-CAS (CASMINI) SYSTEM FOR EUKARYOTIC GENOME ENGINEERING

CROSS-REFERENCE TO RELATED APPLICATIONS

The present application claims priority to U.S. Provisional Application No. 63/073,377 filed Sep. 1, 2020, and U.S. Provisional Application No. 63/191,611 filed May 21, 2021, the full disclosures of which are incorporated by reference in their entirety for all purposes.

SEQUENCE LISTING

A Sequence Listing conforming to the rules of WIPO Standard ST.26 is hereby incorporated by reference. Said Sequence Listing has been filed as an electronic document via PatentCenter encoded as XML in UTF-8 text. The electronic document, created on Jan. 12, 2024, is entitled "079445-007620US-1374494_SL_ST26.xml", and is 409,367 bytes in size.

BACKGROUND

Techniques involving Clustered Regularly Interspaced Short Palindromic Repeat (CRISPR)-associated (Cas) protein have brought revolutionary capability to genome engineering applications (M. Jinek et al., Science 337, (2012): 816-21; L. Cong et al., Science 339, (2013): 819-23. While Cas nucleases (e.g., *Streptococcus pyogenes* Cas9, Lachnospiraceae bacterium Cas12a) allow for efficient and specific genome editing, nuclease-deactivated Cas (dCas) molecules fused with transcriptional and epigenome effectors enable targeted regulation of endogenous genes in mammalian cells (L. S. Qi et al., Cell 152, (2013): 1173-83; B. Zetsche et al., Cell 163, (2015): 759-71; Y. E. Tak et al., Nat. Methods 14, (2017): 1163-66; B. P. Kleinstiver et al., Nat. Biotechnol. 37, (2019): 276-82; X. Xu & S. L. Qi, J. Mol. Biol. 431, (2019): 34-47; D. C. Swarts, J. van der Oost, & M. Jinek, Mol. Cell 66, (2017): 221-33). These systems offer promising approaches to gene therapies against genetic diseases (B. I. Hilton et al., Nat. Biotechnol. 33, (2015): 510-17; T. S. Klann et al., Nat. Biotechnol. 35, (2017): 561-68; C. Fellmann, B. G. Gowen, P. C. Lin, J. A. Doudna, & J. E. Corn, Nat. Rev. Drug Discov. 16, (2017): 89-100). However, their large size usually prohibits applications. For example, adeno-associated virus (AAV) has a limited payload packaging capacity (<4.5 kb), and many Cas effectors or fusion proteins are beyond this limit.

The discovery of naturally occurring Cas effectors, including Cas14 (Cas12f) and CasΦ, having smaller sizes when compared to Cas9 or Cas12a (usually 1000 to 1500 amino acids) has offered a natural reservoir of compact Cas effectors (L. B. Harrington et al., Science 362, (2018): 839-42; T. Karvelis et al., Nucleic Acids Res. 48, (2020): 5016-23; S. N. Takeda et al., Mol. Cell 81, (2021): 558-70; P. Pausch et al., Science 369, (2020): 330-37) (FIG. 1). For example, the class 2 type V-F system, CRISPR-Cas14 (400-700 amino acids) is a family of exceptionally compact RNA-guided nucleases from uncultivated archaea. The compact Cas14 effector has not, though, been shown useful in mammalian cells (L. B. Harrington et al., Science 362, (2018): 839-42; T. Karvelis et al., Nucleic Acids Res. 48, (2020): 5016-23). Similarly, the reported compact CasΦ has been found to exhibit only moderate activity in eukaryotic cells (P. Pausch et al., Science 369, (2020): 330-37).

In view of these and other challenges associated with the use of many existing CRISPR-Cas systems, there is a need in the art for improved CRISPR-Cas system components, e.g., compact and highly efficient Cas effectors and/or related guide RNA molecules, for genome engineering applications. In particular, there is a need for improved CRISPR-Cas systems capable of sufficient functioning in mammalian cells. The present disclosure addresses this need and provides associated and other advantages.

BRIEF SUMMARY

In general, provided herein are miniature Cas effectors engineered, for example, from the type V-F Cas14 (529 amino acids) for efficient gene activation and base editing in mammalian cells. In cases where a natural Cas effector fails to work in mammalian cells, the provided engineered Cas effectors, via guide RNA and protein engineering, can exhibit thousands-fold improvements in activation levels of reporter and endogenous genes in these cell types. The engineered Cas effectors can further have high specificity with no detected off-targets, and allow for robust base editing when fused with an adenine base editor, and robust deletion-insertion gene editing. The synthetic materials and related methods disclosed herein thus provide useful tools for broad applications including those in the fields of gene therapy and cell engineering.

In one aspect, the disclosure provides an engineered Clustered Regularly Interspaced Short Palindromic Repeat (CRISPR)-associated (Cas) protein that is functional in eukaryotic cells. The Cas protein includes a modified amino acid sequence that is at least 80% identical to a native amino acid sequence of a wild-type Cas protein. The native amino acid sequence has a length of less than 700 amino acids and includes a (D/E/K/N)X(R/F)(E/K)N (SEQ ID NO: 253) motif. The modified amino acid sequence includes one or more substitutions in the native amino acid sequence. At least one of the one or more substitutions is at a position either (1) within or no more than 30 amino acids upstream or downstream of the (D/E/K/N)X(R/F)(E/K)N (SEQ ID NO: 253) motif, (2) at or no more than 30 amino acids upstream or downstream of position 241 of the native amino acid sequence, (3) at or no more than 30 amino acids upstream or downstream of position 516 of the native amino acid sequence, or (4) having an electrically charged amino acid in the native amino acid sequence.

In another aspect, the disclosure provides a single-guide RNA (sgRNA) including an engineered CRISPR RNA (crRNA/trans-activating CRISPR RNA (tracrRNA) fusion nucleotide sequence that is at least 60% identical to a wild-type crRNA/tracrRNA fusion nucleotide sequence. The wild-type crRNA/tracrRNA fusion nucleotide sequence includes (1) a 3' region corresponding to an RNA stem-loop hairpin structure, (2) a poly-U region proximate to the 3' region, and (3) a 5' poly-G region. The engineered crRNA/tracrRNA fusion nucleotide sequence includes one or more modifications to the wild-type crRNA/tracrRNA fusion nucleotide sequence. The modifications include substitution of at least one U of the poly-U region, e.g., with a G, deletion of at least a portion of the 3' region, deletion of at least a portion of the 5' poly-G region, or a combination of any of these modifications.

In another aspect, the disclosure provides a nucleic acid encoding any of the engineered Cas proteins disclosed herein. In another aspect, the disclosure provides a nucleic acid encoding any of the sgRNA molecules disclosed herein.

In another aspect, the disclosure provides a vector including a nucleic acid encoding any of the engineered Cas proteins disclosed herein, a nucleic acid encoding any of the sgRNA molecules disclosed herein, or a combination thereof.

In another aspect, the disclosure provides a system including an sgRNA and any of the engineered Cas proteins disclosed herein. In another aspect, the disclosure provides a Cas protein and any of the sgRNA molecules disclosed herein. In another aspect, the disclosure provides a system including both a nucleic acid encoding an sgRNA, and a nucleic acid encoding any of the engineered Cas proteins disclosed herein. In another aspect, the disclosure provides a system including both a nucleic acid encoding a Cas protein, and a nucleic acid encoding any of the sgRNA molecules disclosed herein.

In another aspect, the disclosure provides a method of modulating one or more target nucleic acids in a cell. The method includes contacting the cell with any of the engineered Cas proteins disclosed herein, any of the sgRNA molecules disclosed herein, any of the nucleic acids disclosed herein, any of the vectors disclosed herein, or any of the systems disclosed herein.

In another aspect, the disclosure provides a pharmaceutical composition. The pharmaceutical composition includes any of the engineered Cas proteins disclosed herein, any of the sgRNA molecules disclosed herein, any of the nucleic acids disclosed herein, any of the vectors disclosed herein, or any of the systems disclosed herein.

In another aspect, the disclosure provides a method of preventing or treating a disorder, e.g., a genetic disorder, in a subject. The method includes administering to the subject an amount of any of the pharmaceutical compositions disclosed herein, where the amount is sufficient to modulate one or more target nucleic acids associated with the disorder.

In another aspect, the disclosure provides a method of treating an infection in a subject. The method includes administering to the subject an amount of any of the pharmaceutical compositions disclosed herein, where the amount is sufficient to modulate one or more target nucleic acids associated with the infection.

BRIEF DESCRIPTION OF THE DRAWINGS

FIG. 14 is a graph showing mean activated GFP values characterizing gene activation activity of the different dCas14-VPR fusions of FIG. 12. Dots represent three biological replicates. Dash line represents the GFP mean value of the non-targeting sgRNA. Values showing the fold of activation normalized to the non-target sgRNA are labeled.

FIG. 15 presents an overview of the iterative protein engineering strategy. The TRE3G-GFP HEK293T cell line is used to measure GFP activation efficiency of dCas14-VPR variants by flow cytometry 48 h post transfection. The best dCas14-VPR variant for GFP activation is used as the starting sequence for the next round of screening.

FIG. 16 shows alignment of Cas14 to reported Cas12a protein and DtTnpB, with the conserved active residues of three RuvC domains indicated. FIG. 16 discloses SEQ ID NOS 177-194, respectively, in order of appearance.

FIG. 29 discloses SEQ ID NOS 195-204, respectively, in order of appearance.

FIG. 30 presents schematic illustrations of constructs used to test endogenous gene activation by a dCasMINI-VPR system, and confocal microscopy images showing expression and nuclear localization. Cell nuclei are stained using Hoechst 33342. Bars, 20 μm.

FIG. 31 presents results from gene activation of endogenous HBG in HEK293T cells using dCasMINI-VPR with various single sgRNAs. Top, a schematic illustration of the sgRNA distributions and PAMs. Transcriptional start site (TSS) is designated as '0', and the positions of the first 'T' in each PAM are labeled. Bottom, fold changes of top sgRNAs are shown.

FIG. 38 presents schematic illustrations of constructs used for dCasMINI-VPR, dCas14-VPR, and sgRNA to compare CasMINI and Cas14.

FIG. 39 presents graphs comparing endogenous IFNγ gene activation by dCasMINI-VPR and dCas14-VPR. Fold changes of improvement of dCasMINI-VPR over dCas14-VPR are shown.

FIG. 40 presents graphs comparing endogenous HBB gene activation by dCasMINI-VPR and dCas14-VPR. Fold changes of improvement of dCasMINI-VPR over dCas14-VPR are shown.

FIG. 41 presents graphs comparing endogenous CD2 gene activation by dCasMINI-VPR and dCas14-VPR. Fold changes of improvement of dCasMINI-VPR over dCas14-VPR are shown.

FIG. 43 discloses SEQ ID NO: 205.

FIG. 46 is a graph showing RNA-seq data of cell samples transfected with the targeting sgRNA vs. the non-targeting sgRNA and dCasMINI-VPR from the comparison of FIG. 43. Mean values of two biological replicates are plotted. The data points for GFP transcripts are labeled.

FIG. 47 is a graph showing RNA-seq data of cell samples transfected with the targeting sgRNA vs. the non-targeting sgRNA and dCas12a-VPR from the comparison of FIG. 43. Mean values of two biological replicates are plotted. The data points for GFP transcripts are labeled.

FIG. 48 presents graphs showing comparisons of biological replicates for each condition tested in the experiment of FIGS. 43-47. From top left to bottom right, dCasMINI-VPR+non-targeting sgRNA, dCasMINI-VPR+targeting sgRNA, dCas12a-VPR+non-targeting sgRNA, dCas12-VPR+targeting sgRNA. The calculated Pearson Correlation for each condition is shown.

FIG. 49 presents graphs showing correlation of side-by-side comparison of dCasMINI-VPR vs. dCas12a-VPR for the non-targeting guide (left) and the targeting guide (right). The calculated Pearson Correlation for each condition is shown.

FIG. 50 is a graph overlaying the data of FIGS. 46 and 47.

FIG. 51 is a graph from the comparison of FIG. 43 showing the distribution of standard deviations for $\log_{10}$ [transcripts per million (TPM)+1] values of all genes in RNA sequencing library among non-targeting and targeting replicates for each gene for dCasMINI-VPR and LbdCas12a-VPR, respectively.

FIG. 52 illustrates a comparison of base editing activity using dCasMINI or dCas12a fused to the same ABE8e editor. The schematic diagram shows the constructs used in the experiments. The graph shows the percentage of A·T to G·C conversion observed when using dCas12a-ABE and dCasMINI-ABE for selected genomic sites. NT, non-targeting sgRNA or crRNA. T, T1, T2, targeting sgRNAs or crRNAs.

FIG. 54 presents graphs showing the percentage of gene editing indels, including deletions, insertions, and substitutions, observed when using systems including one of three provided Cas proteins and one of eleven different sgRNAs.

Figure 55:
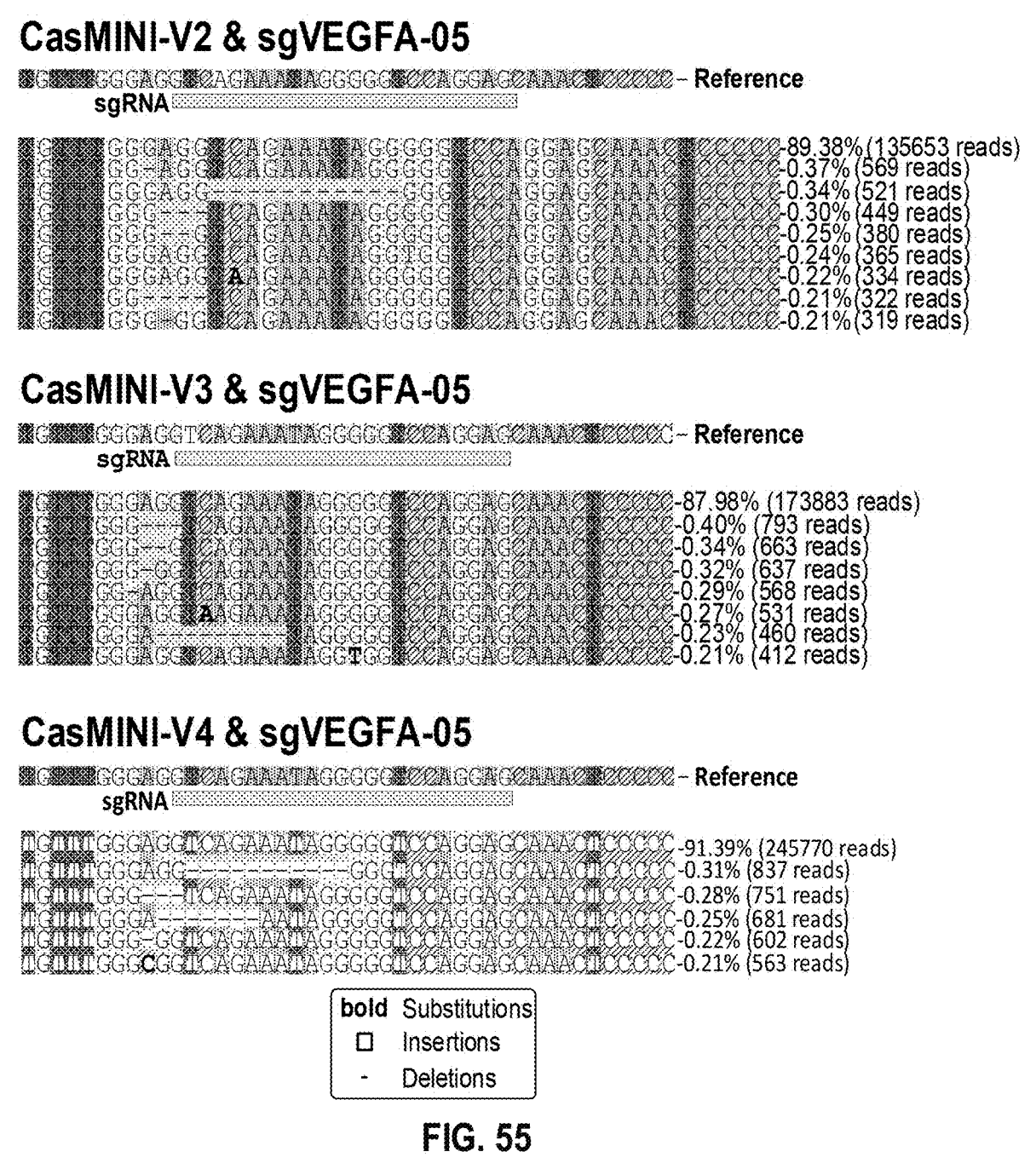

FIG. 55 shows representative sequences from the genomic region targeted by sgVEGFA05 and the corresponding percentages of the sgRNA in the gene editing tests of FIG. 54. FIG. 55 discloses SEQ ID NOS 206-215, 206, 210-211, 215, 208, 213, 216, 212, 206, 209, 210, 217, 215, and 218, respectively, in order of appearance.

FIG. 61 discloses SEQ ID NOS 219-234, respectively, in order of appearance.

FIG. 66 discloses SEQ ID NOS 235-241, 236, 242-244, 238, 237, 240, 245-246, 236, 242, 237, 240, 244, 247, 243, 246, 248-249, 241, 250, 238, 251, 236, 242, 250, and 237, respectively, in order of appearance.

Figure 69:
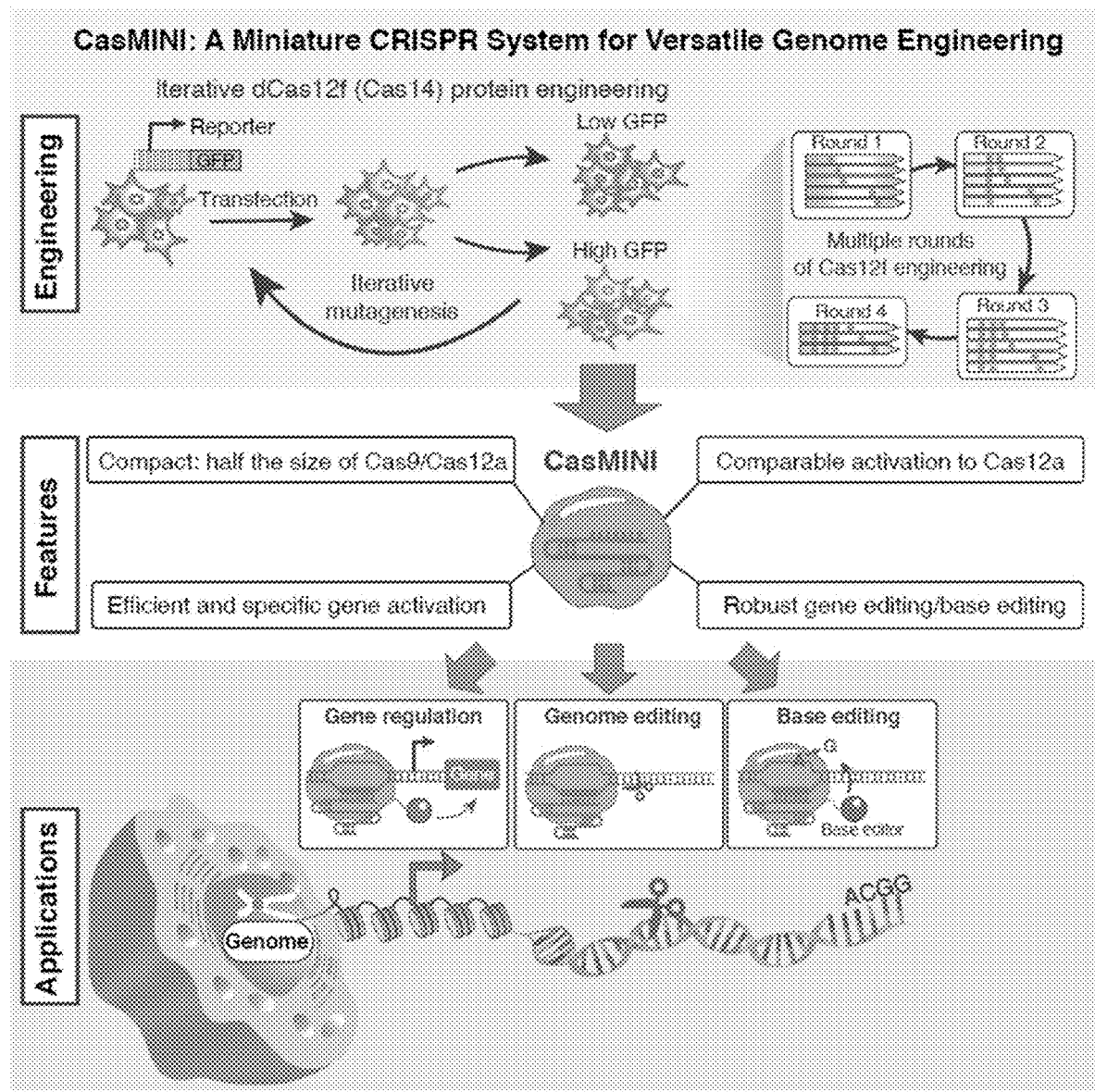

FIG. 69 presents an illustration of the engineering, features, and applications of the provided Cas system.

DETAILED DESCRIPTION

Provided herein are materials and methods involving synthetic compact, efficient, and specific genome engineering systems that advantageously are highly effective in mammalian cells. The provided systems have been developed through particular improvement strategies involving, for example, optimization of the single guide RNA (sgRNA) design and targeted Cas protein engineering (M. T. Reetz & J. D. Carballeira, Mat. Protoc. 2, (2007): 891-903; G. Qu, A. Li, C. G Acevedo-Rocha, Z. Sun, & M. T. Reetz, Angew Chem Int. Ed. Engl. 59, (2020): 13204-31; X. Xu et al., Chembiochem 17 (2016): 56-64). Many of the optimization and engineering approaches described herein use principles not previously appreciated or implemented. As a result of these approaches, the provided variants can, for example, efficiently activate reporter and endogenous gene expression in eukaryotic, e.g., mammalian, cells. Notably, the provided systems exhibit 2 to 3 logs of improvement over the wild-type Cas14, outperform the type V-A dCas12a system, and are specific in mammalian cells without detectable off-targets. Further, when fused to an adenine base editor, the systems can allow robust conversion of A·T to G·C. Thus, the systems and processes disclosed herein provide useful tools for a variety of genome engineering applications, including those within eukaryotic cells and/or those that require compact effector sizes for delivery and function.

Certain embodiments provide an engineered miniature Cas effector, named CasMINI, derived from the naturally occurring type V-F Cas12f (Cas14) system, which was only 529 amino acids compared to 1,368 amino acids of commonly used SpCas9 or 1,228 amino acid of LbCas12a. While the natural Cas14 shows no activity in mammalian cells, synthetic CasMINI engineered via iterative protein screening and optimized sgRNA designs exhibits highly efficient activation of target genes. The efficiency of activation is, for example, comparable to or better than that of the Cas12a system. Also beneficially, no significant detectable off-target activity is detected with the CasMINI system, and the system has been shown useful for other genetic engineering applications such as base editing.

Despite the rapid advancement of CRISPR-Cas systems, a biotechnological challenge for cell engineering or in vivo delivery remains, particular with respect to eukaryotic cells, due to the large size of Cas effectors. The engineered compact molecules disclosed herein have greatly reduced sizes, making them more suitable than other Cas effectors for medical treatment methods. For example, the small size of the CasMINI system makes it compatible with adeno-associated virus (AAV) packaging and can enhance delivery efficiency when using lipid nanoparticles to carry mRNA payloads. Furthermore, the small size advantageously makes the provided materials less immunogenic when compared to large protein payloads. Moreover, the general RNA and protein engineering approach used in the work also makes it possible to engineer Cas effectors, e.g., Cas14/Cas12f effectors, from other bacterial species.

I. CAS PROTEINS

In one aspect, an engineered Cas protein is provided. The engineered Cas protein disclosed herein provides surprising improvements in its ability to function in eukaryotic cells. The engineered Cas protein has a modified amino acid sequence that is at least 80% identical to a native amino acid sequence of a wild-type Cas protein. The modified amino acid sequence of the engineered Cas protein can be, for example, at least 80%, at least 82%, at least 84%, at least 86%, at least 88%, at least 90%, at least 91%, at least 92%, at least 93%, at least 94%, at least 95%, at least 96%, at least 97%, at least 98%, or at least 99% identical to a native amino acid sequence of a wild-type Cas protein.

CRISPR systems are generally divided into two classes, with class 1 systems using a complex of multiple Cas proteins to degrade foreign nucleic acids, and class 2 systems using a single, generally larger, Cas protein for the same purpose. Class 1 is divided into types I, III, and IV, and class 2 is divided into types II, V, and VI. In some embodiments, the wild-type Cas protein that the engineered Cas protein is a modification of is a type V Cas protein. The wild-type Cas protein can be, for example, a type V-A Cas protein, a type V-B Cas protein, a type V-C Cas protein, a type V-D Cas protein, a type V-E Cas protein, a type V-F Cas protein, a type V-G Cas protein, a type V-H Cas protein, a type V-I Cas protein, a type V-J Cas protein, a type V-K Cas protein, or a type V-U Cas protein. In some embodiments, the wild-type Cas protein is a type V-J protein, such as a wild-type CasΦ (Cas 12J) protein.

In some embodiments, the wild-type Cas protein is a type V-F Cas protein such as Cas14. In some embodiments, the wild-type Cas protein is a Cas14 (Cas12f) protein having the native amino sequence of SEQ ID NO: 1. Cas14 proteins are Type V subtype F RNA-guided nucleic acid-binding proteins that can be targeted to DNA and/or RNA, and are much smaller than typical CRISPR effectors, ranging in size from about 400 amino acids to about 700 amino acids. At least 24 different Cas14 variants have been identified that cluster into three subgroups, Cas14a, Cas14b, and Cas14c, based on sequence comparison, all of which share a predicted RuvC nuclease domain characteristic of type V CRISPR-Cas DNA-targeting enzymes. The small size of Cas14 proteins allows Cas14 proteins and effector domain fusions thereof to be paired with a CRISPR array encoding multiple guide RNAs while remaining under the packaging size limit of the versatile adeno-associated virus (AAV) delivery vehicle for primary cell and in vivo delivery. Targeted AAV delivery of dCas14 systems to cells can allow for long-term expression of a corrective payload that avoids permanent genetic modifications or frequent re-administration, complementing other nucleic acid-targeting technologies such as DNA nuclease editing or antisense oligonucleotides. CRISPR-Cas14 and engineered variants such as dCas14 allow for flexible nucleic acid engineering, regulation of gene expression, and therapeutics, expanding the genome editing and regulation toolbox.

In some embodiments, the wild-type Cas protein that the engineered Cas protein is a modification of has a native amino acid sequence with a length of less than 700 amino acids. This relatively small size provides several advantages to the provided engineered Cas protein. For example, the small size can allow the Cas protein to be delivered to a host cell, e.g., a cell of a human patient, via a single adeno-associated virus delivery system that would be otherwise incapable of delivering a larger protein. The native amino acid sequence can have a length that is, for example, between 500 amino acids and 700 amino acids, e.g., between 500 amino acids and 620 amino acids, between 540 amino acids and 660 amino acids, between 560 amino acids and 680 amino acids, or between 580 amino acids and 700 amino acids. In terms of upper limits, the native amino acid sequence can have a length that is less than 700 amino acids, e.g., less than 680 amino acids, less than 660 amino acids, less than 640 amino acids, less than 620 amino acids, less than 600 amino acids, less than 580 amino acids, less than 560 amino acids, less than 540 amino acids, or less than 520 amino acids. In terms of lower limits, the native amino acid sequence can have a length that is greater than 500 amino acids, e.g., greater than 520 amino acids, greater than 540 amino acid, greater than 560 amino acids, greater than 580 amino acids, greater than 600 amino acids, greater than 620 amino acids, greater than 640 amino acids, greater than 660 amino acids, or greater than 700 amino acids. Larger lengths, e.g., greater than 700 amino acids, and smaller lengths, e.g., less than 500 amino acids, are also contemplated.

In some embodiments, the modified amino acid sequence of the engineered Cas protein includes one or more substitutions in the native amino acid sequence, where the positions of at least some of these substitutions follow one or more particular rules determined to have surprising advantages for the characteristics of the engineered Cas protein. For example, the particular substitution rules have been selected for their ability to produce engineered Cas proteins capable of functioning within eukaryotic cells. According to these particular rules, all or some of the one or more substitutions in the native amino acid sequence are either (1) within or no more than 30 amino acids downstream of a (D/E/K/N)X(R/F)(E/K)N (SEQ ID NO: 253) motif of the native amino acid sequence, (2) at or no more than 30 amino acids upstream or downstream of position 241 of the native amino acid sequence, (3) at or no more than 30 amino acids upstream or downstream of position 516 of the native amino acid sequence, or (4) having an electrically charged amino acid in the native amino acid sequence.

In some embodiments, the one or more substitutions in the native amino acid sequence include substitutions in one of the above four categories. The one or more substitutions can include substitutions in one category that is either category (1), (2), (3) or (4). The one or more substitutions can consist of substitutions in one category that is either category (1), (2), (3), or (4). In some embodiments, the one or more substitutions are each independently in one of two categories selected from categories (1) and (2), (1) and (3), (1) and (4), (2) and (3), (2) and (4), or (3) and (4). In some embodiments, the one or more substitutions include substitutions in each of the two categories (1) and (2), (1) and (3), (1) and (4), (2) and (3), (2) and (4), or (3) and (4). In some embodiments, the one or more substitutions consist of substitutions in each of the two categories (1) and (2), (1) and (3), (1) and (4), (2) and (3), (2) and (4), or (3) and (4). In some embodiments, the one or more substitutions are each independently in one of the three categories (1), (2) and (3); (1), (2), and (4); (1), (3), and (4); or (2), (3), and (4). In some embodiments, the one or more substitutions include substitutions in each of the three categories (1), (2) and (3); (1), (2), and (4); (1), (3), and (4); or (2), (3), and (4). In some embodiments, the one or more substitutions consist of substitutions in each of the three categories (1), (2) and (3); (1), (2), and (4); (1), (3), and (4); or (2), (3), and (4). In some embodiments, the one or more substitutions include substitutions in each of the four categories.

Further, in some embodiments, additional substitution rules are followed wherein all or some of the one or more amino acid substitutions in the native amino acid sequence are to a small amino acid, e.g., arginine (R), alanine (A), serine(S), or glycine (G). In some embodiments, the one or more substitutions includes a substitution to R. In some embodiments, each of the one or more substitutions is a substitution to R. In some embodiments, the one or more substitutions includes a substitution to A. In some embodiments, each of the one or more substitutions is a substitution to A. In some embodiments, the one or more substitutions includes a substitution to S. In some embodiments, each of the one or more substitutions is a substitution to S. In some embodiments, the one or more substitutions includes a substitution to G. In some embodiments, each of the one or more substitutions is a substitution to G. In some embodiments, the one or more substitutions include substitutions to the two amino acids R and A, R and S, R and G, A and S, A and G, or S and G. In some embodiments, the one or more substitutions consist of substitutions that are each independently to one of the two amino acids R and A, R and S, R and G, A and S, A and G, or S and G. In some embodiments, the one or more substitutions consist of substitutions to each of the two amino acids R and A, R and S, R and G, A and S, A and G, or S and G. In some embodiments, the one or more substitutions include substitutions to the three amino acids R, A, and S; R, A, and G; R, S, and G; or A, S, and G. In some embodiments, the one or more substitutions consist of substitutions that are each independently to one of the three amino acids R, A, and S; R, A, and G; R, S, and G; or A, S, and G. In some embodiments, the one or more substitutions consist of substitutions to each of the three amino acids R, A, and S; R, A, and G; R, S, and G; or A, S, and G. In some embodiments, the one or more substitutions include substitutions to the four amino acids R, A, S, and G. In some embodiments, the one or more substitutions consist of substitutions that are each independently to one of the four amino acids R, A, S, and G. In some embodiments, the one or more substitutions consist of substitutions to each of the four amino acids R, A, S, and G.

In some embodiments, the native amino acid sequence includes a (D/E/K/N)X(R/F)(E/K)N (SEQ ID NO: 253) motif, and the modified amino acid sequence includes one or more substitutions at positions within or no more than 30 amino acids upstream or downstream of the motif. The modified amino acid sequence can include, for example, one, two, three, four, five, six, seven, eight, nine, ten, or more than ten substitutions within or no more than 30 amino acids upstream or downstream of the motif. At least one of the one or more substitutions to the native amino acid sequence can be, for example, within or no more than 28 amino acids, 26 amino acids, 24 amino acids, 22 amino acids, 20 amino acids, 18 amino acids, 16 amino acids, 14 amino acids, 12 amino acids, or 10 amino acids of the motif. In some embodiments, at least one of the one or more substitutions within or no more than 30 amino acids upstream or downstream of the motif is to an R, A, S, or G. In some embodiments, each of the one or more substitutions within or no more than 30 amino acids upstream or downstream of the motif is independently to an R, A, S, or G. In some embodiments, all of the substitutions to the native amino acid sequence are at positions within or no more than 30 amino acids upstream or downstream of the motif.

The one or more substitutions at positions within or no more than 30 amino acids upstream or downstream of the (D/E/K/N)X(R/F)(E/K)N (SEQ ID NO: 253) motif of the native amino acid sequence can include, for example, one or more substitutions at positions selected from positions 143, 147, 151, and 154 of the native amino acid sequence. In some embodiments, e.g., when the native amino acid sequence is the sequence of SEQ ID NO: 1, the one or more substitutions include substitutions are at one or more positions selected from D143, T147, E151, and K154. In some embodiments, e.g., when the native amino acid sequence is the sequence of SEQ ID NO: 1, the one or more substitutions include one or more substitutions selected from D143R, T147R, E151R, and K154R.

In some embodiments, the modified amino acid sequence includes one or more substitutions at or no more than 30 amino acids upstream or downstream of position 241 of the native amino acid sequence. The modified amino acid sequence can include, for example, one, two, three, four, five, six, seven, eight, nine, ten, or more than ten substitutions within or no more than 30 amino acids upstream or downstream of position 241. At least one of the one or more substitutions to the native amino acid sequence can be, for example, within or no more than 28 amino acids, 26 amino acids, 24 amino acids, 22 amino acids, 20 amino acids, 18 amino acids, 16 amino acids, 14 amino acids, 12 amino acids, or 10 amino acids of position 241. In some embodiments, at least one of the one or more substitutions within or no more than 30 amino acids upstream or downstream of position 241 is to an R, A, S, or G. In some embodiments, each of the one or more substitutions within or no more than 30 amino acids upstream or downstream of position 241 is independently to an R, A, S, or G. In some embodiments, all of the substitutions to the native amino acid sequence are at positions within or no more than 30 amino acids upstream or downstream of position 241.

The one or more substitutions at positions within or no more than 30 amino acids upstream or downstream of position 241 of the native amino acid sequence can include, for example, a substitution at positions 241 of the native amino acid sequence. In some embodiments, e.g., when the native amino acid sequence is the sequence of SEQ ID NO: 1, the one or more substitutions include a substitution at position E241. In some embodiments, e.g., when the native amino acid sequence is the sequence of SEQ ID NO: 1, the one or more substitutions include an E241 substitution.

In some embodiments, the modified amino acid sequence includes one or more substitutions at or no more than 30 amino acids upstream or downstream of position 516 of the native amino acid sequence. The modified amino acid sequence can include, for example, one, two, three, four, five, six, seven, eight, nine, ten, or more than ten substitutions within or no more than 30 amino acids upstream or downstream of position 516. At least one of the one or more substitutions to the native amino acid sequence can be, for example, within or no more than 28 amino acids, 26 amino acids, 24 amino acids, 22 amino acids, 20 amino acids, 18 amino acids, 16 amino acids, 14 amino acids, 12 amino acids, or 10 amino acids of position 516. In some embodiments, at least one of the one or more substitutions within or no more than 30 amino acids upstream or downstream of position 516 is to an R, A, S, or G. In some embodiments, each of the one or more substitutions within or no more than 30 amino acids upstream or downstream of position 516 is independently to an R, A, S, or G. In some embodiments, all of the substitutions to the native amino acid sequence are at positions within or no more than 30 amino acids upstream or downstream of position 516.

The one or more substitutions at positions within or no more than 30 amino acids upstream or downstream of position 516 of the native amino acid sequence can include, for example, one or more substitutions at positions selected from positions 504, 507, 516, 519, 527, and 528 of the native amino acid sequence. In some embodiments, e.g., when the native amino acid sequence is the sequence of SEQ ID NO: 1, the one or more substitutions include substitutions are at one or more positions selected from N504, E507, N516, N519, E527, and E528. In some embodiments, e.g., when the native amino acid sequence is the sequence of SEQ ID NO: 1, the one or more substitutions include one or more substitutions selected from N504R, E507R, N516R, N519R, E527R, and E528R.

In some embodiments, the modified amino acid sequence includes one or more substitutions at positions of the native amino acid sequence having an electrically charged amino acid. The modified amino acid sequence can include, for example, substitutions at positions having an aspartic acid (D), glutamic acid (E), lysine (K), arginine (R), or histidine (H). In some embodiments, at least one of the one or more substitutions for an electrically charged amino acid is to an R, A, S, or G. In some embodiments, each of the one or more substitutions for an electrically charged amino acid is independently to an R, A, S, or G. In some embodiments, all of the substitutions to the native amino acid sequence are at positions having an electrically charged amino acid.

In some embodiments, e.g., when the native amino acid sequence is the sequence of SEQ ID NO: 1, the one or more substitutions at positions having an electrically charged amino include substitutions are at one or more positions selected from K11, K73, D143, E151, K154, E241, D318, K330, K457, E425, E462, E507, E527, and E528. In some embodiments, e.g., when the native amino acid sequence is the sequence of SEQ ID NO: 1, the one or more substitutions include one or more substitutions selected from K11R, K73R, D143R, E151R, K154R, E241R, D318R, K330R, E425N, K457R, E462R, E507R, E527R, and E528R. In some embodiments, the modified amino acid sequence includes a D143R substitution. In some embodiments, the only substitution in the modified amino acid sequence is D143R. In some embodiments, the modified amino acid sequence is the sequence of SEQ ID NO: 2.

In some embodiments, the modified amino acid sequence of the engineered Cas protein includes two substitutions in the native amino acid sequence. In some embodiments, the modified amino acid sequence has exactly two substitutions in the native amino acid sequence. In some embodiments, the modified amino acid sequence includes two substitutions at positions selected from positions 143, 147, 151, 154, 241, 330, 425, 504, 507, 516, 519, 527, and 528. In some embodiments, the modified amino acid sequence has exactly two substitutions, where the exactly two substitutions are at positions selected from positions 143, 147, 151, 154, 241, 330, 425, 504, 507, 516, 519, 527, and 528. In some embodiments, e.g., when the native amino acid sequence is the sequence of SEQ ID NO: 1, the modified amino acid sequence includes two substitutions at positions selected from D143, T147, E151, K154, E241, K330, E425, N504, E507, N516, N519, E527, and E528. In some embodiments, e.g., when the native amino acid sequence is the sequence of SEQ ID NO: 1, the modified amino acid sequence has exactly two substitutions, where the exactly two substitutions are at positions selected from D143, T147, E151, K154, E241, K330, E425, N504, E507, N516, N519, E527, and E528.

In some embodiments, the modified amino acid sequence includes a substitution at position 143 and a substitution at a position selected from positions 147, 151, 154, 241, 330, 425, 504, 507, 516, 519, 527, and 528. In some embodiments, the modified amino acid includes a substitution at position 143 and exactly one other substitution, where the exactly one other substitution is at a position selected from positions 147, 151, 154, 241, 330, 425, 504, 507, 516, 519, 527, and 528. In some embodiments, e.g., when the native amino acid sequence is the sequence of SEQ ID NO: 1, the modified amino acid sequence includes a substitution at position D143 and a substitution at a position selected from positions T147, E151, K154, E241, K330R, E425N, N504, E507, N516, N519, E527, and E528. In some embodiments, e.g., when the native amino acid sequence is the sequence of SEQ ID NO: 1, the modified amino acid includes a substitution at position D143 and exactly one other substitution, where the exactly one other substitution is at a position selected from positions T147, E151, K154, E241, K330R, E425N, N504, E507, N516, N519, E527, and E528.

In some embodiments, e.g., when the native amino acid sequence is the sequence of SEQ ID NO: 1, the modified amino acid includes two substitutions selected from D143R, T147R, E151R, E151A, K154R, E241R, N504R, E507R, N516R, N519R, E527R, and E528R. In some embodiments, e.g., when the native amino acid sequence is the sequence of SEQ ID NO: 1, the modified amino acid includes exactly two substitutions, where the two substitutions are selected from D143R, T147R, E151R, E151A, K154R, E241R, N504R, E507R, N516R, N519R, E527R, and E528R. In some embodiments, e.g., when the native amino acid sequence is the sequence of SEQ ID NO: 1, the modified amino acid includes two substitutions selected from D143R/T147R, D143R/E151R, D143R/E241R, D143R/E425N, D143R/E507R, D143R/N519R, D143R/E527R, D143R/E528R, D143R/R151S, D143/R151G, and D143R/E151A. In some embodiments, e.g., when the native amino acid sequence is the sequence of SEQ ID NO: 1, the modified amino acid includes exactly two substitutions, where the two substitutions are selected from D143R/T147R, D143R/E151R, D143R/E241R, D143R/E425N, D143R/E507R, D143R/N519R, D143R/E527R, D143R/E528R, D143R/R151S, D143/R151G, and D143R/E151A. In some embodiments, the modified amino acid sequence includes a D143R substitution and a T147R substitution. In some embodiments, the only substitutions in the modified amino acid sequence are a D143R substitution and a T147R substitution. In some embodiments, the modified amino acid sequence is the sequence of SEQ ID NO: 3.

In some embodiments, the modified amino acid sequence of the engineered Cas protein includes three substitutions in the native amino acid sequence. In some embodiments, the modified amino acid sequence has exactly three substitutions in the native amino acid sequence. In some embodiments, the modified amino acid sequence includes three substitutions at positions selected from positions 143, 147, 151, 154, 241, 330, 425, 504, 507, 516, 519, 527, and 528. In some embodiments, the modified amino acid sequence has exactly three substitutions, where the exactly three substitutions are at positions selected from positions 143, 147, 151, 154, 241, 330, 425, 504, 507, 516, 519, 527, and 528. In some embodiments, e.g., when the native amino acid sequence is the sequence of SEQ ID NO: 1, the modified amino acid sequence includes three substitutions at positions selected from D143, T147, E151, K154, E241, K330, E425, N504, E507, N516, N519, E527, and E528. In some embodiments, e.g., when the native amino acid sequence is the sequence of SEQ ID NO: 1, the modified amino acid sequence has exactly three substitutions, where the exactly three substitutions are at positions selected from D143, T147, E151, K154, E241, K330, E425, N504, E507, N516, N519, E527, and E528.

In some embodiments, the modified amino acid sequence includes a substitution at position 143, a substitution at position 147, and a substitution at a position selected from positions 151, 154, 241, 330, 425, 504, 507, 516, 519, 527, and 528. In some embodiments, the modified amino acid includes a substitution at position 143, a substitution at position 147, and exactly one other substitution, where the exactly one other substitution is at a position selected from positions 151, 154, 241, 330, 425, 504, 507, 516, 519, 527, and 528. In some embodiments, e.g., when the native amino acid sequence is the sequence of SEQ ID NO: 1, the modified amino acid sequence includes a substitution at position D143, a substitution at position T147, and a substitution at a position selected from positions E151, K154, E241, K330, E425, N504, E507, N516, N519, E527, and E528. In some embodiments, e.g., when the native amino acid sequence is the sequence of SEQ ID NO: 1, the modified amino acid includes a substitution at position D143, a substitution at position T147, and exactly one other substitution, where the exactly one other substitution is at a position selected from positions E151, K154, E241, K330, E425, N504, E507, N516, N519, E527, and E528.

In some embodiments, e.g., when the native amino acid sequence is the sequence of SEQ ID NO: 1, the modified amino acid includes three substitutions selected from D143R, T147R, E151R, E151A, E151S, E151G, K154R, E241R, K330R, E425N, N504R, E507R, N516R, N519R, E527R, and E528R. In some embodiments, e.g., when the native amino acid sequence is the sequence of SEQ ID NO: 1, the modified amino acid includes exactly three substitutions, where the three substitutions are selected from D143R, T147R, E151R, E151A, E151S, E151G, K154R, E241R, K330R, E425N, N504R, E507R, N516R, N519R, E527R, and E528R. In some embodiments, e.g., when the native amino acid sequence is the sequence of SEQ ID NO: 1, the modified amino acid includes three substitutions selected from D143R/T147R/K330R, D143R/T147R/K154R, D143R/T147R/E241R, D143R/T147R/E507R, D143R/T147R/N519R, D143R/T147R/E527R, D143R/T147R/E528R, D143R/T147R/E151S, D143R/T147R/E151G, and D143R/T147R/E151A. In some embodiments, e.g., when the native amino acid sequence is the sequence of SEQ ID NO: 1, the modified amino acid includes exactly three substitutions, where the three substitutions are selected from D143R/T147R/K330R, D143R/T147R/E241R, D143R/T147R/E507R, D143R/T147R/K154R, D143R/T147R/N519R, D143R/T147R/E527R, D143R/T147R/E528R, D143R/T147R/E151S, D143R/T147R/E151G, and D143R/T147R/E151A. In some embodiments, the modified amino acid sequence includes a D143R substitution, a T147R substitution, and a K330R substitution. In some embodiments, the only substitutions in the modified amino acid sequence are a D143R substitution, a T147R substitution, and a K330R substitution. In some embodiments, the modified amino acid sequence is the sequence of SEQ ID NO: 4.

In some embodiments, the modified amino acid sequence of the engineered Cas protein includes four substitutions in the native amino acid sequence. In some embodiments, the modified amino acid sequence has exactly four substitutions in the native amino acid sequence. In some embodiments, the modified amino acid sequence includes four substitutions at positions selected from positions 143, 147, 151, 154, 241, 330, 425, 504, 507, 516, 519, 527, and 528. In some embodiments, the modified amino acid sequence has exactly four substitutions, where the exactly four substitutions are at positions selected from positions 143, 147, 151, 154, 241, 330, 425, 504, 507, 516, 519, 527, and 528. In some embodiments, e.g., when the native amino acid sequence is the sequence of SEQ ID NO: 1, the modified amino acid sequence includes four substitutions at positions selected from D143, T147, E151, K154, E241, K330, E425, N504, E507, N516, N519, E527, and E528. In some embodiments, e.g., when the native amino acid sequence is the sequence of SEQ ID NO: 1, the modified amino acid sequence has exactly four substitutions, where the exactly four substitutions are at positions selected from D143, T147, E151, K154, E241, K330, E425, N504, E507, N516, N519, E527, and E528.

In some embodiments, the modified amino acid sequence includes a substitution at position 143, a substitution at position 147, a substitution at position 330, and a substitution at a position selected from positions 151, 154, 241, 425, 504, 507, 516, 519, 527, and 528. In some embodiments, the modified amino acid includes a substitution at position 143, a substitution at position 147, a substitution at position 330, and exactly one other substitution, where the exactly one other substitution is at a position selected from positions 151, 154, 241, 425, 504, 507, 516, 519, 527, and 528. In some embodiments, e.g., when the native amino acid sequence is the sequence of SEQ ID NO: 1, the modified amino acid sequence includes a substitution at position D143, a substitution at position T147, a substitution at K330, and a substitution at a position selected from positions E151, K154, E241, E425, N504, E507, N516, N519, E527, and E528. In some embodiments, e.g., when the native amino acid sequence is the sequence of SEQ ID NO: 1, the modified amino acid includes a substitution at position D143, a substitution at position T147, a substitution at position K330, and exactly one other substitution, where the exactly one other substitution is at a position selected from positions E151, K154, E241, E425, N504, E507, N516, N519, E527, and E528.

In some embodiments, e.g., when the native amino acid sequence is the sequence of SEQ ID NO: 1, the modified amino acid includes four substitutions selected from D143R, T147R, E151R, E151A, E151S, E151G, K154R, E241R, K330R, E425N, N504R, E507R, N516R, N519R, E527R, and E528R. In some embodiments, e.g., when the native amino acid sequence is the sequence of SEQ ID NO: 1, the modified amino acid includes exactly four substitutions, where the four substitutions are selected from D143R, T147R, E151R, E151A, E151S, E151G, K154R, E241R, K330R, E425N, N504R, E507R, N516R, N519R, E527R, and E528R. In some embodiments, e.g., when the native amino acid sequence is the sequence of SEQ ID NO: 1, the modified amino acid includes four substitutions selected from D143R/T147R/K330R/E528R, D143R/T147R/K330R/E151A, and D143R/T147R/K330R/E527R. In some embodiments, e.g., when the native amino acid sequence is the sequence of SEQ ID NO: 1, the modified amino acid includes exactly four substitutions, where the four substitutions are selected from D143R/T147R/K330R/E528R, D143R/T147R/K330R/E151A, and D143R/T147R/K330R/E527R. In some embodiments, the modified amino acid sequence includes a D143R substitution, a T147R substitution, a K330R substitution, and an E528R substitution. In some embodiments, the only substitutions in the modified amino acid sequence are a D143R substitution, a T147R substitution, a K330R substitution, and an E528R substitution. In some embodiments, the modified amino acid sequence is the sequence of SEQ ID NO: 5.

In some embodiments, the modified amino acid sequence of the engineered Cas protein includes five substitutions in the native amino acid sequence. In some embodiments, the modified amino acid sequence has exactly five substitutions in the native amino acid sequence. In some embodiments, the modified amino acid sequence includes five substitutions at positions selected from positions 143, 147, 151, 154, 241, 330, 504, 507, 516, 519, 527, and 528. In some embodiments, the modified amino acid sequence has exactly five substitutions, where the exactly five substitutions are at positions selected from positions 143, 147, 151, 154, 241, 330, 504, 507, 516, 519, 527, and 528. In some embodiments, e.g., when the native amino acid sequence is the sequence of SEQ ID NO: 1, the modified amino acid sequence includes five substitutions at positions selected from D143, T147, E151, K154, E241, K330, N504, E507, N516, N519, E527, and E528. In some embodiments, e.g., when the native amino acid sequence is the sequence of SEQ ID NO: 1, the modified amino acid sequence has exactly five substitutions, where the exactly five substitutions are at positions selected from D143, T147, E151, K154, E241, K330, N504, E507, N516, N519, E527, and E528.

In some embodiments, the modified amino acid sequence includes a substitution at position 143, a substitution at position 147, a substitution at position 330, a substitution at position 151, and a substitution at a position selected from positions 154, 241, 504, 507, 516, 519, 527, and 528. In some embodiments, the modified amino acid includes a substitution at position 143, a substitution at position 147, a substitution at position 330, a substitution at position 151, and exactly one other substitution, where the exactly one other substitution is at a position selected from positions 151, 154, 241, 504, 507, 516, 519, 527, and 528. In some embodiments, e.g., when the native amino acid sequence is the sequence of SEQ ID NO: 1, the modified amino acid sequence includes a substitution at position D143, a substitution at position T147, a substitution at K330, a substitution at E151, and a substitution at a position selected from positions K154, E241, E425, N504, E507, N516, N519, E527, and E528. In some embodiments, e.g., when the native amino acid sequence is the sequence of SEQ ID NO: 1, the modified amino acid includes a substitution at position D143, a substitution at position T147, a substitution at position K330, a substitution at E151, and exactly one other substitution, where the exactly one other substitution is at a position selected from positions K154, E241, E425, N504, E507, N516, N519, E527, and E528.

In some embodiments, e.g., when the native amino acid sequence is the sequence of SEQ ID NO: 1, the modified amino acid includes five substitutions selected from D143R, T147R, E151R, E151A, E151S, E151G, K154R, E241R, K330R, N504R, E507R, N516R, N519R, E527R, and E528R. In some embodiments, e.g., when the native amino acid sequence is the sequence of SEQ ID NO: 1, the modified amino acid includes exactly five substitutions, where the five substitutions are selected from D143R, T147R, E151R, E151A, E151S, E151G, K154R, E241R, K330R, N504R, E507R, N516R, N519R, E527R, and E528R. In some embodiments, e.g., when the native amino acid sequence is the sequence of SEQ ID NO: 1, the modified amino acid includes five substitutions selected from D143R/T147R/K330R/E151A/E527R and D143R/T147R/K330R/E151A/E528R. In some embodiments, e.g., when the native amino acid sequence is the sequence of SEQ ID NO: 1, the modified amino acid includes exactly five substitutions, where the five substitutions are selected from D143R/T147R/K330R/E151A/E527R and D143R/T147R/K330R/E151A/E528R. In some embodiments, the modified amino acid sequence includes a D143R substitution, a T147R substitution, a K330R substitution, an E528R substitution, and an E151A substitution. In some embodiments, the only substitutions in the modified amino acid sequence are a D143R substitution, a T147R substitution, a K330R substitution, an E528R substitution, and an E151A substitution. In some embodiments, the modified amino acid sequence is the sequence of SEQ ID NO: 6.

In some embodiments, the engineered Cas protein is further modified such that the Cas protein is a fully or partially nuclease deactivated Cas (dCas) protein. Such alteration or modification includes altering one or more amino acids to inactivate the nuclease activity or the nuclease domain, as well as removing the polypeptide sequence or polypeptide sequences exhibiting nuclease activity, i.e., the nuclease domain, such that the polypeptide sequence or polypeptide sequences exhibiting nuclease activity, i.e. nuclease domain, are absent from the Cas14 protein. Thus, in some embodiments, a nuclease-null Cas14 protein (dCas14) includes polypeptide sequences modified to inactivate nuclease activity or removal of a polypeptide sequence or sequences to inactivate nuclease activity. The dCas14 protein retains the ability to bind to target nucleic acid even though the nuclease activity has been inactivated. Accordingly, the dCas14 protein includes the polypeptide sequence or sequences required for nucleic acid binding. In some embodiments, one or both of D326 and D510 are substituted with an amino acid that reduces, substantially eliminates, or eliminates nuclease activity. In some embodiments, one or both of D326 and D510 are substituted with alanine.

In some embodiments, the engineered Cas protein is attached to, bound to, or fused with an effector domain, such as a transcriptional regulatory domain or an epigenetic modifying domain. In some embodiments, the effector domain is fused to the C-terminus of the engineered Cas protein. In some embodiments, the effector domain is fused to the N-terminus of the engineered Cas protein. In some embodiments, the effector domain comprises a subcellular localization signal. In some embodiments, the subcellular localization signals is an organelle localization signal, such as a nuclear localization signal (NLS), nuclear export signal (NES), or mitochondrial localization signal. In some embodiments, the effector domain comprises a polypeptide that can (i) cleave a nucleic acid (e.g., DNA and/or RNA), (ii) affect RNA stability, (iii) edit a nucleotide, (iv) activate transcription, (v) repress transcription, (iv) activate translation, (v) repress translation, (vi) methylate a nucleic acid (e.g., DNA and/or RNA), (vii) demethylate a nucleic acid (e.g., DNA and/or RNA), (viii) affect RNA splicing, (ix) enable affinity purification or immunoprecipitation (e.g., FLAG, HA, biotin, or HALO tags), and/or (x) enable proximity-based protein labeling and identification.

II. GUIDE RNA

In another aspect, a single-guide RNA (sgRNA) protein is provided. The sgRNA disclosed herein provides surprising improvements in its ability to function in eukaryotic cells. The sgRNA protein has an engineered CRISPR RNA (crRNA)/trans-activating CRISPR RNA (tracrRNA) fusion nucleotide sequence that is at least 60% identical to a wild-type crRNA/tracrRNA fusion nucleotide sequence. The engineered crRNA/tracrRNA fusion nucleotide sequence can be, for example, at least 60%, at least 64%, at least 68%, at least 72%, at least 76%, at least 80%, at least 82%, at least 84%, at least 86%, at least 88%, at least 90%, at least 91%, at least 92%, at least 93%, at least 94%, at least 95%, at least 96%, at least 97%, at least 98%, or at least 99% identical to a wild-type tracrRNA nucleotide sequence. In terms of ranges, in some embodiments the engineered crRNA/tracRNA fusion nucleotide sequence is between 60% and 100% identical to a wild-type crRNA/tracRNA fusion nucleotide sequence, e.g., between 60% and 82%, between 63% and 86%, between 66% and 90%, between 70% and 95%, or between 74% and 100%. In some embodiments, the wild-type crRNA/tracrRNA fusion nucleotide sequence is included in the sequence of SEQ ID NO: 7.

In some embodiments, the engineered crRNA/tracrRNA fusion nucleotide sequence includes one or more modifications to the wild-type crRNA/tracrRNA fusion nucleotide sequence, where the modifications follow one or more particular rules determined to have surprising advantages for the characteristics of the provided sgRNA. For example, the particular modification rules have been selected for their ability to produce sgRNA capable of functioning within eukaryotic cells. According to these particular rules, all or some of the modifications to the wild-type crRNA/tracrRNA fusion nucleotide sequence involve either (1) substitution of at least one U of a poly-U region of the wild-type nucleotide sequence, e.g., with a G, (2) deletion of at least a portion of a 3' region of the wild-type sequence corresponding to an RNA stem-loop hairpin structure, or (3) deletion of at least a portion of a 5' poly-G region of the wild-type nucleotide sequence.

In some embodiments, the one or more modifications to the wild-type crRNA/tracrRNA fusion nucleotide sequence include modifications in one of the above three categories. The one or more modifications can include a modification in one category that is either category (1), (2), or (3). The one or more modifications can consist of a modification in one category that is either category (1), (2), or (3). In some embodiments, the one or more modifications include modifications in each of the two categories (1) and (2), (1) and (3), or (2) and (3). In some embodiments, the one or more modifications consist of modifications in each of the two categories (1) and (2), (1) and (3), or (2) and (3). In some embodiments, the one or more modifications include modifications in each of the three categories (1), (2) and (3).

In some embodiments, the wild-type crRNA/tracrRNA fusion nucleotide sequence includes a poly-U region proximate to the 3' end of the sequence. The poly-U region can include, for example, four uracil nucleotides, five uracil nucleotides, six uracil nucleotide, seven uracil nucleotides, eight uracil nucleotides, or more than eight uracil nucleotides. In some embodiments, the engineered crRNA/tracrRNA fusion nucleotide sequence of the provided sgRNA includes substitution of at least one U of the poly-U region, where each substitution is independently to a G. The engineered crRNA/tracrRNA fusion nucleotide sequence can include substitution of only one uracil nucleotide of the poly-U region to a G, only two uracil nucleotides of the poly-U region each to a G, only thee uracil nucleotides of the poly-U region each to a G, only four uracil nucleotides of the poly-U region each to a G, only five uracil nucleotides of the poly-U region each to a G, only six uracil nucleotides of the poly-U region each to a G, only seven uracil nucleotides of the poly-U region each to a G, only eight uracil nucleotides of the poly-U region each to a G, or more than eight uracil nucleotides of the poly-U region each to a G. In some embodiments, each uracil nucleotide of the poly-U region is substituted with a G. In some embodiments, the substitutions in the poly-U region are contiguous. In some embodiments, the substitutions in the poly-U region are noncontiguous. In some embodiments, the engineered crRNA/tracrRNA fusion nucleotide sequence includes the sequence of SEQ ID NO: 8.

In some embodiments, the wild-type crRNA/tracrRNA fusion nucleotide sequence includes a 3' region corresponding to an RNA stem-loop hairpin structure, and the engineered crRNA/tracrRNA fusion nucleotide sequence of the provided sgRNA includes deletion of at least a portion of the 3' region. The amount of the 3' wild-type crRNA/tracrRNA region corresponding to an RNA hairpin structure that is deleted in creating the engineered crRNA/tracrRNA fusion nucleotide sequence can be, for example, from 1% to 100%, e.g., from 1% to 60%, from 10% to 70%, from 20% to 80%, from 30% to 90%, or from 40% to 100%. In terms of upper limits, the amount of the 3' wild-type crRNA/tracrRNA region corresponding to an RNA hairpin structure that is deleted in creating the engineered crRNA/tracrRNA fusion nucleotide sequence can be less than 100%, e.g., less than 90%, less than 80%, less than 70%, less than 60%, less than 50%, less than 40%, less than 30%, less than 20%, or less than 10%. In terms of lower limits, the amount of the 3' wild-type crRNA/tracrRNA region corresponding to an RNA hairpin structure that is deleted in creating the engineered crRNA/tracrRNA fusion nucleotide sequence can be, for example, at least 1%, e.g., at least 10%, at least 20%, at least 30%, at least 40%, at least 50%, at least 60%, at least 70%, at least 80%, or at least 90%. In some embodiments, the only modification to the wild-type crRNA/tracrRNA fusion nucleotide sequence is deletion of at least a portion of the 3' region corresponding to an RNA hairpin structure. In some embodiments, the engineered crRNA/tracrRNA nucleotide sequence includes the sequence of SEQ ID NO: 9.

In some embodiments, the wild-type crRNA/tracrRNA fusion nucleotide sequence includes a poly-G region proximate to the 5' end of the sequence. The poly-G region can include, for example, three guanine nucleotides, four guanine nucleotides, five guanine nucleotide, six guanine nucleotides, seven guanine nucleotides, or more than seven uracil nucleotides. In some embodiments, the engineered crRNA/tracrRNA fusion nucleotide sequence of the provided sgRNA includes deletion of at least one guanine of the poly-G region. The engineered crRNA/tracrRNA fusion nucleotide sequence can include deletion of only one guanine nucleotide of the poly-G region, only two guanine nucleotides of the poly-G region, only thee guanine nucleotides of the poly-G region, only four guanine nucleotides of the poly-G region, only five guanine nucleotides of the poly-G region, only six guanine nucleotides of the poly-G region, only seven guanine nucleotides of the poly-G region, or more than seven guanine nucleotides of the poly-G region. In some embodiments, each guanine nucleotide of the poly-G region is deleted. In some embodiments, the engineered crRNA/tracrRNA fusion nucleotide sequence includes the sequence of SEQ ID NO: 10.

In some embodiments, the provided sgRNA includes a spacer nucleotide sequence corresponding to a 5' Protospacer Adjacent Motif (PAM) having a 5'-TTTR-3' nucleotide sequence. In some embodiments, the target nucleic acid associated with the provided sgRNA is dsDNA. In such embodiments, dsDNA-targeting specificity is determined, at least in part, by two parameters: the sgRNA spacer targeting a protospacer in the target dsDNA (the sequence in the target dsDNA corresponding to the sgRNA spacer on the non-complementary DNA strand) and a short PAM sequence located immediately 5' (upstream) of the protospacer on the non-complementary DNA strand. In some embodiments, the PAM is 5'-TTTG-3' or 5'-TTTA-3'. In some embodiments, the PAM is 5'-TTTG-3'. In some embodiments, the PAM is 5'-TTTA-3'.

III. NUCLEIC ACIDS

In another aspect, a nucleic acid sequence is provided, where the nucleic acid sequence encodes any of the engineered Cas proteins disclosed herein and described in further detail above, or any of the sgRNA molecules disclosed herein and described in further detail above. In some embodiments, the nucleic acid sequence includes or consists of DNA. In some embodiments, the nucleic acid sequence includes or consists of RNA, e.g., mRNA.

IV. VECTORS

In another aspect, a vector is provided, where the vector includes at least one nucleic acid sequence encoding any of the engineered Cas proteins disclosed herein, or at least one nucleic acid sequence encoding any of the sgRNA molecules disclosed herein. In some embodiments, the provided vector includes at least one nucleic acid sequence encoding any of the engineered Cas proteins disclosed herein, and at least one nucleic acid sequence encoding any of the sgRNA molecules disclosed herein.

In some embodiments, the provided vector includes one or more nuclear localization signals (NLS). In some embodiments, the one or more nuclear localization signals include an SV40 NLS. In some embodiments, the one or more nuclear localization signals include a c-Myc NLS. In some embodiments, the one or more nuclear localization signals include both an SV40 NLS and a c-Myc NLS. In some embodiments, the one or more nuclear localization signals include two or more copies of an SV40 NLS. In some embodiments, the one or more nuclear localization signals include two or more copies of a c-Myc NLS. In some embodiments, the one or more nuclear localization signals include both one or more copies, e.g., two or more copies, of an SV40 NLS and one or more copies, e.g., two or more copies, of a c-Myc NLS.

In some embodiments, the provided vector includes one or more additional nucleic acid sequences that each independently encode a transcriptional activator. Transcriptional activators suitable for use with the provided vectors include, but are not limited to, a VP64 transcriptional activator, a tripartite VP64-p65-Rta (VPR) transcriptional activator, a p300 transcriptional activator, a TET1 transcriptional activator, a TET2 transcriptional activator, an HSF1 transcriptional activator, an NFAT transcriptional activator, an NFkB transcriptional activator, a PRDM transcriptional activator, and combinations thereof.

In some embodiments, the provided vector includes one or more additional nucleic acid sequences that each independently encode a transcriptional repressor. Transcriptional repressors suitable for use with the provided vectors include, but are not limited to, a KRAB transcriptional repressor, a bipartite KRAB-DNMT3L (KL) transcriptional repressor, a tripartite KRAB-DNMT3A-DNMT3L (KAL) transcriptional repressor, a SID transcriptional repressor, an HP1 transcriptional repressor, an EZH2 transcriptional repressor, and combinations thereof.

In some embodiments, the provided vector includes one or more sgRNAs configured to enable the simultaneous activation or repression of two or more reporter genes or endogenous genes.

In some embodiments, the provided vector further includes a base editor. In some embodiments, the provided vector further includes a prime editor. In some embodiments, the provided vector further includes a fluorescent protein. In some embodiments, the provided vector is a viral vector. The provided vector can be, for example, an adeno-associated virus (AAV) vector, an adenovirus vector, a retrovirus vector, a lentivirus vector, or a herpes simplex virus (HSV) vector.

V. SYSTEMS

In another aspect, a system, e.g., a ribonucleotide complex, including a Cas protein and an sgRNA is provided. In some embodiments, the Cas protein of the provided system is any of the engineered Cas proteins disclosed herein and described in further detail above. In some embodiments, the sgRNA of the provided system is any of the sgRNA molecules disclosed herein and described in further detail above. In some embodiments, the provided system includes both one or more, e.g., two or more, Cas proteins disclosed herein, and one or more, e.g., two or more, sgRNA molecules disclosed herein.

In another aspect, a system including a nucleic acid encoding a Cas protein and a nucleic acid encoding an sgRNA is provided. In some embodiments, the nucleic acid encoding a Cas protein is any of those disclosed herein and described in further detail above. In some embodiments, the nucleic acid encoding an sgRNA is any of those disclosed herein and described in further detail above. In some embodiments, the provided system includes both one or more, e.g., two or more, nucleic acids each independently encoding a Cas protein as disclosed herein, and one or more, e.g., two or more, nucleic acids each independently encoding a sgRNA molecule as disclosed herein.

In general, the provided systems are characterized by elements that promote the formation of a nucleic acid-targeting complex including a Cas protein and an sgRNA at the site of a target sequence, which can be present in a DNA molecule or an RNA molecule. As used herein, the term "target sequence" refers to a sequence to which a guide sequence (also referred to herein as a "spacer" or "spacer sequence") in an sgRNA is designed to have complementarity, where hybridization between the target sequence and the sgRNA allows for localization of the Cas protein to the target sequence. Full complementarity is not necessarily required, provided there is sufficient complementarity to allow for hybridization between the target sequence and the sgRNA. In some embodiments, a target sequence is located in the nucleus or cytoplasm of a cell. In some embodiments, the target sequence may be within an organelle of a eukaryotic cell, for example, a mitochondrion or a chloroplast.

In some embodiments, the target nucleotide sequence is present in a gene sequence. In some embodiments, the target nucleotide sequence is present in a promoter region of the gene, and can be present in the sense strand or anti-sense strand of the gene. In some embodiments, the target nucleotide sequence is present in a 5' UTR region of the gene, and can be present in the sense strand or anti-sense strand of the gene. In some embodiments, the target nucleotide sequence is present in a 5' UTR/RBS region of the gene, and can be present in the sense strand or anti-sense strand of the gene. In some embodiments, the target nucleotide sequence is present in a coding region of the gene, and can be present in the sense strand or anti-sense strand of the gene.

In some embodiments, one or more vectors driving expression of one or more elements of the provided system, and are introduced into a host cell such that expression of the elements of the system directs formation of a nucleic acid-targeting complex at one or more target sequence sites in the host cell. For example, a Cas protein and an sgRNA could each be operably linked to separate regulatory elements on separate vectors. Alternatively, two or more of the elements expressed from the same or different regulatory elements can be combined in a single vector, with one or more additional vectors providing any components of the system not included in the first vector. System elements that are combined in a single vector can be arranged in any suitable orientation, such as one element located 5' with respect to ("upstream" of) or 3' with respect to ("downstream" of) a second element. The coding sequence of one element can be located on the same or opposite strand of the coding sequence of a second element, and oriented in the same or opposite direction. In some embodiments, a single promoter drives expression of a transcript encoding a Cas protein and an sgRNA. In some embodiments, the Cas protein and sgRNA are operably linked to and expressed from the same promoter.

VI. PHARMACEUTICAL COMPOSITIONS

In another aspect, a pharmaceutical composition is provided. The provided pharmaceutical composition includes one or more, e.g., two or more of any of the engineered Cas proteins as disclosed herein and described in further detail above; one or more, e.g., two or more, of any of the sgRNA molecules disclosed herein and described in further detail above; one or more, e.g., two or more, of any of the nucleic acids disclosed herein and described in further detail above; one or more, e.g., two or more, of any of the vectors disclosed herein and described in further detail above; one or more, e.g., two or more, of any of the systems disclosed herein and described in further detail above; or any combination thereof.

In some embodiments, the pharmaceutical composition includes a therapeutically effective amount of a pharmaceutically acceptable excipient. In some embodiments, the pharmaceutical composition includes one or more of a diluent, adjuvant, or carrier in a formulation suitable for administration, e.g., administration to a mammal. Suitable diluents, adjuvants, or carriers can include, for example, lipids, e.g., liposomes, e.g., liposome dendrimers; liquids, such as water and oils, including those of petroleum, animal, vegetable or synthetic origin, such as peanut oil, soybean oil, mineral oil, sesame oil and the like; gum acacia; gelatin; starch paste; talc; keratin; colloidal silica; urea; and the like. Additional examples of suitable diluents include distilled water, buffered water, physiological saline, PBS, Ringer's solution, dextrose solution, and Hank's solution. The pharmaceutical compositions can also include additional substances to approximate physiological conditions, such as pH adjusting and buffering agents, toxicity adjusting agents, wetting agents and detergents. In addition, auxiliary, thickening, lubricating and coloring agents can alternatively or additionally be used. Pharmaceutical compositions can be formulated into preparations in solid, semisolid, liquid or gaseous forms, such as tablets, capsules, powders, granules, ointments, solutions, suppositories, injections, inhalants, gels, microspheres, and aerosols.

The provided pharmaceutical composition can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, and/or enhance solubility or uptake). Examples of such modifications or complexing agents include sulfate, gluconate, citrate, and phosphate. The nucleic acids or polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

VII. METHODS OF NUCLEIC ACID MODULATION

In another aspect, a method of modulating one or more target nucleic acids in a cell is provided. The method includes contacting the cell with one or more, e.g., two or more of any of the engineered Cas proteins as disclosed herein and described in further detail above; one or more, e.g., two or more, of any of the sgRNA molecules disclosed herein and described in further detail above; one or more, e.g., two or more, of any of the nucleic acids disclosed herein and described in further detail above; one or more, e.g., two or more, of any of the vectors disclosed herein and described in further detail above; one or more, e.g., two or more, of any of the systems disclosed herein and described in further detail above; or any combination thereof.

In some embodiments, the provided method results in selective modulation of one or more target nucleic acids in a cell. For example, selective modulation can modulate one or more target nucleic acids by at least 10%, e.g., at least 20%, at least 30%, at least 40%, at least 50%, at least 60%, at least 70%, at least 80%, at least 90%, or greater than 90%, compared to the level of modulation of the target nucleic acids in the absence of the contacting, while not substantially modulating any non-target nucleic acids. In some embodiments, selective modulation includes modulating any non-target nucleic acids by, less than 10%, e.g., less than 9%, less than 8%, less than 7%, less than 6%, less than 5%, less than 4%, less than 3%, less than 2%, or less than 1%.

In some embodiments, the provided method results in modulation of the transcription of one or more target nucleic acids. In some embodiments, the method results in the increase or decrease of transcription of target DNA. In some embodiments, the method is used to control the transcription of a targeted gene-coding RNA (protein-encoding mRNA) and/or a targeted non-coding RNA (e.g., tRNA, rRNA, snoRNA, siRNA, miRNA, long ncRNA, etc.). In some embodiments, the method modifies a polypeptide associated with DNA (e.g., histone). In some embodiments, method involves enzymatic activity such as methyltransferase activity, demethylase activity, acetyltransferase activity, deacetylase activity, kinase activity, phosphatase activity, ubiquitin ligase activity (e.g., ubiquitination activity), deubiquitinating activity, adenylation activity, deadenylation activity, SUMOylating activity, deSUMOylating activity, ribosylation activity, deribosylation activity, myristoylation activity, demyristoylation activity glycosylation activity (e.g., from GlcNAc transferase) or deglycosylation activity. The enzymatic activities listed herein catalyze covalent modifications to proteins. Such modifications are known in the art to alter the stability or activity of the target protein (e.g., phosphorylation due to kinase activity can stimulate or silence protein activity depending on the target protein). Of particular interest as protein targets are histones. Histone proteins are known in the art to bind DNA and form complexes known as nucleosomes. Histones can be modified (e.g., by methylation, acetylation, ubiquitination, phosphorylation) to elicit structural changes in the surrounding DNA, thus controlling the accessibility of potentially large portions of DNA to interacting factors such as transcription factors, polymerases and the like. A single histone can be modified in many different ways and in many different combinations (e.g., trimethylation of lysine 27 of histone 3, H3K27, is associated with DNA regions of repressed transcription while trimethylation of lysine 4 of histone 3, H3K4, is associated with DNA regions of active transcription).

In some embodiments, the provided method results in modulation of the translation of one or more target nucleic acids. In some embodiments, the method modulate translation of one or more target RNA molecules.

In some embodiments, the one or more target nucleic acids are in a cell that is a eukaryotic cell. In some embodiments, the one or more target nucleic acids are in a cell that is an animal cell. In some embodiments, the one or more target nucleic acids are in a cell that is a mammalian cell. In some embodiments, the one or more target nucleic acids are in a cell that is a human cell. In some embodiments, the one or more target nucleic acids are in a cell that is a stem cell. In some embodiments, the one or more target nucleic acids are in a cell that is a blood cell. In some embodiments, the one or more target nucleic acids are in a cell that is an immune cell. In some embodiments, the one or more target nucleic acids are in a cell that is a plant cell. In some embodiments, the one or more target nucleic acids are in a cell that is in vivo. In some embodiments, the one or more target nucleic acids are in a cell that is part of an organoid.

In some embodiments, the modulating of the one or more target nucleic acids includes activating at least one of the one or more target nucleic acids. In some embodiments, the modulating of the one or more target nucleic acids includes repressing at least one of the one or more target nucleic acids. In some embodiments, the modulating of the one or more target nucleic acids includes editing at least one of the one or more target nucleic acids. In some embodiments, the modulating of the one or more target nucleic acids includes editing a primer of at least one of the one or more target nucleic acids. In some embodiments, the modulating of the one or more target nucleic acids includes nicking at least one of the one or more target nucleic acids. In some embodiments, the modulating of the one or more target nucleic acids includes labeling at least one of the one or more target nucleic acids. In some embodiments, the modulating of the one or more target nucleic acids includes altering the spatiotemporal positioning of at least one of the one or more target nucleic acids. In some embodiments, the modulating of the one or more target nucleic acids includes altering the methylation of at least one of the one or more target nucleic acids. In some embodiments, the modulating of the one or more target nucleic acids includes altering the acetylation of at least one of the one or more target nucleic acids. In some embodiments, the modulating of the one or more target nucleic acids includes altering the acetylation of at least one histone or nucleosome associated with at least one of the one or more target nucleic acids. In some embodiments, the modulating of the one or more target nucleic acids includes altering the methylation of at least one histone or nucleosome associated with at least one of the one or more target nucleic acids.

VIII. METHODS OF TREATMENT

In another aspect, a method of preventing a disorder, e.g., a genetic disorder, in a subject is provided. The method includes administering to the subject an amount of any of the pharmaceutical compositions disclosed herein and described in further detail above, where the administered amount is sufficient to modulate one or more target nucleic acids associated with the disorder. In some embodiments, the administered amount is sufficient to correct one or more mutations in the one or more target nucleic acids.

Disorders suitable for treating with the provided method include, but are not limited to, X-linked severe combined immune deficiency, sickle cell anemia, thalassemia, hemophilia, neoplasia, cancer, age-related macular degeneration, schizophrenia, trinucleotide repeat disorders, fragile X syndrome, prion-related disorders, amyotrophic lateral sclerosis, drug addiction, autism, Alzheimer's disease, Parkinson's disease, cystic fibrosis, blood and coagulation disease or disorders, inflammation, facioscapulohumeral muscular dystrophy, retinitis pigmentosa, Leber congenital amaurosis, glaucoma, immune-related diseases or disorders, metabolic diseases and disorders, liver diseases and disorders, kidney diseases and disorders, muscular/skeletal diseases and disorders, neurological and neuronal diseases and disorders, cardiovascular diseases and disorders, pulmonary diseases and disorders, and ocular diseases and disorders.

Also provided is a method of treating an infection in a subject. The method includes administering to the subject an amount of any of the pharmaceutical compositions disclosed herein and described in further detail above, where the administered amount is sufficient to modulate one or more target nucleic acids associated with the infection. In some embodiments, the administered amount is sufficient to cut or nick at least one of the one or more target nucleic acids. In some embodiments, the infectious agent is a virus.

In some embodiments, the administering of any of the provided methods is via a delivery system using a virus, a nanoparticle, a liposome, a micelle, a virosome, a nucleic acid complex, a protein-RNA conjugate, and combinations thereof. Administration can be achieved in various ways, including oral, buccal, rectal, parenteral, intraperitoneal, intradermal, transdermal, intra-tracheal, intraocular, etc., administration. The active agent can be systemic after administration or can be localized by the use of regional administration, intramural administration, or use of an implant that acts to retain the active dose at the site of implantation. The active agent can be formulated for immediate activity or it may be formulated for sustained release.

In some embodiments, the administering of any of the provided methods is via a single adeno-associated virus delivery system. In some embodiments, the administering is via a dual adeno-associated virus delivery system.

As used herein, the term "subject" generally refers to a vertebrate, preferably a mammal, more preferably a human. In some cases, a subject is a patient. Mammals include, but are not limited to, murines, simians, humans, farm animals, sport animals, and pets. In some embodiments, the subject of any of the provided methods is human.

IX. EMBODIMENTS

The following embodiments are contemplated. All combinations of features and embodiment are contemplated.

Embodiment 1: An engineered Clustered Regularly Interspaced Short Palindromic Repeat (CRISPR)-associated (Cas) protein that is functional in eukaryotic cells, the Cas protein comprising a modified amino acid sequence that is at least 80% identical to a native amino acid sequence of a wild-type Cas protein, wherein: the native amino acid sequence has a length of less than 700 amino acids and comprises a (D/E/K/N)X(R/F)(E/K)N (SEQ ID NO: 253) motif; and the modified amino acid sequence comprises one or more substitutions in the native amino acid sequence, wherein at least one of the one or more substitutions is at a position either (1) within or no more than 30 amino acids upstream or downstream of the (D/E/K/N)X(R/F)(E/K)N (SEQ ID NO: 253) motif, (2) at or no more than 30 amino acids upstream or downstream of position 241 of the native amino acid sequence, (3) at or no more than 30 amino acids upstream or downstream of position 516 of the native amino acid sequence, or (4) having an electrically charged amino acid in the native amino acid sequence.

Embodiment 2: An embodiment of embodiment 1, wherein at least one of the one or more substitutions is to an amino acid selected from the group consisting of arginine (R), alanine (A), serine(S), and glycine (G).

Embodiment 3: An embodiment of embodiment 1, wherein the wild-type Cas protein is a type V Cas protein.

Embodiment 4: An embodiment of embodiment 1, wherein the wild-type Cas protein is a wild-type V-F (Cas14 or Cas 12f) protein or a wild-type V-J (CasΦ or Cas 12J) protein.

Embodiment 5: An embodiment of embodiment 1, wherein the native amino acid sequence is the sequence of SEQ ID NO: 1.

Embodiment 6: An embodiment of any of the embodiments of embodiment 1-5, wherein the one or more substitutions comprise a substitution at a position selected from the group consisting of D143, K11, K73, T147, E151, K154, E241, D318, K330, K457, E425, E462, N504, E507, N516, N519, E527, and E528.

Embodiment 7: An embodiment of embodiment 6, wherein the substitution is selected from the group consisting of D143R, K11R, K73R, T147R, E151R, K154R, E241R, D318R, K330R, E425N, K457R, E462R, N504R, E507R, N516R, N519R, E527R, and E528R.

Embodiment 8: An embodiment of embodiment 7, wherein the substitution is selected from the group consisting of D143R, T147R, E151R, and E241R.

Embodiment 9: An embodiment of any of the embodiments of embodiment 6-8, wherein the one or more substitutions comprise two substitutions at positions selected from the group consisting of D143, T147, E151, K154, E241, K330, E425, N504, E507, N516, N519, E527, and E528.

Embodiment 10: An embodiment of embodiment 9, wherein the two substitutions comprise a substitution at D143 and a substitution at a position selected from the group consisting of T147, E151, K154, E241, K330R, E425N, N504, E507, N516, N519, E527, and E528.

Embodiment 11: An embodiment of embodiment 9 or 10, wherein the two substitutions are selected from the group consisting of D143R, T147R, E151R, E151A, K154R, E241R, N504R, E507R, N516R, N519R, E527R, and E528R.

Embodiment 12: An embodiment of any of the embodiments of embodiment 11, wherein the two substitutions are selected from the group consisting of D143R/T147R, D143R/E151R, D143R/E241R, D143R/E425N, D143R/E507R, D143R/N519R, D143R/E527R, D143R/E528R, D143R/R151S, D143/R151G, and D143R/E151A.

Embodiment 13: An embodiment of any of the embodiments of embodiment 9-12, wherein the one or more substitutions comprise three substitutions at positions selected from the group consisting of D143, T147, E151, K154, E241, K330, E425, N504, E507, N516, N519, E527, and E528.

Embodiment 14: An embodiment of embodiment 13, wherein the three substitutions comprise substitutions at D143 and T147 and a substitution at a position selected from the group consisting of E151, K154, E241, K330, E425, N504, E507, N516, N519, E527, and E528.

Embodiment 15: An embodiment of embodiment 13 or 14, wherein the three substitutions are selected from the group consisting of D143R, T147R, E151R, E151A, E151S, E151G, K154R, E241R, K330R, E425N, N504R, E507R, N516R, N519R, E527R, and E528R.

Embodiment 16: An embodiment of embodiment 15, wherein the three substitutions are selected from the group consisting of D143R/T147R/K330R, D143R/T147R/K154R, D143R/T147R/E241R, D143R/T147R/E507R, D143R/T147R/N519R, D143R/T147R/E527R, D143R/T147R/E528R, D143R/T147R/E151S, D143R/T147R/E151G, and D143R/T147R/E151A.

Embodiment 17: An embodiment of any of the embodiments of embodiment 13-16, wherein the one or more substitutions comprise four substitutions at positions selected from the group consisting of D143, T147, E151, K154, E241, K330, E425, N504, E507, N516, N519, E527, and E528.

Embodiment 18: An embodiment of embodiment 17, wherein the four substitutions comprise substitutions at D143, T147, and K330 and a substitution at a position selected from the group consisting of E151, K154, E241, E425, N504, E507, N516, N519, E527, and E528.

Embodiment 19: An embodiment of embodiment 17 or 18, wherein the four substitutions are selected from the group consisting of D143R, T147R, E151R, E151A, E151S, E151G, K154R, E241R, K330R, E425N, N504R, E507R, N516R, N519R, E527R, and E528R.

Embodiment 20: An embodiment of embodiment 19, wherein the four substitutions selected from group are the consisting of D143R/T147R/K330R/E528R, D143R/T147R/K330R/E151A, and D143R/T147R/K330R/E527R.

Embodiment 21: An embodiment of any of the embodiments of embodiment 17-20, wherein the one or more substitutions comprise five substitutions at positions selected from the group consisting of D143, T147, E151, K154, E241, K330, N504, E507, N516, N519, E527, and E528.

Embodiment 22: An embodiment of embodiment 21, wherein the five substitutions comprise substitutions at D143, T147, K330, E151, and a substitution at a position selected from the group consisting of. K154, E241, N504, E507, N516, N519, E527, and E528.

Embodiment 23: An embodiment of embodiment 21 or 22, wherein the five substitutions are selected from the group consisting of D143R, T147R, E151R, E151A, K154R, E241R, K330R, N504R, E507R, N516R, N519R, E527R, and E528R.

Embodiment 24: An embodiment of embodiment 23, wherein the five substitutions are selected from the group consisting of D143R/T147R/K330R/E151A/E528R and D143R/T147R/K330R/E151A/E527R.

Embodiment 25: An embodiment of any of the embodiments of embodiment 1-24, wherein the Cas protein is a fully or partially nuclease deactivated Cas (dCas) protein.

Embodiment 26: An embodiment of embodiment 1, wherein the modified amino acid sequence comprises a sequence selected from the group consisting of SEQ ID NOS: 2, 3, 4, 5, and 6.

Embodiment 27: A single-guide RNA (sgRNA) comprising an engineered CRISPR RNA (crRNA)/trans-activating CRISPR RNA (tracrRNA) fusion nucleotide sequence that is at least 60% identical to a wild-type crRNA/tracrRNA fusion nucleotide sequence, wherein: the wild-type crRNA/tracrRNA fusion nucleotide sequence comprises (1) a 3' region corresponding to an RNA stem-loop hairpin structure, (2) a poly-U region proximate to the 3' region, and (3) a 5' poly-G region; and the engineered crRNA/tracrRNA fusion nucleotide sequence comprises one or more modifications to the wild-type crRNA/tracrRNA fusion nucleotide sequence, the modifications selected from the group consisting of: substitution of at least one U of the poly-U region, deletion of at least a portion of the 3' region; and deletion of at least a portion of the 5' poly-G region.

Embodiment 28: An embodiment of embodiment 27, wherein the wild-type crRNA/tracrRNA fusion nucleotide sequence is the sequence of SEQ ID NO: 7.

Embodiment 29: An embodiment of embodiment 27 or 28, wherein the engineered crRNA/tracrRNA fusion nucleotide sequence comprises substitutions of at least one U of the poly-U region with a G.

Embodiment 30: An embodiment of embodiment 29, wherein the engineered crRNA/tracrRNA fusion nucleotide sequence comprises the sequence of SEQ ID NO: 8.

Embodiment 31: An embodiment of embodiment 29, wherein the engineered crRNA/tracrRNA fusion nucleotide sequence comprises deletion of at least a portion of the 3' region.

Embodiment 32: An embodiment of embodiment 31, wherein the engineered crRNA/tracrRNA fusion nucleotide sequence comprises the sequence of SEQ ID NO: 9.

Embodiment 33: An embodiment of embodiment 31, wherein the engineered crRNA/tracrRNA fusion nucleotide sequence comprises deletion of at least a portion of the 5' poly-G region.

Embodiment 34: An embodiment of embodiment 33, wherein the engineered crRNA/tracrRNA fusion nucleotide sequence comprises the sequence of SEQ ID NO: 10.

Embodiment 35: An embodiment of any of the embodiments of embodiment 27-34, further comprising a spacer nucleotide sequence corresponding to a 5' Protospacer Adjacent Motif (PAM) having a 5'-TTTR-3' nucleotide sequence.

Embodiment 36: A nucleic acid sequence encoding the engineered Cas protein of any of the embodiments of embodiment 1-26.

Embodiment 37: A nucleic acid sequence encoding the sgRNA of any of the embodiments of embodiment 27-35.

Embodiment 38: A vector comprising one or both of the nucleic acid of embodiment 36 and the nucleic acid of embodiment 37.

Embodiment 39: An embodiment of embodiment 38, further comprising one or more nuclear localization signals (NLS).

Embodiment 40: An embodiment of embodiment 39, wherein the one or more nuclear localization signals comprise one or both of an SV40 NLS and a c-Myc NLS.

Embodiment 41: An embodiment of any of the embodiments of embodiment 38-40, further comprising one or more additional nucleic acid sequences each independently encoding a transcriptional or epigenetically modifying activator.

Embodiment 42: An embodiment of embodiment 41, wherein the one or more transcriptional or epigenetically modifying activators comprise one or more of a VP64 transcriptional activator, a tripartite VP64-p65-Rta (VPR) transcriptional activator, a p300 transcriptional activator, a TET1 transcriptional activator, a TET2 transcriptional activator, an NFAT transcriptional activator, an NFkB transcriptional activator, and a PRDM transcriptional activator.

Embodiment 43: An embodiment of any of the embodiments of embodiment 38-42, further comprising one or more additional nucleic acid sequences each independently encoding a transcriptional or epigenetically modifying repressor.

Embodiment 44: An embodiment of embodiment 43, wherein the one or more transcriptional or epigenetically modifying repressors comprise one or more of a KRAB transcriptional repressor, a DNMT3A DNA methyltransferase, a DNMT3B DNA methyltransferase, a DNMT3L DNA methyltransferase, a bipartite KRAB-DNMT3A (KA) repressor, a bipartite KRAB-DNMT3L (KL) repressor, a tripartite KRAB-DNMT3A-DNMT3L (KAL) repressor, an SID transcriptional repressor, an EZH2 transcriptional repressor, an HP1 heterochromatin protein, a Gli3 transcriptional repressor, and a MBD3 transcriptional repressor.

Embodiment 45: An embodiment of any of the embodiments of embodiment 38-44, further comprising one or more additional nucleic acid sequences each independently encoding a base editor.

Embodiment 46: An embodiment of any of the embodiments of embodiment 38-45, further comprising one or more additional nucleic acid sequences each independently encoding a prime editor.

Embodiment 47: An embodiment of any of the embodiments of embodiment 38-46, further comprising one or more additional nucleic acid sequences each independently encoding a fluorescent protein.

Embodiment 48: An embodiment of any of the embodiments of embodiment 38-47, further comprising one or more additional nucleic acid sequences each independently encoding a retron element.

Embodiment 49: An embodiment of any of the embodiments of embodiment 38-48, wherein the vector is an adeno-associated virus (AAV) vector, an adenovirus vector, a retrovirus vector, a lentivirus vector, or a herpes simplex virus (HSV) vector.

Embodiment 50: A system comprising: the engineered Cas protein of any of the embodiments of embodiment 1-26; and an sgRNA.

Embodiment 51: A system comprising: a Cas protein; and the sgRNA of any of the embodiments of embodiment 27-35.

Embodiment 52: An embodiment of embodiment 51, wherein the Cas protein is the engineered Cas protein of any of the embodiments of embodiment 1-26.

Embodiment 53: A system comprising: the nucleic acid sequence of embodiment 36; and a nucleic acid sequence encoding an sgRNA.

Embodiment 54: A system comprising: a nucleic acid sequence encoding a Cas protein; and the nucleic acid sequence of embodiment 37.

Embodiment 55: An embodiment of embodiment 54, wherein the nucleic acid encoding a Cas protein is the nucleic acid sequence of embodiment 36.

Embodiment 56: A method of modulating one or more target nucleic acids in a cell, the method comprising contacting the cell with the engineered Cas protein of any of the embodiments of embodiment 1-26, the sgRNA of any of the embodiments of embodiment 27-35, the nucleic acid of any of the embodiments of embodiment 36 or 37, the vector any of the embodiments of embodiment 38-49, or the system of any of the embodiments of embodiment 50-55.

Embodiment 57: An embodiment of embodiment 56, wherein the cell is a eukaryotic cell.

Embodiment 58: An embodiment of embodiment 57, wherein the eukaryotic cell is an animal cell.

Embodiment 59: An embodiment of embodiment 58, wherein the animal cell is a mammalian cell.

Embodiment 60: An embodiment of embodiment 59, wherein the mammalian cell is a human cell.

Embodiment 61: An embodiment of any of the embodiments of embodiment 57-60, wherein the cell is a stem cell.

Embodiment 62: An embodiment of any of the embodiments of embodiment 57-61, wherein the cell is a blood cell.

Embodiment 63: An embodiment of any of the embodiments of embodiment 57-62, wherein the cell is an immune cell.

Embodiment 64: An embodiment of embodiment 57, wherein the cell is a plant cell.

Embodiment 65: An embodiment of any of the embodiments of embodiment 56-64, wherein the cell is in vivo.

Embodiment 66: An embodiment of any of the embodiments of embodiment 56-64, wherein the cell is part of an organoid.

Embodiment 67: An embodiment of any of the embodiments of embodiment 56-66, wherein the modulating comprises activating at least one of the one or more target nucleic acids.

Embodiment 68: An embodiment of any of the embodiments of embodiment 56-67, wherein the modulating comprises repressing at least one of the one or more target nucleic acids.

Embodiment 69: An embodiment of any of the embodiments of embodiment 56-68, wherein the modulating comprises editing at least one of the one or more target nucleic acids.

Embodiment 70: An embodiment of any of the embodiments of embodiment 56-69, wherein the modulating comprises editing a primer of at least one of the one or more target nucleic acids.

Embodiment 71: An embodiment of embodiment 69 or 70, wherein the editing comprises nicking the at least one target nucleic acid.

Embodiment 72: An embodiment of embodiment 69 or 70, wherein the editing comprises performing one or more gene knockouts.

Embodiment 73: An embodiment of embodiment 69 or 70, wherein the editing comprises performing one or more gene knock-ins.

Embodiment 74: An embodiment of embodiment 69 or 70, wherein the editing comprises performing one or more base substitutions.

Embodiment 75: An embodiment of any of the embodiments of embodiment 56-74, wherein the modulating comprises cutting genomic DNA.

Embodiment 76: An embodiment of embodiment 75, wherein the modulating further comprises mutating the genomic DNA.

Embodiment 77: An embodiment of embodiment 76, wherein the mutating comprises one or more insertions, one or more deletions, one or more substitutions, or a combination thereof.

Embodiment 78: An embodiment of any of the embodiments of embodiment 56-77, wherein the modulating comprises labeling at least one of the one or more target nucleic acids.

Embodiment 79: An embodiment of any of the embodiments of embodiment 56-78, wherein the modulating comprises altering the spatiotemporal positioning of at least one of the one or more target nucleic acids within the cell.

Embodiment 80: An embodiment of any of the embodiments of embodiment 56-79, wherein the modulating comprises altering the methylation of at least one of the one or more target nucleic acids.

Embodiment 81: An embodiment of any of the embodiments of embodiment 56-80, wherein the modulating comprises altering the acetylation of at least one of the one or more target nucleic acids.

Embodiment 82: An embodiment of any of the embodiments of embodiment 56-81, wherein the modulating comprises altering the acetylation of at least one histone or nucleosome associated with at least one of the one or more target nucleic acids.

Embodiment 83: An embodiment of any of the embodiments of embodiment 56-82, wherein the modulating comprises altering the methylation of at least one histone or nucleosome associated with at least one of the one or more target nucleic acids.

Embodiment 84: A pharmaceutical composition comprising the engineered Cas protein of any of the embodiments of embodiment 1-26, the sgRNA of any of the embodiments of embodiment 27-35, the nucleic acid of embodiment 36 or 37, the vector of any of the embodiments of embodiment 38-49, or the system of any of the embodiments of embodiment 50-55.

Embodiment 85: An embodiment of embodiment 84, further comprising a therapeutically effective amount of a pharmaceutically acceptable excipient.

Embodiment 86: A method of preventing or treating a genetic disorder in a subject, the method comprising administering to the subject an amount of the pharmaceutical composition of embodiment 84 or 85, wherein the amount is sufficient to modulate one or more target nucleic acids associated with the genetic disorder.

Embodiment 87: An embodiment of embodiment 86, wherein the amount is sufficient to correct one or more mutations in the one or more target nucleic acids.

Embodiment 88: An embodiment of embodiment 86 or 87, wherein the genetic disorder is selected from the group consisting of X-linked severe combined immune deficiency, sickle cell anemia, thalassemia, hemophilia, neoplasia, cancer, age-related macular degeneration, schizophrenia, trinucleotide repeat disorders, fragile X syndrome, prion-related disorders, amyotrophic lateral sclerosis, drug addiction, autism, Alzheimer's disease, Parkinson's disease, cystic fibrosis, blood and coagulation disease or disorders, inflammation, facioscapulohumeral muscular dystrophy, retinitis pigmentosa, Leber congenital amaurosis, glaucoma, immune-related diseases or disorders, metabolic diseases and disorders, liver diseases and disorders, kidney diseases and disorders, muscular/skeletal diseases and disorders, neurological and neuronal diseases and disorders, cardiovascular diseases and disorders, pulmonary diseases and disorders, and ocular diseases and disorders.

Embodiment 89: An embodiment of any of the embodiments of embodiment 86-88, wherein the administering is via a delivery system selected from the group consisting of a virus, a nanoparticle, a liposome, a micelle, a virosome, a nucleic acid complex, a protein-RNA conjugate, and combinations thereof.

Embodiment 90: An embodiment of embodiment 89, wherein the administering is via a single adeno-associated virus delivery system.

Embodiment 91: An embodiment of embodiment 89, wherein the administering is via a dual adeno-associated virus delivery system.

Embodiment 92: An embodiment of any of the embodiments of embodiment 86-91, wherein the subject is human.

Embodiment 93: A method of treating an infection in a subject, the method comprising administering to the subject an amount of the pharmaceutical composition of embodiment 84 or 85, wherein the amount is sufficient to modulate one or more target nucleic acids associated with the infection.

Embodiment 94: An embodiment of embodiment 93, wherein the one or more target nucleic acids are nucleic acids of an infectious agent causing the infection.

Embodiment 95: An embodiment of embodiment 94, wherein the amount is sufficient to cut or nick at least one of the one or more target nucleic acids.

Embodiment 96: An embodiment of embodiment 94 or 95, wherein the infectious agent is a virus.

Embodiment 97: An embodiment of any of the embodiments of embodiment 93-96, wherein the administering is via a delivery system selected from the group consisting of a virus, a nanoparticle, a liposome, a micelle, a virosome, a nucleic acid complex, a protein-RNA conjugate, and combinations thereof.

Embodiment 98: An embodiment of embodiment 97, wherein the administering is via a single adeno-associated virus delivery system.

Embodiment 99: An embodiment of embodiment 97, wherein the administering is via a dual adeno-associated virus delivery system.

Embodiment 100: An embodiment of any of the embodiments of embodiment 93-99, wherein the subject is human.

X. EXAMPLES

The present disclosure will be better understood in view of the following non-limiting examples. The following examples are intended for illustrative purposes only and do not limit in any way the scope of the present invention.

Example 1. Functional Testing of Cas14 in Mammalian Cells

Figure 1:
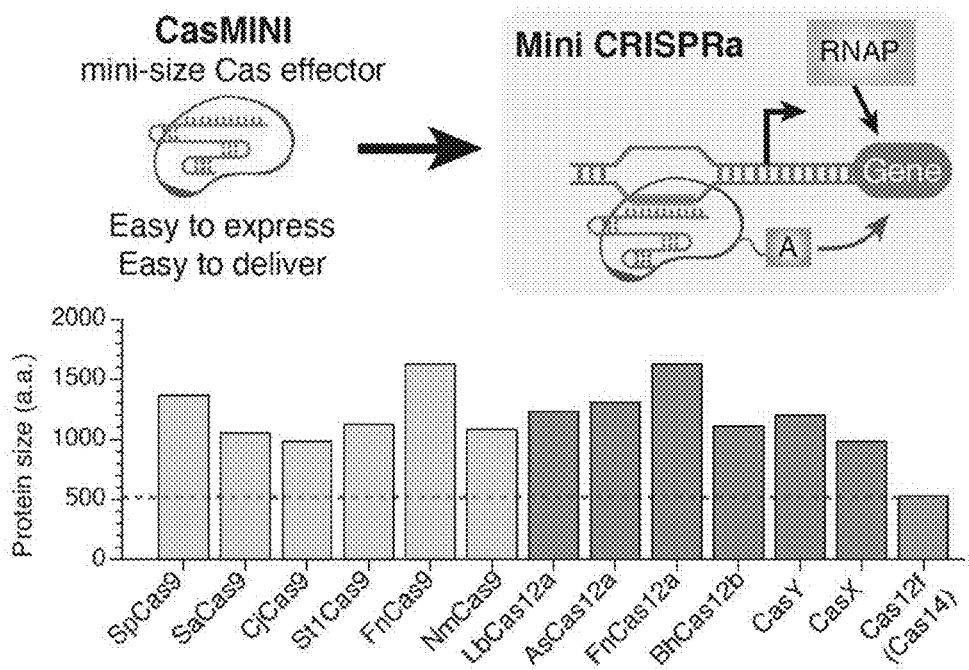
FIG. 1 illustrates that engineered novel miniature Cas effector (CasMINI) can serve as a tool for RNA-guided targeted genome engineering requiring better delivery and expression.
Figure 2:
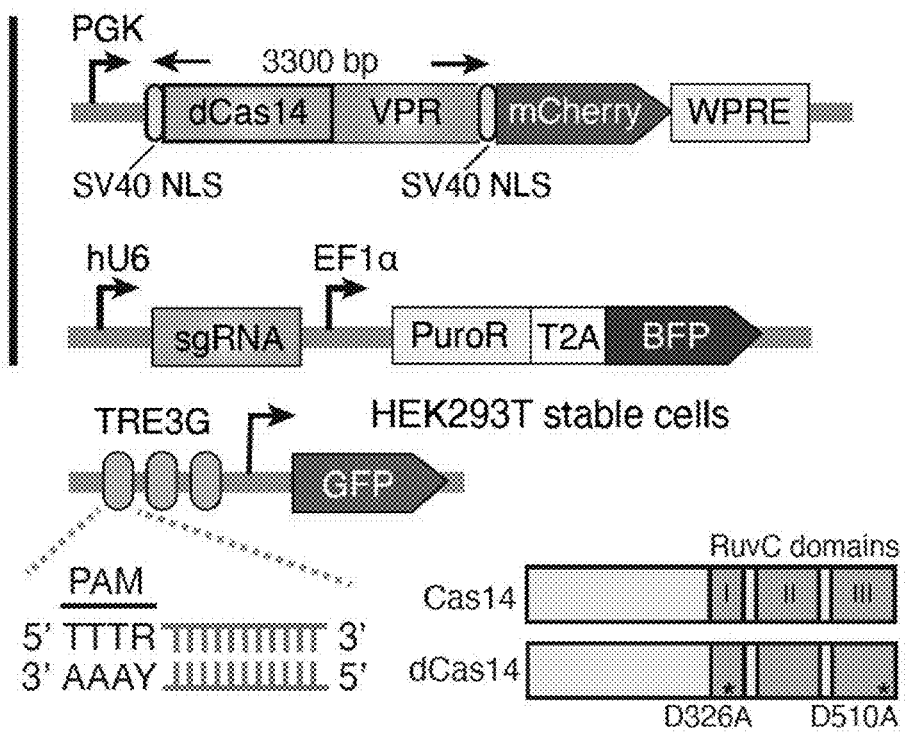
FIG. 2 presents schematic construct designs for testing dCas14-VPR fusion for CRISPR activation in a TRE3G-GFP HEK293T reporter cell line. Two mutations were introduced in the RuvC domain of Cas14 to generate nuclease-deactivated dCas14. The sgRNA targets the TRE3G promoter with a TTTR PAM.

To test whether the naturally occurring Cas14 can function in mammalian cells, nuclease deactivated Cas14 was generated by introducing two mutations to the conserved active sites of Cas14 in the RuvC domains (L. B. Harrington et al., Science 362, (2018): 839-42; T. Karvelis et al., Nucleic Acids Res. 48, (2020): 5016-23). Specifically, the Cas14 sequence was amplified from plasmid Addgene #112500, and the dCas14 was generated by introducing two mutations (D326A and D510A) to the wild-type sequence. The resulting protein was then fused to a tripartite VPR activator (A. Chavez et al. Cell 155, (2016): 563-67) (FIG. 2). This Cas construct and others described in these Examples were cloned using InFusion and Stellar competent cells (Takara Bio).

Using a doxycycline (Dox)-inducible TRE3G-EGFP HEK293T reporter cell line and a sgRNA targeting the promoter, activation efficiency of dCas14-VPR was measured. Wild-type HEK293T cells (ATCC) and the HEK293T TRE3G-GFP reporter line stably encoding EGFP under a Tet-On promoter (pTRE3G) (Y. Gao et al., Genome Res. 22, (2012): 1760-74) were cultured in DMEM with high glucose, sodium pyruvate and GlutaMAX (Thermo Fisher), additionally supplemented with 10% FBS (Sigma). Cells were grown at 37° C. and 5% $CO_2$ and maintained at confluency below 80%. All transfections were performed with TransIT-LT1 transfection reagent (Mirus) at a ratio of 3 μL reagent per μg of plasmid. Cells were plated 1 day before at $1 \times 10^5$ cells/mL. For this and other GFP activation assays described in these Examples, 500 ng of dCas constructs and 250 ng sgRNA or crRNA plasmids were transfected to HEK293T TRE3G-GFP cells in 24-well plates.

Figure 3:
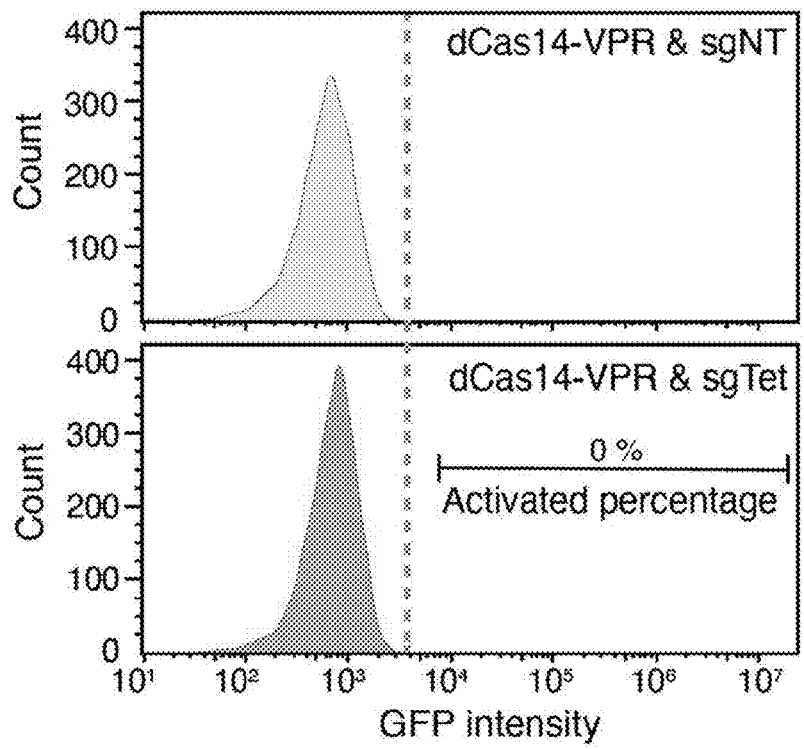
FIG. 3 presents graphs showing performance of GFP activation by the constructs of FIG. 2 as measured by flow cytometry. Representative histograms of target and non-target groups show the percentages of GFP positive population and that dCas14 fails to function in mammalian cells.

Transfected cells were analyzed 2 days post-transfection for GFP activation. Here, no reporter activation was observed (FIG. 3), implying the natural Cas14 system fails to function in the human genome context.

Example 2. Cas14 Guide RNA Engineering

Figure 4:
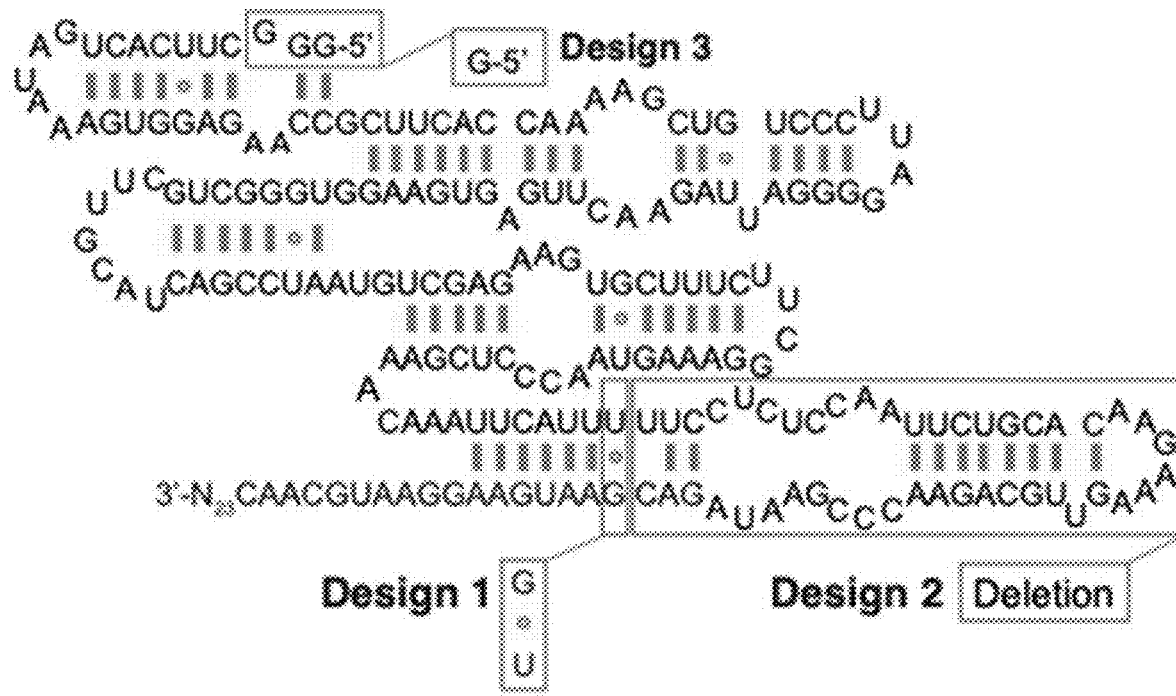
FIG. 4 presents a schematic illustration of strategies for sgRNA engineering (SEQ ID NO: 173). Design 1, G-U swap; Design 2, stem-loop truncation; Design 3, 5' poly G removal.
Figure 5:
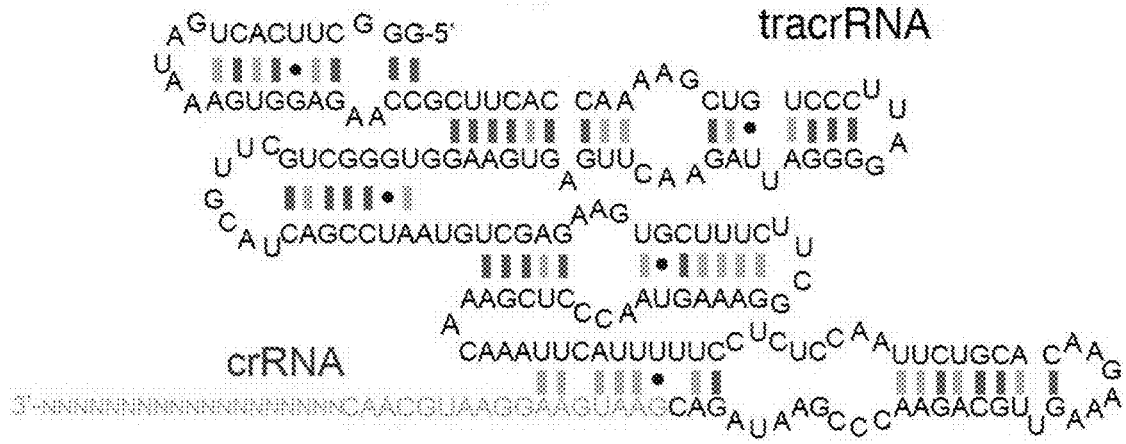
FIG. 5 presents a schematic illustration of wild-type Cas14 sgRNA (SEQ ID NO: 252).
Figure 6:
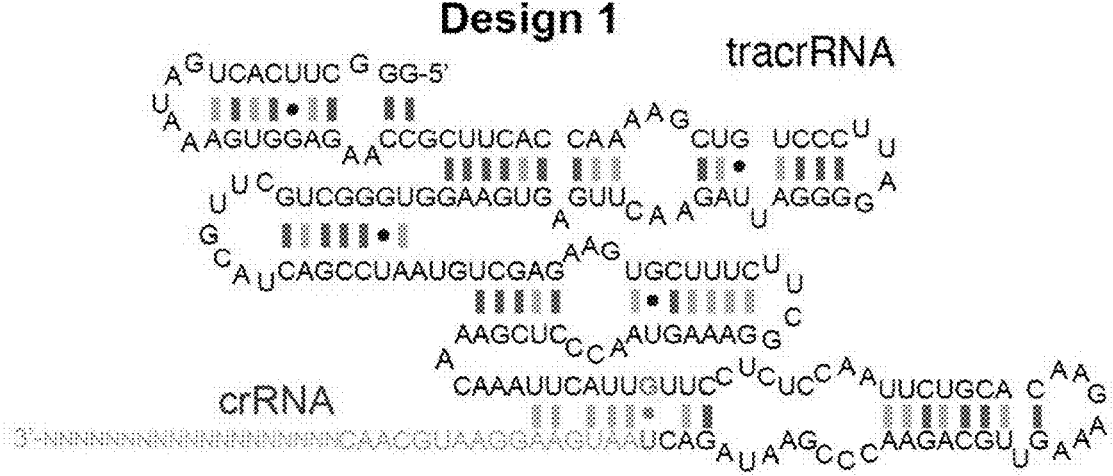
FIG. 6 presents a schematic illustration of sgRNA engineering Design 1 of FIG. 4 (SEQ ID NO: 174).
Figure 7:
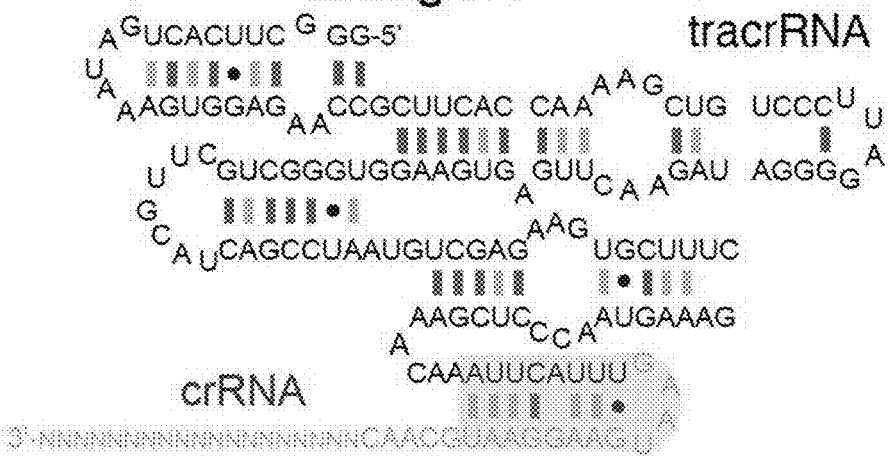
FIG. 7 presents a schematic illustration of sgRNA engineering Design 2 of FIG. 4 (SEQ ID NO: 175).
Figure 8:
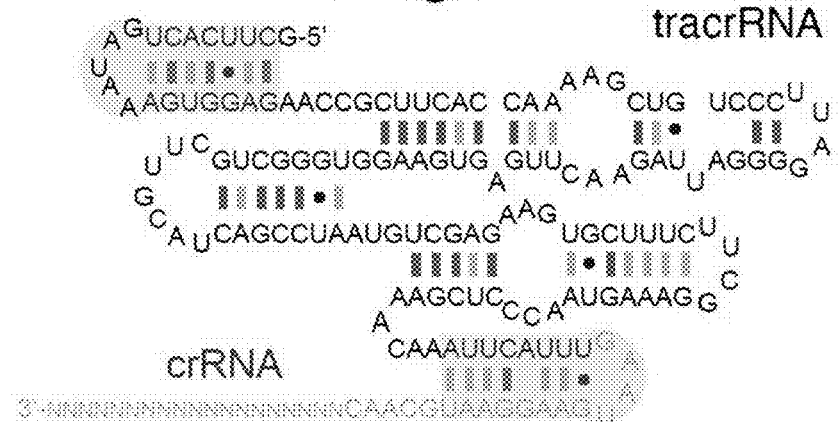
FIG. 8 presents a schematic illustration of sgRNA engineering Design 3 of FIG. 4 (SEQ ID NO: 176).

To test if the lack of Cas14 activity observed in Example 1 could be attributed to suboptimized design of sgRNA and/or the weak binding activity of Cas14 to the chromatin DNA, alternate guide RNA designs were tested (FIG. 4). These alternate designs were based on the natural tracrRNA sequence (FIG. 5), and included a G-U swap to disrupt the poly U sequence (Design 1 in FIG. 4, FIG. 6), RNA hairpin truncation (Design 2 in FIG. 4, FIG. 7), and poly G removal (Design 3 in FIG. 4, FIG. 8) (B. Chen et al., Cell 155, (2013): 1479-91).

The sgRNA backbone fragments were ordered via gBlocks from Integrated DNA Technologies (IDT). The sgRNA and/or crRNA plasmids described in this and other Examples were cloned using T4 DNA Ligase (New England Biolabs). To analyze fluorescent protein expression, cells were dissociated using 0.05% Trypsin EDTA (Life Technologies), resuspended in PBS with 5% FBS, and analyzed by flow cytometry on CytoFLEX S flow cytometer (Beckman Coulter). At least 10,000 cells containing constructs of interest of each sample were analyzed using FlowJo. The analyzed cells were gated for positive fluorescent protein expression based on the non-transfected control corresponding to construct expression.

Figure 9:
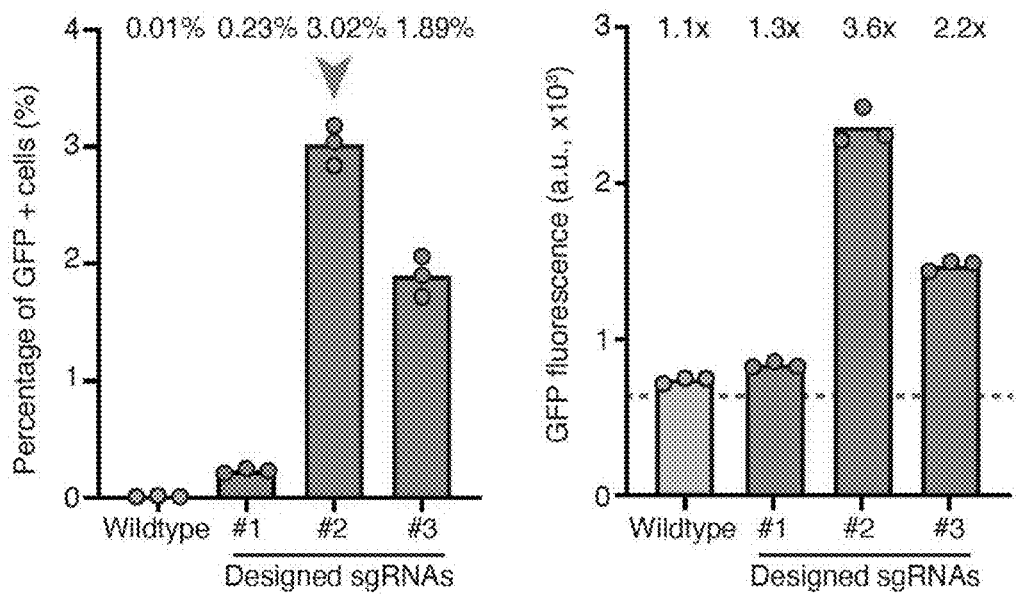
FIG. 9 presents graphs showing performance of GFP activation by transfecting the HEK293T TRE3G reporter line with plasmids containing the dCas14-VPR constructs and four targeting sgRNA of FIGS. 4-8, as well as a non-targeting sgRNA. Left, bars represent activated GFP positive percentage; Right, bars represent GFP mean values; Dash line, the mean value of non-targeting sgRNA group. Dots represent three biological replicates. Fold changes are calculated relative to the non-targeting sgRNA.
Figure 10:
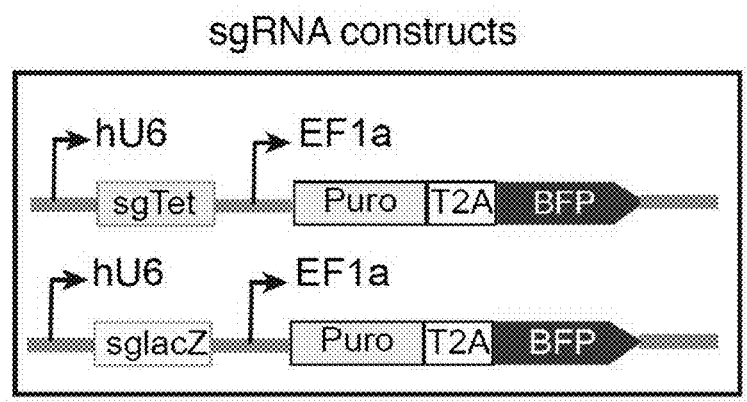
FIG. 10 presents schematic illustrations of the design of sgRNA plasmids with the designs of FIGS. 4-8 for mammalian expression.
Figure 11:
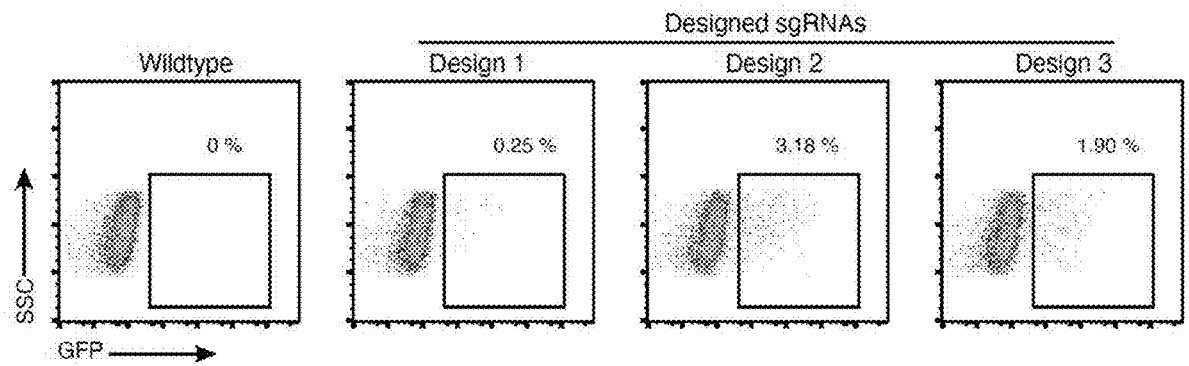
FIG. 11 presents representative flow cytometry scatter plots showing the percentage of GFP positive cells for each of the sgRNA designs of FIGS. 4-8.

Interestingly, each of the tested sgRNA designs improved gene activation, with the Design 2 outperforming the others. While the wild-type sgRNA showed no activation, Design 2 sgRNA exhibited modest activation (3% of GFP+ cells and 3.6-fold upregulation over the non-targeting sgRNA) (FIGS. 9-11). Design 2 was used for later Examples.

Figure 12:
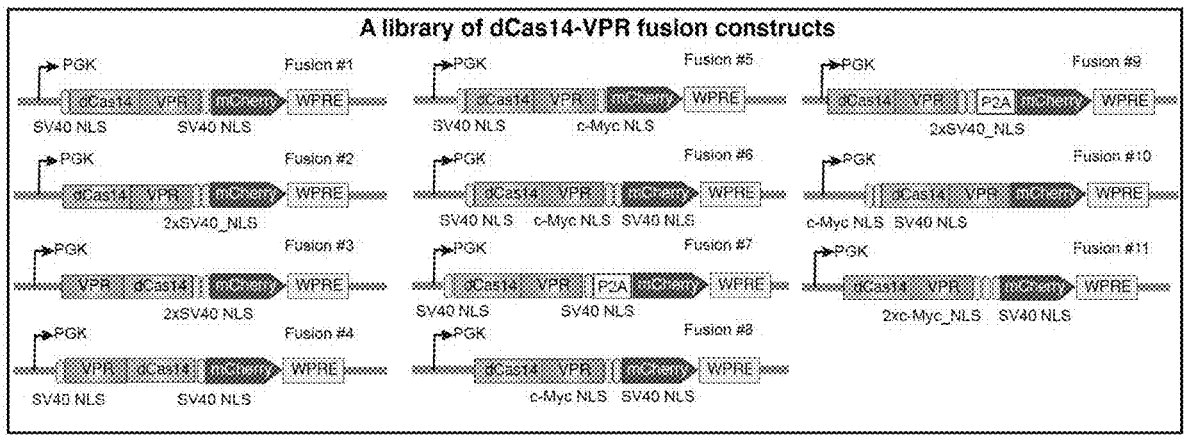
FIG. 12 presents schematic illustrations of a library of designs for dCas14-VPR fusions by fusing VPR to the N or C terminus of dCas14, combining different SV40 or c-MYC nuclear localization signals (NLSs), and different linkers (P2A, glycine-serine linker).
Figure 13:
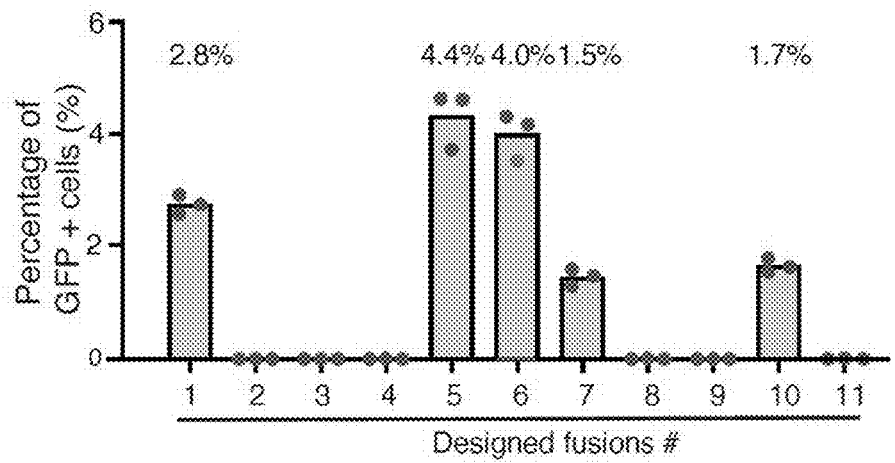
FIG. 13 is a graph showing percentage activated GFP values characterizing gene activation activity of the different dCas14-VPR fusions of FIG. 12. Dots represent three biological replicates. Dash line represents the GFP mean value of the non-targeting sgRNA. Values showing the fold of activation normalized to the non-target sgRNA are labeled.

A library of fusions with different protein fusions, linkers, and nuclear localization signals was also tested (FIG. 12). Using the sgRNA Design 2, we found one protein fusion outperformed other fusions (FIGS. 13 and 14), and was used for later Examples. Despite this optimization, however, other fusions showed only modestly lower reporter activation.

Example 3. Cas14 Protein Engineering

Figure 17:
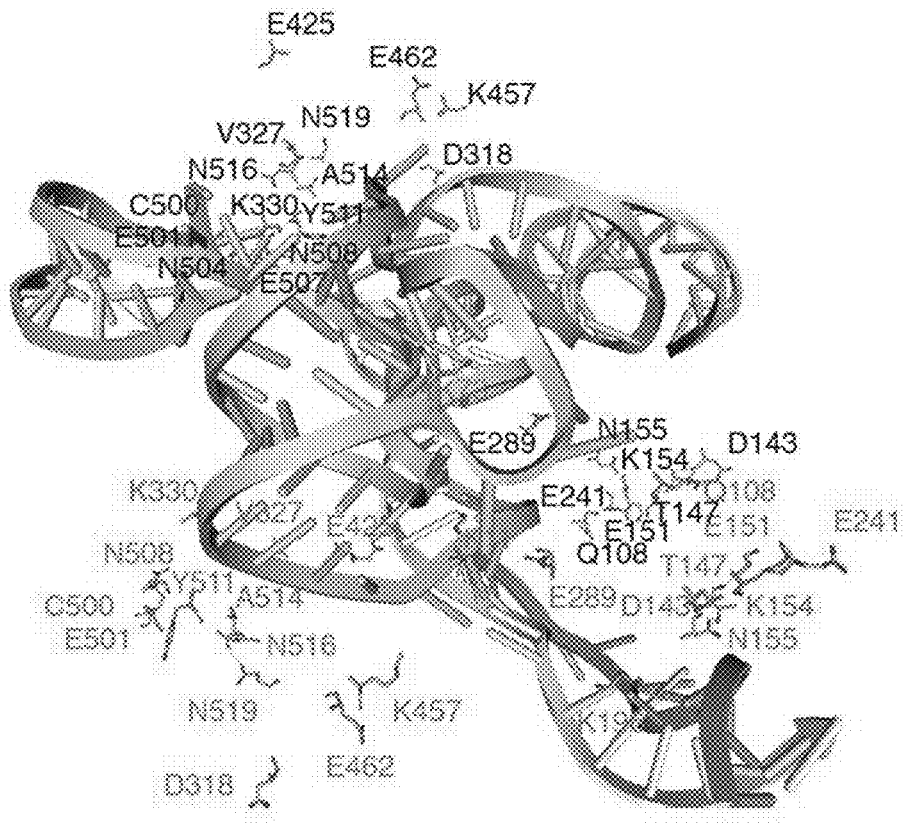
FIG. 17 is a schematic illustration indicating the positions of residues chosen for mutagenesis for iterative engineering of the dCas14 protein.
Figure 18:
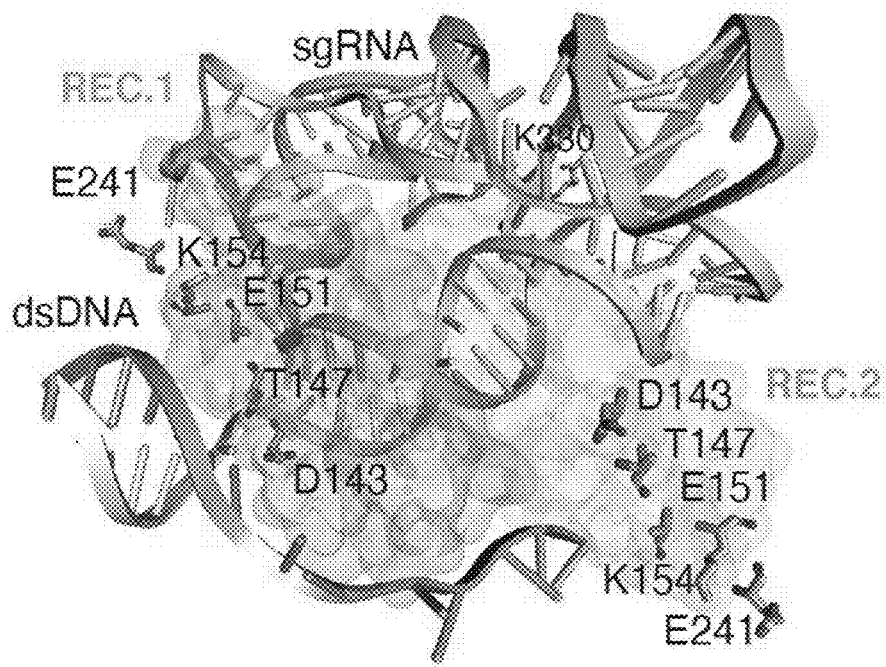
FIG. 18 is a schematic illustration showing dCas14 protein residues targeted for mutagenesis, the double-stranded DNA substrate, the sgRNA, and the binding centers of the dimer.
Figure 19:
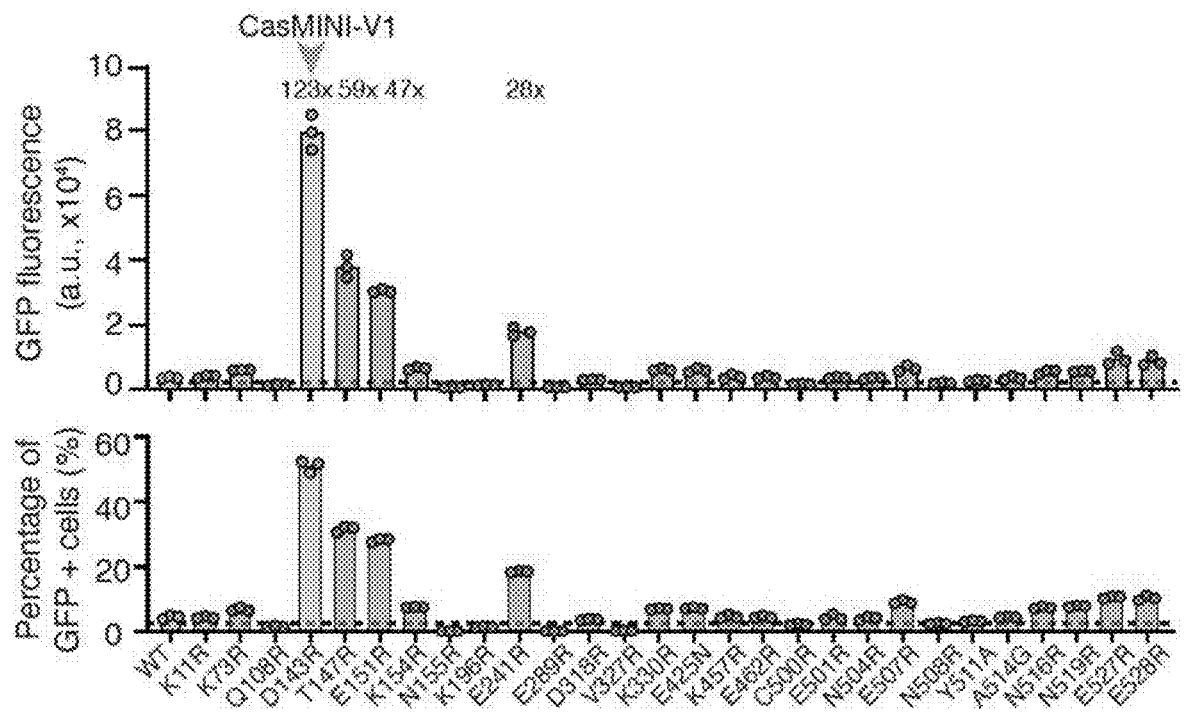
FIG. 19 presents graphs showing the GFP activation performance of 28 variants from the first screening round of the iterative protein engineering strategy of FIG. 15. Top, GFP mean values. Bottom, GFP percentage values. The GFP activation folds normalized to a non-target sgRNA targeting lacZI are labeled.
Figure 20:
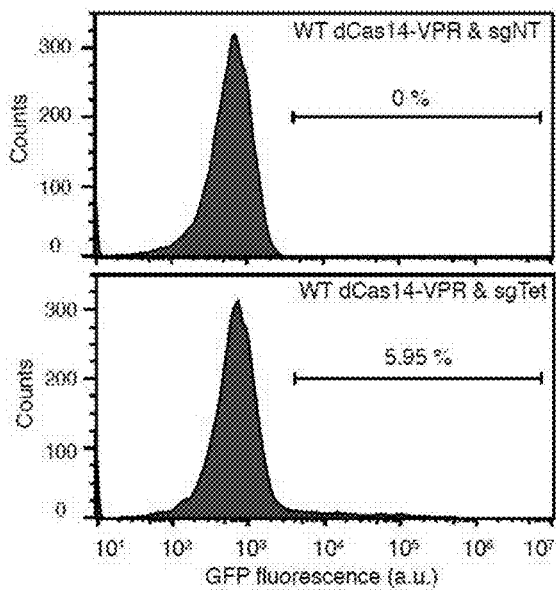
FIG. 20 presents representative flow cytometry histograms showing the percentage of GFP positive cells for wild-type dCas14-VPR using non-targeting sgRNA (top) and targeting sgRNA.
Figure 21:
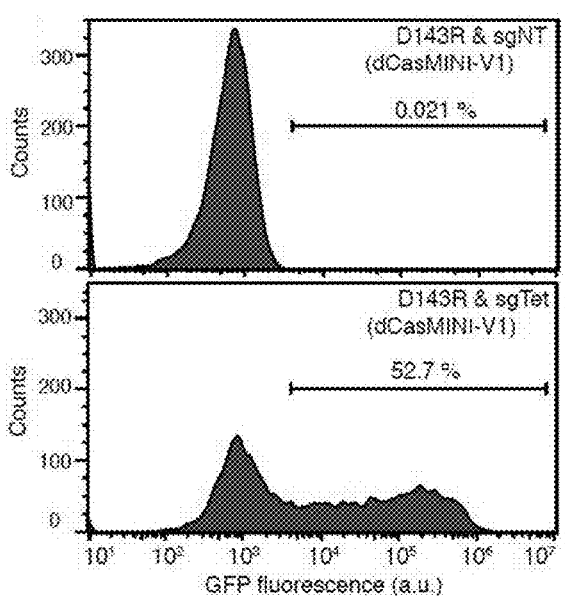
FIG. 21 presents representative flow cytometry histograms showing the percentage of GFP positive cells for wild-type dCasMINI-V1-VPR using non-targeting sgRNA (top) and targeting sgRNA.
Figure 22:
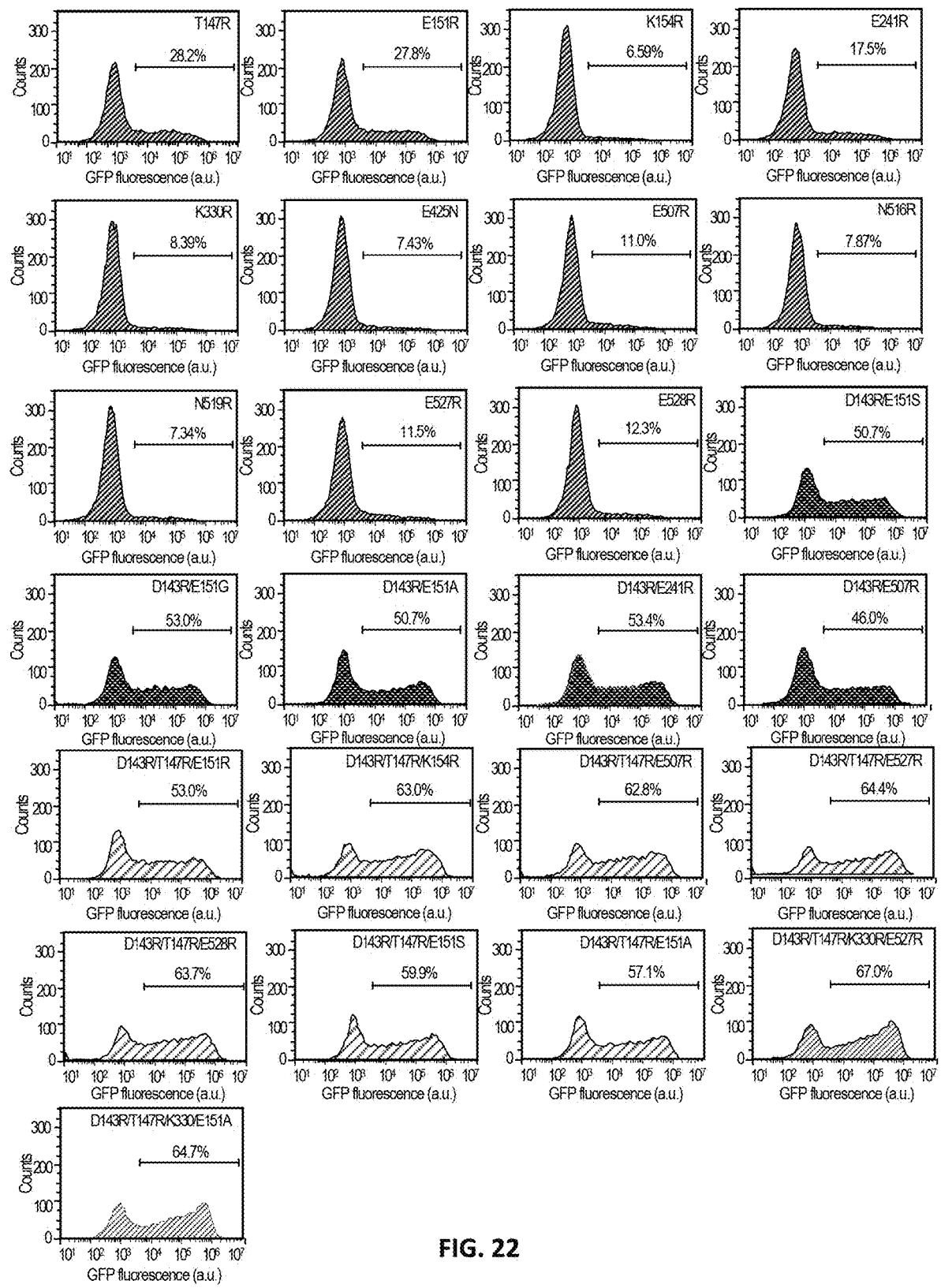
FIG. 22 presents representative flow cytometry histograms showing the percentage of GFP positive cells for variants with single (red), double (blue), triple (green) and quadruple (beige) mutations. Values show the percentage of GFP positive cells.

A guided iterative protein engineering strategy was next used to improve the performance of Cas14 variants as screened via a gene activation assay (FIG. 15). In this assay, variants showing enhanced activation of GFP in each cycle were used as the starting point of the next cycle. For initial mutations, the protein sequences of Cas14 was aligned to a family of Cas12a proteins for identification of predicted conserved motifs and residues in the target DNA binding pocket (FIGS. 16-18). Based on this analysis, 28 variants were engineered by substituting each identified and targeted amino acid to the positively charged arginine (R) that might enhance Cas14-DNA interaction, or by substituting selected individual residues to the conserved residues in Cas12a (FIG. 19). Surprisingly, while most variants showed no improvement of activation over the wild-type dCas14-VPR, a few variants (D143R, T147R, E151R, E241R) significantly enhanced activation (FIGS. 19 and 22). D143R (CasMINI-V1) in particular showed more than 24-fold of improvement over the wild-type (FIGS. 19-21).

Figure 23:
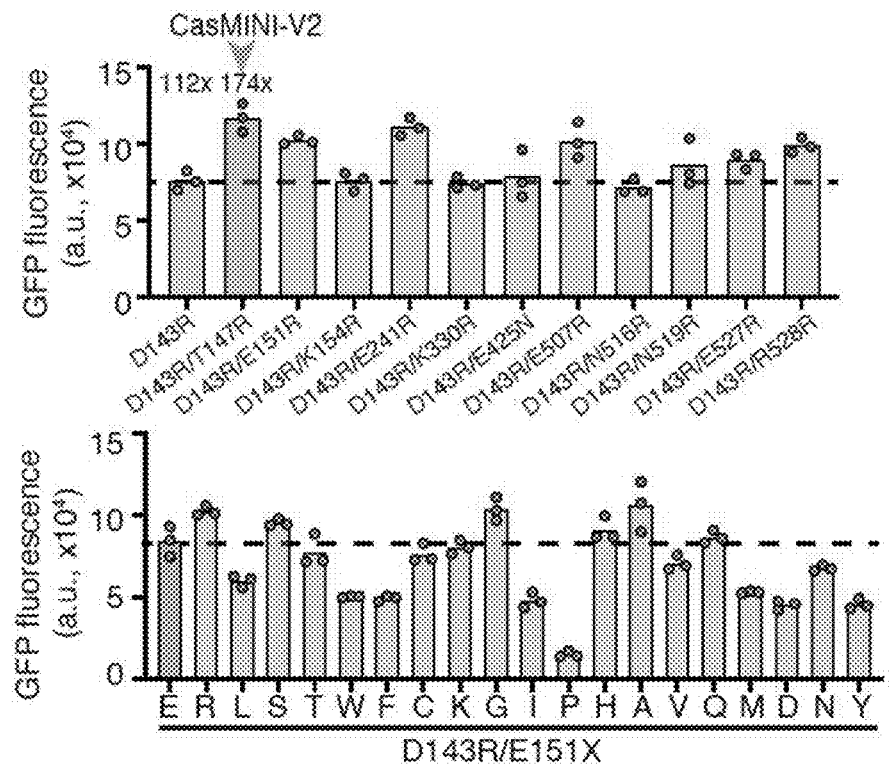
FIG. 23 presents graphs showing the GFP activation performance of variants in two libraries from the second screening round of the iterative protein engineering strategy of FIG. 15.
Figure 24:
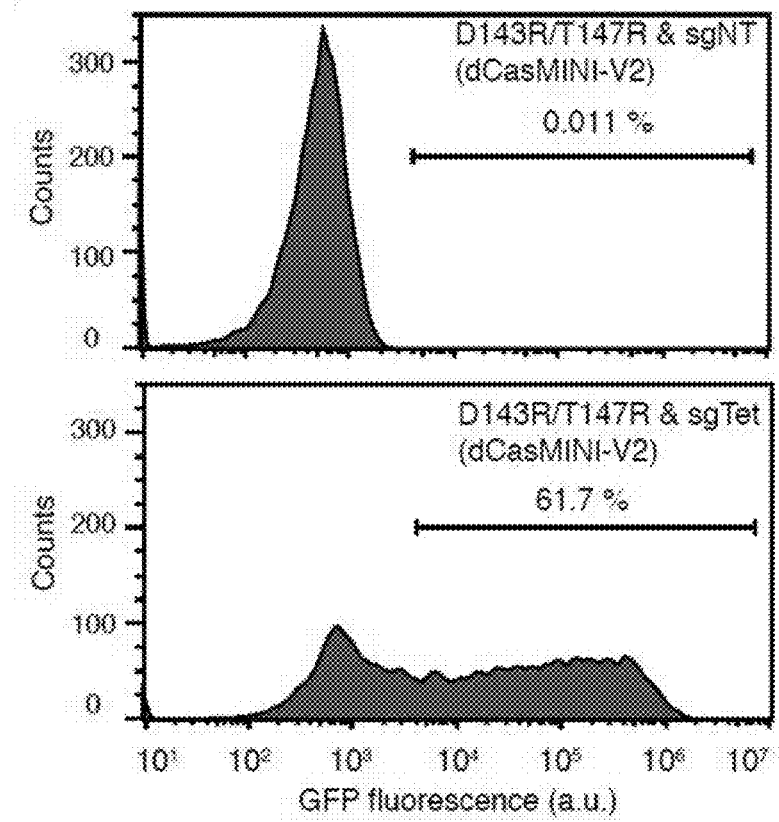
FIG. 24 presents representative flow cytometry histograms showing the percentage of GFP positive cells for wild-type dCasMINI-V2-VPR using non-targeting sgRNA (top) and targeting sgRNA.

Two libraries with double mutations were generated for the second round of screening: one had 11 variants all containing D143R, and the other had 20 variants all containing D143R and a saturation mutation of E151 to all 19 non-glutamic acid (E) amino acids. From the first library, D143R/T147R, D143R/E151R, D143R/E241R, D143R/E507R were shown to exhibit improvement over the D143R variant. The D143R/T147R variant (CasMINI-V2) showed the best improvement (1.55-fold improvement over the best single variant) (FIG. 23). From the second library, in addition to substitutions with R, those with serine(S), glycine (G), or alanine (A) also improved activation (FIG. 23). These results suggest that replacement with small-size amino acids is important for enhanced activity.

Figure 25:
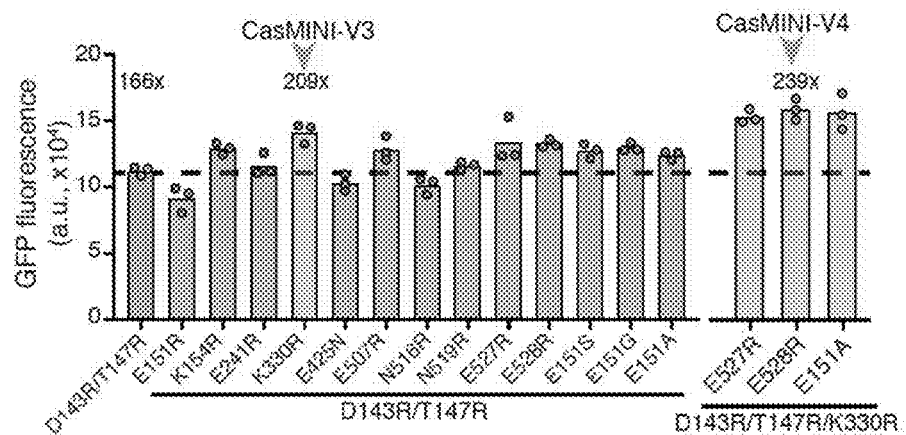
FIG. 25 is a graph showing the GFP activation performance of variants from the third and fourth screening rounds of the iterative protein engineering strategy of FIG. 15.
Figure 26:
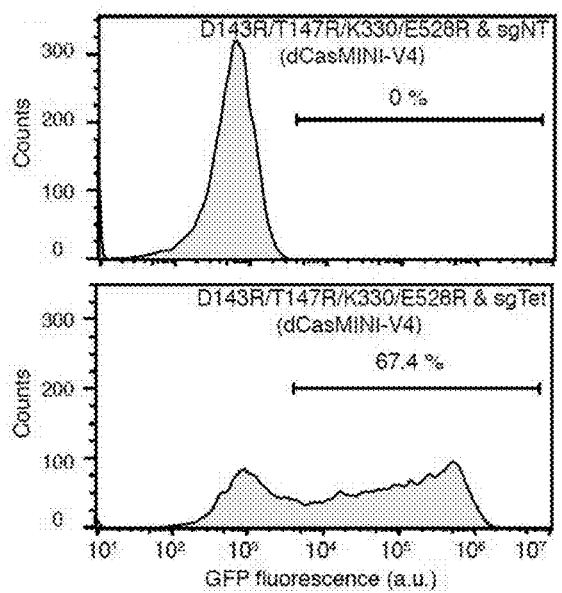
FIG. 26 presents representative flow cytometry histograms showing the percentage of GFP positive cells for wild-type dCasMINI-V3-VPR using non-targeting sgRNA (top) and targeting sgRNA.
Figure 27:
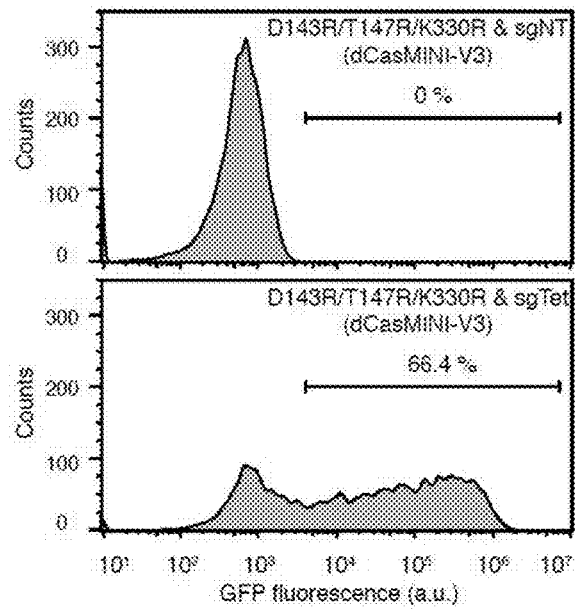
FIG. 27 presents representative flow cytometry histograms showing the percentage of GFP positive cells for wild-type dCasMINI-V4-VPR using non-targeting sgRNA (top) and targeting sgRNA.

The third screening round of screen included 13 triple variants based on D143R/T147R. The D143R/T147R/K330R variant (CasMINI-V3) outperformed other variants (1.26-fold over the best double variant D143R/T147R, FIG. 25). The fourth round of screen testing a quadruple library based on D143R/T147R/K330R showed one variant D143R/T147R/K330R/E528R (CasMINI-V4) with 1.15-fold improvement over the best triple variant (FIG. 25). This variant was chosen as 'CasMINI' for further characterization.

Figure 28:
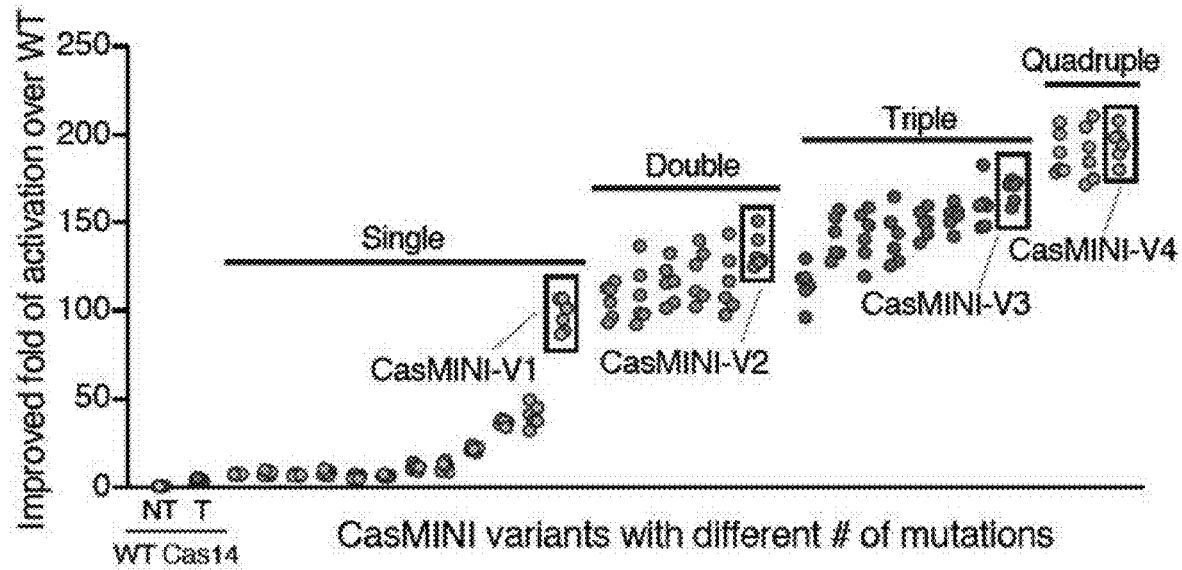
FIG. 28 is a graph showing the gradual improvement of CasMINI performance in terms of GFP activation. The fold change of each group is calculated by normalizing gene activation to wild-type dCas14-VPR.
Figure 29:
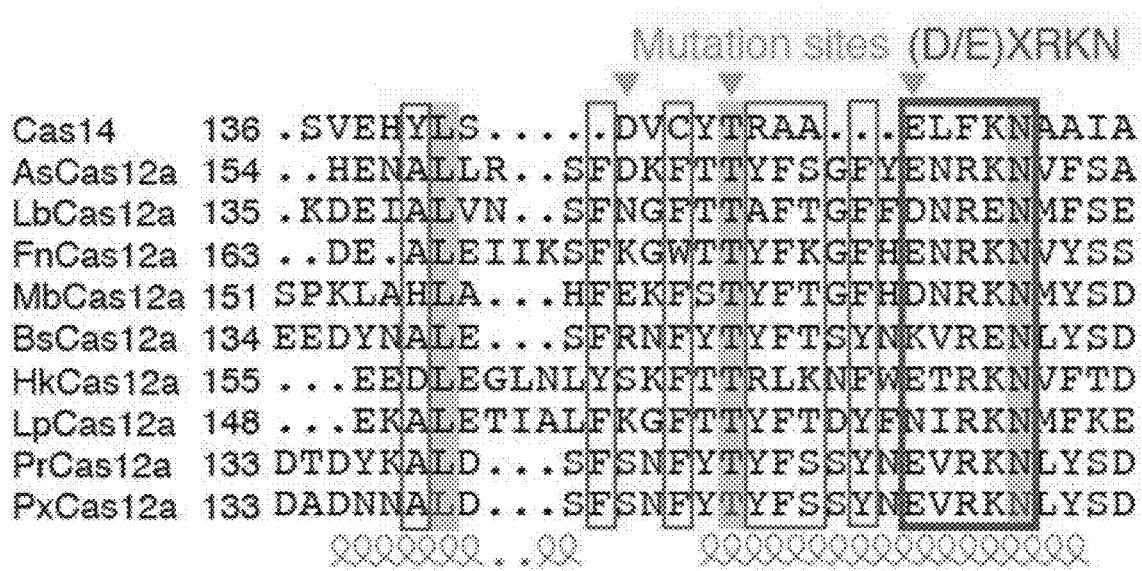
FIG. 29 illustrates sequence alignment between Cas14 and representative Cas12a proteins. The activity-enhancing residues and the conserved motif (D/E) XRKN (SEQ ID NO: 253) are indicated.

The iterative screening altogether yielded a gradually improved Cas14 variant library (FIG. 28). Interestingly, single mutations at D143, T147, and E151 showing improved activity are all at positions close to a (D/E) XRKN (SEQ ID NO: 253) motif that is highly conserved in the Cas12a family (FIG. 29). These results demonstrate that this domain is a likely hotspot for enhancing Cas14-DNA interaction.

Example 4. CasMINI Activation of Endogenous Genes

Figure 32:
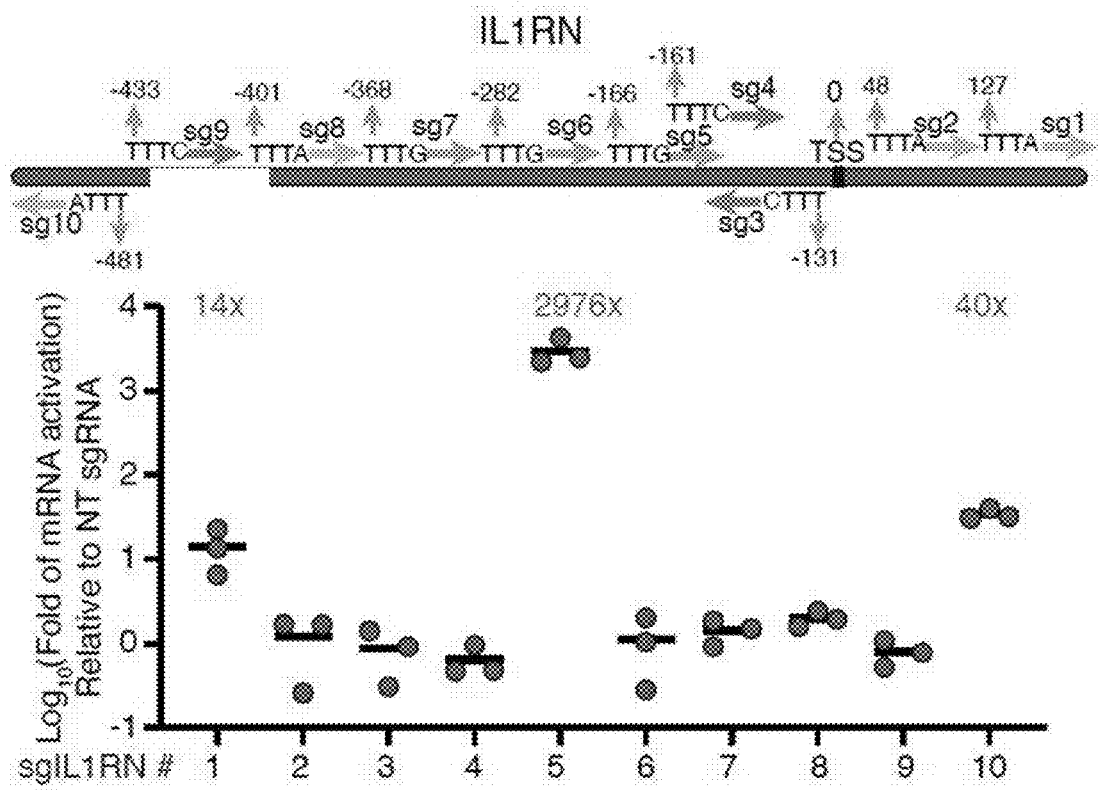
FIG. 32 presents results from gene activation of endogenous IL1RN in HEK293T cells using dCasMINI-VPR with various single sgRNAs. Top, a schematic illustration of the sgRNA distributions and PAMs. Transcriptional start site (TSS) is designated as '0', and the positions of the first 'T' in each PAM are labeled. Bottom, fold changes of top sgRNAs are shown.
Figure 33:
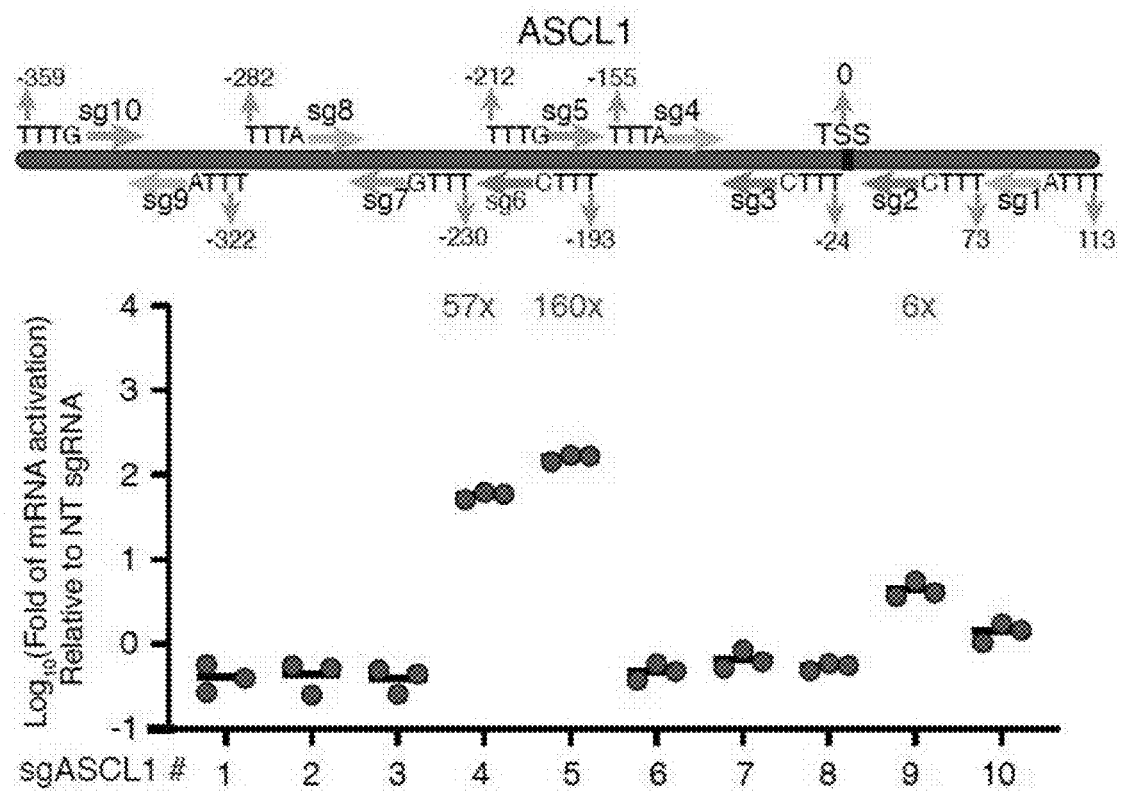
FIG. 33 presents results from gene activation of endogenous ASCL1 in HEK293T cells using dCasMINI-VPR with various single sgRNAs. Top, a schematic illustration of the sgRNA distributions and PAMs. Transcriptional start site (TSS) is designated as '0', and the positions of the first 'T' in each PAM are labeled. Bottom, fold changes of top sgRNAs are shown.

To test whether the engineered protein of Example 3 can activate endogenous genes, dCasMINI was fused to VPR, an N-terminal SV40 NLS, a C-terminal MYC NLS, and mCherry. Nuclear localization was confirmed via confocal microscope fluorescence imaging (FIG. 30). HEK293T cells transduced by dCasMINI-VPR lentivirus was seeded in a 96-well µ-plate (Ibidi, Inc.). Cells were stained with Hoechst 33342 (Thermo Fisher Scientific) to label nucleus at 37° C. for 10 min. Confocal microscopy was performed with a Nikon Spinning Disk Confocal microscope with TIRF. Activation of endogenous genes including HBG, IL1RN, and ASCL1 was tested in the HEK293T cells. For each gene, a panel of 10 sgRNAs was designed, each with different protospacer adjacent motifs (PAMs, TTTA, TTTC, or TTTG) and binding orientation, targeting within 500 bp upstream from the transcriptional start site (TSS) (T. Karvelis et al., Nucleic Acids Res. 48, (2020): 5016-23) (FIGS. 31-33). Oligos for targeting spacers were annealed and ligated into BsmBI digested backbone vectors.

Testing across these sgRNAs showed that gene activation was highly dependent on the sgRNA targeting site. For all three genes, approximately 20-40% of tested sgRNAs showed significant activation, with the best sgRNA activating the target gene by hundreds to thousands of fold improvement of activation. TTTG and TTTA PAMs worked best while TTTC PAM failed to show activation. The results therefore confirmed that TTTR PAM enabled highly efficient gene activation.

Example 5. Comparison of CasMINI and Cas14

The performance of CasMINI relative to that of wild-type Cas14 for gene activation of a panel of endogenous genes, including IFNγ, HBB, CD2, and CXCR4, was next compared. For IFNγ, CD2, and CXCR4, 10 sgRNAs were designed, and for HBB 20 sgRNAs were designed (FIGS. 34-37). To test activation of the endogenous genes, 800 ng of dCas plasmids and 500 ng sgRNA or crRNA plasmids were transfected to HEK293T cells in 24-well plates. The transfected cells were analyzed 3 days post-transfection for endogenous gene activation. Using the TTTR PAM, it was observed that a large portion of sgRNAs activated the target genes efficiently. The fold improvement of activation on these genes was higher if the genes were silenced (IFNγ, CD2, HBB), which was consistent with what has been reported for dCas9-mediated activation (S. Konermann et al., Nature 517, (2015): 583-88).

Activation of IFNγ and HBB was observed using qPCR. The transfected cells as described above were harvested using Accutase (STEMCELL), and total RNA was extracted using RNeasy Plus Mini Kit (Qiagen). cDNA was prepared using iScript cDNA Synthesis kit (Bio-Rad) and stored at −80° C. qPCR reactions were prepared in 384-well plates with iTaq Universal SYBR Green Supermix (Bio-Rad) and run on a CFX384 Touch Real-Time PCR thermocycler (BioRad). All primers were purchased from IDT. Any Cq values over 35 were considered to be 35, as there were fluctuations for transcripts with weak expression level. Samples transfected with non-targeting sgRNA or crRNA plasmids were used as negative controls. The relative expression fold improvements were analyzed using the ΔΔCq method. The levels of activation fold improvement over negative controls were normalized to the expression of GAPDH.

Activation of IFNγ was also observed using ELISA. Supernatants from transfected cell cultures were harvest 3 days post-transfection, and stored at −80° C. The secreted protein was quantified using the ELISA MAX Deluxe kits for human IFNγ on a Synergy H1 plate reader (BioTek). Absorbance at 450 nm and 570 nm was measured and protein concentrations were determined by the standard curve fitted to a power law.

Activation of CD2 and CXCR4 was observed using immunostaining followed by flow cytometry. Cells were dissociated using Accutase (STEMCELL) and stained in 5% FBS in PBS at 4° C. for 30 min. Antibodies and relevant isotypes of CD2 and CXCR4 were purchase from BioLegend (#309224, #306510, #400122, #400220).

Figure 42:
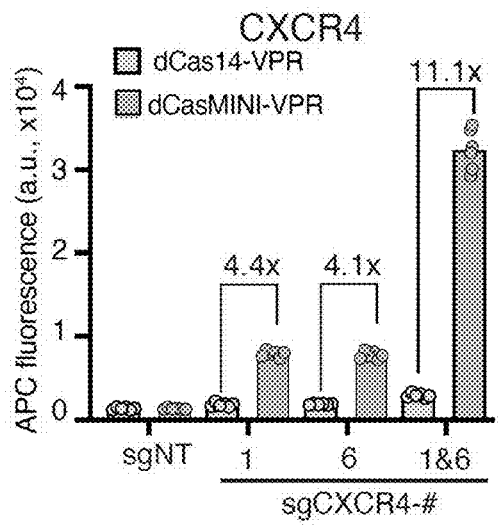
FIG. 42 presents graphs comparing endogenous CXCR4 gene activation by dCasMINI-VPR and dCas14-VPR. Fold changes of improvement of dCasMINI-VPR over dCas14-VPR are shown.

The top sgRNAs were selected for each gene and used to compare dCasMINI-VPR and dCas14-VPR side-by-side (FIG. 38). For all sgRNAs tested, consistent and greatly enhanced activation were observed for each gene. For example, comparing dCasMINI-VPR to dCas14-VPR 45- or 120-fold improvement was observed for IFNγ activation using two different sgRNAs measured by quantitative PCR (qPCR), and 25-fold or 7-fold improvement measured by enzyme-linked immunosorbent assay (ELISA) (FIG. 39). When co-delivering both sgRNAs, even better activation was observed, with improvements that were measured at 300-fold improvement by qPCR and 768-fold improvement by ELISA. Similar improvement was observed for HBB, CD2, and CXCR4 measured by qPCR or flow cytometry: dCasMINI-VPR showed up to 525-fold improvement of HBB activation, 64-fold improvement of CD2 activation, and 11-fold improvement of CXCR4 activation (FIGS. 40-42). The relative lower activation on CXCR4 was likely due to the already high expression level of CXCR4 in HEK293T cells.

Example 6. Comparison of CasMINI and LbCas12

Figure 43:
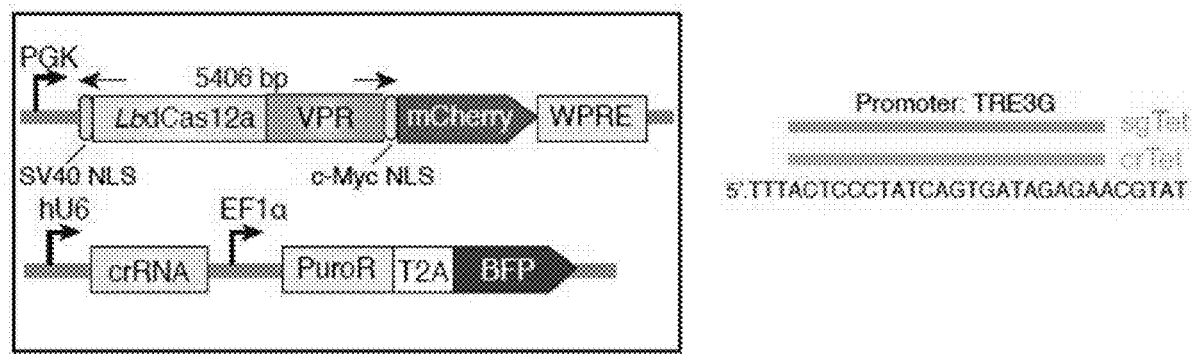
FIG. 43 presents schematic illustrations of dCas12a-VPR and crRNA used for comparisons of dCasMINI-VPR and LbdCas12a-VPR systems using sgRNAs targeting the same genomic sites.

Further experiments tested whether CasMINI performed equally well to LbCas12a. The Cas12a system is a large Cas effector (1228 amino acids), which is more than twice the size of CasMINI (FIG. 43). The Cas12a effector was chosen as a comparator because it shares a similar PAM (TTTV) as dCasMINI (TTTR), making it fair to compare the performance of two systems side-by-side using the sgRNAs targeting the same genomic site. Four genes—GFP, IFNγ, HBB, and CXCR4—were chosen, and Cas12a crRNAs were designed for binding to the same target sites as those of the best performing sgRNA of CasMINI. Nuclease-deactivated LbdCas12a and its crRNA backbone were amplified as described previously (H. R. Kempton, L. E. Goudy, K. S. Love, & L. S. Qi, Mol. Cell 78, (2020): 184-91).

Figure 44:
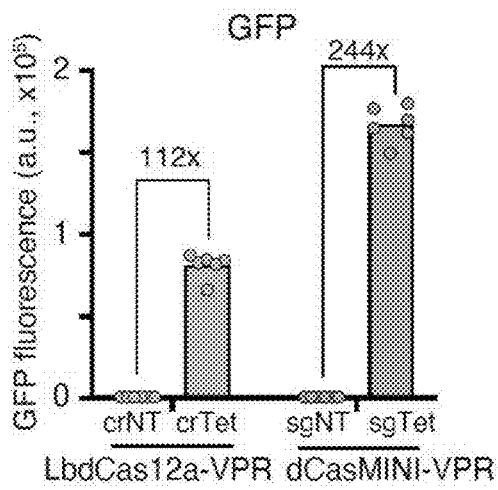
FIG. 44 is a graph showing activation of GFP in the dCasMINI-VPR and LbdCas12a-VPR system comparison of FIG. 43.
Figure 45:
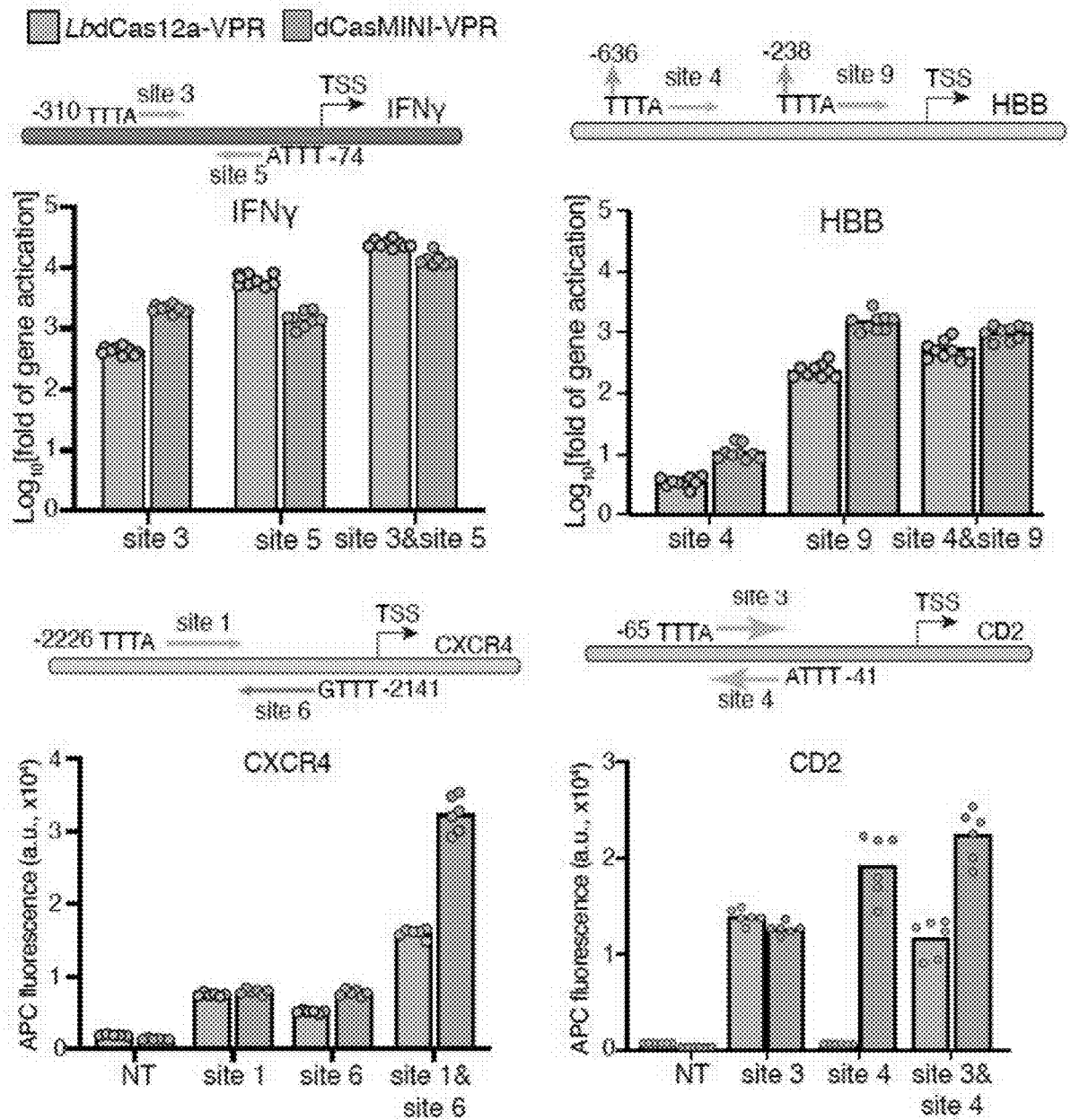
FIG. 45 presents graphs showing activation of endogenous genes in the dCasMINI-VPR and LbdCas12a-VPR system comparison of FIG. 43.

Results indicated that dCasMINI-VPR outperformed dCas12a-VPR for GFP activation by 2-fold (244-fold vs. 112-fold of activation, FIG. 44). Further, for most endogenous genes dCasMINI-VPR was observed to outperformed dCas12a-VPR, suggesting that the CasMINI system is comparable or better than Cas12a for gene activation (FIG. 45). Recent structural studies suggested that Cas14 forms a dimer when binding to the target DNA (S. N. Takeda et al., Mol. Cell 81, (2021): 558-70). It is theorized that for each target site a dimer of dCasMINI-VPR binds to the target site and enhances activation. These findings therefore demonstrate that CasMINI is a small effector comparable to or more effective than the Cas12a system (Y. E. Tak et al., Nat. Methods 14, (2017): 1163-66).

Example 7. Evaluation of CasMINI Specificity in the Mammalian Genome

To test whether CasMINI is specific in the mammalian genome context, whole-transcriptome RNA sequencing (RNA-seq) in HEK293T cells. The TRE3G-GFP HEK293T reporter cell line was transfected with the dCas and relevant sgRNA or crRNA plasmids and purified based on the expression of fluorescence proteins (mCherry and BFP) 2 days post-transfection. Total RNA was isolated using RNeasy Plus Mini Kit (Qiagen). RNA sequencing library preparation and next-generation sequencing were conducted by Novogene Corporation (Chula Vista, CA). The libraries were sequenced on a NovoSeq6000 platform. Paired-end 150-bp reads were acquired and aligned to the hg38 genome with added GFP using STAR. Transcript abundances were estimated using STAR and htseq using the quantmode option. The counts were imported with tximport, and then normalized and statistically compared using DESeq2. hg38 annotations were downloaded from Gencode (J. Harrow et al., Genome Res. 22, (2012): 1760-74). Custom R Scripts were used to perform further tpm normalization and quality control. Downstream plots used the pheatmap, ggplot2, and tidyverse packages including a custom modified EnhancedVolcano function. The variation of LbdCas12a-VPR versus dCasMINI-VPR systems were represented in violin plots by considering the distribution of standard deviations for gene expression across the four replicates (two targeting and two non-targeting replicates). Linear models and correlation coefficients were obtained using QR decomposition and regression In these experiments, prepared HEK293T cells were transfected with dCasMINI-VPR with a targeting or non-targeting sgRNA, and dCas12a-VPR was used with a targeting and non-targeting sgRNA for comparison (FIGS. 46 and 47). The two biological replicates showed consistent RNA-seq profiling (FIGS. 48 and 49). For both dCasMINI-VPR and dCas12a-VPR, no significant off-target effects comparing the targeting sgRNA to the non-targeting sgRNA were detected. Overlaying the RNA-seq data of dCas12a and dCasMINI (two duplicates shown) demonstrated dCasMINI activated GFP with a better efficiency (FIG. 50). The violin plot of the both datasets also confirmed the two Cas effectors had similar off-target profiles for gene activation (D. Kim et al., Nat. Biotechnol. 34, (2016): 863-68) (FIG. 51). These data together demonstrate the high specificity of using CasMINI in mammalian cells.

Example 8. Application of CasMINI to Base Editing in Mammalian Cells

Previously developed base editing systems derived by fusing Cas9 or Cas12 with base editors are too large to fit into the packaging capacity of AAV (~4.5 kb) (M. F. Richter et al., Nat. Biotechnol. 38, (2020): 883-91; X. Li et al., Nat. Biotechnol. 36, (2018): 324-27). In contrast, the greatly reduced size of CasMINI, permits it to reasonably fit it into this size limit. A fusion of the dCasMINI and an adenine base editor (ABE8e) was constructed, resulting in a compact fusion protein (2.4 kb compared to 4.5 kb using dCas12a). Selected genomic sites for converting A·T to G·C were tested using both base editors. Deep sequencing of edited cells was used to measure the frequency of A·T to G·C conversion.

For base editing assays, cells were plated at 40,000 cells per well in 48-well plates and transfected using 750 ng of dCas plasmids and 250 ng of sgRNA or crRNA plasmids. The transfected cells were analyzed 3 days post-transfection for endogenous gene activation. The genomic DNA lysate was prepared as described previously (M. F. Richter et al., Nat. Biotechnol. 38, (2020): 883-91) and used as templates for high-throughput sequencing (HTS). Targeted genomic regions of interest were amplified with Q5 Hot Start High-Fidelity Mastermix, 2×(NEB, #M0494S) using two-round PCRs to add Illumina adaptors and unique barcodes for each sample. Libraries were sequenced with on an Illumina Mi-Seq as previously described (M. F. Richter et al., Nat. Biotechnol. 38, (2020): 883-91). CRISPResso2 was used to process fastq.gz files obtained from the Illumina sequencing run. The "min_average_read_quality" flag was set to 30 to filter out reads with average phred33 quality scores less than 30. For each sample, the Alleles_frequency_table.txt was used to quantify the substitution percentage using the following procedure. For each read: amplicon alignment, all columns with an insertion or deletion were removed, and the columns corresponding to the 5 base pairs at the 5' and 3' ends of the amplicon were also removed. The quantification region was defined as the columns in the alignment corresponding to the sgRNA as well as 10 columns extending from both ends of the guide. If the sgRNA was reverse complemented with respect to the amplicon, a true mutation is defined as a T-to-C mutation; else, a true mutation is defined as an A-to-G mutation. All other substitutions were defined as random mutations. The substitution percentage was defined as the percentage of remaining reads containing at least one true mutation inside the quantification region.

Results indicated that dCasMINI-ABE showed an editing efficiency comparable to that of dCas12a-ABE (FIG. 52). These findings confirmed that CasMINI can be used in broad genome engineering applications.

Figure 56:
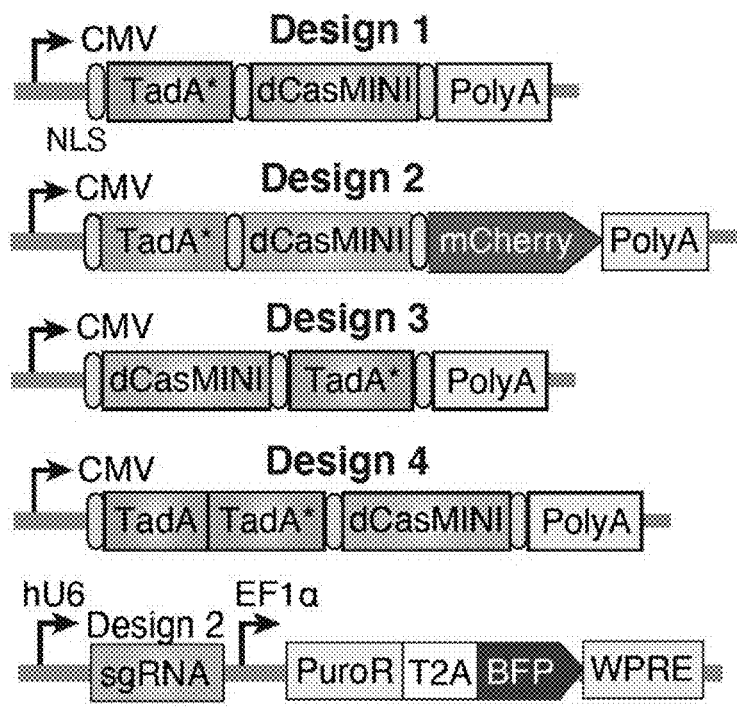
FIG. 56 presents schematic illustrations of constructs for four designs by fusing TadA-8e (TadA*) to dCasMINI at the N terminus without (Design 1) or with mCherry (Design 2), fusing TadA* to dCasMINI at the C terminus (Design 3), or fusing a heterodimer TadA-TadA* to dCasMINI at the N terminus (Design 4). The construct of sgRNA is shown on the bottom.
Figure 57:
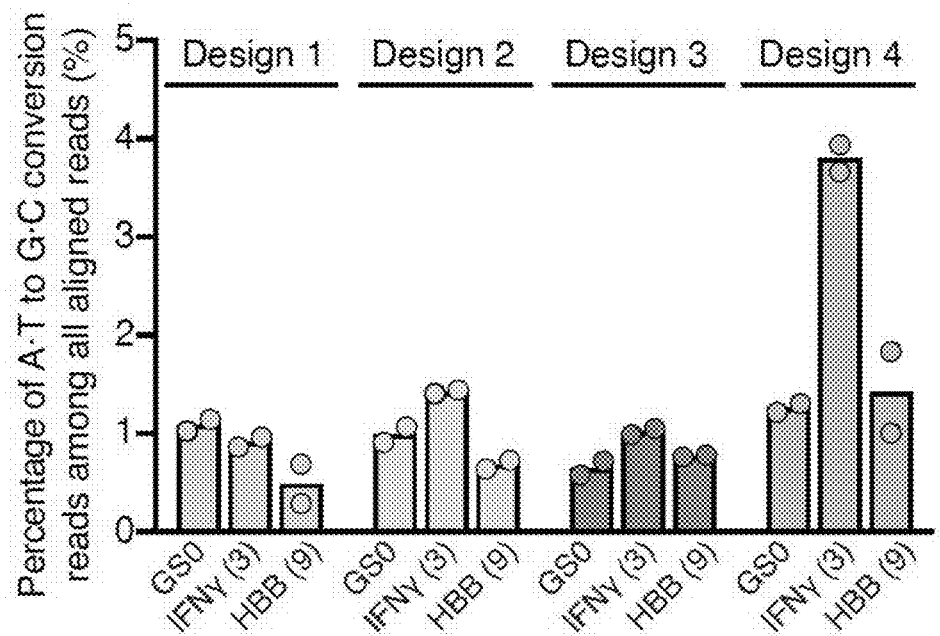
FIG. 57 is a graph comparing four dCasMINI-ABE designs for base editing efficiencies at three different genomic sites in HEK293T cells. The data shown are the percentage of reads with A·T to G·C conversion over the total aligned reads using deep sequencing. Data are representative of three biological replicates. GS0, genomic site 0. Bars represent mean values and points represent two independent biological replicates.
Figure 58:
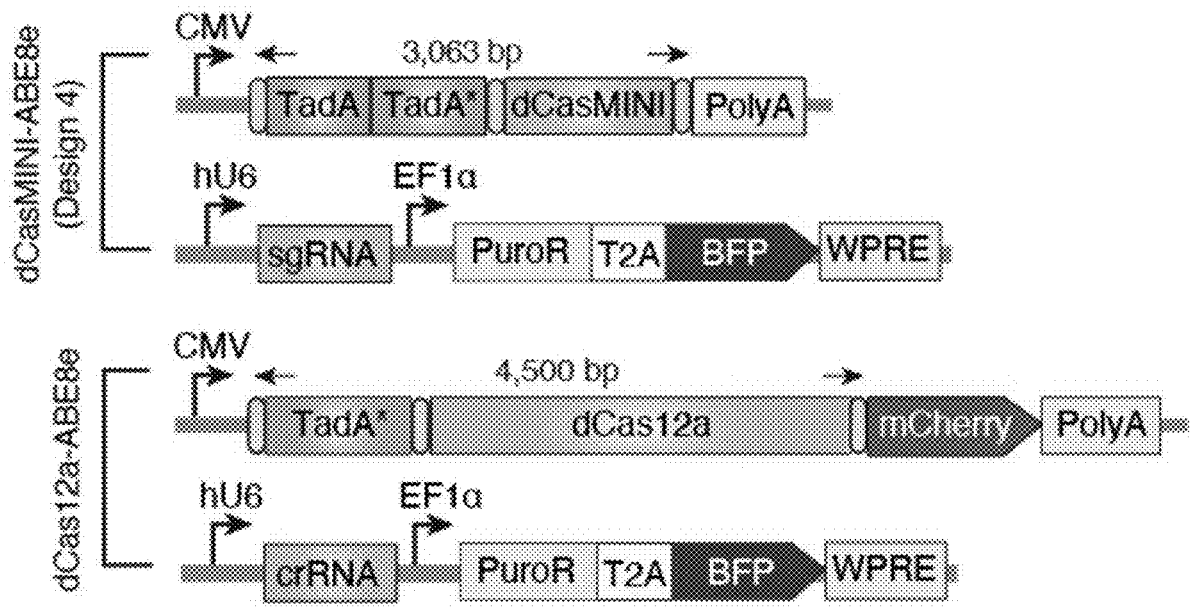
FIG. 58 presents schematic illustrations of constructs for dCasMINI-ABE Design 4 and its sgRNA and constructs for dCas12a-ABE and its crRNA used for side-by-side comparison for base editing.
Figure 59:
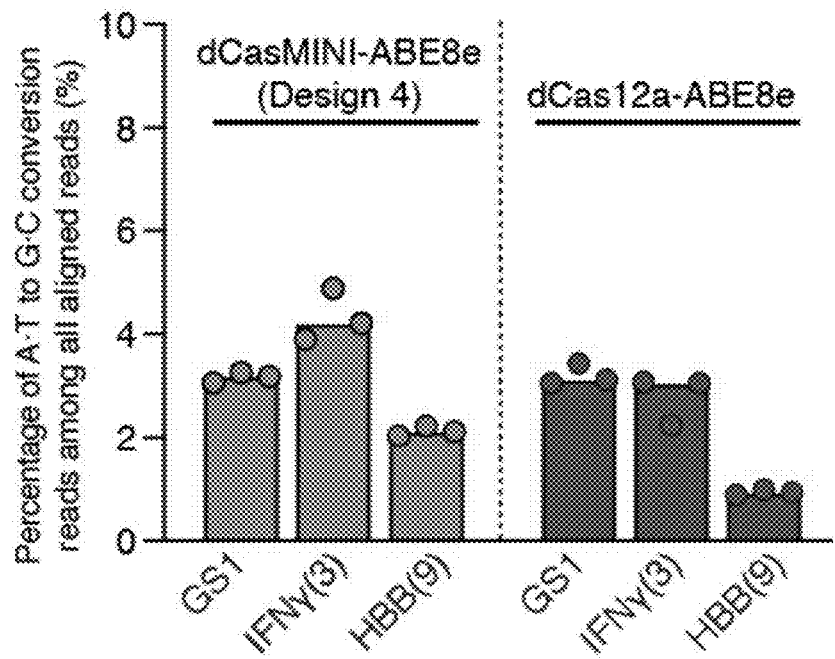
FIG. 59 is a graph showing base editing activity using dCasMINI-ABE and dCas12a-ABE at three genomic sites using sgRNAs or crRNAs targeting the same genomic sites. GS1, genomic site 1. Bars represent mean values, and data represent three biological replicates.

Next, different designs were generated by fusing dCas-MINI to the deoxyadenosine deaminase TadA-8e (TadA*) domain or to a heterodimer TadA-TadA* (Design 1-4 in FIG. 56) (T. P. Huang, G. A. Newby, & D. R. Liu, Nat. Protoc. 16, (2021): 1089; M. F. Richter et al., Nat Biotechnol. 38, (2020): 883). The conversion efficiency of A·T to G·C was measured via high-throughput sequencing (HTS) using these designs at three genomic sites (FIG. 57). Among these protein designs, Design 4 with the TadA-TadA* fusion outperformed others. The frequency of A·T to G·C conversion using dCasMINI-ABE Design 4 (~3.0 kb) and dCas12a-ABE (~4.5 kb) was next compared side-by-side at the same genomic sites and the two systems were found to exhibit similar editing efficiency across these sites (FIGS. 58 and 59).

Figure 60:
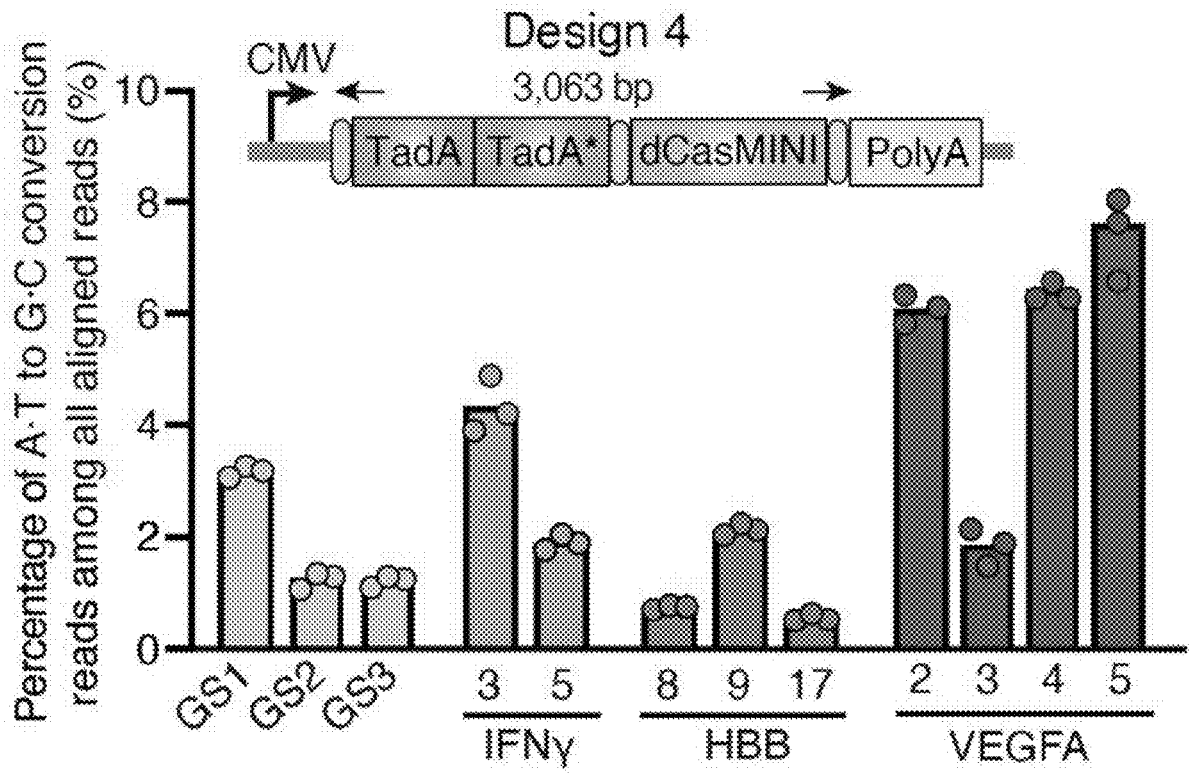
FIG. 60 is a graph showing base editing efficiencies in HEK293T cells of more genomic sites with dCasMINI-ABE Design 4, including two sites in the IFNγ locus, three sites in the HBB locus, and four sites in the VEGFA locus. The data shown are the percentage of reads with A·T to G·C conversion over the total aligned reads using deep sequencing. GS1-3, genomic sites 1-3. Bars represent mean values and points represent three independent biological replicates.
Figure 61:
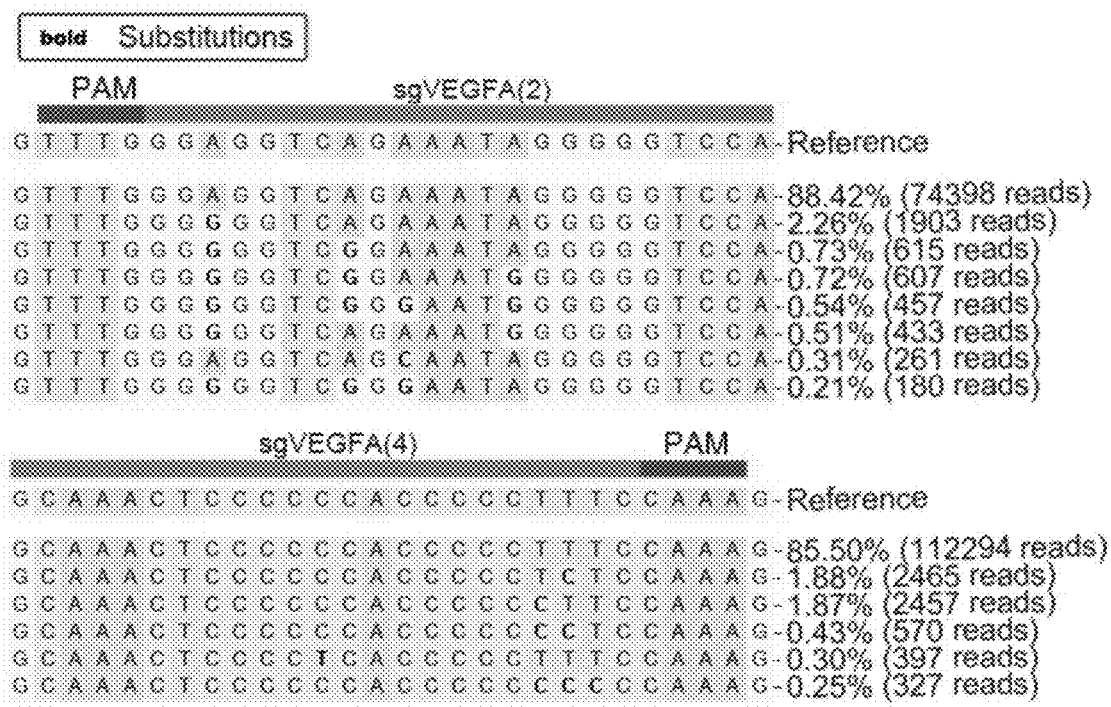
FIG. 61 shows raw sequencing reads from deep sequencing using dCasMINI-ABE and sgRNA targeting site 3 in the IFNγ locus or site 4 in the VEGFA locus. The sequenced reads and percentage among the total aligned reads are shown on the right. Representative variants with >0.2% of the total reads generated by CRISPResso2 are shown.
Figure 62:
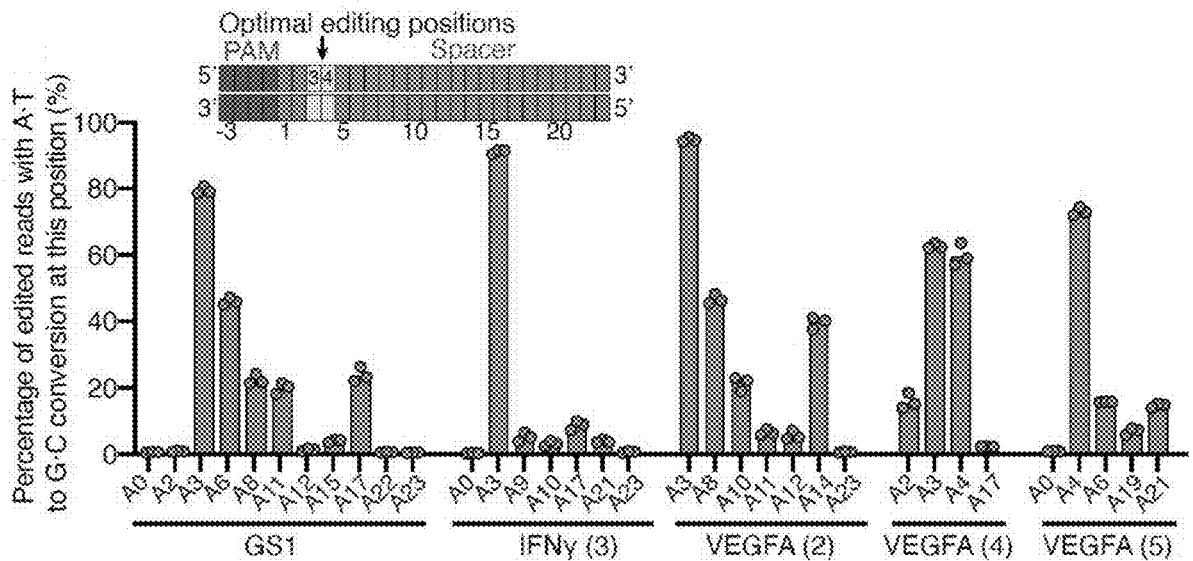
FIG. 62 is a graph showing A·T to G·C conversion base editing frequency in HEK293T cells by dCasMINI-ABE at adenines for five sites. The schematic of the nucleotide position is shown on the top: the 'R' in TTTR PAM is position '0'. The arrowed boxes represent the observed most efficient A·T to G·C conversion positions (position 3 and 4). The data shown is the number of reads with A·T to G·C conversion at a specific position over the total number of reads for A·T to G·C conversion using deep sequencing. GS1, genomic site 1. Bars represent mean values and data represent three independent biological replicates.

The performance of this fusion for A·T to G·C base editing was next characterized at a total of 12 genomic sites, including multiples sites in vicinity regions of IFNγ, HBB, and VEGFA loci. For many genomic sites, detectable A·T to G·C base conversion was observed (FIGS. 60 and 61). The base editing efficiency was dependent on the target site, and the pattern for A·T to G·C conversion was further analyzed. Interestingly, it was observed that most efficient A·T to G·C editing occurred in a narrow window A3-A4 (3-4 bp downstream of the PAM, the 'R' in the TTTR PAM is position '0') (FIG. 62), suggesting that careful sgRNA target design is needed for efficient base editing.

Figure 53:
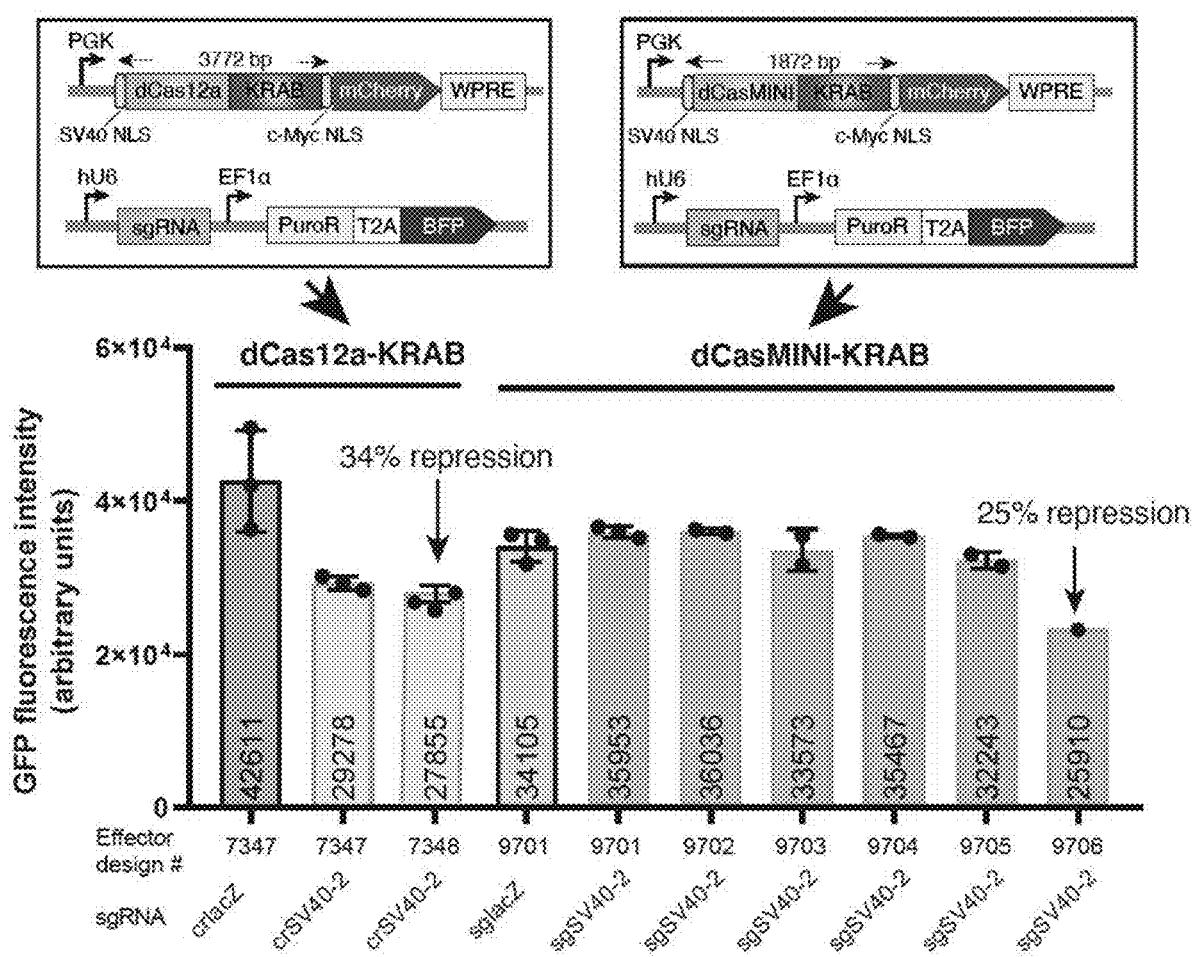
FIG. 53 illustrates the silencing of GFP reporter genes using dCasMINI fused to a transcriptional repressor KRAB. The schematic diagrams show the constructs used in the experiments. The graph shows that repression activity observed with the dCasMINI-KRAB construct is comparable to that observed with dCas12a-KRAB.

Example 9. Application of CasMINI to Transcriptional Repression in Mammalian Cells To evaluate the functionality of the provided CasMINI systems as transcriptional repressors, dCas12a and dCas-MINI (having 4 mutations) were each independently fused to the transcriptional repressor domain KRAB. The resulting fusions were then tested using a single sgRNA targeting the same site on a synthetic reporter system (SV40 promoter driving EGFP, stably inserted into the genome) in HEK293T cells. Observation of the cells transfected with both dCas12a-KRAB+crRNA or dCasMINI-KRAB+sgRNA, resulted in detection of moderate but statistically significant repression of the target GFP gene. As shown in FIG. 53, dCas12a (yellow bars) exhibited up to 34% repression compared to a non-targeting crRNA (grey bar). dCasMINI (blue bars) exhibited up to 25% repression of the target GFP compared to its control group with the non-targeting sgRNA (light grey). These results demonstrate that the provided systems can be used for transcriptional or epigenetic repression of endogenous genes in the genome.

Example 10. Application of CasMINI to Gene Editing in Mammalian Cells

To further evaluate the ability of the provided CasMINI systems to edit genes, three constructs were created. Two of these, CasMINI-V2_E2 and CasMINI-V2_E3, included a Cas protein variant having two substitutions in the Cas14 amino acid sequence, and one, CasMINI-V4_E4, included a Cas protein variant having four substitutions. The E2 construct included a 3×FLAG® tag, while the E3 and E4 constructs included a human influenza hemagglutinin (HA) tag. Additionally, 11 different sgRNAs were constructed as shown in Table 1 below. Each guide RNA targeted either TTTG or TTTA PAMs of template or non-template DNA strands, and the genes DNMT1 or VEGFA of the human genome. For each locus, a PCR primer was designed for performing deep sequencing to quantify the percentage of variants for each mutation, e.g., indels, including insertions and deletions.

TABLE 1 sgRNA constructs.

| Number | Relevant gene | Guide name | Guide sequence | PAM |
|---|---|---|---|---|
| 1 | Human DNMT1 | sgDNMT1-02 | gctcagcaggcacctgcctcagc (SEQ ID NO: 162) | TTTG |
| 2 | Human DNMT1 | sgDNMT1-04 | tttcccttcagCTAAAATAAAGG (SEQ ID NO: 163) | TTTA |
| 3 | Human DNMT1 | sgDNMT1-05 | Gctgaagggaaataaaaggaaaa (SEQ ID NO: 164) | TTTA* |
| 4 | Human DNMT1 | sgDNMT1-07 | ACATGTCAATCTGTCCGTTCACA (SEQ ID NO: 165) | TTTA |
| 5 | Human VEGFA | sgVEGFA-01 | ggaagtgtccagggatgcttccc (SEQ ID NO: 166) | TTTG* |
| 6 | Human VEGFA | sgVEGFA-02 | atgtctgcaggccagatgagggc (SEQ ID NO: 167) | TTTG |
| 7 | Human VEGFA | sgVEGFA-03 | ggactggagttgcttcatgtaca (SEQ ID NO: 168) | TTTG* |
| 8 | Human VEGFA | sgVEGFA-04 | ggaggtcagaaataggggtcca (SEQ ID NO: 169) | TTTG |
| 9 | Human VEGFA | sgVEGFA-05 | ctcctggacccctatttctgac (SEQ ID NO: 170) | TTTG* |
| 10 | Human VEGFA | sgVEGFA-06 | gaaagggggtgggggagtttgc (SEQ ID NO: 171) | TTTG* |
| 11 | Human VEGFA | sgVEGFA-08 | gccagagccggggtgtgcagacg (SEQ ID NO: 172) | TTTA |

*non-template strand

Gene editing results, quantified as the percentage of indels, including deletion, insertion, and substitution allelic mutations in the region within 50 base pairs of the sgRNA, are presented in FIG. 54. The data show that all tested CasMINI systems can induce indels, and thus, gene editing. Among the 11 tested sgRNAs, 4 could induce measurable indels above the background. Among the tested CasMINI constructs, E2 exhibited slightly better gene editing, with 7% of editing efficiency. These results suggests that the performance of gene editing can be dependent on the sgRNA targeting location. Furthermore, the representative sequences presented in FIG. 54 show that the modifications are biased towards the distal region of the target DNA PAM (protospacer adjacent motif, TTTR) by the sgRNA.

Figure 63:
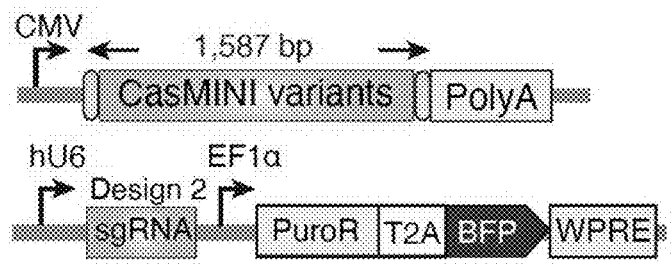
FIG. 63 presents schematic illustrations of constructs encoding the nuclease active CasMINI and its sgRNA for gene editing, and a table showing three CasMINI variants tested. All experiments used sgRNA Design 2.
Figure 64:
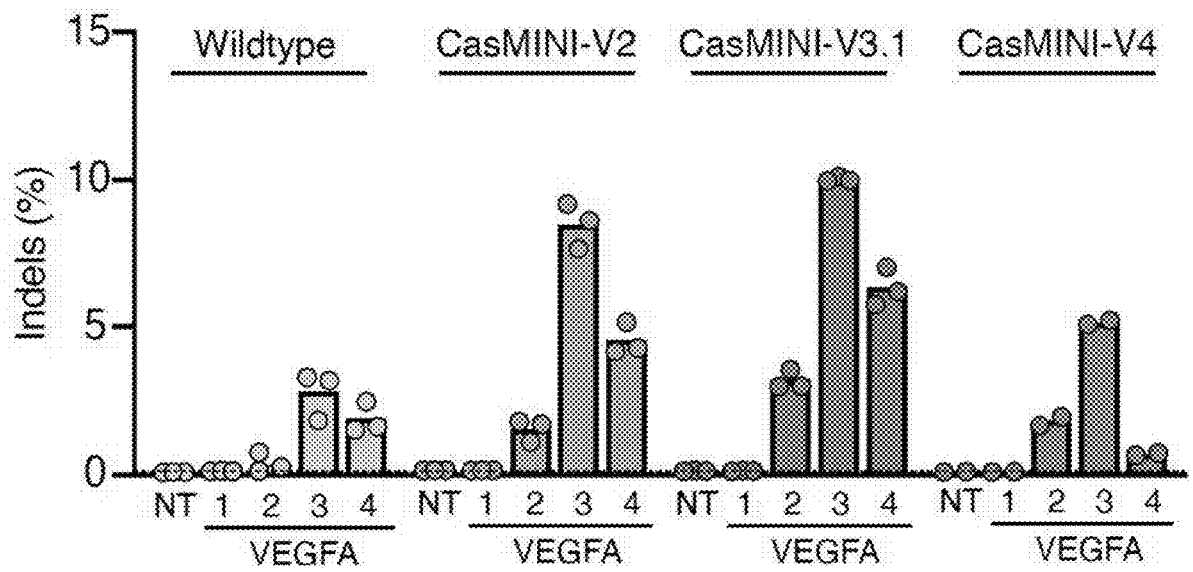
FIG. 64 is a graph showing indel activity of each CasMINI variant at four sites of the VEGFA locus measured by deep sequencing in HEK293T cells. The data using a non-targeting (NT) sgRNA is shown as a representative negative control. The dotted line shows the basal indel level detected from wild type HEK293T cells. Bars represent mean values, and data represent three independent biological replicates.

To further investigate whether nuclease-active versions of dCasMINI variants (CasMINI) could cut and edit genomic DNA in human cells, CasMINI-V2 (D143R/T147R), V3.1 (D143R/T147R/E151A), and V4 (D143R/T147R/K330R/E528R) were compared side-by-side with the wild type Cas12f (FIG. 63). The V2 and V3.1 variants were included due to suspicion that the proximity of the K330R and E528R mutations to the catalytic sites in the RuvC domains might negatively impact the DNA cleavage ability of CasMINI-V4. Using the sgRNA Design 2, all variants were tested by targeting four selected sites in the VEGFA genomic locus and measured indel (insertion/deletion) formation efficiency via deep sequencing. Interestingly, it was observed that CasMINI-V3.1 outperformed V2 and V4, which showed consistently higher indel formation across all tested sites (FIG. 64). The use of Design 2 sgRNA also enabled modest indel formation with the wild type Cas12f in mammalian cells, which has not been observed before.

Figure 34:
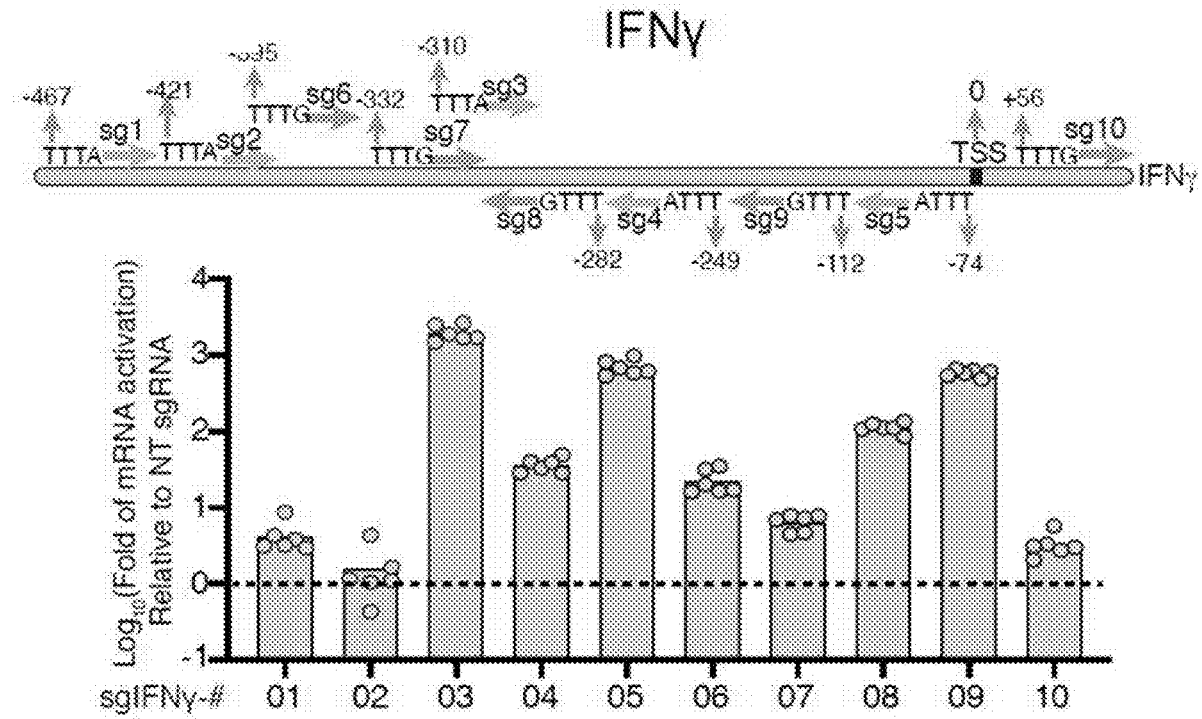
FIG. 34 presents results from characterization of a library of 10 sgRNAs using dCasMINI-VPR for activating the human endogenous IFNγ gene. The top schematic illustration shows the binding sites and PAMs using by each sgRNA, designed to target within 500 bp of the transcriptional start site (TSS, position 0). The position of the first 'T' of each PAM is shown. The bottom diagram shows characterized gene activation activity of all sgRNAs using qPCR. Dots represent biological replicates.
Figure 35:
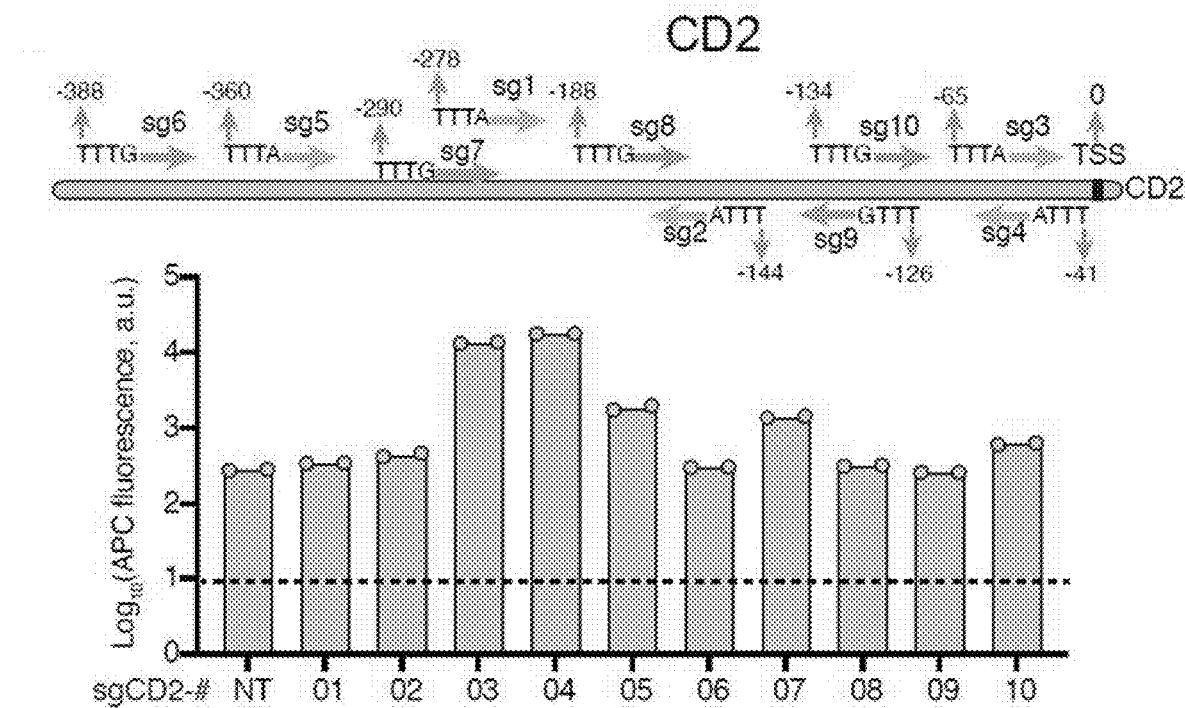
FIG. 35 presents results from characterization of a library of 10 sgRNAs using dCasMINI-VPR for activating the human endogenous CD2 gene. The top schematic illustration shows the binding sites and PAMs using by each sgRNA, designed to target within 500 bp of the transcriptional start site (TSS, position 0). The position of the first 'T' of each PAM is shown. The bottom diagram shows characterized gene activation activity of all sgRNAs using immunostaining followed by flow cytometry. Dots represent biological replicates.
Figure 36:
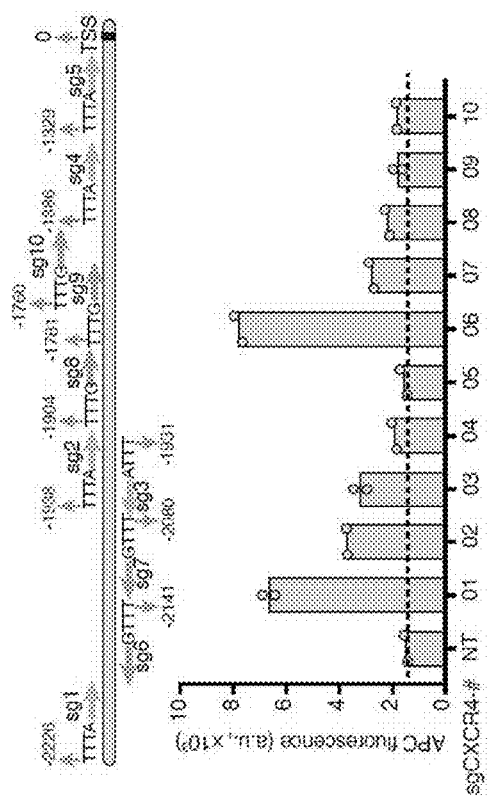
FIG. 36 presents results from characterization of a library of 10 sgRNAs using dCasMINI-VPR for activating the human endogenous CXCR4 gene. The top schematic illustration shows the binding sites and PAMs using by each sgRNA, designed to target within 500 bp of the transcriptional start site (TSS, position 0). The position of the first 'T' of each PAM is shown. The bottom diagram shows characterized gene activation activity of all sgRNAs using immunostaining followed by flow cytometry. Dots represent biological replicates.
Figure 37:
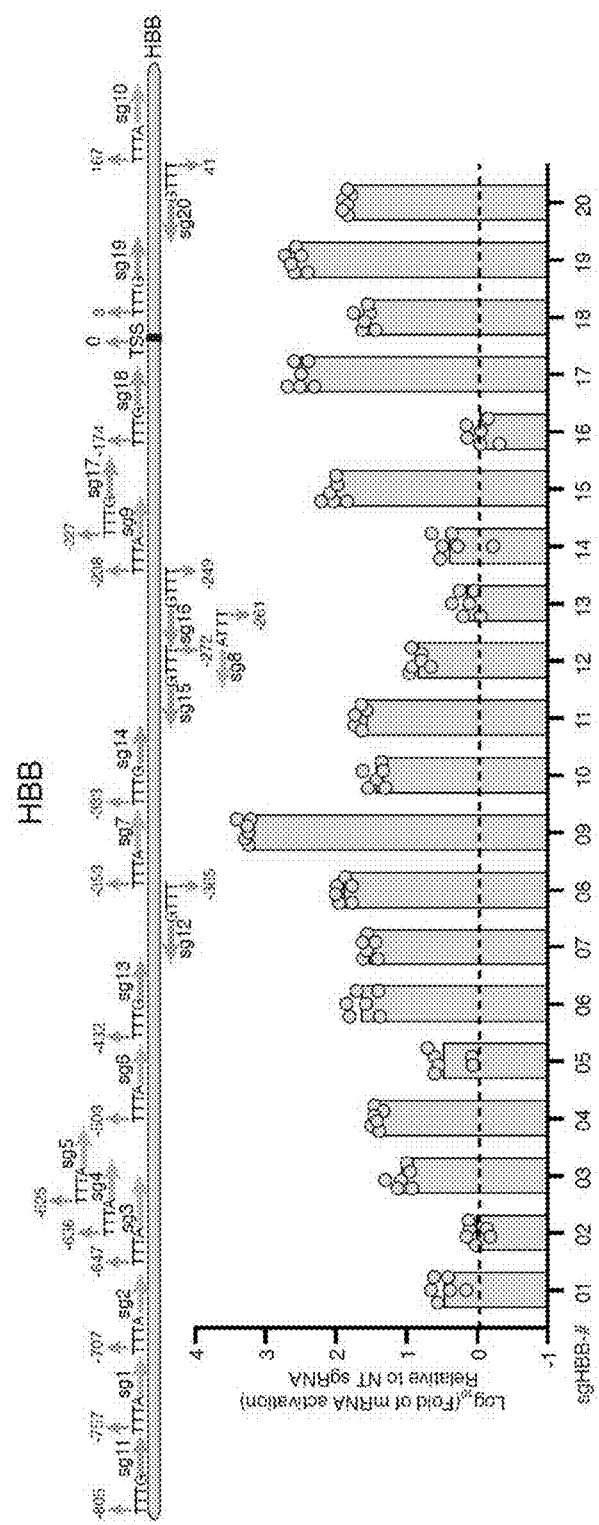
FIG. 37 presents results from characterization of a library of 20 sgRNAs using dCasMINI-VPR for activating the human endogenous IFNγ gene. The top schematic illustration shows the binding sites and PAMs using by each sgRNA, designed to target within 500 bp of the transcriptional start site (TSS, position 0). The position of the first 'T' of each PAM is shown. The bottom diagram shows characterized gene activation activity of all sgRNAs using qPCR. Dots represent biological replicates.
Figure 65:
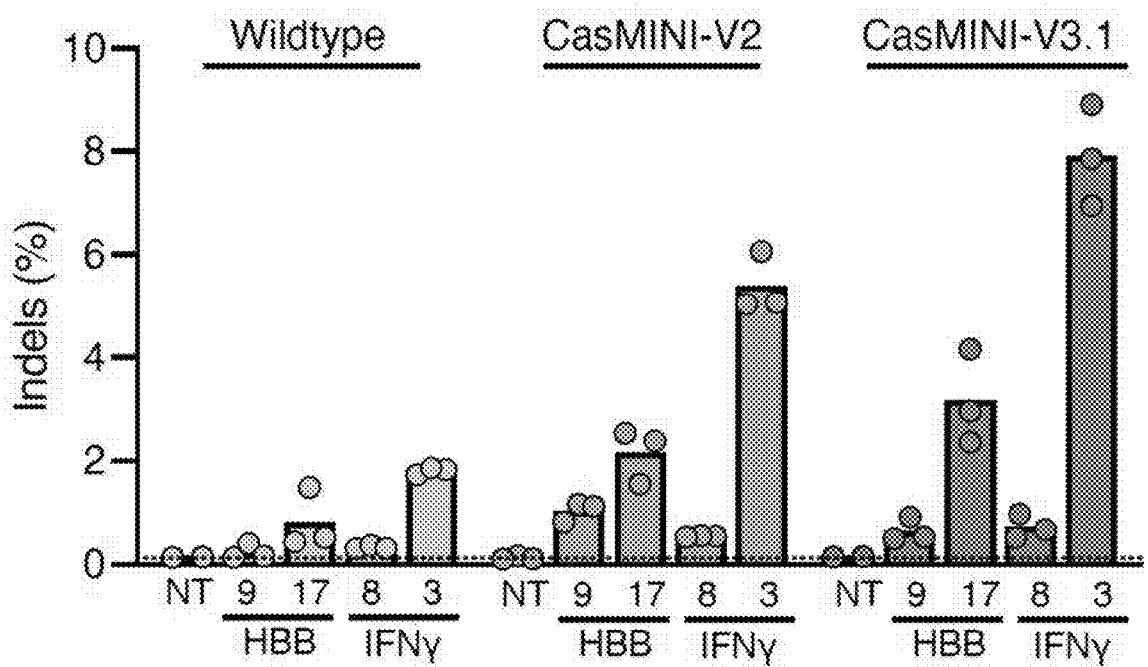
FIG. 65 is a graph showing indel activity of the wild type Cas12f, CasMINI-V2, and CasMINI-V3.1 at two sites of the HBB and IFNγ loci in HEK293T cells. The dotted line shows the data using a sgNT as a representative negative control. Bars represent mean values and data represent three independent biological replicates.
Figure 66:
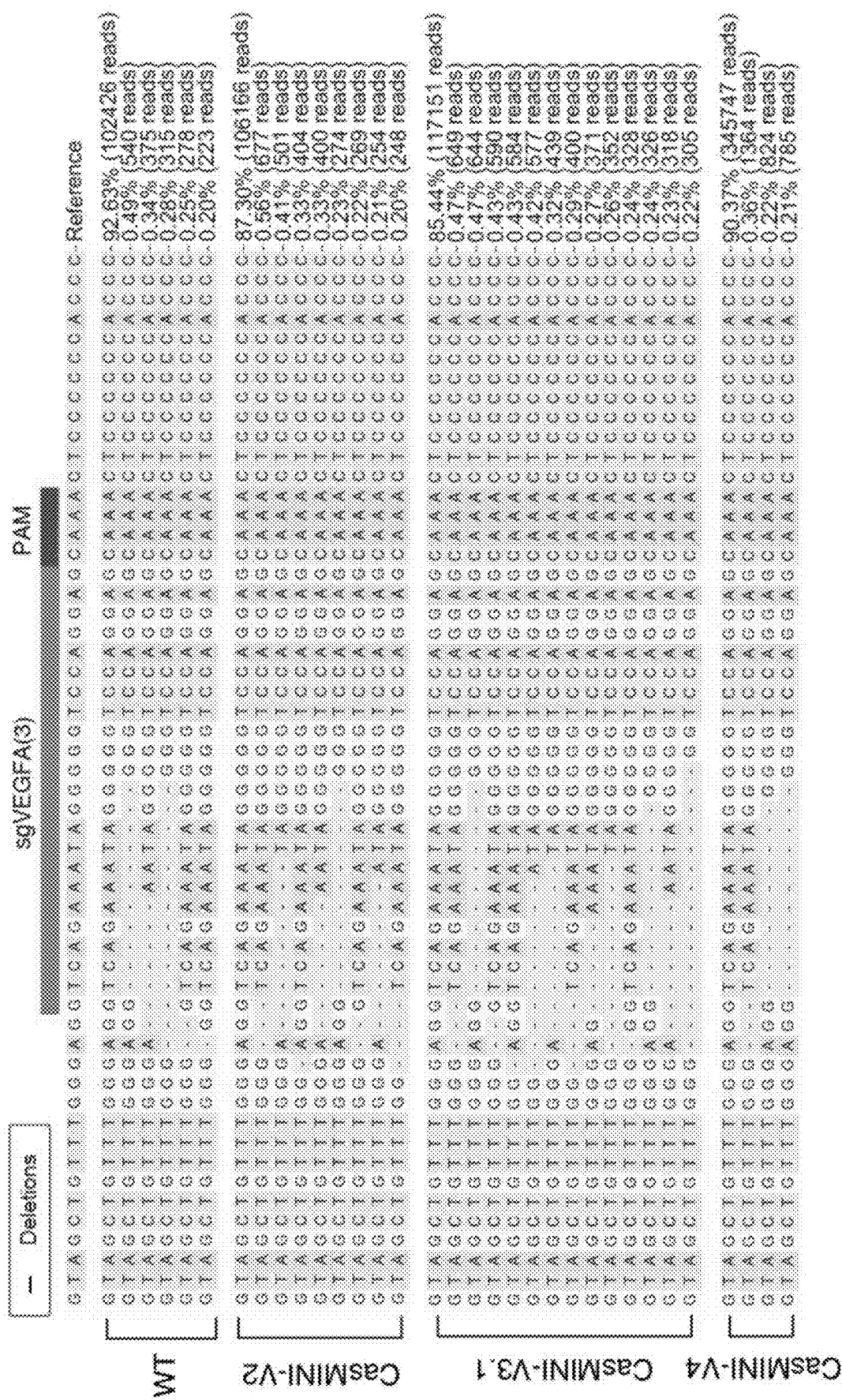
FIG. 66 shows raw sequencing reads from deep sequencing using the wild type Cas12f, CasMINI-V2, CasMINI-V3.1, CasMINI-V4 by targeting the site 3 in the VEGFA locus. The sequenced reads and percentage among the total aligned reads are shown on the right. Representative variants with >0.2% of the total reads generated by CRISPResso2 are shown.

To further characterize gene editing using CasMINI-V3.1, the indel formation efficiency was quantified at four additional genomic sites in HBB or IFNγ (FIGS. 34 and 39). Robust gene editing was observed using CasMINI-V3.1 at these sites, which was more efficient than the wild type Cas12f or CasMINI-V2 (FIGS. 65 and 66). These data suggest that the CasMINI variants enabling optimal gene editing can be different from those used for best gene activation.

Figure 68:
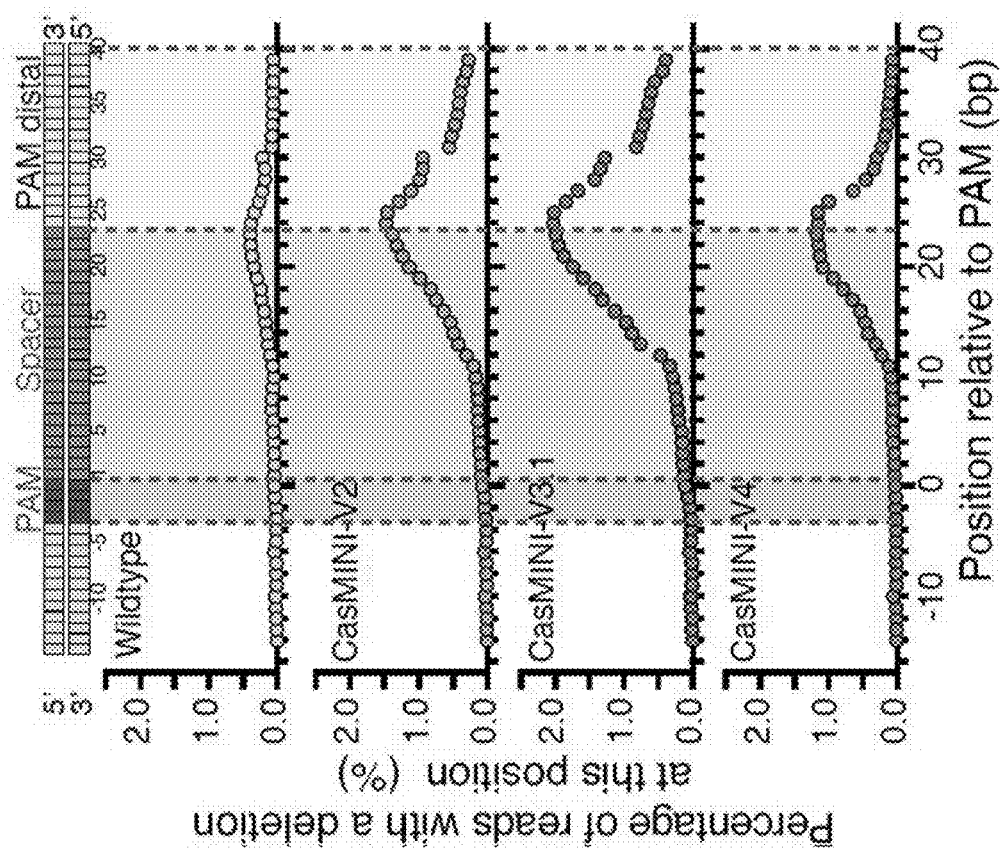
FIG. 68 presents a series of graphs showing indel activity at each nucleotide position during genome editing over eight distinct sites (except for V4 which has four active sites). The data represent the percentage of total reads with a deletion at the position. The schematic on the top show the PAM (4 bp) and the spacer (23 bp), which is aligned to each nucleotide position. The 'R' in TTTR PAM is position '0'.
Figure 67:
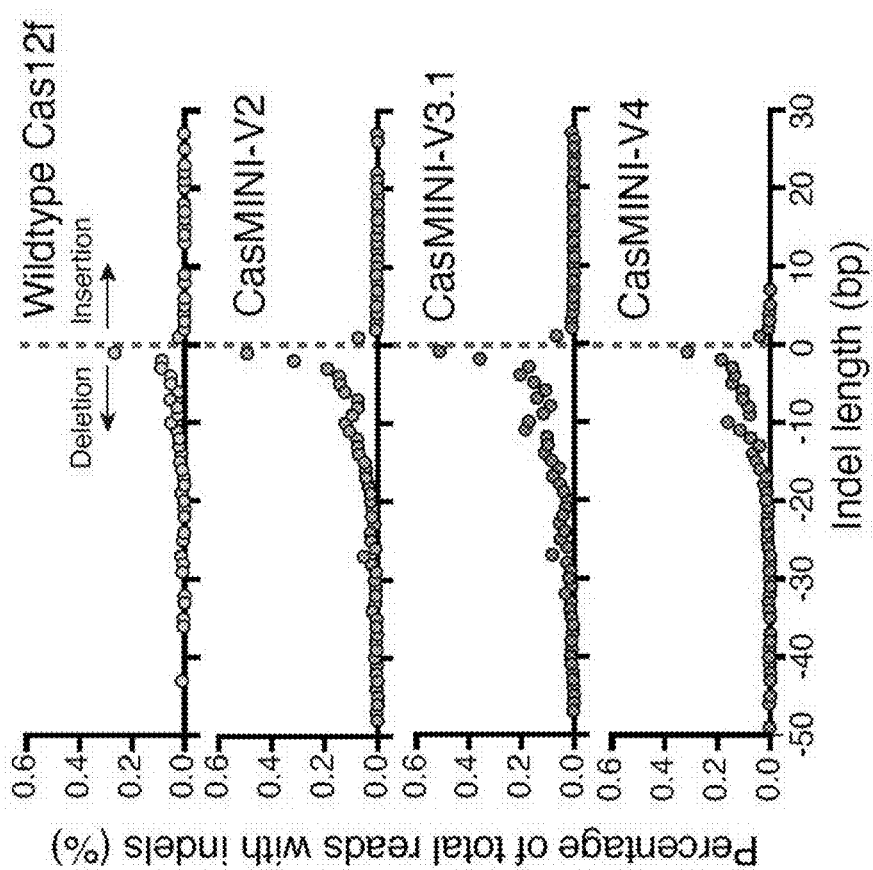
FIG. 67 presents a series of graphs showing the largest indel length during genome editing over eight distinct sites (except for V4 which has four active sites). The data represent the percentage of aligned reads with an insertion or deletion of the given length.

The indel patterns formed by the CasMINI variants were further analyzed by averaging the indel length at top genomic sites. Compared to the wild type Cas12f, CasMINI-V3.1 showed larger deletions (around 20 bp), which was also larger than was reported for Cas9 (FIG. 67) (B. P. Kleinstiver, Nat. Biotechnol. 37, (2019): 276; J. Strecker et al., Nat. Commun. 10, (2019): 212). Indel formation frequency at each nucleotide position was also evaluated. Interestingly, major indel editing was observed at the PAM-distal region spanning outside of the sgRNA-binding sequence (FIG. 68). Previous in vitro assays showed that Cas12f cleavage predominantly centered around positions 20-24 bp relative to the PAM sequence (T. Karvelis et al., Nucleic Acids Res. 48, (2020): 5016). Consistently, our results using CasMINI showed that in vivo gene editing also peaked around positions 20-30 bp relative to PAM (FIG. 68). We thus confirm that CasMINI can be used in broad genome editing applications in addition to gene activation.

XI. INFORMAL SEQUENCE LISTING

| SEQ ID NO | Sequence | Description |
|---|---|---|
| 1 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSDVCYTRAAELFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIDVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCEKCNFKENADYNAALNISNPKLKSTKEEP | Cas14 |
| 2 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSRVCYTRAAELFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIDVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCEKCNFKENADYNAALNISNPKLKSTKEEP | Cas14/D143R (CasMINI-V1) |
| 3 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSRVCYRRAAELFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIDVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCEKCNFKENADYNAALNISNPKLKSTKEEP | Cas14/D143R/T147R (CasMINI-V2) |
| 4 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSRVCYRRAAELFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIDVGVRSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCEKCNFKENADYNAALNISNPKLKSTKEEP | Cas14/D143R/T147R/K330R (Cas-MINI-V3) |
| 5 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSRVCYRRAAELFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIDVGVRSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCEKCNFKENADYNAALNISNPKLKSTKERP | Cas14/D143R/T147R/K330R/E528R (Cas-MINI-V4) |
| 6 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSRVCYRAAALFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIDVGVRSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCEKCNFKENADYNAALNISNPKLKSTKERP | Cas14/D143R/T147R/K330R/E151A/E528R |
| 7 | 5'GGGCTTCACTGATAAAGTGGAGAACCGCTTCACCAAAAGCTGTCCCTTAGGGGATT<br>AGAACTTGAGTGAAGGTGGGCTGCTTGCATCAGCCTAATGTCGAGAAGTGCTTTCTTC<br>GGAAAGTAACCCTCGAAACAAATTCATTTTTCCTCTCCAATTCTGCAAGAAAGTTGC<br>AGAACCCGAATAGACGAATGAAGGAATGCAACNNNNNNNNNNNNNNNNNNNNN<br>N3' | Wild-type sgRNA |
| 8 | 5'GGGCTTCACTGATAAAGTGGAGAACCGCTTCACCAAAAGCTGTCCCTTAGGGGATT<br>AGAACTTGAGTGAAGGTGGGCTGCTTGCATCAGCCTAATGTCGAGAAGTGCTTTCTTC<br>GGAAAGTAACCCTCGAAACAAATTCATTGTTCCTCTCCAATTCTGCAAGAAAGTTGC<br>AGAACCCGAATAGACGAATGAAGGAATGCAACNNNNNNNNNNNNNNNNNNNNN<br>N3' | sgRNA design 1 |

| SEQ ID NO | Sequence | Description |
|---|---|---|
| 9 | 5'GGGCTTCACTGATAAAGTGGAGAACCGCTTCACCAAAAGCTGTCCCTTAGGGGATT<br>AGAACTTGAGTGAAGGTGGGCTGCTTGCATCAGCCTAATGTCGAGAAGTGCTTTCTTC<br>GGAAAGTAACCCTCGAAACAAATTCATTTGAATGAAGGAATGCAACNNNNNNNNNN<br>NNNNNNNNNNNN3' | sgRNA design 2 |
| 10 | 5'GGCTTCACTGATAAAGTGGAGAACCGCTTCACCAAAAGCTGTCCCTTAGGGGATTA<br>GAACTTGAGTGAAGGTGGGCTGCTTGCATCAGCCTAATGTCGAGAAGTGCTTTCTTCG<br>GAAAGTAACCCTCGAAACAAATTCATTTGAATGAAGGAATGCAACNNNNNNNNNN<br>NNNNNNNNNNNN3' | sgRNA design 3 |
| 11 | MAKNTITKTLRLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSDVCYTRAAELFKNAAIASGLRSKIKSNFRLKELKNMKSGLPTTKS<br>DNFPIPLVKQKGGQYTGFEISNHNSDFIIKIPFGRWVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIDVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCEKCNFKENADYNAALNISNPKLKSTKEEP | Cas14/K11R |
| 12 | MAKNTITKTLKLRIVRPYNSAEVEKIVADEKNNREKIALEKNKDKVKEACSKHLKVAAYCTT<br>QVERNACLFCRARKLDDKFYQKLRGQFPDAVFWQEISEIFRQLQKQAAEIYNQSLIELYYEI<br>FIKGKGIANASSVEHYLSDVCYTRAAELFKNAAIASGLRSKIKSNFRLKELKNMKSGLPTTKS<br>DNFPIPLVKQKGGQYTGFEISNHNSDFIIKIPFGRWVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIDVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCEKCNFKENADYNAALNISNPKLKSTKEEP | Cas14/K73R |
| 13 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKRAAEIYNQSLIELYYEIF<br>IKGKGIANASSVEHYLSDVCYTRAAELFKNAAIASGLRSKIKSNFRLKELKNMKSGLPTTKSD<br>NFPIPLVKQKGGQYTGFEISNHNSDFIIKIPFGRWQVKKEIDKYRPWEKFDFEQVQKSPKPI<br>SLLLSTQRRKRNKGWSKDEGTEAEIKKVMNGDYQTSYIEVKRGSKICEKSAWMLNLSIDVP<br>KIDKGVDPSIIGGIDVGVKSPLVCAINNAFSRYSISDNDLFHFNKKMFARRRILLKKNRHKRA<br>GHGAKNKLKPITILTEKSERFRKKLIERWACEIADFFIKNKVGTVQMENLESMKRKEDSYFNI<br>RLRGFWPYAEMQNKIEFKLKQYGIEIRKVAPNNTSKTCSKCGHLNNYFNFEYRKKNKFPHF<br>KCEKCNFKENADYNAALNISNPKLKSTKEEP | Cas14/Q108R |
| 14 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSDVCYRRAAELFKNAAIASGLRSKIKSNFRLKELKNMKSGLPTTKS<br>DNFPIPLVKQKGGQYTGFEISNHNSDFIIKIPFGRWVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIDVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCEKCNFKENADYNAALNISNPKLKSTKEEP | Cas14/T147R |
| 15 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSDVCYTRAARLFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIDVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCEKCNFKENADYNAALNISNPKLKSTKEEP | Cas14/E151R |
| 16 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSDVCYTRAAELFRNAAIASGLRSKIKSNFRLKELKNMKSGLPTTKS<br>DNFPIPLVKQKGGQYTGFEISNHNSDFIIKIPFGRWVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIDVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCEKCNFKENADYNAALNISNPKLKSTKEEP | Cas14/K154R |
| 17 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSDVCYTRAAELFKRAAIASGLRSKIKSNFRLKELKNMKSGLPTTKS<br>DNFPIPLVKQKGGQYTGFEISNHNSDFIIKIPFGRWVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIDVGVKSPLVCAINNAFSRYSISDNDLFHFNKKMFARRRILLKKNRHK | Cas14/N155R |

| SEQ ID NO | Sequence | Description |
|---|---|---|
| | RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCEKCNFKENADYNAALNISNPKLKSTKEEP | |
| 18 | MAKNTITKTLKLRIVRPYNSAEVEKIVADEKNNREKIALEKNKDKVKEACSKHLKVAAYCTT<br>QVERNACLFCKARKLDDKFYQLRGQFPDAVFWQEISEIFRQLQKQAAEIYNQSLIELYYEI<br>FIKGKGIANASSVEHYLSDVCYTRAAELFKNAAIASGLRSKIKSNFRLKELKNMKSGLPTTKS<br>DNFPIPLVRQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIDVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCEKCNFKENADYNAALNISNPKLKSTKEEP | Cas14/K196R |
| 19 | MAKNTITKTLKLRIVRPYNSAEVEKIVADEKNNREKIALEKNKDKVKEACSKHLKVAAYCTT<br>QVERNACLFCKARKLDDKFYQLRGQFPDAVFWQEISEIFRQLQKQAAEIYNQSLIELYYEI<br>FIKGKGIANASSVEHYLSDVCYTRAAELFKNAAIASGLRSKIKSNFRLKELKNMKSGLPTTKS<br>DNFPIPLVKQKGGQYTGFEISNHNSDFIIKIPFGRWQVKKEIDKYRPWEKFDFRQVQKSPK<br>PISLLLSTQRRKRNKGWSKDEGTEAEIKKVMNGDYQTSYIEVKRGSKICEKSAWMLNLSID<br>VPKIDKGVDPSIIGGIDVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCEKCNFKENADYNAALNISNPKLKSTKEEP | Cas14/E241R |
| 20 | MAKNTITKTLKLRIVRPYNSAEVEKIVADEKNNREKIALEKNKDKVKEACSKHLKVAAYCTT<br>QVERNACLFCKARKLDDKFYQLRGQFPDAVFWQEISEIFRQLQKQAAEIYNQSLIELYYEI<br>FIKGKGIANASSVEHYLSDVCYTRAAELFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIRVKRGSKICEKSAWMLNLSID<br>VPKIDKGVDPSIIGGIDVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCEKCNFKENADYNAALNISNPKLKSTKEEP | Cas14/E289R |
| 21 | MAKNTITKTLKLRIVRPYNSAEVEKIVADEKNNREKIALEKNKDKVKEACSKHLKVAAYCTT<br>QVERNACLFCKARKLDDKFYQLRGQFPDAVFWQEISEIFRQLQKQAAEIYNQSLIELYYEI<br>FIKGKGIANASSVEHYLSDVCYTRAAELFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVRPSIIGGIDVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCEKCNFKENADYNAALNISNPKLKSTKEEP | Cas14/D318R |
| 22 | MAKNTITKTLKLRIVRPYNSAEVEKIVADEKNNREKIALEKNKDKVKEACSKHLKVAAYCTT<br>QVERNACLFCKARKLDDKFYQLRGQFPDAVFWQEISEIFRQLQKQAAEIYNQSLIELYYEI<br>FIKGKGIANASSVEHYLSDVCYTRAAELFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIDRGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCEKCNFKENADYNAALNISNPKLKSTKEEP | Cas14/V327R |
| 23 | MAKNTITKTLKLRIVRPYNSAEVEKIVADEKNNREKIALEKNKDKVKEACSKHLKVAAYCTT<br>QVERNACLFCKARKLDDKFYQLRGQFPDAVFWQEISEIFRQLQKQAAEIYNQSLIELYYEI<br>FIKGKGIANASSVEHYLSDVCYTRAAELFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIDVGVRSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCEKCNFKENADYNAALNISNPKLKSTKEEP | Cas14/K330R |
| 24 | MAKNTITKTLKLRIVRPYNSAEVEKIVADEKNNREKIALEKNKDKVKEACSKHLKVAAYCTT<br>QVERNACLFCKARKLDDKFYQLRGQFPDAVFWQEISEIFRQLQKQAAEIYNQSLIELYYEI<br>FIKGKGIANASSVEHYLSDVCYTRAAELFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIDVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLNSMKRKEDSY<br>FNIRLRGFWPYAEMQNKIEFKLKQYGIEIRKVAPNNTSKTCSKCGHLNNYFNFEYRKKNKF<br>PHFKCEKCNFKENADYNAALNISNPKLKSTKEEP | Cas14/E425N |
| 25 | MAKNTITKTLKLRIVRPYNSAEVEKIVADEKNNREKIALEKNKDKVKEACSKHLKVAAYCTT<br>QVERNACLFCKARKLDDKFYQLRGQFPDAVFWQEISEIFRQLQKQAAEIYNQSLIELYYEI | Cas14/K457R |

| SEQ ID NO | Sequence | Description |
|---|---|---|
|  | FIKGKGIANASSVEHYLSDVCYTRAAELFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIDVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLRQYGIEIRKVAPNNTSKTCSKCGHLNNYFNFEYRKKNKF<br>PHFKCEKCNFKENADYNAALNISNPKLKSTKEEP |  |
| 26 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSDVCYTRAAELFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIDVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIRIRKVAPNNTSKTCSKCGHLNNYFNFEYRKKNKF<br>PHFKCEKCNFKENADYNAALNISNPKLKSTKEEP | Cas14/E462R |
| 27 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSDVCYTRAAELFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIDVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKREKCNFKENADYNAALNISNPKLKSTKEEP | Cas14/C500R |
| 28 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSDVCYTRAAELFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIDVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFRREKCNFKENADYNAALNISNPKLKSTKEEP | Cas14/K499R/C500R |
| 29 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSDVCYTRAAELFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIDVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCRKCNFKENADYNAALNISNPKLKSTKEEP | Cas14/E501R |
| 30 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSDVCYTRAAELFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIDVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCEKCRFKENADYNAALNISNPKLKSTKEEP | Cas14/E504R |
| 31 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSDVCYTRAAELFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIDVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCEKCNFKRNADYNAALNISNPKLKSTKEEP | Cas14/E507R |

| SEQ ID NO | Sequence | Description |
|---|---|---|
| 32 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSDVCYTRAAELFKNAAIASGLRSKIKSNFRLKELKNMKSGLPTTKS DNFPIPLVKQKGGQYTGFEISNHNSDFIIKIPFGRWQVKKEIDKYRPWEKFDFEQVQKSPK PISLLLSTQRRKRNKGWSKDEGTEAEIKKVMNGDYQTSYIEVKRGSKICEKSAWMLNLSID VPKIDKGVDPSIIGGIDVGVKSPLVCAINNAFSRYSISDNDLFHFNKKMFARRRILLKKNRHK RAGHGAKNKLKPITILTEKSERFRKKLIERWACEIADFFIKNKVGTVQMENLESMKRKEDSY FNIRLRGFWPYAEMQNKIEFKLKQYGIEIRKVAPNNTSKTCSKCGHLNNYFNFEYRKKNKF PHFKCEKCNFKEDADYNAALNISNPKLKSTKEEP | Cas14/N508D |
| 33 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSDVCYTRAAELFKNAAIASGLRSKIKSNFRLKELKNMKSGLPTTKS DNFPIPLVKQKGGQYTGFEISNHNSDFIIKIPFGRWQVKKEIDKYRPWEKFDFEQVQKSPK PISLLLSTQRRKRNKGWSKDEGTEAEIKKVMNGDYQTSYIEVKRGSKICEKSAWMLNLSID VPKIDKGVDPSIIGGIDVGVKSPLVCAINNAFSRYSISDNDLFHFNKKMFARRRILLKKNRHK RAGHGAKNKLKPITILTEKSERFRKKLIERWACEIADFFIKNKVGTVQMENLESMKRKEDSY FNIRLRGFWPYAEMQNKIEFKLKQYGIEIRKVAPNNTSKTCSKCGHLNNYFNFEYRKKNKF PHFKCEKCNFKENADANAALNISNPKLKSTKEEP | Cas14/Y511A |
| 34 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSDVCYTRAAELFKNAAIASGLRSKIKSNFRLKELKNMKSGLPTTKS DNFPIPLVKQKGGQYTGFEISNHNSDFIIKIPFGRWQVKKEIDKYRPWEKFDFEQVQKSPK PISLLLSTQRRKRNKGWSKDEGTEAEIKKVMNGDYQTSYIEVKRGSKICEKSAWMLNLSID VPKIDKGVDPSIIGGIDVGVKSPLVCAINNAFSRYSISDNDLFHFNKKMFARRRILLKKNRHK RAGHGAKNKLKPITILTEKSERFRKKLIERWACEIADFFIKNKVGTVQMENLESMKRKEDSY FNIRLRGFWPYAEMQNKIEFKLKQYGIEIRKVAPNNTSKTCSKCGHLNNYFNFEYRKKNKF PHFKCEKCNFKENADYNAGLNISNPKLKSTKEEP | Cas14/A514G |
| 35 | AKNTITKTLKLRIVRPYNSAEVEKIVADEKNNREKIALEKNKDKVKEACSKHLKVAAYCTTQV ERNACLFCKARKLDDKFYQKLRGQFPDAVFWQEISEIFRQLQKQAAEIYNQSLIELYYEIFIK GKGIANASSVEHYLSDVCYTRAAELFKNAAIASGLRSKIKSNFRLKELKNMKSGLPTTKSDNF PIPLVKQKGGQYTGFEISNHNSDFIIKIPFGRWQVKKEIDKYRPWEKFDFEQVQKSPKPISLL LSTQRRKRNKGWSKDEGTEAEIKKVMNGDYQTSYIEVKRGSKICEKSAWMLNLSIDVPKID KGVDPSIIGGIDVGVKSPLVCAINNAFSRYSISDNDLFHFNKKMFARRRILLKKNRHKRAGH GAKNKLKPITILTEKSERFRKKLIERWACEIADFFIKNKVGTVQMENLESMKRKEDSYFNIRL RGFWPYAEMQNKIEFKLKQYGIEIRKVAPNNTSKTCSKCGHLNNYFNFEYRKKNKFPHFKC EKCNFKENADYNAALRISNPKLKSTKEEP | Cas14/N516R |
| 36 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSDVCYTRAAELFKNAAIASGLRSKIKSNFRLKELKNMKSGLPTTKS DNFPIPLVKQKGGQYTGFEISNHNSDFIIKIPFGRWQVKKEIDKYRPWEKFDFEQVQKSPK PISLLLSTQRRKRNKGWSKDEGTEAEIKKVMNGDYQTSYIEVKRGSKICEKSAWMLNLSID VPKIDKGVDPSIIGGIDVGVKSPLVCAINNAFSRYSISDNDLFHFNKKMFARRRILLKKNRHK RAGHGAKNKLKPITILTEKSERFRKKLIERWACEIADFFIKNKVGTVQMENLESMKRKEDSY FNIRLRGFWPYAEMQNKIEFKLKQYGIEIRKVAPNNTSKTCSKCGHLNNYFNFEYRKKNKF PHFKCEKCNFKENADYNAALNISRPKLKSTKEEP | Cas14/N519R |
| 37 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSDVCYTRAAELFKNAAIASGLRSKIKSNFRLKELKNMKSGLPTTKS DNFPIPLVKQKGGQYTGFEISNHNSDFIIKIPFGRWQVKKEIDKYRPWEKFDFEQVQKSPK PISLLLSTQRRKRNKGWSKDEGTEAEIKKVMNGDYQTSYIEVKRGSKICEKSAWMLNLSID VPKIDKGVDPSIIGGIDVGVKSPLVCAINNAFSRYSISDNDLFHFNKKMFARRRILLKKNRHK RAGHGAKNKLKPITILTEKSERFRKKLIERWACEIADFFIKNKVGTVQMENLESMKRKEDSY FNIRLRGFWPYAEMQNKIEFKLKQYGIEIRKVAPNNTSKTCSKCGHLNNYFNFEYRKKNKF PHFKCEKCNFKENADYNAALNISNPKLKSTKREP | Cas14/E527R |
| 38 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSDVCYTRAAELFKNAAIASGLRSKIKSNFRLKELKNMKSGLPTTKS DNFPIPLVKQKGGQYTGFEISNHNSDFIIKIPFGRWQVKKEIDKYRPWEKFDFEQVQKSPK PISLLLSTQRRKRNKGWSKDEGTEAEIKKVMNGDYQTSYIEVKRGSKICEKSAWMLNLSID VPKIDKGVDPSIIGGIDVGVKSPLVCAINNAFSRYSISDNDLFHFNKKMFARRRILLKKNRHK RAGHGAKNKLKPITILTEKSERFRKKLIERWACEIADFFIKNKVGTVQMENLESMKRKEDSY FNIRLRGFWPYAEMQNKIEFKLKQYGIEIRKVAPNNTSKTCSKCGHLNNYFNFEYRKKNKF PHFKCEKCNFKENADYNAALNISNPKLKSTKERP | Cas14/E528R |
| 39 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSRVCYTRAARLFKNAAIASGLRSKIKSNFRLKELKNMKSGLPTTKS DNFPIPLVKQKGGQYTGFEISNHNSDFIIKIPFGRWQVKKEIDKYRPWEKFDFEQVQKSPK PISLLLSTQRRKRNKGWSKDEGTEAEIKKVMNGDYQTSYIEVKRGSKICEKSAWMLNLSID VPKIDKGVDPSIIGGIDVGVKSPLVCAINNAFSRYSISDNDLFHFNKKMFARRRILLKKNRHK | Cas14/D143R/E151R |

| SEQ ID NO | Sequence | Description |
|---|---|---|
| | RAGHGAKNKLKPITILTEKSERFRKKLIERWACEIADFFIKNKVGTVQMENLESMKRKEDSY FNIRLRGFWPYAEMQNKIEFKLKQYGIEIRKVAPNNTSKTCSKCGHLNNYFNFEYRKKNKF PHFKCEKCNFKENADYNAALNISNPKLKSTKEEP | |
| 40 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSRVCYTRAAELFRNAAIASGLRSKIKSNFRLKELKNMKSGLPTTKS DNFPIPLVKQKGGQYTGFEISNHNSDFIIKIPFGRWQVKKEIDKYRPWEKFDFEQVQKSPK PISLLLSTQRRKRNKGWSKDEGTEAEIKKVMNGDYQTSYIEVKRGSKICEKSAWMLNLSID VPKIDKGVDPSIIGGIDVGVKSPLVCAINNAFSRYSISDNDLFHFNKKMFARRRILLKKNRHK RAGHGAKNKLKPITILTEKSERFRKKLIERWACEIADFFIKNKVGTVQMENLESMKRKEDSY FNIRLRGFWPYAEMQNKIEFKLKQYGIEIRKVAPNNTSKTCSKCGHLNNYFNFEYRKKNKF PHFKCEKCNFKENADYNAALNISNPKLKSTKEEP | Cas14/D143R/K154R |
| 41 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSRVCYTRAAELFKNAAIASGLRSKIKSNFRLKELKNMKSGLPTTKS DNFPIPLVKQKGGQYTGFEISNHNSDFIIKIPFGRWQVKKEIDKYRPWEKFDFRQVQKSPK PISLLLSTQRRKRNKGWSKDEGTEAEIKKVMNGDYQTSYIEVKRGSKICEKSAWMLNLSID VPKIDKGVDPSIIGGIDVGVKSPLVCAINNAFSRYSISDNDLFHFNKKMFARRRILLKKNRHK RAGHGAKNKLKPITILTEKSERFRKKLIERWACEIADFFIKNKVGTVQMENLESMKRKEDSY FNIRLRGFWPYAEMQNKIEFKLKQYGIEIRKVAPNNTSKTCSKCGHLNNYFNFEYRKKNKF PHFKCEKCNFKENADYNAALNISNPKLKSTKEEP | Cas14/D143R/E241R |
| 42 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSRVCYTRAAELFKNAAIASGLRSKIKSNFRLKELKNMKSGLPTTKS DNFPIPLVKQKGGQYTGFEISNHNSDFIIKIPFGRWQVKKEIDKYRPWEKFDFEQVQKSPK PISLLLSTQRRKRNKGWSKDEGTEAEIKKVMNGDYQTSYIEVKRGSKICEKSAWMLNLSID VPKIDKGVDPSIIGGIDVGVRSPLVCAINNAFSRYSISDNDLFHFNKKMFARRRILLKKNRHK RAGHGAKNKLKPITILTEKSERFRKKLIERWACEIADFFIKNKVGTVQMENLESMKRKEDSY FNIRLRGFWPYAEMQNKIEFKLKQYGIEIRKVAPNNTSKTCSKCGHLNNYFNFEYRKKNKF PHFKCEKCNFKENADYNAALNISNPKLKSTKEEP | Cas14/D143R/K330R |
| 43 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSRVCYTRAAELFKNAAIASGLRSKIKSNFRLKELKNMKSGLPTTKS DNFPIPLVKQKGGQYTGFEISNHNSDFIIKIPFGRWQVKKEIDKYRPWEKFDFEQVQKSPK PISLLLSTQRRKRNKGWSKDEGTEAEIKKVMNGDYQTSYIEVKRGSKICEKSAWMLNLSID VPKIDKGVDPSIIGGIDVGVKSPLVCAINNAFSRYSISDNDLFHFNKKMFARRRILLKKNRHK RAGHGAKNKLKPITILTEKSERFRKKLIERWACEIADFFIKNKVGTVQMENLNSMKRKEDSY FNIRLRGFWPYAEMQNKIEFKLKQYGIEIRKVAPNNTSKTCSKCGHLNNYFNFEYRKKNKF PHFKCEKCNFKENADYNAALNISNPKLKSTKEEP | Cas14/D143R/E245N |
| 44 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSRVCYTRAAELFKNAAIASGLRSKIKSNFRLKELKNMKSGLPTTKS DNFPIPLVKQKGGQYTGFEISNHNSDFIIKIPFGRWQVKKEIDKYRPWEKFDFEQVQKSPK PISLLLSTQRRKRNKGWSKDEGTEAEIKKVMNGDYQTSYIEVKRGSKICEKSAWMLNLSID VPKIDKGVDPSIIGGIDVGVKSPLVCAINNAFSRYSISDNDLFHFNKKMFARRRILLKKNRHK RAGHGAKNKLKPITILTEKSERFRKKLIERWACEIADFFIKNKVGTVQMENLESMKRKEDSY FNIRLRGFWPYAEMQNKIEFKLKQYGIEIRKVAPNNTSKTCSKCGHLNNYFNFEYRKKNKF PHFKCEKCNFKRNADYNAALNISNPKLKSTKEEP | Cas14/D143R/E507R |
| 45 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSRVCYTRAAELFKNAAIASGLRSKIKSNFRLKELKNMKSGLPTTKS DNFPIPLVKQKGGQYTGFEISNHNSDFIIKIPFGRWQVKKEIDKYRPWEKFDFEQVQKSPK PISLLLSTQRRKRNKGWSKDEGTEAEIKKVMNGDYQTSYIEVKRGSKICEKSAWMLNLSID VPKIDKGVDPSIIGGIDVGVKSPLVCAINNAFSRYSISDNDLFHFNKKMFARRRILLKKNRHK RAGHGAKNKLKPITILTEKSERFRKKLIERWACEIADFFIKNKVGTVQMENLESMKRKEDSY FNIRLRGFWPYAEMQNKIEFKLKQYGIEIRKVAPNNTSKTCSKCGHLNNYFNFEYRKKNKF PHFKCEKCNFKENADYNAALRISNPKLKSTKEEP | Cas14/D143R/N516R |
| 46 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSRVCYTRAAELFKNAAIASGLRSKIKSNFRLKELKNMKSGLPTTKS DNFPIPLVKQKGGQYTGFEISNHNSDFIIKIPFGRWQVKKEIDKYRPWEKFDFEQVQKSPK PISLLLSTQRRKRNKGWSKDEGTEAEIKKVMNGDYQTSYIEVKRGSKICEKSAWMLNLSID VPKIDKGVDPSIIGGIDVGVKSPLVCAINNAFSRYSISDNDLFHFNKKMFARRRILLKKNRHK RAGHGAKNKLKPITILTEKSERFRKKLIERWACEIADFFIKNKVGTVQMENLESMKRKEDSY FNIRLRGFWPYAEMQNKIEFKLKQYGIEIRKVAPNNTSKTCSKCGHLNNYFNFEYRKKNKF PHFKCEKCNFKENADYNAALNISRPKLKSTKEEP | Cas14/D143R/N519R |
| 47 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI | Cas14/D143R/E527R |

| SEQ ID NO | Sequence | Description |
|---|---|---|
| | FIKGKGIANASSVEHYLSRVCYTRAAELFKNAAIASGLRSKIKSNFRLKELKNMKSGLPTTKS<br>DNFPIPLVKQKGGQYTGFEISNHNSDFIIKIPFGRWVKKEIDKYRPEFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIDVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMRKKEDSY<br>FNIRLRGFWPYAEMQNKIEFKLKQYGIEIRKVAPNNTSKTCSKCGHLNNYFNFEYRKKNKF<br>PHFKCEKCNFKENADYNAALNISNPKLKSTKREP | |
| 48 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSRVCYTRAAELFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIDVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMRKKEDSY<br>FNIRLRGFWPYAEMQNKIEFKLKQYGIEIRKVAPNNTSKTCSKCGHLNNYFNFEYRKKNKF<br>PHFKCEKCNFKENADYNAALNISNPKLKSTKERP | Cas14/D143R/E528R |
| 49 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSRVCYRRAARLFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIDVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMRKKEDSY<br>FNIRLRGFWPYAEMQNKIEFKLKQYGIEIRKVAPNNTSKTCSKCGHLNNYFNFEYRKKNKF<br>PHFKCEKCNFKENADYNAALNISNPKLKSTKEEP | Cas14/D143R/T147R/E151R |
| 50 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSRVCYRRAAELFRNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIDVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMRKKEDSY<br>FNIRLRGFWPYAEMQNKIEFKLKQYGIEIRKVAPNNTSKTCSKCGHLNNYFNFEYRKKNKF<br>PHFKCEKCNFKENADYNAALNISNPKLKSTKEEP | Cas14/D143R/T147R/K154R |
| 51 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSRVCYRRAAELFKNAAIASGLRSKIKSNFRLKELKNMKSGLPTTKS<br>DNFPIPLVKQKGGQYTGFEISNHNSDFIIKIPFGRWQVKKEIDKYRPWEKFDFRQVQKSPK<br>PISLLLSTQRRKRNKGWSKDEGTEAEIKKVMNGDYQTSYIEVKRGSKICEKSAWMLNLSID<br>VPKIDKGVDPSIIGGIDVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMRKKEDSY<br>FNIRLRGFWPYAEMQNKIEFKLKQYGIEIRKVAPNNTSKTCSKCGHLNNYFNFEYRKKNKF<br>PHFKCEKCNFKENADYNAALNISNPKLKSTKEEP | Cas14/D143R/T147R/E241R |
| 52 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSRVCYRRAAELFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIDVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLNSMRKKEDSY<br>FNIRLRGFWPYAEMQNKIEFKLKQYGIEIRKVAPNNTSKTCSKCGHLNNYFNFEYRKKNKF<br>PHFKCEKCNFKENADYNAALNISNPKLKSTKEEP | Cas14/D143R/T147R/E425N |
| 53 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSRVCYRRAAELFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIDVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMRKKEDSY<br>FNIRLRGFWPYAEMQNKIEFKLKQYGIEIRKVAPNNTSKTCSKCGHLNNYFNFEYRKKNKF<br>PHFKCEKCNFKRNADYNAALNISNPKLKSTKEEP | Cas14/D143R/T147R/E507R |
| 54 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSRVCYRRAAELFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID | Cas14/D143R/T147R/N516R |

| SEQ ID NO | Sequence | Description |
|---|---|---|
| | VPKIDKGVDPSIIGGIDVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCEKCNFKENADYNAALRISNPKLSTKEEP | |
| 55 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSRVCYRRAAELFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIDVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCEKCNFKENADYNAALNISRPKLSTKEEP | Cas14/D143R/T147R/<br>N519R |
| 56 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSRVCYRRAAELFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIDVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCEKCNFKENADYNAALNISNPKLSTKREP | Cas14/D143R/T147R/<br>E527R |
| 57 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSRVCYRRAAELFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIDVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKREDSY<br>FNIRLRGFWPYAEMQNKIEFKLKQYGIEIRKVAPNNTSKTCSKCGHLNNYFNFEYRKKNKF<br>PHFKCEKCNFKENADYNAALNISNPKLSTKERP | Cas14/D143R/T147R/<br>E528R |
| 58 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSRVCYRRAASLFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIDVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCEKCNFKENADYNAALNISNPKLSTKEEP | Cas14/D143R/T147R/<br>E151S |
| 59 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSRVCYRRAAGLFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIDVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCEKCNFKENADYNAALNISNPKLSTKEEP | Cas14/D143R/T147R/<br>E151G |
| 60 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSRVCYRRAAALFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIDVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCEKCNFKENADYNAALNISNPKLSTKEEP | Cas14/D143R/T147R/<br>E151A |
| 61 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSRVCYTRAALLFKNAAIASGLRSKIKSNFRLKELKNMKSGLPTTKSD<br>NFPIPLVKQKGGQYTGFEISNHNSDFIIKIPFGRWQVKKEIDKYRPWEKFDFEQVQKSPKPI<br>SLLLSTQRRKRNKGWSKDEGTEAEIKKVMNGDYQTSYIEVKRGSKICEKSAWMLNLSIDVP<br>KIDKGVDPSIIGGIDVGVKSPLVCAINNAFSRYSISDNDLFHFNKKMFARRRILLKKNRHKRA<br>GHGAKNKLKPITILTEKSERFRKKLIERWACEIADFFIKNKVGTVQMENLESMKREDSYFNI<br>RLRGFWPYAEMQNKIEFKLKQYGIEIRKVAPNNTSKTCSKCGHLNNYFNFEYRKKNKFPHF<br>KCEKCNFKENADYNAALNISNPKLSTKEEP | Cas14/D143R/E151L |

| SEQ ID NO | Sequence | Description |
|---|---|---|
| 62 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSRVCYTRAASLFKNAAIASGLRSKIKSNFRLKELKNMKSGLPTTKS DNFPIPLVKQKGGQYTGFEISNHNSDFIIKIPFGRWQVKKEIDKYRPWEKFDFEQVQKSPK PISLLLSTQRRKRNKGWSKDEGTEAEIKKVMNGDYQTSYIEVKRGSKICEKSAWMLNLSID VPKIDKGVDPSIIGGIDVGVKSPLVCAINNAFSRYSISDNDLFHFNKKMFARRRILLKKNRHK RAGHGAKNKLKPITILTEKSERFRKKLIERWACEIADFFIKNKVGTVQMENLESMKRKEDSY FNIRLRGFWPYAEMQNKIEFKLKQYGIEIRKVAPNNTSKTCSKCGHLNNYFNFEYRKKNKF PHFKCEKCNFKENADYNAALNISNPKLKSTKEEP | Cas14/D143R/E151S |
| 63 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSRVCYTRAATLFKNAAIASGLRSKIKSNFRLKELKNMKSGLPTTKS DNFPIPLVKQKGGQYTGFEISNHNSDFIIKIPFGRWQVKKEIDKYRPWEKFDFEQVQKSPK PISLLLSTQRRKRNKGWSKDEGTEAEIKKVMNGDYQTSYIEVKRGSKICEKSAWMLNLSID VPKIDKGVDPSIIGGIDVGVKSPLVCAINNAFSRYSISDNDLFHFNKKMFARRRILLKKNRHK RAGHGAKNKLKPITILTEKSERFRKKLIERWACEIADFFIKNKVGTVQMENLESMKRKEDSY FNIRLRGFWPYAEMQNKIEFKLKQYGIEIRKVAPNNTSKTCSKCGHLNNYFNFEYRKKNKF PHFKCEKCNFKENADYNAALNISNPKLKSTKEEP | Cas14/D143R/E151T |
| 64 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSRVCYTRAAWLFKNAAIASGLRSKIKSNFRLKELKNMKSGLPTTKS DNFPIPLVKQKGGQYTGFEISNHNSDFIIKIPFGRWQVKKEIDKYRPWEKFDFEQVQKSPK PISLLLSTQRRKRNKGWSKDEGTEAEIKKVMNGDYQTSYIEVKRGSKICEKSAWMLNLSID VPKIDKGVDPSIIGGIDVGVKSPLVCAINNAFSRYSISDNDLFHFNKKMFARRRILLKKNRHK RAGHGAKNKLKPITILTEKSERFRKKLIERWACEIADFFIKNKVGTVQMENLESMKRKEDSY FNIRLRGFWPYAEMQNKIEFKLKQYGIEIRKVAPNNTSKTCSKCGHLNNYFNFEYRKKNKF PHFKCEKCNFKENADYNAALNISNPKLKSTKEEP | Cas14/D143R/E151W |
| 65 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSRVCYTRAAFLFKNAAIASGLRSKIKSNFRLKELKNMKSGLPTTKS DNFPIPLVKQKGGQYTGFEISNHNSDFIIKIPFGRWQVKKEIDKYRPWEKFDFEQVQKSPK PISLLLSTQRRKRNKGWSKDEGTEAEIKKVMNGDYQTSYIEVKRGSKICEKSAWMLNLSID VPKIDKGVDPSIIGGIDVGVKSPLVCAINNAFSRYSISDNDLFHFNKKMFARRRILLKKNRHK RAGHGAKNKLKPITILTEKSERFRKKLIERWACEIADFFIKNKVGTVQMENLESMKRKEDSY FNIRLRGFWPYAEMQNKIEFKLKQYGIEIRKVAPNNTSKTCSKCGHLNNYFNFEYRKKNKF PHFKCEKCNFKENADYNAALNISNPKLKSTKEEP | Cas14/D143R/E151F |
| 66 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSRVCYTRAACLFKNAAIASGLRSKIKSNFRLKELKNMKSGLPTTKS DNFPIPLVKQKGGQYTGFEISNHNSDFIIKIPFGRWQVKKEIDKYRPWEKFDFEQVQKSPK PISLLLSTQRRKRNKGWSKDEGTEAEIKKVMNGDYQTSYIEVKRGSKICEKSAWMLNLSID VPKIDKGVDPSIIGGIDVGVKSPLVCAINNAFSRYSISDNDLFHFNKKMFARRRILLKKNRHK RAGHGAKNKLKPITILTEKSERFRKKLIERWACEIADFFIKNKVGTVQMENLESMKRKEDSY FNIRLRGFWPYAEMQNKIEFKLKQYGIEIRKVAPNNTSKTCSKCGHLNNYFNFEYRKKNKF PHFKCEKCNFKENADYNAALNISNPKLKSTKEEP | Cas14/D143R/E151C |
| 67 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSRVCYTRAAKLFKNAAIASGLRSKIKSNFRLKELKNMKSGLPTTKS DNFPIPLVKQKGGQYTGFEISNHNSDFIIKIPFGRWQVKKEIDKYRPWEKFDFEQVQKSPK PISLLLSTQRRKRNKGWSKDEGTEAEIKKVMNGDYQTSYIEVKRGSKICEKSAWMLNLSID VPKIDKGVDPSIIGGIDVGVKSPLVCAINNAFSRYSISDNDLFHFNKKMFARRRILLKKNRHK RAGHGAKNKLKPITILTEKSERFRKKLIERWACEIADFFIKNKVGTVQMENLESMKRKEDSY FNIRLRGFWPYAEMQNKIEFKLKQYGIEIRKVAPNNTSKTCSKCGHLNNYFNFEYRKKNKF PHFKCEKCNFKENADYNAALNISNPKLKSTKEEP | Cas14/D143R/E151K |
| 68 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSRVCYTRAAGLFKNAAIASGLRSKIKSNFRLKELKNMKSGLPTTKS DNFPIPLVKQKGGQYTGFEISNHNSDFIIKIPFGRWQVKKEIDKYRPWEKFDFEQVQKSPK PISLLLSTQRRKRNKGWSKDEGTEAEIKKVMNGDYQTSYIEVKRGSKICEKSAWMLNLSID VPKIDKGVDPSIIGGIDVGVKSPLVCAINNAFSRYSISDNDLFHFNKKMFARRRILLKKNRHK RAGHGAKNKLKPITILTEKSERFRKKLIERWACEIADFFIKNKVGTVQMENLESMKRKEDSY FNIRLRGFWPYAEMQNKIEFKLKQYGIEIRKVAPNNTSKTCSKCGHLNNYFNFEYRKKNKF PHFKCEKCNFKENADYNAALNISNPKLKSTKEEP | Cas14/D143R/E151G |
| 69 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSRVCYTRAAILFKNAAIASGLRSKIKSNFRLKELKNMKSGLPTTKSD NFPIPLVKQKGGQYTGFEISNHNSDFIIKIPFGRWQVKKEIDKYRPWEKFDFEQVQKSPKPI SLLLSTQRRKRNKGWSKDEGTEAEIKKVMNGDYQTSYIEVKRGSKICEKSAWMLNLSIDVP KIDKGVDPSIIGGIDVGVKSPLVCAINNAFSRYSISDNDLFHFNKKMFARRRILLKKNRHKRA | Cas14/D143R/E151I |

| SEQ ID NO | Sequence | Description |
|---|---|---|
| | GHGAKNKLKPITILTEKSERFRKKLIERWACEIADFFIKNKVGTVQMENLESMKRKEDSYFNI RLRGFWPYAEMQNKIEFKLKQYGIEIRKVAPNNTSKTCSKCGHLNNYFNFEYRKKNKFPHF KCEKCNFKENADYNAALNISNPKLSTKEEP | |
| 70 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSRVCYTRAAPLFKNAAIASGLRSKIKSNFRLKELKNMKSGLPTTKS DNFPIPLVKQKGGQYTGFEISNHNSDFIIKIPFGRWQVKKEIDKYRPWEKFDFEQVQKSPK PISLLLSTQRRKRNKGWSKDEGTEAEIKKVMNGDYQTSYIEVKRGSKICEKSAWMLNLSID VPKIDKGVDPSIIGGIDVGVKSPLVCAINNAFSRYSISDNDLFHFNKKMFARRRILLKKNRHK RAGHGAKNKLKPITILTEKSERFRKKLIERWACEIADFFIKNKVGTVQMENLESMKRKEDSY FNIRLRGFWPYAEMQNKIEFKLKQYGIEIRKVAPNNTSKTCSKCGHLNNYFNFEYRKKNKF PHFKCEKCNFKENADYNAALNISNPKLSTKEEP | Cas14/D143R/E151P |
| 71 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSRVCYTRAAHLFKNAAIASGLRSKIKSNFRLKELKNMKSGLPTTKS DNFPIPLVKQKGGQYTGFEISNHNSDFIIKIPFGRWQVKKEIDKYRPWEKFDFEQVQKSPK PISLLLSTQRRKRNKGWSKDEGTEAEIKKVMNGDYQTSYIEVKRGSKICEKSAWMLNLSID VPKIDKGVDPSIIGGIDVGVKSPLVCAINNAFSRYSISDNDLFHFNKKMFARRRILLKKNRHK RAGHGAKNKLKPITILTEKSERFRKKLIERWACEIADFFIKNKVGTVQMENLESMKRKEDSY FNIRLRGFWPYAEMQNKIEFKLKQYGIEIRKVAPNNTSKTCSKCGHLNNYFNFEYRKKNKF PHFKCEKCNFKENADYNAALNISNPKLSTKEEP | Cas14/D143R/E151H |
| 72 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSRVCYTRAAALFKNAAIASGLRSKIKSNFRLKELKNMKSGLPTTKS DNFPIPLVKQKGGQYTGFEISNHNSDFIIKIPFGRWQVKKEIDKYRPWEKFDFEQVQKSPK PISLLLSTQRRKRNKGWSKDEGTEAEIKKVMNGDYQTSYIEVKRGSKICEKSAWMLNLSID VPKIDKGVDPSIIGGIDVGVKSPLVCAINNAFSRYSISDNDLFHFNKKMFARRRILLKKNRHK RAGHGAKNKLKPITILTEKSERFRKKLIERWACEIADFFIKNKVGTVQMENLESMKRKEDSY FNIRLRGFWPYAEMQNKIEFKLKQYGIEIRKVAPNNTSKTCSKCGHLNNYFNFEYRKKNKF PHFKCEKCNFKENADYNAALNISNPKLSTKEEP | Cas14/D143R/E151A |
| 73 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSRVCYTRAAVLFKNAAIASGLRSKIKSNFRLKELKNMKSGLPTTKS DNFPIPLVKQKGGQYTGFEISNHNSDFIIKIPFGRWQVKKEIDKYRPWEKFDFEQVQKSPK PISLLLSTQRRKRNKGWSKDEGTEAEIKKVMNGDYQTSYIEVKRGSKICEKSAWMLNLSID VPKIDKGVDPSIIGGIDVGVKSPLVCAINNAFSRYSISDNDLFHFNKKMFARRRILLKKNRHK RAGHGAKNKLKPITILTEKSERFRKKLIERWACEIADFFIKNKVGTVQMENLESMKRKEDSY FNIRLRGFWPYAEMQNKIEFKLKQYGIEIRKVAPNNTSKTCSKCGHLNNYFNFEYRKKNKF PHFKCEKCNFKENADYNAALNISNPKLSTKEEP | Cas14/D143R/E151V |
| 74 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSRVCYTRAAQLFKNAAIASGLRSKIKSNFRLKELKNMKSGLPTTKS DNFPIPLVKQKGGQYTGFEISNHNSDFIIKIPFGRWQVKKEIDKYRPWEKFDFEQVQKSPK PISLLLSTQRRKRNKGWSKDEGTEAEIKKVMNGDYQTSYIEVKRGSKICEKSAWMLNLSID VPKIDKGVDPSIIGGIDVGVKSPLVCAINNAFSRYSISDNDLFHFNKKMFARRRILLKKNRHK RAGHGAKNKLKPITILTEKSERFRKKLIERWACEIADFFIKNKVGTVQMENLESMKRKEDSY FNIRLRGFWPYAEMQNKIEFKLKQYGIEIRKVAPNNTSKTCSKCGHLNNYFNFEYRKKNKF PHFKCEKCNFKENADYNAALNISNPKLSTKEEP | Cas14/D143R/E151Q |
| 75 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSRVCYTRAAMLFKNAAIASGLRSKIKSNFRLKELKNMKSGLPTTKS DNFPIPLVKQKGGQYTGFEISNHNSDFIIKIPFGRWQVKKEIDKYRPWEKFDFEQVQKSPK PISLLLSTQRRKRNKGWSKDEGTEAEIKKVMNGDYQTSYIEVKRGSKICEKSAWMLNLSID VPKIDKGVDPSIIGGIDVGVKSPLVCAINNAFSRYSISDNDLFHFNKKMFARRRILLKKNRHK RAGHGAKNKLKPITILTEKSERFRKKLIERWACEIADFFIKNKVGTVQMENLESMKRKEDSY FNIRLRGFWPYAEMQNKIEFKLKQYGIEIRKVAPNNTSKTCSKCGHLNNYFNFEYRKKNKF PHFKCEKCNFKENADYNAALNISNPKLSTKEEP | Cas14/D143R/E151M |
| 76 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSRVCYTRAADLFKNAAIASGLRSKIKSNFRLKELKNMKSGLPTTKS DNFPIPLVKQKGGQYTGFEISNHNSDFIIKIPFGRWQVKKEIDKYRPWEKFDFEQVQKSPK PISLLLSTQRRKRNKGWSKDEGTEAEIKKVMNGDYQTSYIEVKRGSKICEKSAWMLNLSID VPKIDKGVDPSIIGGIDVGVKSPLVCAINNAFSRYSISDNDLFHFNKKMFARRRILLKKNRHK RAGHGAKNKLKPITILTEKSERFRKKLIERWACEIADFFIKNKVGTVQMENLESMKRKEDSY FNIRLRGFWPYAEMQNKIEFKLKQYGIEIRKVAPNNTSKTCSKCGHLNNYFNFEYRKKNKF PHFKCEKCNFKENADYNAALNISNPKLSTKEEP | Cas14/D143R/E151D |
| 77 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI | Cas14/D143R/E151N |

| SEQ ID NO | Sequence | Description |
|---|---|---|
| | FIKGKGIANASSVEHYLSRVCYTRAANLFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIDVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCEKCNFKENADYNAALNISNPKLKSTKEEP | |
| 78 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSRVCYRRAAYLFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIDVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCEKCNFKENADYNAALNISNPKLKSTKEEP | Cas14/D143R/E151Y |
| 79 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSRVCYRRAALFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIDVGVRSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCEKCNFKENADYNAALNISNPKLKSTKREP | Cas14/D143R/T147R/<br>K330R/E151A/E527R |
| 80 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSDVCYTRAAELFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIAVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCEKCNFKENAAYNAALNISNPKLKSTKEEP | Cas14/D326A/D510A |
| 81 | MAKNTITKTLRLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSDVCYTRAAELFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIAVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCEKCNFKENAAYNAALNISNPKLKSTKEEP | Cas14/D326A/D510A/<br>K11R |
| 82 | MAKNTITKTLKLRIVRPYNSAEVEKIVADEKNNREKIALEKNKDKVKEACSKHLKVAAYCTT<br>QVERNACLFCRARKLDDKFYQKLRGQFPDAVFWQEISEIFRQLQKQAAEIYNQSLIELYYEI<br>FIKGKGIANASSVEHYLSDVCYTRAAELFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIAVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCEKCNFKENAAYNAALNISNPKLKSTKEEP | Cas14/D326A/D510A/<br>K73R |
| 83 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKRAAEIYNQSLIELYYEIF<br>IKGKGIANASSVEHYLSDVCYTRAAELFKNAAIASGLRSKIKSNFRLKELKNMKSGLPTTKSD<br>NFPIPLVKQKGGQYTGFEISNHNSDFIIKIPFGRWQVKKEIDKYRPWEKFDFEQVQKSPKPI<br>SLLLSTQRRKRNKGWSKDEGTEAEIKKVMNGDYQTSYIEVKRGSKICEKSAWMLNLSIDVP<br>KIDKGVDPSIIGGIAVGVKSPLVCAINNAFSRYSISDNDLFHFNKKMFARRRILLKKNRHKRA<br>GHGAKNKLKPITILTEKSERFRKKLIERWACEIADFFIKNKVGTVQMENLESMKRKEDSYENI<br>RLRGFWPYAEMQNKIEFKLKQYGIEIRKVAPNNTSKTCSKCGHLNNYFNFEYRKKNKFPHF<br>KCEKCNFKENAAYNAALNISNPKLKSTKEEP | Cas14/D326A/D510A/<br>Q108R |

| SEQ ID NO | Sequence | Description |
|---|---|---|
| 84 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSRVCYTRAAELFKNAAIASGLRSKIKSNFRLKELKNMKSGLPTTKS DNFPIPLVKQKGGQYTGFEISNHNSDFIIKIPFGRWQVKKEIDKYRPWEKFDFEQVQKSPK PISLLLSTQRRKRNKGWSKDEGTEAEIKKVMNGDYQTSYIEVKRGSKICEKSAWMLNLSID VPKIDKGVDPSIIGGIAVGVKSPLVCAINNAFSRYSISDNDLFHFNKKMFARRRILLKKNRHK RAGHGAKNKLKPITILTEKSERFRKKLIERWACEIADFFIKNKVGTVQMENLESMKRKEDSY FNIRLRGFWPYAEMQNKIEFKLKQYGIEIRKVAPNNTSKTCSKCGHLNNYFNFEYRKKNKF PHFKCEKCNFKENAAYNAALNISNPKLKSTKEEP | Cas14/D326A/D510A/ D143R |
| 85 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSDVCYRRAAELFKNAAIASGLRSKIKSNFRLKELKNMKSGLPTTKS DNFPIPLVKQKGGQYTGFEISNHNSDFIIKIPFGRWQVKKEIDKYRPWEKFDFEQVQKSPK PISLLLSTQRRKRNKGWSKDEGTEAEIKKVMNGDYQTSYIEVKRGSKICEKSAWMLNLSID VPKIDKGVDPSIIGGIAVGVKSPLVCAINNAFSRYSISDNDLFHFNKKMFARRRILLKKNRHK RAGHGAKNKLKPITILTEKSERFRKKLIERWACEIADFFIKNKVGTVQMENLESMKRKEDSY FNIRLRGFWPYAEMQNKIEFKLKQYGIEIRKVAPNNTSKTCSKCGHLNNYFNFEYRKKNKF PHFKCEKCNFKENAAYNAALNISNPKLKSTKEEP | Cas14/D326A/D510A/ T147R |
| 86 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSDVCYTRAARLFKNAAIASGLRSKIKSNFRLKELKNMKSGLPTTKS DNFPIPLVKQKGGQYTGFEISNHNSDFIIKIPFGRWQVKKEIDKYRPWEKFDFEQVQKSPK PISLLLSTQRRKRNKGWSKDEGTEAEIKKVMNGDYQTSYIEVKRGSKICEKSAWMLNLSID VPKIDKGVDPSIIGGIAVGVKSPLVCAINNAFSRYSISDNDLFHFNKKMFARRRILLKKNRHK RAGHGAKNKLKPITILTEKSERFRKKLIERWACEIADFFIKNKVGTVQMENLESMKRKEDSY FNIRLRGFWPYAEMQNKIEFKLKQYGIEIRKVAPNNTSKTCSKCGHLNNYFNFEYRKKNKF PHFKCEKCNFKENAAYNAALNISNPKLKSTKEEP | Cas14/D326A/D510A/ E151R |
| 87 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSDVCYTRAAELFRNAAIASGLRSKIKSNFRLKELKNMKSGLPTTKS DNFPIPLVKQKGGQYTGFEISNHNSDFIIKIPFGRWQVKKEIDKYRPWEKFDFEQVQKSPK PISLLLSTQRRKRNKGWSKDEGTEAEIKKVMNGDYQTSYIEVKRGSKICEKSAWMLNLSID VPKIDKGVDPSIIGGIAVGVKSPLVCAINNAFSRYSISDNDLFHFNKKMFARRRILLKKNRHK RAGHGAKNKLKPITILTEKSERFRKKLIERWACEIADFFIKNKVGTVQMENLESMKRKEDSY FNIRLRGFWPYAEMQNKIEFKLKQYGIEIRKVAPNNTSKTCSKCGHLNNYFNFEYRKKNKF PHFKCEKCNFKENAAYNAALNISNPKLKSTKEEP | Cas14/D326A/D510A/ K154R |
| 88 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSDVCYTRAAELFKRAAIASGLRSKIKSNFRLKELKNMKSGLPTTKS DNFPIPLVKQKGGQYTGFEISNHNSDFIIKIPFGRWQVKKEIDKYRPWEKFDFEQVQKSPK PISLLLSTQRRKRNKGWSKDEGTEAEIKKVMNGDYQTSYIEVKRGSKICEKSAWMLNLSID VPKIDKGVDPSIIGGIAVGVKSPLVCAINNAFSRYSISDNDLFHFNKKMFARRRILLKKNRHK RAGHGAKNKLKPITILTEKSERFRKKLIERWACEIADFFIKNKVGTVQMENLESMKRKEDSY FNIRLRGFWPYAEMQNKIEFKLKQYGIEIRKVAPNNTSKTCSKCGHLNNYFNFEYRKKNKF PHFKCEKCNFKENAAYNAALNISNPKLKSTKEEP | Cas14/D326A/D510A/ N155R |
| 89 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSDVCYTRAAELFKNAAIASGLRSKIKSNFRLKELKNMKSGLPTTKS DNFPIPLVRQKGGQYTGFEISNHNSDFIIKIPFGRWQVKKEIDKYRPWEKFDFEQVQKSPK PISLLLSTQRRKRNKGWSKDEGTEAEIKKVMNGDYQTSYIEVKRGSKICEKSAWMLNLSID VPKIDKGVDPSIIGGIAVGVKSPLVCAINNAFSRYSISDNDLFHFNKKMFARRRILLKKNRHK RAGHGAKNKLKPITILTEKSERFRKKLIERWACEIADFFIKNKVGTVQMENLESMKRKEDSY FNIRLRGFWPYAEMQNKIEFKLKQYGIEIRKVAPNNTSKTCSKCGHLNNYFNFEYRKKNKF PHFKCEKCNFKENAAYNAALNISNPKLKSTKEEP | Cas14/D326A/D510A/ K196R |
| 90 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSDVCYTRAAELFKNAAIASGLRSKIKSNFRLKELKNMKSGLPTTKS DNFPIPLVKQKGGQYTGFEISNHNSDFIIKIPFGRWQVKKEIDKYRPWEKFDFRQVQKSPK PISLLLSTQRRKRNKGWSKDEGTEAEIKKVMNGDYQTSYIEVKRGSKICEKSAWMLNLSID VPKIDKGVDPSIIGGIAVGVKSPLVCAINNAFSRYSISDNDLFHFNKKMFARRRILLKKNRHK RAGHGAKNKLKPITILTEKSERFRKKLIERWACEIADFFIKNKVGTVQMENLESMKRKEDSY FNIRLRGFWPYAEMQNKIEFKLKQYGIEIRKVAPNNTSKTCSKCGHLNNYFNFEYRKKNKF PHFKCEKCNFKENAAYNAALNISNPKLKSTKEEP | Cas14/D326A/D510A/ E241R |
| 91 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSDVCYTRAAELFKNAAIASGLRSKIKSNFRLKELKNMKSGLPTTKS DNFPIPLVKQKGGQYTGFEISNHNSDFIIKIPFGRWQVKKEIDKYRPWEKFDFEQVQKSPK PISLLLSTQRRKRNKGWSKDEGTEAEIKKVMNGDYQTSYIRVKRGSKICEKSAWMLNLSID VPKIDKGVDPSIIGGIAVGVKSPLVCAINNAFSRYSISDNDLFHFNKKMFARRRILLKKNRHK | Cas14/D326A/D510A/ E289R |

| SEQ ID NO | Sequence | Description |
|---|---|---|
| | RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCEKCNFKENAAYNAALNISNPKLSTKEEP | |
| 92 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSDVCYTRAAELFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVRPSIIGGIAVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCEKCNFKENAAYNAALNISNPKLSTKEEP | Cas14/D326A/D510A/<br>D318R |
| 93 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSDVCYTRAAELFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIARGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCEKCNFKENAAYNAALNISNPKLSTKEEP | Cas14/D326A/D510A/<br>V327R |
| 94 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSDVCYTRAAELFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIAVGVRSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCEKCNFKENAAYNAALNISNPKLSTKEEP | Cas14/D326A/D510A/<br>K330R |
| 95 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSDVCYTRAAELFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIAVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLNSMKRKEDSY<br>FNIRLRGFWPYAEMQNKIEFKLKQYGIEIRKVAPNNTSKTCSKCGHLNNYFNFEYRKKNKF<br>PHFKCEKCNFKENAAYNAALNISNPKLSTKEEP | Cas14/D326A/D510A/<br>E425N |
| 96 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSDVCYTRAAELFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIAVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLRQYGIEIRKVAPNNTSKTCSKCGHLNNYFNFEYRKKNKF<br>PHFKCEKCNFKENAAYNAALNISNPKLSTKEEP | Cas14/D326A/D510A/<br>K457R |
| 97 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSDVCYTRAAELFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIAVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIRIRKVAPNNTSKTCSKCGHLNNYFNFEYRKKNKF<br>PHFKCEKCNFKENAAYNAALNISNPKLSTKEEP | Cas14/D326A/D510A/<br>E462R |
| 98 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSDVCYTRAAELFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIAVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKREKCNFKENAAYNAALNISNPKLSTKEEP | Cas14/D326A/D510A/<br>C500R |
| 99 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI | Cas14/D326A/D510A/<br>K499R/C500R |

| SEQ ID NO | Sequence | Description |
|---|---|---|
|  | FIKGKGIANASSVEHYLSDVCYTRAAELFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIAVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFRREKCNFKENAAYNAALNISNPKLKSTKEEP |  |
| 100 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSDVCYTRAAELFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIAVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCRKCNFKENAAYNAALNISNPKLKSTKEEP | Cas14/D326A/D510A/<br>E501R |
| 101 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSDVCYTRAAELFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIAVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCEKCRFKENAAYNAALNISNPKLKSTKEEP | Cas14/D326A/D510A/<br>E504R |
| 102 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSDVCYTRAAELFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIAVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCEKCNFKRNAAYNAALNISNPKLKSTKEEP | Cas14/D326A/D510A/<br>E507R |
| 103 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSDVCYTRAAELFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIAVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCEKCNFKEDAAYNAALNISNPKLKSTKEEP | Cas14/D326A/D510A/<br>N508D |
| 104 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSDVCYTRAAELFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIAVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCEKCNFKENAAANAALNISNPKLKSTKEEP | Cas14/D326A/D510A/<br>Y511A |
| 105 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSDVCYTRAAELFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIAVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCEKCNFKENAAYNAGLNISNPKLKSTKEEP | Cas14/D326A/D510A/<br>A514G |
| 106 | AKNTITKTLKLRIVRPYNSAEVEKIVADEKNNREKIALEKNKDKVKEACSKHLKVAAYCTTQV<br>ERNACLFCKARKLDDKFYQKLRGQFPDAVFWQEISEIFRQLQKQAAEIYNQSLIELYYEIFIK<br>GKGIANASSVEHYLSDVCYTRAAELFKNAAIASGLRSKIKSNFRLKELKNMKSGLPTTKSDNF<br>PIPLVKQKGGQYTGFEISNHNSDFIIKIPFGRWQVKKEIDKYRPWEKFDFEQVQKSPKPISLL<br>LSTQRRKRNKGWSKDEGTEAEIKKVMNGDYQTSYIEVKRGSKICEKSAWMLNLSIDVPKID | Cas14/D326A/D510A/<br>IN516R |

| SEQ ID NO | Sequence | Description |
|---|---|---|
| | KGVDPSIIGGIAVGVKSPLVCAINNAFSRYSISDNDLFHFNKKMFARRRILLKKNRHKRAGH GAKNLKPITILTEKSERFRKKLIERWACEIADFFIKNKVGTVQMENLESMKRKEDSYFNIRL RGFWPYAEMQNKIEFKLKQYGIEIRKVAPNNTSKTCSKCGHLNNYFNFEYRKKNKFPHFKC EKCNFKENAAYNAALRISNPKLSTKEEP | |
| 107 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSDVCYTRAAELFKNAAIASGLRSKIKSNFRLKELKNMKSGLPTTKS DNFPIPLVKQKGGQYTGFEISNHNSDFIIKIPFGRWQVKKEIDKYRPWEKFDFEQVQKSPK PISLLLSTQRRKRNKGWSKDEGTEAEIKKVMNGDYQTSYIEVKRGSKICEKSAWMLNLSID VPKIDKGVDPSIIGGIAVGVKSPLVCAINNAFSRYSISDNDLFHFNKKMFARRRILLKKNRHK RAGHGAKNKLKPITILTEKSERFRKKLIERWACEIADFFIKNKVGTVQMENLESMKRKEDSY FNIRLRGFWPYAEMQNKIEFKLKQYGIEIRKVAPNNTSKTCSKCGHLNNYFNFEYRKKNKF PHFKCEKCNFKENAAYNAALNISRPKLSTKEEP | Cas14/D326A/D510A/ N519R |
| 108 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSDVCYTRAAELFKNAAIASGLRSKIKSNFRLKELKNMKSGLPTTKS DNFPIPLVKQKGGQYTGFEISNHNSDFIIKIPFGRWQVKKEIDKYRPWEKFDFEQVQKSPK PISLLLSTQRRKRNKGWSKDEGTEAEIKKVMNGDYQTSYIEVKRGSKICEKSAWMLNLSID VPKIDKGVDPSIIGGIAVGVKSPLVCAINNAFSRYSISDNDLFHFNKKMFARRRILLKKNRHK RAGHGAKNKLKPITILTEKSERFRKKLIERWACEIADFFIKNKVGTVQMENLESMKRKEDSY FNIRLRGFWPYAEMQNKIEFKLKQYGIEIRKVAPNNTSKTCSKCGHLNNYFNFEYRKKNKF PHFKCEKCNFKENAAYNAALNISNPKLSTKREP | Cas14/D326A/D510A/ E527R |
| 109 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSDVCYTRAAELFKNAAIASGLRSKIKSNFRLKELKNMKSGLPTTKS DNFPIPLVKQKGGQYTGFEISNHNSDFIIKIPFGRWQVKKEIDKYRPWEKFDFEQVQKSPK PISLLLSTQRRKRNKGWSKDEGTEAEIKKVMNGDYQTSYIEVKRGSKICEKSAWMLNLSID VPKIDKGVDPSIIGGIAVGVKSPLVCAINNAFSRYSISDNDLFHFNKKMFARRRILLKKNRHK RAGHGAKNKLKPITILTEKSERFRKKLIERWACEIADFFIKNKVGTVQMENLESMKREDSY FNIRLRGFWPYAEMQNKIEFKLKQYGIEIRKVAPNNTSKTCSKCGHLNNYFNFEYRKKNKF PHFKCEKCNFKENAAYNAALNISNPKLSTKERP | Cas14/D326A/D510A/ E528R |
| 110 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSRVCYRRAAELFKNAAIASGLRSKIKSNFRLKELKNMKSGLPTTKS DNFPIPLVKQKGGQYTGFEISNHNSDFIIKIPFGRWQVKKEIDKYRPWEKFDFEQVQKSPK PISLLLSTQRRKRNKGWSKDEGTEAEIKKVMNGDYQTSYIEVKRGSKICEKSAWMLNLSID VPKIDKGVDPSIIGGIAVGVKSPLVCAINNAFSRYSISDNDLFHFNKKMFARRRILLKKNRHK RAGHGAKNKLKPITILTEKSERFRKKLIERWACEIADFFIKNKVGTVQMENLESMKRKEDSY FNIRLRGFWPYAEMQNKIEFKLKQYGIEIRKVAPNNTSKTCSKCGHLNNYFNFEYRKKNKF PHFKCEKCNFKENAAYNAALNISNPKLSTKEEP | Cas14/D326A/D510A/ D143R/T147R |
| 111 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSRVCYTRAARLFKNAAIASGLRSKIKSNFRLKELKNMKSGLPTTKS DNFPIPLVKQKGGQYTGFEISNHNSDFIIKIPFGRWQVKKEIDKYRPWEKFDFEQVQKSPK PISLLLSTQRRKRNKGWSKDEGTEAEIKKVMNGDYQTSYIEVKRGSKICEKSAWMLNLSID VPKIDKGVDPSIIGGIAVGVKSPLVCAINNAFSRYSISDNDLFHFNKKMFARRRILLKKNRHK RAGHGAKNKLKPITILTEKSERFRKKLIERWACEIADFFIKNKVGTVQMENLESMKRKEDSY FNIRLRGFWPYAEMQNKIEFKLKQYGIEIRKVAPNNTSKTCSKCGHLNNYFNFEYRKKNKF PHFKCEKCNFKENAAYNAALNISNPKLSTKEEP | Cas14/D326A/D510A/ D143R/E151R |
| 112 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSRVCYTRAAELFRNAAIASGLRSKIKSNFRLKELKNMKSGLPTTKS DNFPIPLVKQKGGQYTGFEISNHNSDFIIKIPFGRWQVKKEIDKYRPWEKFDFEQVQKSPK PISLLLSTQRRKRNKGWSKDEGTEAEIKKVMNGDYQTSYIEVKRGSKICEKSAWMLNLSID VPKIDKGVDPSIIGGIAVGVKSPLVCAINNAFSRYSISDNDLFHFNKKMFARRRILLKKNRHK RAGHGAKNKLKPITILTEKSERFRKKLIERWACEIADFFIKNKVGTVQMENLESMKRKEDSY FNIRLRGFWPYAEMQNKIEFKLKQYGIEIRKVAPNNTSKTCSKCGHLNNYFNFEYRKKNKF PHFKCEKCNFKENAAYNAALNISNPKLSTKEEP | Cas14/D326A/D510A/ D143R/K154R |
| 113 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSRVCYTRAAELFKNAAIASGLRSKIKSNFRLKELKNMKSGLPTTKS DNFPIPLVKQKGGQYTGFEISNHNSDFIIKIPFGRWQVKKEIDKYRPWEKFDFRQVQKSPK PISLLLSTQRRKRNKGWSKDEGTEAEIKKVMNGDYQTSYIEVKRGSKICEKSAWMLNLSID VPKIDKGVDPSIIGGIAVGVKSPLVCAINNAFSRYSISDNDLFHFNKKMFARRRILLKKNRHK RAGHGAKNKLKPITILTEKSERFRKKLIERWACEIADFFIKNKVGTVQMENLESMKRKEDSY FNIRLRGFWPYAEMQNKIEFKLKQYGIEIRKVAPNNTSKTCSKCGHLNNYFNFEYRKKNKF PHFKCEKCNFKENAAYNAALNISNPKLSTKEEP | Cas14/D326A/D510A/ D143R/E241R |

| SEQ ID NO | Sequence | Description |
|---|---|---|
| 114 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSRVCYTRAAELFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIAVGVRSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCEKCNFKENAAYNAALNISNPKLKSTKEEP | Cas14/D326A/D510A/<br>D143R/K330R |
| 115 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSRVCYTRAAELFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIAVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLNSMKRKEDSY<br>FNIRLRGFWPYAEMQNKIEFKLKQYGIEIRKVAPNNTSKTCSKCGHLNNYFNFEYRKKNKF<br>PHFKCEKCNFKENAAYNAALNISNPKLKSTKEEP | Cas14/D326A/D510A/<br>D143R/E245N |
| 116 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSRVCYTRAAELFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIAVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCEKCNFKRNAAYNAALNISNPKLKSTKEEP | Cas14/D326A/D510A/<br>D143R/E507R |
| 117 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSRVCYTRAAELFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIAVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCEKCNFKENAAYNAALRISNPKLKSTKEEP | Cas14/D326A/D510A/<br>D143R/N516R |
| 118 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSRVCYTRAAELFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIAVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCEKCNFKENAAYNAALNISRPKLKSTKEEP | Cas14/D326A/D510A/<br>D143R/N519R |
| 119 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSRVCYTRAAELFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIAVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCEKCNFKENAAYNAALNISNPKLKSTKREP | Cas14/D326A/D510A/<br>D143R/E527R |
| 120 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSRVCYTRAAELFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIAVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCEKCNFKENAAYNAALNISNPKLKSTKERP | Cas14/D326A/D510A/<br>D143R/E528R |
| 121 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSRVCYRAARLFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIAVGVKSPLVCAINNAFSRYSISDNDLFHFNKKMFARRRILLKKNRHK | Cas14/D326A/D510A/<br>D143R/T147R/E151R |

| SEQ ID NO | Sequence | Description |
|---|---|---|
| | RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCEKCNFKENAAYNAALNISNPKLKSTKEEP | |
| 122 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSRVCYRRAAELFRNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIAVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCEKCNFKENAAYNAALNISNPKLKSTKEEP | Cas14/D326A/D510A/<br>D143R/T147R/K154R |
| 123 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSRVCYRRAAELFKNAAIASGLRSKIKSNFRLKELKNMKSGLPTTKS<br>DNFPIPLVKQKGGQYTGFEISNHNSDFIIKIPFGRWQVKKEIDKYRPWEKFDFRQVQKSPK<br>PISLLLSTQRRKRNKGWSKDEGTEAEIKKVMNGDYQTSYIEVKRGSKICEKSAWMLNLSID<br>VPKIDKGVDPSIIGGIAVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCEKCNFKENAAYNAALNISNPKLKSTKEEP | Cas14/D326A/D510A/<br>D143R/T147R/E241R |
| 124 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSRVCYRRAAELFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIAVGVRSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCEKCNFKENAAYNAALNISNPKLKSTKEEP | Cas14/D326A/D510A/<br>D143R/T147R/K330R |
| 125 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSRVCYRRAAELFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIAVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLNSMKRKEDSY<br>FNIRLRGFWPYAEMQNKIEFKLKQYGIEIRKVAPNNTSKTCSKCGHLNNYFNFEYRKKNKF<br>PHFKCEKCNFKENAAYNAALNISNPKLKSTKEEP | Cas14/D326A/D510A/<br>D143R/T147R/E425N |
| 126 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSRVCYRRAAELFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIAVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCEKCNFKRNAAYNAALNISNPKLKSTKEEP | Cas14/D326A/D510A/<br>D143R/T147R/E507R |
| 127 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSRVCYRRAAELFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIAVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCEKCNFKENAAYNAALRISNPKLKSTKEEP | Cas14/D326A/D510A/<br>D143R/T147R/N516R |
| 128 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSRVCYRRAAELFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIAVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCEKCNFKENAAYNAALNISRPKLKSTKEEP | Cas14/D326A/D510A/<br>D143R/T147R/N519R |
| 129 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI | Cas14/D326A/D510A/<br>D143R/T147R/E527R |

-continued

| SEQ ID NO | Sequence | Description |
|---|---|---|
| | FIKGKGIANASSVEHYLSRVCYRRAAELFKNAAIASGLRSKIKSNFRLKELKNMKSGLPTTKS DNFPIPLVKQKGGQYTFEISNHNSDFIIKIPFGRWQVKKEIDKYRPWEKFDFEQVQKSPK PISLLLSTQRRKRNKGWSKDEGTEAEIKKVMNGDYQTSYIEVKRGSKICEKSAWMLNLSID VPKIDKGVDPSIIGGIAVGVKSPLVCAINNAFSRYSISDNDLFHFNKKMFARRRILLKKNRHK RAGHGAKNKLKPITILTEKSERFRKKLIERWACEIADFFIKNKVGTVQMENLESMKRKEDSY FNIRLRGFWPYAEMQNKIEFKLKQYGIEIRKVAPNNTSKTCSKCGHLNNYFNFEYRKKNKF PHFKCEKCNFKENAAYNAALNISNPKLKSTKREP | |
| 130 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSRVCYRRAAELFKNAAIASGLRSKIKSNFRLKELKNMKSGLPTTKS DNFPIPLVKQKGGQYTFEISNHNSDFIIKIPFGRWQVKKEIDKYRPWEKFDFEQVQKSPK PISLLLSTQRRKRNKGWSKDEGTEAEIKKVMNGDYQTSYIEVKRGSKICEKSAWMLNLSID VPKIDKGVDPSIIGGIAVGVKSPLVCAINNAFSRYSISDNDLFHFNKKMFARRRILLKKNRHK RAGHGAKNKLKPITILTEKSERFRKKLIERWACEIADFFIKNKVGTVQMENLESMKRKEDSY FNIRLRGFWPYAEMQNKIEFKLKQYGIEIRKVAPNNTSKTCSKCGHLNNYFNFEYRKKNKF PHFKCEKCNFKENAAYNAALNISNPKLKSTKERP | Cas14/D326A/D510A/ D143R/T147R/E528R |
| 131 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSRVCYRRAASLFKNAAIASGLRSKIKSNFRLKELKNMKSGLPTTKS DNFPIPLVKQKGGQYTFEISNHNSDFIIKIPFGRWQVKKEIDKYRPWEKFDFEQVQKSPK PISLLLSTQRRKRNKGWSKDEGTEAEIKKVMNGDYQTSYIEVKRGSKICEKSAWMLNLSID VPKIDKGVDPSIIGGIAVGVKSPLVCAINNAFSRYSISDNDLFHFNKKMFARRRILLKKNRHK RAGHGAKNKLKPITILTEKSERFRKKLIERWACEIADFFIKNKVGTVQMENLESMKRKEDSY FNIRLRGFWPYAEMQNKIEFKLKQYGIEIRKVAPNNTSKTCSKCGHLNNYFNFEYRKKNKF PHFKCEKCNFKENAAYNAALNISNPKLKSTKEEP | Cas14/D326A/D510A/ D143R/T147R/E151S |
| 132 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSRVCYRRAAGLFKNAAIASGLRSKIKSNFRLKELKNMKSGLPTTKS DNFPIPLVKQKGGQYTFEISNHNSDFIIKIPFGRWQVKKEIDKYRPWEKFDFEQVQKSPK PISLLLSTQRRKRNKGWSKDEGTEAEIKKVMNGDYQTSYIEVKRGSKICEKSAWMLNLSID VPKIDKGVDPSIIGGIAVGVKSPLVCAINNAFSRYSISDNDLFHFNKKMFARRRILLKKNRHK RAGHGAKNKLKPITILTEKSERFRKKLIERWACEIADFFIKNKVGTVQMENLESMKRKEDSY FNIRLRGFWPYAEMQNKIEFKLKQYGIEIRKVAPNNTSKTCSKCGHLNNYFNFEYRKKNKF PHFKCEKCNFKENAAYNAALNISNPKLKSTKEEP | Cas14/D326A/D510A/ D143R/T147R/E151G |
| 133 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSRVCYRRAAALFKNAAIASGLRSKIKSNFRLKELKNMKSGLPTTKS DNFPIPLVKQKGGQYTFEISNHNSDFIIKIPFGRWQVKKEIDKYRPWEKFDFEQVQKSPK PISLLLSTQRRKRNKGWSKDEGTEAEIKKVMNGDYQTSYIEVKRGSKICEKSAWMLNLSID VPKIDKGVDPSIIGGIAVGVKSPLVCAINNAFSRYSISDNDLFHFNKKMFARRRILLKKNRHK RAGHGAKNKLKPITILTEKSERFRKKLIERWACEIADFFIKNKVGTVQMENLESMKRKEDSY FNIRLRGFWPYAEMQNKIEFKLKQYGIEIRKVAPNNTSKTCSKCGHLNNYFNFEYRKKNKF PHFKCEKCNFKENAAYNAALNISNPKLKSTKEEP | Cas14/D326A/D510A/ D143R/T147R/E151A |
| 134 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSRVCYRTAALLFKNAAIASGLRSKIKSNFRLKELKNMKSGLPTTKSD NFPIPLVKQKGGQYTFEISNHNSDFIIKIPFGRWQVKKEIDKYRPWEKFDFEQVQKSPKPI SLLLSTQRRKRNKGWSKDEGTEAEIKKVMNGDYQTSYIEVKRGSKICEKSAWMLNLSIDVP KIDKGVDPSIIGGIAVGVKSPLVCAINNAFSRYSISDNDLFHFNKKMFARRRILLKKNRHKRA GHGAKNKLKPITILTEKSERFRKKLIERWACEIADFFIKNKVGTVQMENLESMKRKEDSYFNI RLRGFWPYAEMQNKIEFKLKQYGIEIRKVAPNNTSKTCSKCGHLNNYFNFEYRKKNKFPHF KCEKCNFKENAAYNAALNISNPKLKSTKEEP | dCasMINI (Cas14/D326A/D510A/ D143R/E151L) |
| 135 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSRVCYRTAASLFKNAAIASGLRSKIKSNFRLKELKNMKSGLPTTKS DNFPIPLVKQKGGQYTFEISNHNSDFIIKIPFGRWQVKKEIDKYRPWEKFDFEQVQKSPK PISLLLSTQRRKRNKGWSKDEGTEAEIKKVMNGDYQTSYIEVKRGSKICEKSAWMLNLSID VPKIDKGVDPSIIGGIAVGVKSPLVCAINNAFSRYSISDNDLFHFNKKMFARRRILLKKNRHK RAGHGAKNKLKPITILTEKSERFRKKLIERWACEIADFFIKNKVGTVQMENLESMKRKEDSY FNIRLRGFWPYAEMQNKIEFKLKQYGIEIRKVAPNNTSKTCSKCGHLNNYFNFEYRKKNKF PHFKCEKCNFKENAAYNAALNISNPKLKSTKEEP | Cas14/D326A/D510A/ D143R/E151S |
| 136 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSRVCYRTAATLFKNAAIASGLRSKIKSNFRLKELKNMKSGLPTTKS DNFPIPLVKQKGGQYTFEISNHNSDFIIKIPFGRWQVKKEIDKYRPWEKFDFEQVQKSPK PISLLLSTQRRKRNKGWSKDEGTEAEIKKVMNGDYQTSYIEVKRGSKICEKSAWMLNLSID | Cas14/D326A/D510A/ D143R/E151T |

| SEQ ID NO | Sequence | Description |
|---|---|---|
| | VPKIDKGVDPSIIGGIAVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLQYGIEIRKVAPNNTSKTCSKCGHLNNYFNFEYRKKNKF<br>PHFKCEKCNFKENAAYNAALNISNPKLKSTKEEP | |
| 137 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSRVCYTRAAWLFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIAVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLQYGIEIRKVAPNNTSKTCSKCGHLNNYFNFEYRKKNKF<br>PHFKCEKCNFKENAAYNAALNISNPKLKSTKEEP | Cas14/D326A/D510A/<br>D143R/E151W |
| 138 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSRVCYTRAAFLFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIAVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLQYGIEIRKVAPNNTSKTCSKCGHLNNYFNFEYRKKNKF<br>PHFKCEKCNFKENAAYNAALNISNPKLKSTKEEP | Cas14/D326A/D510A/<br>D143R/E151F |
| 139 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSRVCYTRAACLFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIAVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLQYGIEIRKVAPNNTSKTCSKCGHLNNYFNFEYRKKNKF<br>PHFKCEKCNFKENAAYNAALNISNPKLKSTKEEP | Cas14/D326A/D510A/<br>D143R/E151C |
| 140 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSRVCYTRAAKLFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIAVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLQYGIEIRKVAPNNTSKTCSKCGHLNNYFNFEYRKKNKF<br>PHFKCEKCNFKENAAYNAALNISNPKLKSTKEEP | Cas14/D326A/D510A/<br>D143R/E151K |
| 141 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSRVCYTRAAGLFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIAVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLQYGIEIRKVAPNNTSKTCSKCGHLNNYFNFEYRKKNKF<br>PHFKCEKCNFKENAAYNAALNISNPKLKSTKEEP | Cas14/D326A/D510A/<br>D143R/E151G |
| 142 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSRVCYTRAAILFKNAAIASGLRSKIKSNFRLKELKNMKSGLPTTKSD<br>NFPIPLVKQKGGQYTGFEISNHNSDFIIKIPFGRWQVKKEIDKYRPWEKFDFEQVQKSPKPI<br>SLLLSTQRRKRNKGWSKDEGTEAEIKKVMNGDYQTSYIEVKRGSKICEKSAWMLNLSIDVP<br>KIDKGVDPSIIGGIAVGVKSPLVCAINNAFSRYSISDNDLFHFNKKMFARRRILLKKNRHKRA<br>GHGAKNKLKPITILTEKSERFRKKLIERWACEIADFFIKNKVGTVQMENLESMKRKEDSYFNI<br>RLRGFWPYAEMQNKIEFKLQYGIEIRKVAPNNTSKTCSKCGHLNNYFNFEYRKKNKFPHF<br>KCEKCNFKENAAYNAALNISNPKLKSTKEEP | Cas14/D326A/D510A/<br>D143R/E151 |
| 143 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSRVCYTRAAPLFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIAVGVKSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLQYGIEIRKVAPNNTSKTCSKCGHLNNYFNFEYRKKNKF<br>PHFKCEKCNFKENAAYNAALNISNPKLKSTKEEP | Cas14/D326A/D510A/<br>D143R/E151P |

| SEQ ID NO | Sequence | Description |
|---|---|---|
| 144 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSRVCYTRAAHLFKNAAIASGLRSKIKSNFRLKELKNMKSGLPTTKS DNFPIPLVKQKGGQYTGFEISNHNSDFIIKIPFGRWQVKKEIDKYRPWEKFDFEQVQKSPK PISLLLSTQRRKRNKGWSKDEGTEAEIKKVMNGDYQTSYIEVKRGSKICEKSAWMLNLSID VPKIDKGVDPSIIGGIAVGVKSPLVCAINNAFSRYSISDNDLFHFNKKMFARRRILLKKNRHK RAGHGAKNKLKPITILTEKSERFRKKLIERWACEIADFFIKNKVGTVQMENLESMKRKEDSY FNIRLRGFWPYAEMQNKIEFKLKQYGIEIRKVAPNNTSKTCSKCGHLNNYFNFEYRKKNKF PHFKCEKCNFKENAAYNAALNISNPKLKSTKEEP | Cas14/D326A/D510A/ D143R/E151H |
| 145 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSRVCYTRAAALFKNAAIASGLRSKIKSNFRLKELKNMKSGLPTTKS DNFPIPLVKQKGGQYTGFEISNHNSDFIIKIPFGRWQVKKEIDKYRPWEKFDFEQVQKSPK PISLLLSTQRRKRNKGWSKDEGTEAEIKKVMNGDYQTSYIEVKRGSKICEKSAWMLNLSID VPKIDKGVDPSIIGGIAVGVKSPLVCAINNAFSRYSISDNDLFHFNKKMFARRRILLKKNRHK RAGHGAKNKLKPITILTEKSERFRKKLIERWACEIADFFIKNKVGTVQMENLESMKRKEDSY FNIRLRGFWPYAEMQNKIEFKLKQYGIEIRKVAPNNTSKTCSKCGHLNNYFNFEYRKKNKF PHFKCEKCNFKENAAYNAALNISNPKLKSTKEEP | Cas14/D326A/D510A/ D143R/E151A |
| 146 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSRVCYTRAAVLFKNAAIASGLRSKIKSNFRLKELKNMKSGLPTTKS DNFPIPLVKQKGGQYTGFEISNHNSDFIIKIPFGRWQVKKEIDKYRPWEKFDFEQVQKSPK PISLLLSTQRRKRNKGWSKDEGTEAEIKKVMNGDYQTSYIEVKRGSKICEKSAWMLNLSID VPKIDKGVDPSIIGGIAVGVKSPLVCAINNAFSRYSISDNDLFHFNKKMFARRRILLKKNRHK RAGHGAKNKLKPITILTEKSERFRKKLIERWACEIADFFIKNKVGTVQMENLESMKRKEDSY FNIRLRGFWPYAEMQNKIEFKLKQYGIEIRKVAPNNTSKTCSKCGHLNNYFNFEYRKKNKF PHFKCEKCNFKENAAYNAALNISNPKLKSTKEEP | Cas14/D326A/D510A/ D143R/E151V |
| 147 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSRVCYTRAAQLFKNAAIASGLRSKIKSNFRLKELKNMKSGLPTTKS DNFPIPLVKQKGGQYTGFEISNHNSDFIIKIPFGRWQVKKEIDKYRPWEKFDFEQVQKSPK PISLLLSTQRRKRNKGWSKDEGTEAEIKKVMNGDYQTSYIEVKRGSKICEKSAWMLNLSID VPKIDKGVDPSIIGGIAVGVKSPLVCAINNAFSRYSISDNDLFHFNKKMFARRRILLKKNRHK RAGHGAKNKLKPITILTEKSERFRKKLIERWACEIADFFIKNKVGTVQMENLESMKRKEDSY FNIRLRGFWPYAEMQNKIEFKLKQYGIEIRKVAPNNTSKTCSKCGHLNNYFNFEYRKKNKF PHFKCEKCNFKENAAYNAALNISNPKLKSTKEEP | Cas14/D326A/D510A/ D143R/E151Q |
| 148 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSRVCYTRAAMLFKNAAIASGLRSKIKSNFRLKELKNMKSGLPTTKS DNFPIPLVKQKGGQYTGFEISNHNSDFIIKIPFGRWQVKKEIDKYRPWEKFDFEQVQKSPK PISLLLSTQRRKRNKGWSKDEGTEAEIKKVMNGDYQTSYIEVKRGSKICEKSAWMLNLSID VPKIDKGVDPSIIGGIAVGVKSPLVCAINNAFSRYSISDNDLFHFNKKMFARRRILLKKNRHK RAGHGAKNKLKPITILTEKSERFRKKLIERWACEIADFFIKNKVGTVQMENLESMKRKEDSY FNIRLRGFWPYAEMQNKIEFKLKQYGIEIRKVAPNNTSKTCSKCGHLNNYFNFEYRKKNKF PHFKCEKCNFKENAAYNAALNISNPKLKSTKEEP | Cas14/D326A/D510A/ D143R/E151M |
| 149 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSRVCYTRAADLFKNAAIASGLRSKIKSNFRLKELKNMKSGLPTTKS DNFPIPLVKQKGGQYTGFEISNHNSDFIIKIPFGRWQVKKEIDKYRPWEKFDFEQVQKSPK PISLLLSTQRRKRNKGWSKDEGTEAEIKKVMNGDYQTSYIEVKRGSKICEKSAWMLNLSID VPKIDKGVDPSIIGGIAVGVKSPLVCAINNAFSRYSISDNDLFHFNKKMFARRRILLKKNRHK RAGHGAKNKLKPITILTEKSERFRKKLIERWACEIADFFIKNKVGTVQMENLESMKRKEDSY FNIRLRGFWPYAEMQNKIEFKLKQYGIEIRKVAPNNTSKTCSKCGHLNNYFNFEYRKKNKF PHFKCEKCNFKENAAYNAALNISNPKLKSTKEEP | Cas14/D326A/D510A/ D143R/E151D |
| 150 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSRVCYTRAANLFKNAAIASGLRSKIKSNFRLKELKNMKSGLPTTKS DNFPIPLVKQKGGQYTGFEISNHNSDFIIKIPFGRWQVKKEIDKYRPWEKFDFEQVQKSPK PISLLLSTQRRKRNKGWSKDEGTEAEIKKVMNGDYQTSYIEVKRGSKICEKSAWMLNLSID VPKIDKGVDPSIIGGIAVGVKSPLVCAINNAFSRYSISDNDLFHFNKKMFARRRILLKKNRHK RAGHGAKNKLKPITILTEKSERFRKKLIERWACEIADFFIKNKVGTVQMENLESMKRKEDSY FNIRLRGFWPYAEMQNKIEFKLKQYGIEIRKVAPNNTSKTCSKCGHLNNYFNFEYRKKNKF PHFKCEKCNFKENAAYNAALNISNPKLKSTKEEP | Cas14/D326A/D510A/ D143R/E151N |
| 151 | MAKNTITKTLKLRIVRPYNSAEVEKIVADEKNNREKIALEKNKDKVKEACSKHLKVAAYCTT QVERNACLFCKARKLDDKFYQKLRGQFPDAVFWQEISEIFRQLQKQAAEIYNQSLIELYYEI FIKGKGIANASSVEHYLSRVCYRRAAYLFKNAAIASGLRSKIKSNFRLKELKNMKSGLPTTKS DNFPIPLVKQKGGQYTGFEISNHNSDFIIKIPFGRWQVKKEIDKYRPWEKFDFEQVQKSPK PISLLLSTQRRKRNKGWSKDEGTEAEIKKVMNGDYQTSYIEVKRGSKICEKSAWMLNLSID VPKIDKGVDPSIIGGIAVGVKSPLVCAINNAFSRYSISDNDLFHFNKKMFARRRILLKKNRHK | Cas14/D326A/D510A/ D143R/E151Y |

| SEQ ID NO | Sequence | Description |
|---|---|---|
| | RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCEKCNFKENAAYNAALNISNPKLKSTKEEP | |
| 152 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLKQAAEIYNQSLIELYYEI<br>FIKGKGIANASSVEHYLSRVCYRRAAALFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIAVGVRSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCEKCNFKENAAYNAALNISNPKLKSTKREP | Cas14/D326A/D510A/<br>D143R/T147R/K330R/<br>E151A/E527R |
| 153 | MAKNTITKTLKLRIVRPYNSAEVEKIVADEKNNREKIALEKNKDKVKEACSKHLKVAAYCTT<br>QVERNACLFCKARKLDDKFYQKLRGQFPDAVFWQEISEIFRQLQKQAAEIYNQSLIELYYEI<br>FIKGKGIANASSVEHYLSRVCYRRAAALFKNAAIASGLRSKIKSNFRLKELKNMKSGLPTTKS<br>DNFPIPLVKQKGGQYTGFEISNHNSDFIIKIPFGRWQVKKEIDKYRPWEKFDFEQVQKSPK<br>PISLLLSTQRRKRNKGWSKDEGTEAEIKKVMNGDYQTSYIEVKRGSKICEKSAWMLNLSID<br>VPKIDKGVDPSIIGGIAVGVRSPLVCAINNAFSRYSISDNDLFHFNKKMFARRRILLKKNRHK<br>RAGHGAKNKLKPITILTEKSERFRKKLIERWACEIADFFIKNKVGTVQMENLESMKRKEDSY<br>FNIRLRGFWPYAEMQNKIEFKLKQYGIEIRKVAPNNTSKTCSKCGHLNNYFNFEYRKKNKF<br>PHFKCEKCNFKENAAYNAALNISNPKLKSTKERP | Cas14/D326A/D510A/<br>D143R/T147R/K330R/<br>E151A/E528R |
| 154 | PKKKRKVGSGSSKLEKFTNCYSLSKTLRFKAIPVGKTQENIDNKRLLVEDEKRAEDYKGVKKL<br>LDRYYLSFINDVLHSIKLKNLNNYISLFRKKTRTEKENKELENLEINLRKEIAKAFKGNEGYKSL<br>FKKDIIETILPEFLDDKDEIALVSNFNGFTTAFTGFFDNRENMFSEEAKSTSIAFRCINENLTRY<br>ISNMDIFEKVDAIFDKHEVQEIKEKILNSDYDVEDFFEGEFFNFVLTQEGIDVYNAIIGGFVTE<br>SGEKIKGLNEYINLYNQKTKQLPKFKPLYKQVLSDRESLSFYGEGYTSDEEVLEVFRNTLNK<br>NSEIFSSIKKLEKLFKNFDEYSSAGIFVKNGPAISTISKDIFGEWNVIRDKWNAEYDDIHLKKK<br>AVVTEKYEDDRRKSFKKIGSFSLEQLQEYADADLSVVEKLKEIIIQKVDEIYKVYGSSEKLFDA<br>DFVLEKSLKKNDAVVAIMKDLLDSVKSFENYIKAFFGEGKETNRDESFYGDFVLAYDILLKVD<br>HIYDAIRNYVTQKPYSKDKFKLYFQNPQFMGGWDKDKETDYRATILRYGSKYYAIMDKKY<br>AKCLQKIDKDDVNGNYEKINYKLLPGPNKMLPKVFFSKKWMAYYNPSEDIQKIYKNGTFKK<br>GDMFNLNDCHKLIDFFKDSISRYPKWSNAYDFNFSETEKYKDIAGFYREVEEQGYKVSFES<br>ASKKEVDKLVEEGKLYMFQIYNKDFSDKSHGTPNLHTMYFKLLFDENNHGQIRLSGGAELF<br>MRRASLKKEELVVHPANSPIANKNPDNPKKTTTLSYDVYKDKRFSEDQYELHIPIAINKCPK<br>NIFKINTEVRVLLKHDDNPYVIGIARGERNLLYIVVVDGKGNIVEQYSLNEIINNENGIRIKTD<br>YHSLLDKKEKERFEARQNWTSIENIKELKAGYISQVVHKICELVEKYDAVIALEDLNSGFKNS<br>RVKVEKQVYQKFEKMLIDKLNYMVDKKSNPCATGGALKGYQITNKFESFKSMSTQNGFIF<br>YIPAWLTSKIDPSTGFVNLLKTKYTSIADSKKFISSFDRIMYVPEEDLFEFALDYKNFSRTDAD<br>YIKKWKLYSYGNRIRIFRNPKKNNVFDWEEVCLTSAYKELFNKYGINYQQGDIRALLCEQSD<br>KAFYSSFMALMSLMLQMRNSITGRTDVDFLISPVKNSDGIFYDSRNYEAQENAILPKNAD<br>ANGAYNIARKVLWAIGQFKKAEDEKLDKVKIAISNKEWLEYAQTSVKHGSYPYDVPDYASL<br>GSGDGIGSGSNGSSLMDAKSLTAWSRTLVTFKDVFVDFTREEWKLLDTAQQIVYRNVML<br>ENYKNLVSLGYQLTKPDVILRLEKGEEPHMGGGSGEDPAAKRVKLDMGSGATNFSLLKQA<br>GDVEENPGPVSKGEEDNMAIIKEFMRFKVHMEGSVNGHEFEIEGEGEGRPYEGTQTAKL<br>KVTKGGPLPFAWDILSPQFMYGSKAYVKHPADIPDYLKLSFPEGFKWERVMNFEDGGVV<br>TVTQDSSLQDGEFIYKVKLRGTNFPSDGPVMQKKTMGWEASSERMYPEDGALKGEIKQR<br>LKLKDGGHYDAEVKTTYKAKKPVQLPGAYNVNIKLDITSHNEDYTIVEQYERAEGRHSTGG<br>MDELYK* | pSLQ7347<br>pHR-PGK-SV40_NLS-<br>dLbCpf1-KOX1_KRAB-c-<br>Myc_NLS-P2A-<br>mCherry-WPRE<br>SV40_NLS-dLbCpf1-<br>KOX1_KRAB-c-<br>Myc_NLS-P2A-mCherry |
| 155 | PKKKRKVGSGSSKLEKFTNCYSLSKTLRFKAIPVGKTQENIDNKRLLVEDEKRAEDYKGVKKL<br>LDRYYLSFINDVLHSIKLKNLNNYISLFRKKTRTEKENKELENLEINLRKEIAKAFKGNEGYKSL<br>FKKDIIETILPEFLDDKDEIALVSNFNGFTTAFTGFFDNRENMFSEEAKSTSIAFRCINENLTRY<br>ISNMDIFEKVDAIFDKHEVQEIKEKILNSDYDVEDFFEGEFFNFVLTQEGIDVYNAIIGGFVTE<br>SGEKIKGLNEYINLYNQKTKQLPKFKPLYKQVLSDRESLSFYGEGYTSDEEVLEVFRNTLNK<br>NSEIFSSIKKLEKLFKNFDEYSSAGIFVKNGPAISTISKDIFGEWNVIRDKWNAEYDDIHLKKK<br>AVVTEKYEDDRRKSFKKIGSFSLEQLQEYADADLSVVEKLKEIIIQKVDEIYKVYGSSEKLFDA<br>DFVLEKSLKKNDAVVAIMKDLLDSVKSFENYIKAFFGEGKETNRDESFYGDFVLAYDILLKVD<br>HIYDAIRNYVTQKPYSKDKFKLYFQNPQFMGGWDKDKETDYRATILRYGSKYYAIMDKKY<br>AKCLQKIDKDDVNGNYEKINYKLLPGPNKMLPKVFFSKKWMAYYNPSEDIQKIYKNGTFKK<br>GDMFNLNDCHKLIDFFKDSISRYPKWSNAYDFNFSETEKYKDIAGFYREVEEQGYKVSFES<br>ASKKEVDKLVEEGKLYMFQIYNKDFSDKSHGTPNLHTMYFKLLFDENNHGQIRLSGGAELF<br>MRRASLKKEELVVHPANSPIANKNPDNPKKTTTLSYDVYKDKRFSEDQYELHIPIAINKCPK<br>NIFKINTEVRVLLKHDDNPYVIGIARGERNLLYIVVVDGKGNIVEQYSLNEIINNFNGIRIKTD<br>YHSLLDKKEKERFEARQNWTSIENIKELKAGYISQVVHKICELVEKYDAVIALEDLNSGFKNS<br>RVKVEKQVYQKFEKMLIDKLNYMVDKKSNPCATGGALKGYQITNKFESFKSMSTQNGFIF<br>YIPAWLTSKIDPSTGFVNLLKTKYTSIADSKKFISSFDRIMYVPEEDLFEFALDYKNFSRTDAD<br>YIKKWKLYSYGNRIRIFRNPKKNNVFDWEEVCLTSAYKELFNKYGINYQQGDIRALLCEQSD<br>KAFYSSFMALMSLMLQMRNSITGRTDVDFLISPVKNSDGIFYSRNYEAQENAILPKNAD<br>ANGAYNIARKVLWAIGQFKKAEDEKLDKVKIAISNKEWLEYAQTSVKHGSYPYDVPDYASL<br>GSGDGIGSGSNGSSLMNSQGRVTFEDVTVNFTQGEWQRLNPEQRNLYRDVMLENYS<br>NLVSVGQETTKPDVILRLEQGKEPWLEEEEVLGSGRAEKNGDIGGGQIWKPKDVKESLAR<br>EVPSINKEHMGGGSGEDPAAKRVKLDMGSGATNFSLLKQAGDVEENPGPVSKGEEDNM<br>AIIKEFMRFKVHMEGSVNGHEFEIEGEGEGRPYEGTQTAKLKVTKGGPLPFAWDILSPQF | pSLQ7348<br>pHR-PGK-SV40_NLS-<br>dLbCpf1-ZIM3_KRAB-c-<br>Myc_NLS-P2A-<br>mCherry-WPRE<br>SV40_NLS-dLbCpf1-<br>ZIM3_KRAB-c-<br>Myc_NLS-P2A-mCherry |

| SEQ ID NO | Sequence | Description |
|---|---|---|
| | MYGSKAYVKHPADIPDYLKLSFPEGFKWERVMNFEDGGVVTVTQDSSLQDGEFIYKVKLR<br>GTNFPSDGPVMQKKTMGWEASSERMYPEDGALKGEIKQRLKLKDGGHYDAEVKTTYKA<br>KKPVQLPGAYNVNIKLDITSHNEDYTIVEQYERAEGRHSTGGMDELYK* | |
| 156 | PKKKRKVGSGSAKNTITKTLKLRIVRPYNSAEVEKIVADEKNNREKIALEKNKDKVKEACSKH<br>LKVAAYCTTQVERNACLFCKARKLDDKFYQKLRGQFPDAVFWQEISEIFRQLQKQAAEIYN<br>QSLIELYYEIFIKGKGIANASSVEHYLSDVCYTRAAELFKNAAIASGLRSKIKSNFRLKELKNMK<br>SGLPTTKSDNFPIPLVKQKGGQYTGFEISNHNSDFIIKIPFGRWQVKKEIDKYRPWEKFDFE<br>QVQKSPKPISLLLSTQRRKRNKGWSKDEGTEAEIKKVMNGDYQTSYIEVKRGSKICEKSAW<br>MLNLSIDVPKIDKGVDPSIIGGIAVGVKSPLVCAINNAFSRYSISDNDLFHFNKKMFARRRIL<br>LKKNRHKRAGHGAKNKLKPITILTEKSERFRKKLIERWACEIADFFIKNKVGTVQMENLESM<br>KRKEDSYFNIRLRGFWPYAEMQNKIEFKLKQYGIEIRKVAPNNTSKTCSKCGHLNNYFNFEY<br>RKKNKFPHFKCEKCNFKENAAYNAALNISNPKLKSTKEEPAYPYDVPDYASLGSGDGIGSGS<br>NGSSLMDAKSLTAWSRTLVTFKDVFVDFTREEWKLLDTAQQIVYRNVMLENYKNLVSLGY<br>QLTKPDVILRLEKGEEPHMGGGSGEDPAAKRVKLDMGSGVSKGEEDNMAIIKEFMRFKV<br>HMEGSVNGHEFEIEGEGEGRPYEGTQTAKLKVTKGGPLPFAWDILSPQFMYGSKAYVKH<br>PADIPDYLKLSFPEGFKWERVMNFEDGGVVTVTQDSSLQDGEFIYKVKLRGTNFPSDGPV<br>MQKKTMGWEASSERMYPEDGALKGEIKQRLKLKDGGHYDAEVKTTYKAKKPVQLPGAY<br>NVNIKLDITSHNEDYTIVEQYERAEGRHSTGGMDELYK* | pSL9701<br>pHR-PGK-SV40_NLS-<br>Cas14/D326A/D510A-<br>KOX1_KRAB-c-<br>Myc_NLS-mCherry-<br>WPRE<br>SV40_NLS-<br>Cas14/D326A/D510A-<br>KOX1_KRAB-c-<br>Myc_NLS-mCherry |
| 157 | PKKKRKVGSGSAKNTITKTLKLRIVRPYNSAEVEKIVADEKNNREKIALEKNKDKVKEACSKH<br>LKVAAYCTTQVERNACLFCKARKLDDKFYQKLRGQFPDAVFWQEISEIFRQLQKQAAEIYN<br>QSLIELYYEIFIKGKGIANASSVEHYLSDVCYTRAAELFKNAAIASGLRSKIKSNFRLKELKNMK<br>SGLPTTKSDNFPIPLVKQKGGQYTGFEISNHNSDFIIKIPFGRWQVKKEIDKYRPWEKFDFE<br>QVQKSPKPISLLLSTQRRKRNKGWSKDEGTEAEIKKVMNGDYQTSYIEVKRGSKICEKSAW<br>MLNLSIDVPKIDKGVDPSIIGGIAVGVKSPLVCAINNAFSRYSISDNDLFHFNKKMFARRRIL<br>LKKNRHKRAGHGAKNKLKPITILTEKSERFRKKLIERWACEIADFFIKNKVGTVQMENLESM<br>KRKEDSYFNIRLRGFWPYAEMQNKIEFKLKQYGIEIRKVAPNNTSKTCSKCGHLNNYENFEY<br>RKKNKFPHFKCEKCNFKENAAYNAALNISNPKLKSTKEEPAYPYDVPDYASLGSGDGIGSGS<br>NGSSLMNNSQGRVTFEDVTVNFTQGEWQRLNPEQRNLYRDVMLENYSNLVSVGQET<br>TKPDVILRLEQGKEPWLEEEEVLGSGRAEKNGDIGGQIWKPKDVKESLAREVPSINKEHM<br>GGGSGEDPAAKRVKLDMGSGVSKGEEDNMAIIKEFMRFKVHMEGSVNGHEFEIEGEGE<br>GRPYEGTQTAKLKVTKGGPLPFAWDILSPQFMYGSKAYVKHPADIPDYLKLSFPEGFKWE<br>RVMNFEDGGVVTVTQDSSLQDGEFIYKVKLRGTNFPSDGPVMQKKTMGWEASSERMY<br>PEDGALKGEIKQRLKLKDGGHYDAEVKTTYKAKKPVQLPGAYNVNIKLDITSHNEDYTIVEQ<br>YERAEGRHSTGGMDELYK* | pSL9702<br>pHR-PGK-SV40_NLS-<br>Cas14/D326A/D510A-<br>ZIM3_KRAB-c-<br>Myc_NLS-mCherry-<br>WPRE<br>SV40_NLS-<br>Cas14/D326A/D510A-<br>ZIM3_KRAB-c-<br>Myc_NLS-mCherry |
| 158 | PKKKRKVGSGSAKNTITKTLKLRIVRPYNSAEVEKIVADEKNNREKIALEKNKDKVKEACSKH<br>LKVAAYCTTQVERNACLFCKARKLDDKFYQKLRGQFPDAVFWQEISEIFRQLQKQAAEIYN<br>QSLIELYYEIFIKGKGIANASSVEHYLSRVCYTRAAELFKNAAIASGLRSKIKSNFRLKELKNMK<br>SGLPTTKSDNFPIPLVKQKGGQYTGFEISNHNSDFIIKIPFGRWQVKKEIDKYRPWEKFDFE<br>QVQKSPKPISLLLSTQRRKRNKGWSKDEGTEAEIKKVMNGDYQTSYIEVKRGSKICEKSAW<br>MLNLSIDVPKIDKGVDPSIIGGIAVGVKSPLVCAINNAFSRYSISDNDLFHFNKKMFARRRIL<br>LKKNRHKRAGHGAKNKLKPITILTEKSERFRKKLIERWACEIADFFIKNKVGTVQMENLESM<br>KRKEDSYFNIRLRGFWPYAEMQNKIEFKLKQYGIEIRKVAPNNTSKTCSKCGHLNNYFNFEY<br>RKKNKFPHFKCEKCNFKENAAYNAALNISNPKLKSTKEEPAYPYDVPDYASLGSGDGIGSGS<br>NGSSLMDAKSLTAWSRTLVTFKDVFVDFTREEWKLLDTAQQIVYRNVMLENYKNLVSLGY<br>QLTKPDVILRLEKGEEPHMGGGSGEDPAAKRVKLDMGSGVSKGEEDNMAIIKEFMRFKV<br>HMEGSVNGHEFEIEGEGEGRPYEGTQTAKLKVTKGGPLPFAWDILSPQFMYGSKAYVKH<br>PADIPDYLKLSFPEGFKWERVMNFEDGGVVTVTQDSSLQDGEFIYKVKLRGTNFPSDGPV<br>MQKKTMGWEASSERMYPEDGALKGEIKQRLKLKDGGHYDAEVKTTYKAKKPVQLPGAY<br>NVNIKLDITSHNEDYTIVEQYERAEGRHSTGGMDELYK* | pSL9703<br>pHR-PGK-SV40_NLS-<br>Cas14/D143R/D326A/<br>D510A-KOX1_KRAB-c-<br>Myc_NLS-mCherry-<br>WPRE<br>SV40_NLS-<br>Cas14/D143R/D326A/<br>D510A-KOX1_KRAB-c-<br>Myc_NLS-mCherry |
| 159 | PKKKRKVGSGSAKNTITKTLKLRIVRPYNSAEVEKIVADEKNNREKIALEKNKDKVKEACSKH<br>LKVAAYCTTQVERNACLFCKARKLDDKFYQKLRGQFPDAVFWQEISEIFRQLQKQAAEIYN<br>QSLIELYYEIFIKGKGIANASSVEHYLSRVCYTRAAELFKNAAIASGLRSKIKSNFRLKELKNMK<br>SGLPTTKSDNFPIPLVKQKGGQYTGFEISNHNSDFIIKIPFGRWQVKKEIDKYRPWEKFDFE<br>QVQKSPKPISLLLSTQRRKRNKGWSKDEGTEAEIKKVMNGDYQTSYIEVKRGSKICEKSAW<br>MLNLSIDVPKIDKGVDPSIIGGIAVGVKSPLVCAINNAFSRYSISDNDLFHFNKKMFARRRIL<br>LKKNRHKRAGHGAKNKLKPITILTEKSERFRKKLIERWACEIADFFIKNKVGTVQMENLESM<br>KRKEDSYFNIRLRGFWPYAEMQNKIEFKLKQYGIEIRKVAPNNTSKTCSKCGHLNNYENFEY<br>RKKNKFPHFKCEKCNFKENAAYNAALNISNPKLKSTKEEPAYPYDVPDYASLGSGDGIGSGS<br>NGSSLMNNSQGRVTFEDVTVNFTQGEWQRLNPEQRNLYRDVMLENYSNLVSVGQET<br>TKPDVILRLEQGKEPWLEEEEVLGSGRAEKNGDIGGQIWKPKDVKESLAREVPSINKEHM<br>GGGSGEDPAAKRVKLDMGSGVSKGEEDNMAIIKEFMRFKVHMEGSVNGHEFEIEGEGE<br>GRPYEGTQTAKLKVTKGGPLPFAWDILSPQFMYGSKAYVKHPADIPDYLKLSFPEGFKWE<br>RVMNFEDGGVVTVTQDSSLQDGEFIYKVKLRGTNFPSDGPVMQKKTMGWEASSERMY<br>PEDGALKGEIKQRLKLKDGGHYDAEVKTTYKAKKPVQLPGAYNVNIKLDITSHNEDYTIVEQ<br>YERAEGRHSTGGMDELYK* | pSL9704<br>pHR-PGK-SV40_NLS-<br>Cas14a1/D143R/D326A/<br>D510A-ZIM3_KRAB-c-<br>Myc_NLS-mCherry-<br>WPRE<br>SV40_NLS-<br>Cas14a1/D143R/D326A/<br>D510A-ZIM3_KRAB-c-<br>Myc_NLS-mCherry |
| 160 | PKKKRKVGSGSAKNTITKTLKLRIVRPYNSAEVEKIVADEKNNREKIALEKNKDKVKEACSKH<br>LKVAAYCTTQVERNACLFCKARKLDDKFYQKLRGQFPDAVFWQEISEIFRQLQKQAAEIYN<br>QSLIELYYEIFIKGKGIANASSVEHYLSRVCYRRAAELFKNAAIASGLRSKIKSNFRLKELKNMK<br>SGLPTTKSDNFPIPLVKQKGGQYTGFEISNHNSDFIIKIPFGRWQVKKEIDKYRPWEKFDFE<br>QVQKSPKPISLLLSTQRRKRNKGWSKDEGTEAEIKKVMNGDYQTSYIEVKRGSKICEKSAW<br>MLNLSIDVPKIDKGVDPSIIGGIAVGVKSPLVCAINNAFSRYSISDNDLFHFNKKMFARRRIL | pSL9705<br>pHR-PGK-SV40_NLS-<br>Cas14a1/D143R/T147R/<br>D326A/D510A-<br>KOX1_<br>KRAB-c- |

| SEQ ID NO | Sequence | Description |
|---|---|---|
| | LKKNRHKRAGHGAKNKLKPITILTEKSERFRKKLIERWACEIADFFIKNKVGTVQMENLESM<br>KRKEDSYFNIRLRGFWPYAEMQNKIEFKLKQYGIEIRKVAPNNTSKTCSKCGHLNNYFNFEY<br>RKKNKFPHFKCEKCNFKENAAYNAALNISNPKLKSTKEEPAYPYDVPDYASLGSGDGIGSGS<br>NGSSLMDAKSLTAWSRTLVTFKDVFVDFTREEWKLLDTAQQIVYRNVMLENYKNLVSLGY<br>QLTKPDVILRLEKGEEPHMGGGSGEDPAAKRVKLDMGSGVSKGEEDNMAIIKEFMRFKV<br>HMEGSVNGHEFEIEGEGEGRPYEGTQTAKLKVTKGGPLPFAWDILSPQFMYGSKAYVKH<br>PADIPDYLKLSFPEGFKWERVMNFEDGGVVTVTQDSSLQDGEFIYKVKLRGTNFPSDGPV<br>MQKKTMGWEASSERMYPEDGALKGEIKQRLKLKDGGHYDAEVKTTYKAKKPVQLPGAY<br>NVNIKLDITSHNEDYTIVEQYERAEGRHSTGGMDELYK* | Myc_NLS-mCherry-<br>WPRE<br>SV40_NLS-<br>Cas14a1/D143R/T147R/<br>D326A/D510A-<br>KOX1_KRAB-c-<br>Myc_NLS-mCherry |
| 161 | PKKKRKVGSGSAKNTITKTLKLRIVRPYNSAEVEKIVADEKNNREKIALEKNKDKVKEACSKH<br>LKVAAYCTTQVERNACLFCKARKLDDKFYQKLRGQFPDAVFWQEISEIFRQLQKQAAEIYN<br>QSLIELYYEIFIKGKGIANASSVEHYLSRVCYRRAAELFKNAAIASGLRSKIKSNFRLKELKNMK<br>SGLPTTKSDNFPIPLVKQKGGQYTGFEISNHNSDFIIKIPFGRWQVKKEIDKYRPWEKFDFE<br>QVQKSPKPISLLLSTQRRKRNKGWSKDEGTEAEIKKVMNGDYQTSYIEVKRGSKICEKSAW<br>MLNLSIDVPKIDKGVDPSIIGGIAVGVKSPLVCAINNAFSRYSISDNDLFHFNKKMFARRRIL<br>LKKNRHKRAGHGAKNKLKPITILTEKSERFRKKLIERWACEIADFFIKNKVGTVQMENLESM<br>KRKEDSYFNIRLRGFWPYAEMQNKIEFKLKQYGIEIRKVAPNNTSKTCSKCGHLNNYFNFEY<br>RKKNKFPHFKCEKCNFKENAAYNAALNISNPKLKSTKEEPAYPYDVPDYASLGSGDGIGSGS<br>NGSSLMNNSQGRVTFEDVTVNFTQGEWQRLNPEQRNLYRDVMLENYSNLVSVGQGET<br>TKPDVILRLEQGKEPWLEEEEVLGSGRAEKNGDIGGQIWKPKDVKESLAREVPSINKEHM<br>GGGSGEDPAAKRVKLDMGSGVSKGEEDNMAIIKEFMRFKVHMEGSVNGHEFEIEGEGE<br>GRPYEGTQTAKLKVTKGGPLPFAWDILSPQFMYGSKAYVKHPADIPDYLKLSFPEGFKWE<br>RVMNFEDGGVVTVTQDSSLQDGEFIYKVKLRGTNFPSDGPVMQKKTMGWEASSERMY<br>PEDGALKGEIKQRLKLKDGGHYDAEVKTTYKAKKPVQLPGAYNVNIKLDITSHNEDYTIVEQ<br>YERAEGRHSTGGMDELYK* | pSL9706<br>pHR-PGK-SV40_NLS-<br>Cas14a1/D143R/T147R/<br>D326A/D510A-<br>ZIM3_KRAB-c-<br>Myc_NLS-mCherry-<br>WPRE<br>SV40_NLS-<br>Cas14a1/D143R/T147R/<br>D326A/D510A-<br>ZIM3_KRAB-c-<br>Myc_NLS-mCherry |

Although the foregoing disclosure has been described in some detail by way of illustration and example for purpose of clarity of understanding, one of skill in the art will appreciate that certain changes and modifications within the spirit and scope of the disclosure may be practiced, e.g., within the scope of the appended claims. It should also be understood that aspects of the disclosure and portions of various recited embodiments and features can be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the disclosure. In addition, each reference provided herein is incorporated by reference in its entirety for all purposes to the same extent as if each reference was individually incorporated by reference.

```
                        SEQUENCE LISTING

Sequence total quantity: 253
SEQ ID NO: 1           moltype = AA  length = 529
FEATURE                Location/Qualifiers
REGION                 1..529
                       note = Description of Unknown: Cas14 sequence
source                 1..529
                       mol_type = protein
                       organism = unidentified
SEQUENCE: 1
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSDVCYTRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIDVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAD YNAALNISNP KLKSTKEEP              529

SEQ ID NO: 2           moltype = AA  length = 529
FEATURE                Location/Qualifiers
REGION                 1..529
                       note = Description of sequence: Modified CAS protein
source                 1..529
                       mol_type = protein
                       organism = synthetic construct
SEQUENCE: 2
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSRVCYTRAA ELFKNAAIAS GLRSKIKSNF RLKELKNMKS   180
```

```
GLPTTKSDNF PIPLVKQKGG QYTGFEISNH NSDFIIKIPF GRWQVKKEID KYRPWEKFDF  240
EQVQKSPKPI SLLLSTQRRK RNKGWSKDEG TEAEIKKVMN GDYQTSYIEV KRGSKICEKS  300
AWMLNLSIDV PKIDKGVDPS IIGGIDVGVK SPLVCAINNA FSRYSISDND LFHFNKKMFA  360
RRRILLKKNR HKRAGHGAKN KLKPITILTE KSERFRKKLI ERWACEIADF FIKNKVGTVQ  420
MENLESMKRK EDSYFNIRLR GFWPYAEMQN KIEFKLKQYG IEIRKVAPNN TSKTCSKCGH  480
LNNYFNFEYR KKNKFPHFKC EKCNFKENAD YNAALNISNP KLKSTKEEP              529

SEQ ID NO: 3               moltype = AA  length = 529
FEATURE                    Location/Qualifiers
REGION                     1..529
                           note = Description of sequence: Modified CAS protein
source                     1..529
                           mol_type = protein
                           organism = synthetic construct
SEQUENCE: 3
MAKNTITKTL KLRIVRPYNS AEVEKIVADE KNNREKIALE KNKDKVKEAC SKHLKVAAYC   60
TTQVERNACL FCKARKLDDK FYQKLRGQFP DAVFWQEISE IFRQLQKQAA EIYNQSLIEL  120
YYEIFIKGKG IANASSVEHY LSRVCYRRAA ELFKNAAIAS GLRSKIKSNF RLKELKNMKS  180
GLPTTKSDNF PIPLVKQKGG QYTGFEISNH NSDFIIKIPF GRWQVKKEID KYRPWEKFDF  240
EQVQKSPKPI SLLLSTQRRK RNKGWSKDEG TEAEIKKVMN GDYQTSYIEV KRGSKICEKS  300
AWMLNLSIDV PKIDKGVDPS IIGGIDVGVK SPLVCAINNA FSRYSISDND LFHFNKKMFA  360
RRRILLKKNR HKRAGHGAKN KLKPITILTE KSERFRKKLI ERWACEIADF FIKNKVGTVQ  420
MENLESMKRK EDSYFNIRLR GFWPYAEMQN KIEFKLKQYG IEIRKVAPNN TSKTCSKCGH  480
LNNYFNFEYR KKNKFPHFKC EKCNFKENAD YNAALNISNP KLKSTKEEP              529

SEQ ID NO: 4               moltype = AA  length = 529
FEATURE                    Location/Qualifiers
REGION                     1..529
                           note = Description of sequence: Modified CAS protein
source                     1..529
                           mol_type = protein
                           organism = synthetic construct
SEQUENCE: 4
MAKNTITKTL KLRIVRPYNS AEVEKIVADE KNNREKIALE KNKDKVKEAC SKHLKVAAYC   60
TTQVERNACL FCKARKLDDK FYQKLRGQFP DAVFWQEISE IFRQLQKQAA EIYNQSLIEL  120
YYEIFIKGKG IANASSVEHY LSRVCYRRAA ELFKNAAIAS GLRSKIKSNF RLKELKNMKS  180
GLPTTKSDNF PIPLVKQKGG QYTGFEISNH NSDFIIKIPF GRWQVKKEID KYRPWEKFDF  240
EQVQKSPKPI SLLLSTQRRK RNKGWSKDEG TEAEIKKVMN GDYQTSYIEV KRGSKICEKS  300
AWMLNLSIDV PKIDKGVDPS IIGGIDVGVR SPLVCAINNA FSRYSISDND LFHFNKKMFA  360
RRRILLKKNR HKRAGHGAKN KLKPITILTE KSERFRKKLI ERWACEIADF FIKNKVGTVQ  420
MENLESMKRK EDSYFNIRLR GFWPYAEMQN KIEFKLKQYG IEIRKVAPNN TSKTCSKCGH  480
LNNYFNFEYR KKNKFPHFKC EKCNFKENAD YNAALNISNP KLKSTKEEP              529

SEQ ID NO: 5               moltype = AA  length = 529
FEATURE                    Location/Qualifiers
REGION                     1..529
                           note = Description of sequence: Modified CAS protein
source                     1..529
                           mol_type = protein
                           organism = synthetic construct
SEQUENCE: 5
MAKNTITKTL KLRIVRPYNS AEVEKIVADE KNNREKIALE KNKDKVKEAC SKHLKVAAYC   60
TTQVERNACL FCKARKLDDK FYQKLRGQFP DAVFWQEISE IFRQLQKQAA EIYNQSLIEL  120
YYEIFIKGKG IANASSVEHY LSRVCYRRAA ELFKNAAIAS GLRSKIKSNF RLKELKNMKS  180
GLPTTKSDNF PIPLVKQKGG QYTGFEISNH NSDFIIKIPF GRWQVKKEID KYRPWEKFDF  240
EQVQKSPKPI SLLLSTQRRK RNKGWSKDEG TEAEIKKVMN GDYQTSYIEV KRGSKICEKS  300
AWMLNLSIDV PKIDKGVDPS IIGGIDVGVK SPLVCAINNA FSRYSISDND LFHFNKKMFA  360
RRRILLKKNR HKRAGHGAKN KLKPITILTE KSERFRKKLI ERWACEIADF FIKNKVGTVQ  420
MENLESMKRK EDSYFNIRLR GFWPYAEMQN KIEFKLKQYG IEIRKVAPNN TSKTCSKCGH  480
LNNYFNFEYR KKNKFPHFKC EKCNFKENAD YNAALNISNP KLKSTKERP              529

SEQ ID NO: 6               moltype = AA  length = 529
FEATURE                    Location/Qualifiers
REGION                     1..529
                           note = Description of sequence: Modified CAS protein
source                     1..529
                           mol_type = protein
                           organism = synthetic construct
SEQUENCE: 6
MAKNTITKTL KLRIVRPYNS AEVEKIVADE KNNREKIALE KNKDKVKEAC SKHLKVAAYC   60
TTQVERNACL FCKARKLDDK FYQKLRGQFP DAVFWQEISE IFRQLQKQAA EIYNQSLIEL  120
YYEIFIKGKG IANASSVEHY LSRVCYRRAA ALFKNAAIAS GLRSKIKSNF RLKELKNMKS  180
GLPTTKSDNF PIPLVKQKGG QYTGFEISNH NSDFIIKIPF GRWQVKKEID KYRPWEKFDF  240
EQVQKSPKPI SLLLSTQRRK RNKGWSKDEG TEAEIKKVMN GDYQTSYIEV KRGSKICEKS  300
AWMLNLSIDV PKIDKGVDPS IIGGIDVGVR SPLVCAINNA FSRYSISDND LFHFNKKMFA  360
RRRILLKKNR HKRAGHGAKN KLKPITILTE KSERFRKKLI ERWACEIADF FIKNKVGTVQ  420
MENLESMKRK EDSYFNIRLR GFWPYAEMQN KIEFKLKQYG IEIRKVAPNN TSKTCSKCGH  480
LNNYFNFEYR KKNKFPHFKC EKCNFKENAD YNAALNISNP KLKSTKERP              529
```

```
SEQ ID NO: 7                moltype = DNA  length = 228
FEATURE                     Location/Qualifiers
misc_feature                1..228
                            note = Description of Unknown: sgRNA sequence
variation                   206..228
                            note = n = a, c, t, g, unknown or other
source                      1..228
                            mol_type = genomic DNA
                            organism = unidentified
SEQUENCE: 7
gggcttcact gataaagtgg agaaccgctt caccaaaagc tgtcccttag gggattagaa    60
cttgagtgaa ggtgggctgc ttgcatcagc ctaatgtcga gaagtgcttt cttcggaaag   120
taaccctcga aacaaattca ttttcctct ccaattctgc acaagaaagt tgcagaaccc   180
gaatagacga atgaaggaat gcaacnnnnn nnnnnnnnnn nnnnnnnn                228

SEQ ID NO: 8                moltype = DNA  length = 228
FEATURE                     Location/Qualifiers
misc_feature                1..228
                            note = Description of sequence: Synthetic polynucleotide
variation                   206..228
                            note = n = a, c, t, g, unknown or other
source                      1..228
                            mol_type = other DNA
                            organism = synthetic construct
SEQUENCE: 8
gggcttcact gataaagtgg agaaccgctt caccaaaagc tgtcccttag gggattagaa    60
cttgagtgaa ggtgggctgc ttgcatcagc ctaatgtcga gaagtgcttt cttcggaaag   120
taaccctcga aacaaattca ttgttcctct ccaattctgc acaagaaagt tgcagaaccc   180
gaatagacga atgaaggaat gcaacnnnnn nnnnnnnnnn nnnnnnnn                228

SEQ ID NO: 9                moltype = DNA  length = 182
FEATURE                     Location/Qualifiers
misc_feature                1..182
                            note = Description of sequence: Synthetic polynucleotide
variation                   161..182
                            note = n = a, c, t, g, unknown or other
source                      1..182
                            mol_type = other DNA
                            organism = synthetic construct
SEQUENCE: 9
gggcttcact gataaagtgg agaaccgctt caccaaaagc tgtcccttag gggattagaa    60
cttgagtgaa ggtgggctgc ttgcatcagc ctaatgtcga gaagtgcttt cttcggaaag   120
taaccctcga aacaaattca tttgaatgaa ggaatgcaac nnnnnnnnnn nnnnnnnnnn   180
nn                                                                  182

SEQ ID NO: 10               moltype = DNA  length = 181
FEATURE                     Location/Qualifiers
misc_feature                1..181
                            note = Description of sequence: Synthetic polynucleotide
variation                   160..181
                            note = n = a, c, t, g, unknown or other
source                      1..181
                            mol_type = other DNA
                            organism = synthetic construct
SEQUENCE: 10
ggcttcactg ataaagtgga gaaccgcttc accaaaagct gtcccttagg ggattagaac    60
ttgagtgaag gtgggctgct tgcatcagcc taatgtcgag aagtgctttc ttcggaaagt   120
aaccctcgaa acaaattcat ttgaatgaag gaatgcaacn nnnnnnnnnn nnnnnnnnnn   180
n                                                                   181

SEQ ID NO: 11               moltype = AA  length = 529
FEATURE                     Location/Qualifiers
REGION                      1..529
                            note = Description of sequence: Modified CAS protein
source                      1..529
                            mol_type = protein
                            organism = synthetic construct
SEQUENCE: 11
MAKNTITKTL RLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSDVCYTRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIDVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAD YNAALNISNP KLKSTKEEP               529

SEQ ID NO: 12               moltype = AA  length = 529
```

```
FEATURE                 Location/Qualifiers
REGION                  1..529
                        note = Description of sequence: Modified CAS protein
source                  1..529
                        mol_type = protein
                        organism = synthetic construct
SEQUENCE: 12
MAKNTITKTL KLRIVRPYNS AEVEKIVADE KNNREKIALE KNKDKVKEAC SKHLKVAAYC    60
TTQVERNACL FCRARKLDDK FYQKLRGQFP DAVFWQEISE IFRQLQKQAA EIYNQSLIEL   120
YYEIFIKGKG IANASSVEHY LSDVCYTRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIDVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAD YNAALNISNP KLKSTKEEP              529

SEQ ID NO: 13           moltype = AA  length = 529
FEATURE                 Location/Qualifiers
REGION                  1..529
                        note = Description of sequence: Modified CAS protein
source                  1..529
                        mol_type = protein
                        organism = synthetic construct
SEQUENCE: 13
MAKNTITKTL KLRIVRPYNS AEVEKIVADE KNNREKIALE KNKDKVKEAC SKHLKVAAYC    60
TTQVERNACL FCRARKLDDK FYQKLRGQFP DAVFWQEISE IFRQLQKRAA EIYNQSLIEL   120
YYEIFIKGKG IANASSVEHY LSDVCYTRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIDVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAD YNAALNISNP KLKSTKEEP              529

SEQ ID NO: 14           moltype = AA  length = 529
FEATURE                 Location/Qualifiers
REGION                  1..529
                        note = Description of sequence: Modified CAS protein
source                  1..529
                        mol_type = protein
                        organism = synthetic construct
SEQUENCE: 14
MAKNTITKTL KLRIVRPYNS AEVEKIVADE KNNREKIALE KNKDKVKEAC SKHLKVAAYC    60
TTQVERNACL FCRARKLDDK FYQKLRGQFP DAVFWQEISE IFRQLQKQAA EIYNQSLIEL   120
YYEIFIKGKG IANASSVEHY LSDVCYRRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIDVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAD YNAALNISNP KLKSTKEEP              529

SEQ ID NO: 15           moltype = AA  length = 529
FEATURE                 Location/Qualifiers
REGION                  1..529
                        note = Description of sequence: Modified CAS protein
source                  1..529
                        mol_type = protein
                        organism = synthetic construct
SEQUENCE: 15
MAKNTITKTL KLRIVRPYNS AEVEKIVADE KNNREKIALE KNKDKVKEAC SKHLKVAAYC    60
TTQVERNACL FCRARKLDDK FYQKLRGQFP DAVFWQEISE IFRQLQKQAA EIYNQSLIEL   120
YYEIFIKGKG IANASSVEHY LSDVCYTRAA RLFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIDVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAD YNAALNISNP KLKSTKEEP              529

SEQ ID NO: 16           moltype = AA  length = 529
FEATURE                 Location/Qualifiers
REGION                  1..529
                        note = Description of sequence: Modified CAS protein
source                  1..529
                        mol_type = protein
                        organism = synthetic construct
SEQUENCE: 16
```

```
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSDVCYTRAA ELFRNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIDVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAD YNAALNISNP KLKSTKEEP              529

SEQ ID NO: 17          moltype = AA  length = 529
FEATURE                Location/Qualifiers
REGION                 1..529
                       note = Description of sequence: Modified CAS protein
source                 1..529
                       mol_type = protein
                       organism = synthetic construct
SEQUENCE: 17
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSDVCYTRAA ELFKRAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIDVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAD YNAALNISNP KLKSTKEEP              529

SEQ ID NO: 18          moltype = AA  length = 529
FEATURE                Location/Qualifiers
REGION                 1..529
                       note = Description of sequence: Modified CAS protein
source                 1..529
                       mol_type = protein
                       organism = synthetic construct
SEQUENCE: 18
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSDVCYTRAA ELFKNAAIAS GLRSKIKSNF RLKELKNMKS   180
GLPTTKSDNF PIPLVRQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIDVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAD YNAALNISNP KLKSTKEEP              529

SEQ ID NO: 19          moltype = AA  length = 529
FEATURE                Location/Qualifiers
REGION                 1..529
                       note = Description of sequence: Modified CAS protein
source                 1..529
                       mol_type = protein
                       organism = synthetic construct
SEQUENCE: 19
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSDVCYTRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
RQVQKSPKPI SLLLSTQRRK RNKGWSKDEG TEAEIKKVMN GDYQTSYIEV KRGSKICEKS   300
AWMLNLSIDV PKIDKGVDPS IIGGIDVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAD YNAALNISNP KLKSTKEEP              529

SEQ ID NO: 20          moltype = AA  length = 529
FEATURE                Location/Qualifiers
REGION                 1..529
                       note = Description of sequence: Modified CAS protein
source                 1..529
                       mol_type = protein
                       organism = synthetic construct
SEQUENCE: 20
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSDVCYTRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIRV KRGSKICEKS   300
AWMLNLSIDV PKIDKGVDPS IIGGIDVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
```

```
MENLESMKRK EDSYFNIRLR GFWPYAEMQN KIEFKLKQYG IEIRKVAPNN TSKTCSKCGH    480
LNNYFNFEYR KKNKFPHFKC EKCNFKENAD YNAALNISNP KLKSTKEEP               529

SEQ ID NO: 21              moltype = AA  length = 529
FEATURE                    Location/Qualifiers
REGION                     1..529
                           note = Description of sequence: Modified CAS protein
source                     1..529
                           mol_type = protein
                           organism = synthetic construct
SEQUENCE: 21
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSDVCYTRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVRPS IIGGIDVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAD YNAALNISNP KLKSTKEEP              529

SEQ ID NO: 22              moltype = AA  length = 529
FEATURE                    Location/Qualifiers
REGION                     1..529
                           note = Description of sequence: Modified CAS protein
source                     1..529
                           mol_type = protein
                           organism = synthetic construct
SEQUENCE: 22
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSDVCYTRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIDRGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAD YNAALNISNP KLKSTKEEP              529

SEQ ID NO: 23              moltype = AA  length = 529
FEATURE                    Location/Qualifiers
REGION                     1..529
                           note = Description of sequence: Modified CAS protein
source                     1..529
                           mol_type = protein
                           organism = synthetic construct
SEQUENCE: 23
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSDVCYTRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIDVGVR SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAD YNAALNISNP KLKSTKEEP              529

SEQ ID NO: 24              moltype = AA  length = 529
FEATURE                    Location/Qualifiers
REGION                     1..529
                           note = Description of sequence: Modified CAS protein
source                     1..529
                           mol_type = protein
                           organism = synthetic construct
SEQUENCE: 24
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSDVCYTRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIDVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLNSMKRK EDSYFNIRLR GFWPYAEMQN KIEFKLKQYG IEIRKVAPNN TSKTCSKCGH   480
LNNYFNFEYR KKNKFPHFKC EKCNFKENAD YNAALNISNP KLKSTKEEP              529

SEQ ID NO: 25              moltype = AA  length = 529
FEATURE                    Location/Qualifiers
REGION                     1..529
                           note = Description of sequence: Modified CAS protein
```

```
source                  1..529
                        mol_type = protein
                        organism = synthetic construct
SEQUENCE: 25
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSDVCYTRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIDVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLRQYG IEIRKVAPNN TSKTCSKCGH   480
LNNYFNFEYR KKNKFPHFKC EKCNFKENAD YNAALNISNP KLKSTKEEP              529

SEQ ID NO: 26           moltype = AA  length = 529
FEATURE                 Location/Qualifiers
REGION                  1..529
                        note = Description of sequence: Modified CAS protein
source                  1..529
                        mol_type = protein
                        organism = synthetic construct
SEQUENCE: 26
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSDVCYTRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIDVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IRIRKVAPNN TSKTCSKCGH   480
LNNYFNFEYR KKNKFPHFKC EKCNFKENAD YNAALNISNP KLKSTKEEP              529

SEQ ID NO: 27           moltype = AA  length = 529
FEATURE                 Location/Qualifiers
REGION                  1..529
                        note = Description of sequence: Modified CAS protein
source                  1..529
                        mol_type = protein
                        organism = synthetic construct
SEQUENCE: 27
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSDVCYTRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIDVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKR EKCNFKENAD YNAALNISNP KLKSTKEEP              529

SEQ ID NO: 28           moltype = AA  length = 529
FEATURE                 Location/Qualifiers
REGION                  1..529
                        note = Description of sequence: Modified CAS protein
source                  1..529
                        mol_type = protein
                        organism = synthetic construct
SEQUENCE: 28
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSDVCYTRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIDVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFRR EKCNFKENAD YNAALNISNP KLKSTKEEP              529

SEQ ID NO: 29           moltype = AA  length = 529
FEATURE                 Location/Qualifiers
REGION                  1..529
                        note = Description of sequence: Modified CAS protein
source                  1..529
                        mol_type = protein
                        organism = synthetic construct
SEQUENCE: 29
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSDVCYTRAA ELFKNAAIAS GLRSKIKSNF RLKELKNMKS   180
```

```
GLPTTKSDNF PIPLVKQKGG QYTGFEISNH NSDFIIKIPF GRWQVKKEID KYRPWEKFDF    240
EQVQKSPKPI SLLLSTQRRK RNKGWSKDEG TEAEIKKVMN GDYQTSYIEV KRGSKICEKS    300
AWMLNLSIDV PKIDKGVDPS IIGGIDVGVK SPLVCAINNA FSRYSISDND LFHFNKKMFA    360
RRRILLKKNR HKRAGHGAKN KLKPITILTE KSERFRKKLI ERWACEIADF FIKNKVGTVQ    420
MENLESMKRK EDSYFNIRLR GFWPYAEMQN KIEFKLKQYG IEIRKVAPNN TSKTCSKCGH    480
LNNYFNFEYR KKNKFPHFKC RKCNFKENAD YNAALNISNP KLKSTKEEP               529

SEQ ID NO: 30              moltype = AA   length = 529
FEATURE                    Location/Qualifiers
REGION                     1..529
                           note = Description of sequence: Modified CAS protein
source                     1..529
                           mol_type = protein
                           organism = synthetic construct
SEQUENCE: 30
MAKNTITKTL KLRIVRPYNS AEVEKIVADE KNNREKIALE KNKDKVKEAC SKHLKVAAYC     60
TTQVERNACL FCKARKLDDK FYQKLRGQFP DAVFWQEISE IFRQLQKQAA EIYNQSLIEL    120
YYEIFIKGKG IANASSVEHY LSDVCYTRAA ELFKNAAIAS GLRSKIKSNF RLKELKNMKS    180
GLPTTKSDNF PIPLVKQKGG QYTGFEISNH NSDFIIKIPF GRWQVKKEID KYRPWEKFDF    240
EQVQKSPKPI SLLLSTQRRK RNKGWSKDEG TEAEIKKVMN GDYQTSYIEV KRGSKICEKS    300
AWMLNLSIDV PKIDKGVDPS IIGGIDVGVK SPLVCAINNA FSRYSISDND LFHFNKKMFA    360
RRRILLKKNR HKRAGHGAKN KLKPITILTE KSERFRKKLI ERWACEIADF FIKNKVGTVQ    420
MENLESMKRK EDSYFNIRLR GFWPYAEMQN KIEFKLKQYG IEIRKVAPNN TSKTCSKCGH    480
LNNYFNFEYR KKNKFPHFKC EKCRFKENAD YNAALNISNP KLKSTKEEP               529

SEQ ID NO: 31              moltype = AA   length = 529
FEATURE                    Location/Qualifiers
REGION                     1..529
                           note = Description of sequence: Modified CAS protein
source                     1..529
                           mol_type = protein
                           organism = synthetic construct
SEQUENCE: 31
MAKNTITKTL KLRIVRPYNS AEVEKIVADE KNNREKIALE KNKDKVKEAC SKHLKVAAYC     60
TTQVERNACL FCKARKLDDK FYQKLRGQFP DAVFWQEISE IFRQLQKQAA EIYNQSLIEL    120
YYEIFIKGKG IANASSVEHY LSDVCYTRAA ELFKNAAIAS GLRSKIKSNF RLKELKNMKS    180
GLPTTKSDNF PIPLVKQKGG QYTGFEISNH NSDFIIKIPF GRWQVKKEID KYRPWEKFDF    240
EQVQKSPKPI SLLLSTQRRK RNKGWSKDEG TEAEIKKVMN GDYQTSYIEV KRGSKICEKS    300
AWMLNLSIDV PKIDKGVDPS IIGGIDVGVK SPLVCAINNA FSRYSISDND LFHFNKKMFA    360
RRRILLKKNR HKRAGHGAKN KLKPITILTE KSERFRKKLI ERWACEIADF FIKNKVGTVQ    420
MENLESMKRK EDSYFNIRLR GFWPYAEMQN KIEFKLKQYG IEIRKVAPNN TSKTCSKCGH    480
LNNYFNFEYR KKNKFPHFKC EKCNFKRNAD YNAALNISNP KLKSTKEEP               529

SEQ ID NO: 32              moltype = AA   length = 529
FEATURE                    Location/Qualifiers
REGION                     1..529
                           note = Description of sequence: Modified CAS protein
source                     1..529
                           mol_type = protein
                           organism = synthetic construct
SEQUENCE: 32
MAKNTITKTL KLRIVRPYNS AEVEKIVADE KNNREKIALE KNKDKVKEAC SKHLKVAAYC     60
TTQVERNACL FCKARKLDDK FYQKLRGQFP DAVFWQEISE IFRQLQKQAA EIYNQSLIEL    120
YYEIFIKGKG IANASSVEHY LSDVCYTRAA ELFKNAAIAS GLRSKIKSNF RLKELKNMKS    180
GLPTTKSDNF PIPLVKQKGG QYTGFEISNH NSDFIIKIPF GRWQVKKEID KYRPWEKFDF    240
EQVQKSPKPI SLLLSTQRRK RNKGWSKDEG TEAEIKKVMN GDYQTSYIEV KRGSKICEKS    300
AWMLNLSIDV PKIDKGVDPS IIGGIDVGVK SPLVCAINNA FSRYSISDND LFHFNKKMFA    360
RRRILLKKNR HKRAGHGAKN KLKPITILTE KSERFRKKLI ERWACEIADF FIKNKVGTVQ    420
MENLESMKRK EDSYFNIRLR GFWPYAEMQN KIEFKLKQYG IEIRKVAPNN TSKTCSKCGH    480
LNNYFNFEYR KKNKFPHFKC EKCNFKEDAD YNAALNISNP KLKSTKEEP               529

SEQ ID NO: 33              moltype = AA   length = 529
FEATURE                    Location/Qualifiers
REGION                     1..529
                           note = Description of sequence: Modified CAS protein
source                     1..529
                           mol_type = protein
                           organism = synthetic construct
SEQUENCE: 33
MAKNTITKTL KLRIVRPYNS AEVEKIVADE KNNREKIALE KNKDKVKEAC SKHLKVAAYC     60
TTQVERNACL FCKARKLDDK FYQKLRGQFP DAVFWQEISE IFRQLQKQAA EIYNQSLIEL    120
YYEIFIKGKG IANASSVEHY LSDVCYTRAA ELFKNAAIAS GLRSKIKSNF RLKELKNMKS    180
GLPTTKSDNF PIPLVKQKGG QYTGFEISNH NSDFIIKIPF GRWQVKKEID KYRPWEKFDF    240
EQVQKSPKPI SLLLSTQRRK RNKGWSKDEG TEAEIKKVMN GDYQTSYIEV KRGSKICEKS    300
AWMLNLSIDV PKIDKGVDPS IIGGIDVGVK SPLVCAINNA FSRYSISDND LFHFNKKMFA    360
RRRILLKKNR HKRAGHGAKN KLKPITILTE KSERFRKKLI ERWACEIADF FIKNKVGTVQ    420
MENLESMKRK EDSYFNIRLR GFWPYAEMQN KIEFKLKQYG IEIRKVAPNN TSKTCSKCGH    480
LNNYFNFEYR KKNKFPHFKC EKCNFKENAD ANAALNISNP KLKSTKEEP               529
```

```
SEQ ID NO: 34            moltype = AA  length = 529
FEATURE                  Location/Qualifiers
REGION                   1..529
                         note = Description of sequence: Modified CAS protein
source                   1..529
                         mol_type = protein
                         organism = synthetic construct
SEQUENCE: 34
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSDVCYTRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIDVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAD YNAGLNISNP KLKSTKEEP              529

SEQ ID NO: 35            moltype = AA  length = 528
FEATURE                  Location/Qualifiers
REGION                   1..528
                         note = Description of sequence: Modified CAS protein
source                   1..528
                         mol_type = protein
                         organism = synthetic construct
SEQUENCE: 35
AKNTITKTLK LRIVRPYNSA EVEKIVADEK NNREKIALEK NKDKVKEACS KHLKVAAYCT    60
TQVERNACLF CKARKLDDKF YQKLRGQFPD AVFWQEISEI FRQLQKQAAE IYNQSLIELY   120
YEIFIKGKGI ANASSVEHYL SDVCYTRAAE LFKNAAIASG LRSKIKSNFR LKELKNMKSG   180
LPTTKSDNFP IPLVKQKGGQ YTGFEISNHN SDFIIKIPPG RWQVKKEIDK YRPWEKFDFE   240
QVQKSPKPIS LLLSTQRRKR NKGWSKDEGT EAEIKKVMNG DYQTSYIEVK RGSKICEKSA   300
WMLNLSIDVP KIDKGVDPSI IGGIDVGVKS PLVCAINNAF SRYSISDNDL PHFNKKMFAR   360
RRILLKKNRH KRAGHGAKNK LKPITILTEK SERFRKKLIE RWACEIADFF IKNKVGTVQM   420
ENLESMKRKE DSYFNIRLRG FWPYAEMQNK IEFKLKQYGI EIRKVAPNNT SKTCSKCGHL   480
NNYFNFEYRK KNKFPHFKCE KCNFKENADY NAALRISNPK LKSTKEEP                528

SEQ ID NO: 36            moltype = AA  length = 529
FEATURE                  Location/Qualifiers
REGION                   1..529
                         note = Description of sequence: Modified CAS protein
source                   1..529
                         mol_type = protein
                         organism = synthetic construct
SEQUENCE: 36
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSDVCYTRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIDVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAD YNAALNISRP KLKSTKEEP              529

SEQ ID NO: 37            moltype = AA  length = 529
FEATURE                  Location/Qualifiers
REGION                   1..529
                         note = Description of sequence: Modified CAS protein
source                   1..529
                         mol_type = protein
                         organism = synthetic construct
SEQUENCE: 37
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSDVCYTRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIDVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAD YNAALNISNP KLKSTKREP              529

SEQ ID NO: 38            moltype = AA  length = 529
FEATURE                  Location/Qualifiers
REGION                   1..529
                         note = Description of sequence: Modified CAS protein
source                   1..529
                         mol_type = protein
                         organism = synthetic construct
```

```
SEQUENCE: 38
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKAA  EIYNQSLIEL   120
YYEIFIKGKG IANASSVEHY LSDVCYTRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIDVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAD YNAALNISNP KLKSTKERP              529

SEQ ID NO: 39           moltype = AA  length = 529
FEATURE                 Location/Qualifiers
REGION                  1..529
                        note = Description of sequence: Modified CAS protein
source                  1..529
                        mol_type = protein
                        organism = synthetic construct
SEQUENCE: 39
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKAA  EIYNQSLIEL   120
YYEIFIKGKG IANASSVEHY LSRVCYTRAA RLFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIDVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAD YNAALNISNP KLKSTKEEP              529

SEQ ID NO: 40           moltype = AA  length = 529
FEATURE                 Location/Qualifiers
REGION                  1..529
                        note = Description of sequence: Modified CAS protein
source                  1..529
                        mol_type = protein
                        organism = synthetic construct
SEQUENCE: 40
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKAA  EIYNQSLIEL   120
YYEIFIKGKG IANASSVEHY LSRVCYTRAA ELFRNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIDVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAD YNAALNISNP KLKSTKEEP              529

SEQ ID NO: 41           moltype = AA  length = 529
FEATURE                 Location/Qualifiers
REGION                  1..529
                        note = Description of sequence: Modified CAS protein
source                  1..529
                        mol_type = protein
                        organism = synthetic construct
SEQUENCE: 41
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKAA  EIYNQSLIEL   120
YYEIFIKGKG IANASSVEHY LSRVCYTRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
RQVQKSPKPI SLLLSTQRRK RNKGWSKDEG TEAEIKKVMN GDYQTSYIEV KRGSKICEKS   300
AWMLNLSIDV PKIDKGVDPS IIGGIDVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAD YNAALNISNP KLKSTKEEP              529

SEQ ID NO: 42           moltype = AA  length = 529
FEATURE                 Location/Qualifiers
REGION                  1..529
                        note = Description of sequence: Modified CAS protein
source                  1..529
                        mol_type = protein
                        organism = synthetic construct
SEQUENCE: 42
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKAA  EIYNQSLIEL   120
YYEIFIKGKG IANASSVEHY LSRVCYTRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIDVGVR SPLVCAINNA FSRYSISDND LFHFNKKMFA   360
```

```
RRRILLKKNR HKRAGHGAKN KLKPITILTE KSERFRKKLI ERWACEIADF FIKNKVGTVQ    420
MENLESMKRK EDSYFNIRLR GFWPYAEMQN KIEFKLKQYG IEIRKVAPNN TSKTCSKCGH    480
LNNYFNFEYR KKNKFPHFKC EKCNFKENAD YNAALNISNP KLKSTKEEP               529

SEQ ID NO: 43             moltype = AA   length = 529
FEATURE                   Location/Qualifiers
REGION                    1..529
                          note = Description of sequence: Modified CAS protein
source                    1..529
                          mol_type = protein
                          organism = synthetic construct
SEQUENCE: 43
MAKNTITKTL KLRIVRPYNS AEVEKIVADE KNNREKIALE KNKDKVKEAC SKHLKVAAYC     60
TTQVERNACL FCKARKLDDK FYQKLRGQFP DAVFWQEISE IFRQLQKQAA EIYNQSLIEL    120
YYEIFIKGKG IANASSVEHY LSRVCYTRAA ELFKNAAIAS GLRSKIKSNF RLKELKNMKS    180
GLPTTKSDNF PIPLVKQKGG QYTGFEISNH NSDFIIKIPF GRWQVKKEID KYRPWEKFDF    240
EQVQKSPKPI SLLLSTQRRK RNKGWSKDEG TEAEIKKVMN GDYQTSYIEV KRGSKICEKS    300
AWMLNLSIDV PKIDKGVDPS IIGGIDVGVK SPLVCAINNA FSRYSISDND LFHFNKKMFA    360
RRRILLKKNR HKRAGHGAKN KLKPITILTE KSERFRKKLI ERWACEIADF FIKNKVGTVQ    420
MENLNSMKRK EDSYFNIRLR GFWPYAEMQN KIEFKLKQYG IEIRKVAPNN TSKTCSKCGH    480
LNNYFNFEYR KKNKFPHFKC EKCNFKENAD YNAALNISNP KLKSTKEEP               529

SEQ ID NO: 44             moltype = AA   length = 529
FEATURE                   Location/Qualifiers
REGION                    1..529
                          note = Description of sequence: Modified CAS protein
source                    1..529
                          mol_type = protein
                          organism = synthetic construct
SEQUENCE: 44
MAKNTITKTL KLRIVRPYNS AEVEKIVADE KNNREKIALE KNKDKVKEAC SKHLKVAAYC     60
TTQVERNACL FCKARKLDDK FYQKLRGQFP DAVFWQEISE IFRQLQKQAA EIYNQSLIEL    120
YYEIFIKGKG IANASSVEHY LSRVCYTRAA ELFKNAAIAS GLRSKIKSNF RLKELKNMKS    180
GLPTTKSDNF PIPLVKQKGG QYTGFEISNH NSDFIIKIPF GRWQVKKEID KYRPWEKFDF    240
EQVQKSPKPI SLLLSTQRRK RNKGWSKDEG TEAEIKKVMN GDYQTSYIEV KRGSKICEKS    300
AWMLNLSIDV PKIDKGVDPS IIGGIDVGVK SPLVCAINNA FSRYSISDND LFHFNKKMFA    360
RRRILLKKNR HKRAGHGAKN KLKPITILTE KSERFRKKLI ERWACEIADF FIKNKVGTVQ    420
MENLESMKRK EDSYFNIRLR GFWPYAEMQN KIEFKLKQYG IEIRKVAPNN TSKTCSKCGH    480
LNNYFNFEYR KKNKFPHFKC EKCNFKRNAD YNAALNISNP KLKSTKEEP               529

SEQ ID NO: 45             moltype = AA   length = 529
FEATURE                   Location/Qualifiers
REGION                    1..529
                          note = Description of sequence: Modified CAS protein
source                    1..529
                          mol_type = protein
                          organism = synthetic construct
SEQUENCE: 45
MAKNTITKTL KLRIVRPYNS AEVEKIVADE KNNREKIALE KNKDKVKEAC SKHLKVAAYC     60
TTQVERNACL FCKARKLDDK FYQKLRGQFP DAVFWQEISE IFRQLQKQAA EIYNQSLIEL    120
YYEIFIKGKG IANASSVEHY LSRVCYTRAA ELFKNAAIAS GLRSKIKSNF RLKELKNMKS    180
GLPTTKSDNF PIPLVKQKGG QYTGFEISNH NSDFIIKIPF GRWQVKKEID KYRPWEKFDF    240
EQVQKSPKPI SLLLSTQRRK RNKGWSKDEG TEAEIKKVMN GDYQTSYIEV KRGSKICEKS    300
AWMLNLSIDV PKIDKGVDPS IIGGIDVGVK SPLVCAINNA FSRYSISDND LFHFNKKMFA    360
RRRILLKKNR HKRAGHGAKN KLKPITILTE KSERFRKKLI ERWACEIADF FIKNKVGTVQ    420
MENLESMKRK EDSYFNIRLR GFWPYAEMQN KIEFKLKQYG IEIRKVAPNN TSKTCSKCGH    480
LNNYFNFEYR KKNKFPHFKC EKCNFKENAD YNAALRISNP KLKSTKEEP               529

SEQ ID NO: 46             moltype = AA   length = 529
FEATURE                   Location/Qualifiers
REGION                    1..529
                          note = Description of sequence: Modified CAS protein
source                    1..529
                          mol_type = protein
                          organism = synthetic construct
SEQUENCE: 46
MAKNTITKTL KLRIVRPYNS AEVEKIVADE KNNREKIALE KNKDKVKEAC SKHLKVAAYC     60
TTQVERNACL FCKARKLDDK FYQKLRGQFP DAVFWQEISE IFRQLQKQAA EIYNQSLIEL    120
YYEIFIKGKG IANASSVEHY LSRVCYTRAA ELFKNAAIAS GLRSKIKSNF RLKELKNMKS    180
GLPTTKSDNF PIPLVKQKGG QYTGFEISNH NSDFIIKIPF GRWQVKKEID KYRPWEKFDF    240
EQVQKSPKPI SLLLSTQRRK RNKGWSKDEG TEAEIKKVMN GDYQTSYIEV KRGSKICEKS    300
AWMLNLSIDV PKIDKGVDPS IIGGIDVGVK SPLVCAINNA FSRYSISDND LFHFNKKMFA    360
RRRILLKKNR HKRAGHGAKN KLKPITILTE KSERFRKKLI ERWACEIADF FIKNKVGTVQ    420
MENLESMKRK EDSYFNIRLR GFWPYAEMQN KIEFKLKQYG IEIRKVAPNN TSKTCSKCGH    480
LNNYFNFEYR KKNKFPHFKC EKCNFKENAD YNAALNISRP KLKSTKEEP               529

SEQ ID NO: 47             moltype = AA   length = 529
FEATURE                   Location/Qualifiers
REGION                    1..529
```

```
                       note = Description of sequence: Modified CAS protein
source                 1..529
                       mol_type = protein
                       organism = synthetic construct
SEQUENCE: 47
MAKNTITKTL KLRIVRPYNS AEVEKIVADE KNNREKIALE KNKDKVKEAC SKHLKVAAYC  60
TTQVERNACL FCKARKLDDK FYQKLRGQFP DAVFWQEISE IFRQLQKQAA EIYNQSLIEL  120
YYEIFIKGKG IANASSVEHY LSRVCYTRAA ELFKNAAIAS GLRSKIKSNF RLKELKNMKS  180
GLPTTKSDNF PIPLVKQGG QYTGFEISNH NSDFIIKIPF GRWQVKKEID KYRPWEKFDF  240
EQVQKSPKPI SLLLSTQRRK RNKGWSKDEG TEAEIKKVMN GDYQTSYIEV KRGSKICEKS  300
AWMLNLSIDV PKIDKGVDPS IIGGIDVGVK SPLVCAINNA FSRYSISDND LFHFNKKMFA  360
RRRILLKKNR HKRAGHGAKN KLKPITILTE KSERFRKKLI ERWACEIADF FIKNKVGTVQ  420
MENLESMKRK EDSYFNIRLR GFWPYAEMQN KIEFKLKQYG IEIRKVAPNN TSKTCSKCGH  480
LNNYFNFEYR KKNKFPHFKC EKCNFKENAD YNAALNISNP KLKSTKREP             529

SEQ ID NO: 48          moltype = AA  length = 529
FEATURE                Location/Qualifiers
REGION                 1..529
                       note = Description of sequence: Modified CAS protein
source                 1..529
                       mol_type = protein
                       organism = synthetic construct
SEQUENCE: 48
MAKNTITKTL KLRIVRPYNS AEVEKIVADE KNNREKIALE KNKDKVKEAC SKHLKVAAYC  60
TTQVERNACL FCKARKLDDK FYQKLRGQFP DAVFWQEISE IFRQLQKQAA EIYNQSLIEL  120
YYEIFIKGKG IANASSVEHY LSRVCYTRAA ELFKNAAIAS GLRSKIKSNF RLKELKNMKS  180
GLPTTKSDNF PIPLVKQGG QYTGFEISNH NSDFIIKIPF GRWQVKKEID KYRPWEKFDF  240
EQVQKSPKPI SLLLSTQRRK RNKGWSKDEG TEAEIKKVMN GDYQTSYIEV KRGSKICEKS  300
AWMLNLSIDV PKIDKGVDPS IIGGIDVGVK SPLVCAINNA FSRYSISDND LFHFNKKMFA  360
RRRILLKKNR HKRAGHGAKN KLKPITILTE KSERFRKKLI ERWACEIADF FIKNKVGTVQ  420
MENLESMKRK EDSYFNIRLR GFWPYAEMQN KIEFKLKQYG IEIRKVAPNN TSKTCSKCGH  480
LNNYFNFEYR KKNKFPHFKC EKCNFKENAD YNAALNISNP KLKSTKERP             529

SEQ ID NO: 49          moltype = AA  length = 529
FEATURE                Location/Qualifiers
REGION                 1..529
                       note = Description of sequence: Modified CAS protein
source                 1..529
                       mol_type = protein
                       organism = synthetic construct
SEQUENCE: 49
MAKNTITKTL KLRIVRPYNS AEVEKIVADE KNNREKIALE KNKDKVKEAC SKHLKVAAYC  60
TTQVERNACL FCKARKLDDK FYQKLRGQFP DAVFWQEISE IFRQLQKQAA EIYNQSLIEL  120
YYEIFIKGKG IANASSVEHY LSRVCYRRAA RLFKNAAIAS GLRSKIKSNF RLKELKNMKS  180
GLPTTKSDNF PIPLVKQGG QYTGFEISNH NSDFIIKIPF GRWQVKKEID KYRPWEKFDF  240
EQVQKSPKPI SLLLSTQRRK RNKGWSKDEG TEAEIKKVMN GDYQTSYIEV KRGSKICEKS  300
AWMLNLSIDV PKIDKGVDPS IIGGIDVGVK SPLVCAINNA FSRYSISDND LFHFNKKMFA  360
RRRILLKKNR HKRAGHGAKN KLKPITILTE KSERFRKKLI ERWACEIADF FIKNKVGTVQ  420
MENLESMKRK EDSYFNIRLR GFWPYAEMQN KIEFKLKQYG IEIRKVAPNN TSKTCSKCGH  480
LNNYFNFEYR KKNKFPHFKC EKCNFKENAD YNAALNISNP KLKSTKEEP             529

SEQ ID NO: 50          moltype = AA  length = 529
FEATURE                Location/Qualifiers
REGION                 1..529
                       note = Description of sequence: Modified CAS protein
source                 1..529
                       mol_type = protein
                       organism = synthetic construct
SEQUENCE: 50
MAKNTITKTL KLRIVRPYNS AEVEKIVADE KNNREKIALE KNKDKVKEAC SKHLKVAAYC  60
TTQVERNACL FCKARKLDDK FYQKLRGQFP DAVFWQEISE IFRQLQKQAA EIYNQSLIEL  120
YYEIFIKGKG IANASSVEHY LSRVCYRRAA ELFRNAAIAS GLRSKIKSNF RLKELKNMKS  180
GLPTTKSDNF PIPLVKQGG QYTGFEISNH NSDFIIKIPF GRWQVKKEID KYRPWEKFDF  240
EQVQKSPKPI SLLLSTQRRK RNKGWSKDEG TEAEIKKVMN GDYQTSYIEV KRGSKICEKS  300
AWMLNLSIDV PKIDKGVDPS IIGGIDVGVK SPLVCAINNA FSRYSISDND LFHFNKKMFA  360
RRRILLKKNR HKRAGHGAKN KLKPITILTE KSERFRKKLI ERWACEIADF FIKNKVGTVQ  420
MENLESMKRK EDSYFNIRLR GFWPYAEMQN KIEFKLKQYG IEIRKVAPNN TSKTCSKCGH  480
LNNYFNFEYR KKNKFPHFKC EKCNFKENAD YNAALNISNP KLKSTKEEP             529

SEQ ID NO: 51          moltype = AA  length = 529
FEATURE                Location/Qualifiers
REGION                 1..529
                       note = Description of sequence: Modified CAS protein
source                 1..529
                       mol_type = protein
                       organism = synthetic construct
SEQUENCE: 51
MAKNTITKTL KLRIVRPYNS AEVEKIVADE KNNREKIALE KNKDKVKEAC SKHLKVAAYC  60
TTQVERNACL FCKARKLDDK FYQKLRGQFP DAVFWQEISE IFRQLQKQAA EIYNQSLIEL  120
```

```
YYEIFIKGKG IANASSVEHY LSRVCYRRAA ELFKNAAIAS GLRSKIKSNF RLKELKNMKS 180
GLPTTKSDNF PIPLVKQKGG QYTGFEISNH NSDFIIKIPF GRWQVKKEID KYRPWEKFDF 240
RQVQKSPKPI SLLLSTQRRK RNKGWSKDEG TEAEIKKVMN GDYQTSYIEV KRGSKICEKS 300
AWMLNLSIDV PKIDKGVDPS IIGGIDVGVK SPLVCAINNA FSRYSISDND LFHFNKKMFA 360
RRRILLKKNR HKRAGHGAKN KLKPITILTE KSERFRKKLI ERWACEIADF FIKNKVGTVQ 420
MENLESMKRK EDSYFNIRLR GFWPYAEMQN KIEFKLKQYG IEIRKVAPNN TSKTCSKCGH 480
LNNYFNFEYR KKNKFPHFKC EKCNFKENAD YNAALNISNP KLKSTKEEP            529

SEQ ID NO: 52              moltype = AA  length = 529
FEATURE                    Location/Qualifiers
REGION                     1..529
                           note = Description of sequence: Modified CAS protein
source                     1..529
                           mol_type = protein
                           organism = synthetic construct
SEQUENCE: 52
MAKNTITKTL KLRIVRPYNS AEVEKIVADE KNNREKIALE KNKDKVKEAC SKHLKVAAYC 60
TTQVERNACL FCKARKLDDK FYQKLRGQFP DAVFWQEISE IFRQLQKQAA EIYNQSLIEL 120
YYEIFIKGKG IANASSVEHY LSRVCYRRAA ELFKNAAIAS GLRSKIKSNF RLKELKNMKS 180
GLPTTKSDNF PIPLVKQKGG QYTGFEISNH NSDFIIKIPF GRWQVKKEID KYRPWEKFDF 240
EQVQKSPKPI SLLLSTQRRK RNKGWSKDEG TEAEIKKVMN GDYQTSYIEV KRGSKICEKS 300
AWMLNLSIDV PKIDKGVDPS IIGGIDVGVK SPLVCAINNA FSRYSISDND LFHFNKKMFA 360
RRRILLKKNR HKRAGHGAKN KLKPITILTE KSERFRKKLI ERWACEIADF FIKNKVGTVQ 420
MENLNSMKRK EDSYFNIRLR GFWPYAEMQN KIEFKLKQYG IEIRKVAPNN TSKTCSKCGH 480
LNNYFNFEYR KKNKFPHFKC EKCNFKENAD YNAALNISNP KLKSTKEEP            529

SEQ ID NO: 53              moltype = AA  length = 529
FEATURE                    Location/Qualifiers
REGION                     1..529
                           note = Description of sequence: Modified CAS protein
source                     1..529
                           mol_type = protein
                           organism = synthetic construct
SEQUENCE: 53
MAKNTITKTL KLRIVRPYNS AEVEKIVADE KNNREKIALE KNKDKVKEAC SKHLKVAAYC 60
TTQVERNACL FCKARKLDDK FYQKLRGQFP DAVFWQEISE IFRQLQKQAA EIYNQSLIEL 120
YYEIFIKGKG IANASSVEHY LSRVCYRRAA ELFKNAAIAS GLRSKIKSNF RLKELKNMKS 180
GLPTTKSDNF PIPLVKQKGG QYTGFEISNH NSDFIIKIPF GRWQVKKEID KYRPWEKFDF 240
EQVQKSPKPI SLLLSTQRRK RNKGWSKDEG TEAEIKKVMN GDYQTSYIEV KRGSKICEKS 300
AWMLNLSIDV PKIDKGVDPS IIGGIDVGVK SPLVCAINNA FSRYSISDND LFHFNKKMFA 360
RRRILLKKNR HKRAGHGAKN KLKPITILTE KSERFRKKLI ERWACEIADF FIKNKVGTVQ 420
MENLESMKRK EDSYFNIRLR GFWPYAEMQN KIEFKLKQYG IEIRKVAPNN TSKTCSKCGH 480
LNNYFNFEYR KKNKFPHFKC EKCNFKRNAD YNAALNISNP KLKSTKEEP            529

SEQ ID NO: 54              moltype = AA  length = 529
FEATURE                    Location/Qualifiers
REGION                     1..529
                           note = Description of sequence: Modified CAS protein
source                     1..529
                           mol_type = protein
                           organism = synthetic construct
SEQUENCE: 54
MAKNTITKTL KLRIVRPYNS AEVEKIVADE KNNREKIALE KNKDKVKEAC SKHLKVAAYC 60
TTQVERNACL FCKARKLDDK FYQKLRGQFP DAVFWQEISE IFRQLQKQAA EIYNQSLIEL 120
YYEIFIKGKG IANASSVEHY LSRVCYRRAA ELFKNAAIAS GLRSKIKSNF RLKELKNMKS 180
GLPTTKSDNF PIPLVKQKGG QYTGFEISNH NSDFIIKIPF GRWQVKKEID KYRPWEKFDF 240
EQVQKSPKPI SLLLSTQRRK RNKGWSKDEG TEAEIKKVMN GDYQTSYIEV KRGSKICEKS 300
AWMLNLSIDV PKIDKGVDPS IIGGIDVGVK SPLVCAINNA FSRYSISDND LFHFNKKMFA 360
RRRILLKKNR HKRAGHGAKN KLKPITILTE KSERFRKKLI ERWACEIADF FIKNKVGTVQ 420
MENLESMKRK EDSYFNIRLR GFWPYAEMQN KIEFKLKQYG IEIRKVAPNN TSKTCSKCGH 480
LNNYFNFEYR KKNKFPHFKC EKCNFKENAD YNAALRISNP KLKSTKEEP            529

SEQ ID NO: 55              moltype = AA  length = 529
FEATURE                    Location/Qualifiers
REGION                     1..529
                           note = Description of sequence: Modified CAS protein
source                     1..529
                           mol_type = protein
                           organism = synthetic construct
SEQUENCE: 55
MAKNTITKTL KLRIVRPYNS AEVEKIVADE KNNREKIALE KNKDKVKEAC SKHLKVAAYC 60
TTQVERNACL FCKARKLDDK FYQKLRGQFP DAVFWQEISE IFRQLQKQAA EIYNQSLIEL 120
YYEIFIKGKG IANASSVEHY LSRVCYRRAA ELFKNAAIAS GLRSKIKSNF RLKELKNMKS 180
GLPTTKSDNF PIPLVKQKGG QYTGFEISNH NSDFIIKIPF GRWQVKKEID KYRPWEKFDF 240
EQVQKSPKPI SLLLSTQRRK RNKGWSKDEG TEAEIKKVMN GDYQTSYIEV KRGSKICEKS 300
AWMLNLSIDV PKIDKGVDPS IIGGIDVGVK SPLVCAINNA FSRYSISDND LFHFNKKMFA 360
RRRILLKKNR HKRAGHGAKN KLKPITILTE KSERFRKKLI ERWACEIADF FIKNKVGTVQ 420
MENLESMKRK EDSYFNIRLR GFWPYAEMQN KIEFKLKQYG IEIRKVAPNN TSKTCSKCGH 480
LNNYFNFEYR KKNKFPHFKC EKCNFKENAD YNAALNISRP KLKSTKEEP            529
```

```
SEQ ID NO: 56          moltype = AA  length = 529
FEATURE                Location/Qualifiers
REGION                 1..529
                       note = Description of sequence: Modified CAS protein
source                 1..529
                       mol_type = protein
                       organism = synthetic construct
SEQUENCE: 56
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSRVCYRRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIDVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAD YNAALNISNP KLKSTKREP              529

SEQ ID NO: 57          moltype = AA  length = 529
FEATURE                Location/Qualifiers
REGION                 1..529
                       note = Description of sequence: Modified CAS protein
source                 1..529
                       mol_type = protein
                       organism = synthetic construct
SEQUENCE: 57
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSRVCYRRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIDVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAD YNAALNISNP KLKSTKERP              529

SEQ ID NO: 58          moltype = AA  length = 529
FEATURE                Location/Qualifiers
REGION                 1..529
                       note = Description of sequence: Modified CAS protein
source                 1..529
                       mol_type = protein
                       organism = synthetic construct
SEQUENCE: 58
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSRVCYRRAA SLFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIDVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAD YNAALNISNP KLKSTKEEP              529

SEQ ID NO: 59          moltype = AA  length = 529
FEATURE                Location/Qualifiers
REGION                 1..529
                       note = Description of sequence: Modified CAS protein
source                 1..529
                       mol_type = protein
                       organism = synthetic construct
SEQUENCE: 59
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSRVCYRRAA GLFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIDVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAD YNAALNISNP KLKSTKEEP              529

SEQ ID NO: 60          moltype = AA  length = 529
FEATURE                Location/Qualifiers
REGION                 1..529
                       note = Description of sequence: Modified CAS protein
source                 1..529
                       mol_type = protein
```

```
                         organism = synthetic construct
SEQUENCE: 60
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSRVCYRRAA ALFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIDVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAD YNAALNISNP KLKSTKEEP              529

SEQ ID NO: 61               moltype = AA  length = 529
FEATURE                     Location/Qualifiers
REGION                      1..529
                            note = Description of sequence: Modified CAS protein
source                      1..529
                            mol_type = protein
                            organism = synthetic construct
SEQUENCE: 61
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSRVCYTRAA LLFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIDVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAD YNAALNISNP KLKSTKEEP              529

SEQ ID NO: 62               moltype = AA  length = 529
FEATURE                     Location/Qualifiers
REGION                      1..529
                            note = Description of sequence: Modified CAS protein
source                      1..529
                            mol_type = protein
                            organism = synthetic construct
SEQUENCE: 62
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSRVCYTRAA SLFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIDVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAD YNAALNISNP KLKSTKEEP              529

SEQ ID NO: 63               moltype = AA  length = 529
FEATURE                     Location/Qualifiers
REGION                      1..529
                            note = Description of sequence: Modified CAS protein
source                      1..529
                            mol_type = protein
                            organism = synthetic construct
SEQUENCE: 63
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSRVCYTRAA TLFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIDVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAD YNAALNISNP KLKSTKEEP              529

SEQ ID NO: 64               moltype = AA  length = 529
FEATURE                     Location/Qualifiers
REGION                      1..529
                            note = Description of sequence: Modified CAS protein
source                      1..529
                            mol_type = protein
                            organism = synthetic construct
SEQUENCE: 64
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSRVCYTRAA WLFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
```

```
AWMLNLSIDV PKIDKGVDPS IIGGIDVGVK SPLVCAINNA FSRYSISDND LFHFNKKMFA     360
RRRILLKKNR HKRAGHGAKN KLKPITILTE KSERFRKKLI ERWACEIADF FIKNKVGTVQ     420
MENLESMKRK EDSYFNIRLR GFWPYAEMQN KIEFKLKQYG IEIRKVAPNN TSKTCSKCGH     480
LNNYFNFEYR KKNKFPHFKC EKCNFKENAD YNAALNISNP KLKSTKEEP                529

SEQ ID NO: 65            moltype = AA   length = 529
FEATURE                  Location/Qualifiers
REGION                   1..529
                         note = Description of sequence: Modified CAS protein
source                   1..529
                         mol_type = protein
                         organism = synthetic construct
SEQUENCE: 65
MAKNTITKTL KLRIVRPYNS AEVEKIVADE KNNREKIALE KNKDKVKEAC SKHLKVAAYC      60
TTQVERNACL FCKARKLDDK FYQKLRGQFP DAVFWQEISE IFRQLQKQAA EIYNQSLIEL     120
YYEIFIKGKG IANASSVEHY LSRVCYTRAA FLFKNAAIAS GLRSKIKSNF RLKELKNMKS     180
GLPTTKSDNF PIPLVKQKGG QYTGFEISNH NSDFIIKIPF GRWQVKKEID KYRPWEKFDF     240
EQVQKSPKPI SLLLSTQRRK RNKGWSKDEG TEAEIKKVMN GDYQTSYIEV KRGSKICEKS     300
AWMLNLSIDV PKIDKGVDPS IIGGIDVGVK SPLVCAINNA FSRYSISDND LFHFNKKMFA     360
RRRILLKKNR HKRAGHGAKN KLKPITILTE KSERFRKKLI ERWACEIADF FIKNKVGTVQ     420
MENLESMKRK EDSYFNIRLR GFWPYAEMQN KIEFKLKQYG IEIRKVAPNN TSKTCSKCGH     480
LNNYFNFEYR KKNKFPHFKC EKCNFKENAD YNAALNISNP KLKSTKEEP                529

SEQ ID NO: 66            moltype = AA   length = 529
FEATURE                  Location/Qualifiers
REGION                   1..529
                         note = Description of sequence: Modified CAS protein
source                   1..529
                         mol_type = protein
                         organism = synthetic construct
SEQUENCE: 66
MAKNTITKTL KLRIVRPYNS AEVEKIVADE KNNREKIALE KNKDKVKEAC SKHLKVAAYC      60
TTQVERNACL FCKARKLDDK FYQKLRGQFP DAVFWQEISE IFRQLQKQAA EIYNQSLIEL     120
YYEIFIKGKG IANASSVEHY LSRVCYTRAA CLFKNAAIAS GLRSKIKSNF RLKELKNMKS     180
GLPTTKSDNF PIPLVKQKGG QYTGFEISNH NSDFIIKIPF GRWQVKKEID KYRPWEKFDF     240
EQVQKSPKPI SLLLSTQRRK RNKGWSKDEG TEAEIKKVMN GDYQTSYIEV KRGSKICEKS     300
AWMLNLSIDV PKIDKGVDPS IIGGIDVGVK SPLVCAINNA FSRYSISDND LFHFNKKMFA     360
RRRILLKKNR HKRAGHGAKN KLKPITILTE KSERFRKKLI ERWACEIADF FIKNKVGTVQ     420
MENLESMKRK EDSYFNIRLR GFWPYAEMQN KIEFKLKQYG IEIRKVAPNN TSKTCSKCGH     480
LNNYFNFEYR KKNKFPHFKC EKCNFKENAD YNAALNISNP KLKSTKEEP                529

SEQ ID NO: 67            moltype = AA   length = 529
FEATURE                  Location/Qualifiers
REGION                   1..529
                         note = Description of sequence: Modified CAS protein
source                   1..529
                         mol_type = protein
                         organism = synthetic construct
SEQUENCE: 67
MAKNTITKTL KLRIVRPYNS AEVEKIVADE KNNREKIALE KNKDKVKEAC SKHLKVAAYC      60
TTQVERNACL FCKARKLDDK FYQKLRGQFP DAVFWQEISE IFRQLQKQAA EIYNQSLIEL     120
YYEIFIKGKG IANASSVEHY LSRVCYTRAA KLFKNAAIAS GLRSKIKSNF RLKELKNMKS     180
GLPTTKSDNF PIPLVKQKGG QYTGFEISNH NSDFIIKIPF GRWQVKKEID KYRPWEKFDF     240
EQVQKSPKPI SLLLSTQRRK RNKGWSKDEG TEAEIKKVMN GDYQTSYIEV KRGSKICEKS     300
AWMLNLSIDV PKIDKGVDPS IIGGIDVGVK SPLVCAINNA FSRYSISDND LFHFNKKMFA     360
RRRILLKKNR HKRAGHGAKN KLKPITILTE KSERFRKKLI ERWACEIADF FIKNKVGTVQ     420
MENLESMKRK EDSYFNIRLR GFWPYAEMQN KIEFKLKQYG IEIRKVAPNN TSKTCSKCGH     480
LNNYFNFEYR KKNKFPHFKC EKCNFKENAD YNAALNISNP KLKSTKEEP                529

SEQ ID NO: 68            moltype = AA   length = 529
FEATURE                  Location/Qualifiers
REGION                   1..529
                         note = Description of sequence: Modified CAS protein
source                   1..529
                         mol_type = protein
                         organism = synthetic construct
SEQUENCE: 68
MAKNTITKTL KLRIVRPYNS AEVEKIVADE KNNREKIALE KNKDKVKEAC SKHLKVAAYC      60
TTQVERNACL FCKARKLDDK FYQKLRGQFP DAVFWQEISE IFRQLQKQAA EIYNQSLIEL     120
YYEIFIKGKG IANASSVEHY LSRVCYTRAA GLFKNAAIAS GLRSKIKSNF RLKELKNMKS     180
GLPTTKSDNF PIPLVKQKGG QYTGFEISNH NSDFIIKIPF GRWQVKKEID KYRPWEKFDF     240
EQVQKSPKPI SLLLSTQRRK RNKGWSKDEG TEAEIKKVMN GDYQTSYIEV KRGSKICEKS     300
AWMLNLSIDV PKIDKGVDPS IIGGIDVGVK SPLVCAINNA FSRYSISDND LFHFNKKMFA     360
RRRILLKKNR HKRAGHGAKN KLKPITILTE KSERFRKKLI ERWACEIADF FIKNKVGTVQ     420
MENLESMKRK EDSYFNIRLR GFWPYAEMQN KIEFKLKQYG IEIRKVAPNN TSKTCSKCGH     480
LNNYFNFEYR KKNKFPHFKC EKCNFKENAD YNAALNISNP KLKSTKEEP                529

SEQ ID NO: 69            moltype = AA   length = 529
FEATURE                  Location/Qualifiers
```

```
REGION                  1..529
                        note = Description of sequence: Modified CAS protein
source                  1..529
                        mol_type = protein
                        organism = synthetic construct
SEQUENCE: 69
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSRVCYTRAA ILFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIDVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAD YNAALNISNP KLKSTKEEP              529

SEQ ID NO: 70           moltype = AA   length = 529
FEATURE                 Location/Qualifiers
REGION                  1..529
                        note = Description of sequence: Modified CAS protein
source                  1..529
                        mol_type = protein
                        organism = synthetic construct
SEQUENCE: 70
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSRVCYTRAA PLFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIDVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAD YNAALNISNP KLKSTKEEP              529

SEQ ID NO: 71           moltype = AA   length = 529
FEATURE                 Location/Qualifiers
REGION                  1..529
                        note = Description of sequence: Modified CAS protein
source                  1..529
                        mol_type = protein
                        organism = synthetic construct
SEQUENCE: 71
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSRVCYTRAA HLFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIDVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAD YNAALNISNP KLKSTKEEP              529

SEQ ID NO: 72           moltype = AA   length = 529
FEATURE                 Location/Qualifiers
REGION                  1..529
                        note = Description of sequence: Modified CAS protein
source                  1..529
                        mol_type = protein
                        organism = synthetic construct
SEQUENCE: 72
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSRVCYTRAA ALFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIDVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAD YNAALNISNP KLKSTKEEP              529

SEQ ID NO: 73           moltype = AA   length = 529
FEATURE                 Location/Qualifiers
REGION                  1..529
                        note = Description of sequence: Modified CAS protein
source                  1..529
                        mol_type = protein
                        organism = synthetic construct
SEQUENCE: 73
MAKNTITKTL KLRIVRPYNS AEVEKIVADE KNNREKIALE KNKDKVKEAC SKHLKVAAYC    60
```

```
TTQVERNACL FCKARKLDDK FYQKLRGQFP DAVFWQEISE IFRQLQKQAA EIYNQSLIEL    120
YYEIFIKGKG IANASSVEHY LSRVCYTRAA VLFKNAAIAS GLRSKIKSNF RLKELKNMKS    180
GLPTTKSDNF PIPLVKQKGG QYTGFEISNH NSDFIIKIPF GRWQVKKEID KYRPWEKFDF    240
EQVQKSPKPI SLLLSTQRRK RNKGWSKDEG TEAEIKKVMN GDYQTSYIEV KRGSKICEKS    300
AWMLNLSIDV PKIDKGVDPS IIGGIDVGVK SPLVCAINNA FSRYSISDND LFHFNKKMFA    360
RRRILLKKNR HKRAGHGAKN KLKPITILTE KSERFRKKLI ERWACEIADF FIKNKVGTVQ    420
MENLESMKRK EDSYFNIRLR GFWPYAEMQN KIEFKLKQYG IEIRKVAPNN TSKTCSKCGH    480
LNNYFNFEYR KKNKFPHFKC EKCNFKENAD YNAALNISNP KLKSTKEEP              529

SEQ ID NO: 74        moltype = AA  length = 529
FEATURE              Location/Qualifiers
REGION               1..529
                     note = Description of sequence: Modified CAS protein
source               1..529
                     mol_type = protein
                     organism = synthetic construct
SEQUENCE: 74
MAKNTITKTL KLRIVRPYNS AEVEKIVADE KNNREKIALE KNKDKVKEAC SKHLKVAAYC     60
TTQVERNACL FCKARKLDDK FYQKLRGQFP DAVFWQEISE IFRQLQKQAA EIYNQSLIEL    120
YYEIFIKGKG IANASSVEHY LSRVCYTRAA QLFKNAAIAS GLRSKIKSNF RLKELKNMKS    180
GLPTTKSDNF PIPLVKQKGG QYTGFEISNH NSDFIIKIPF GRWQVKKEID KYRPWEKFDF    240
EQVQKSPKPI SLLLSTQRRK RNKGWSKDEG TEAEIKKVMN GDYQTSYIEV KRGSKICEKS    300
AWMLNLSIDV PKIDKGVDPS IIGGIDVGVK SPLVCAINNA FSRYSISDND LFHFNKKMFA    360
RRRILLKKNR HKRAGHGAKN KLKPITILTE KSERFRKKLI ERWACEIADF FIKNKVGTVQ    420
MENLESMKRK EDSYFNIRLR GFWPYAEMQN KIEFKLKQYG IEIRKVAPNN TSKTCSKCGH    480
LNNYFNFEYR KKNKFPHFKC EKCNFKENAD YNAALNISNP KLKSTKEEP              529

SEQ ID NO: 75        moltype = AA  length = 529
FEATURE              Location/Qualifiers
REGION               1..529
                     note = Description of sequence: Modified CAS protein
source               1..529
                     mol_type = protein
                     organism = synthetic construct
SEQUENCE: 75
MAKNTITKTL KLRIVRPYNS AEVEKIVADE KNNREKIALE KNKDKVKEAC SKHLKVAAYC     60
TTQVERNACL FCKARKLDDK FYQKLRGQFP DAVFWQEISE IFRQLQKQAA EIYNQSLIEL    120
YYEIFIKGKG IANASSVEHY LSRVCYTRAA MLFKNAAIAS GLRSKIKSNF RLKELKNMKS    180
GLPTTKSDNF PIPLVKQKGG QYTGFEISNH NSDFIIKIPF GRWQVKKEID KYRPWEKFDF    240
EQVQKSPKPI SLLLSTQRRK RNKGWSKDEG TEAEIKKVMN GDYQTSYIEV KRGSKICEKS    300
AWMLNLSIDV PKIDKGVDPS IIGGIDVGVK SPLVCAINNA FSRYSISDND LFHFNKKMFA    360
RRRILLKKNR HKRAGHGAKN KLKPITILTE KSERFRKKLI ERWACEIADF FIKNKVGTVQ    420
MENLESMKRK EDSYFNIRLR GFWPYAEMQN KIEFKLKQYG IEIRKVAPNN TSKTCSKCGH    480
LNNYFNFEYR KKNKFPHFKC EKCNFKENAD YNAALNISNP KLKSTKEEP              529

SEQ ID NO: 76        moltype = AA  length = 529
FEATURE              Location/Qualifiers
REGION               1..529
                     note = Description of sequence: Modified CAS protein
source               1..529
                     mol_type = protein
                     organism = synthetic construct
SEQUENCE: 76
MAKNTITKTL KLRIVRPYNS AEVEKIVADE KNNREKIALE KNKDKVKEAC SKHLKVAAYC     60
TTQVERNACL FCKARKLDDK FYQKLRGQFP DAVFWQEISE IFRQLQKQAA EIYNQSLIEL    120
YYEIFIKGKG IANASSVEHY LSRVCYTRAA DLFKNAAIAS GLRSKIKSNF RLKELKNMKS    180
GLPTTKSDNF PIPLVKQKGG QYTGFEISNH NSDFIIKIPF GRWQVKKEID KYRPWEKFDF    240
EQVQKSPKPI SLLLSTQRRK RNKGWSKDEG TEAEIKKVMN GDYQTSYIEV KRGSKICEKS    300
AWMLNLSIDV PKIDKGVDPS IIGGIDVGVK SPLVCAINNA FSRYSISDND LFHFNKKMFA    360
RRRILLKKNR HKRAGHGAKN KLKPITILTE KSERFRKKLI ERWACEIADF FIKNKVGTVQ    420
MENLESMKRK EDSYFNIRLR GFWPYAEMQN KIEFKLKQYG IEIRKVAPNN TSKTCSKCGH    480
LNNYFNFEYR KKNKFPHFKC EKCNFKENAD YNAALNISNP KLKSTKEEP              529

SEQ ID NO: 77        moltype = AA  length = 529
FEATURE              Location/Qualifiers
REGION               1..529
                     note = Description of sequence: Modified CAS protein
source               1..529
                     mol_type = protein
                     organism = synthetic construct
SEQUENCE: 77
MAKNTITKTL KLRIVRPYNS AEVEKIVADE KNNREKIALE KNKDKVKEAC SKHLKVAAYC     60
TTQVERNACL FCKARKLDDK FYQKLRGQFP DAVFWQEISE IFRQLQKQAA EIYNQSLIEL    120
YYEIFIKGKG IANASSVEHY LSRVCYTRAA NLFKNAAIAS GLRSKIKSNF RLKELKNMKS    180
GLPTTKSDNF PIPLVKQKGG QYTGFEISNH NSDFIIKIPF GRWQVKKEID KYRPWEKFDF    240
EQVQKSPKPI SLLLSTQRRK RNKGWSKDEG TEAEIKKVMN GDYQTSYIEV KRGSKICEKS    300
AWMLNLSIDV PKIDKGVDPS IIGGIDVGVK SPLVCAINNA FSRYSISDND LFHFNKKMFA    360
RRRILLKKNR HKRAGHGAKN KLKPITILTE KSERFRKKLI ERWACEIADF FIKNKVGTVQ    420
MENLESMKRK EDSYFNIRLR GFWPYAEMQN KIEFKLKQYG IEIRKVAPNN TSKTCSKCGH    480
```

```
LNNYFNFEYR KKNKFPHFKC EKCNFKENAD YNAALNISNP KLKSTKEEP            529

SEQ ID NO: 78              moltype = AA   length = 529
FEATURE                    Location/Qualifiers
REGION                     1..529
                           note = Description of sequence: Modified CAS protein
source                     1..529
                           mol_type = protein
                           organism = synthetic construct
SEQUENCE: 78
MAKNTITKTL KLRIVRPYNS AEVEKIVADE KNNREKIALE KNKDKVKEAC SKHLKVAAYC  60
TTQVERNACL FCKARKLDDK FYQKLRGQFP DAVFWQEISE IFRQLQKQAA EIYNQSLIEL 120
YYEIFIKGKG IANASSVEHY LSRVCYRRAA YLFKNAAIAS GLRSKIKSNF RLKELKNMKS 180
GLPTTKSDNF PIPLVKQKGG QYTGFEISNH NSDFIIKIPF GRWQVKKEID KYRPWEKFDF 240
EQVQKSPKPI SLLLSTQRRK RNKGWSKDEG TEAEIKKVMN GDYQTSYIEV KRGSKICEKS 300
AWMLNLSIDV PKIDKGVDPS IIGGIDVGVK SPLVCAINNA FSRYSISDND LFHFNKKMFA 360
RRRILLKKNR HKRAGHGAKN KLKPITILTE KSERFRKKLI ERWACEIADF FIKNKVGTVQ 420
MENLESMKRK EDSYFNIRLR GFWPYAEMQN KIEFKLKQYG IEIRKVAPNN TSKTCSKCGH 480
LNNYFNFEYR KKNKFPHFKC EKCNFKENAD YNAALNISNP KLKSTKEEP            529

SEQ ID NO: 79              moltype = AA   length = 529
FEATURE                    Location/Qualifiers
REGION                     1..529
                           note = Description of sequence: Modified CAS protein
source                     1..529
                           mol_type = protein
                           organism = synthetic construct
SEQUENCE: 79
MAKNTITKTL KLRIVRPYNS AEVEKIVADE KNNREKIALE KNKDKVKEAC SKHLKVAAYC  60
TTQVERNACL FCKARKLDDK FYQKLRGQFP DAVFWQEISE IFRQLQKQAA EIYNQSLIEL 120
YYEIFIKGKG IANASSVEHY LSRVCYRRAA ALFKNAAIAS GLRSKIKSNF RLKELKNMKS 180
GLPTTKSDNF PIPLVKQKGG QYTGFEISNH NSDFIIKIPF GRWQVKKEID KYRPWEKFDF 240
EQVQKSPKPI SLLLSTQRRK RNKGWSKDEG TEAEIKKVMN GDYQTSYIEV KRGSKICEKS 300
AWMLNLSIDV PKIDKGVDPS IIGGIDVGVR SPLVCAINNA FSRYSISDND LFHFNKKMFA 360
RRRILLKKNR HKRAGHGAKN KLKPITILTE KSERFRKKLI ERWACEIADF FIKNKVGTVQ 420
MENLESMKRK EDSYFNIRLR GFWPYAEMQN KIEFKLKQYG IEIRKVAPNN TSKTCSKCGH 480
LNNYFNFEYR KKNKFPHFKC EKCNFKENAD YNAALNISNP KLKSTKREP            529

SEQ ID NO: 80              moltype = AA   length = 529
FEATURE                    Location/Qualifiers
REGION                     1..529
                           note = Description of sequence: Modified CAS protein
source                     1..529
                           mol_type = protein
                           organism = synthetic construct
SEQUENCE: 80
MAKNTITKTL KLRIVRPYNS AEVEKIVADE KNNREKIALE KNKDKVKEAC SKHLKVAAYC  60
TTQVERNACL FCKARKLDDK FYQKLRGQFP DAVFWQEISE IFRQLQKQAA EIYNQSLIEL 120
YYEIFIKGKG IANASSVEHY LSDVCYTRAA ELFKNAAIAS GLRSKIKSNF RLKELKNMKS 180
GLPTTKSDNF PIPLVKQKGG QYTGFEISNH NSDFIIKIPF GRWQVKKEID KYRPWEKFDF 240
EQVQKSPKPI SLLLSTQRRK RNKGWSKDEG TEAEIKKVMN GDYQTSYIEV KRGSKICEKS 300
AWMLNLSIDV PKIDKGVDPS IIGGIAVGVK SPLVCAINNA FSRYSISDND LFHFNKKMFA 360
RRRILLKKNR HKRAGHGAKN KLKPITILTE KSERFRKKLI ERWACEIADF FIKNKVGTVQ 420
MENLESMKRK EDSYFNIRLR GFWPYAEMQN KIEFKLKQYG IEIRKVAPNN TSKTCSKCGH 480
LNNYFNFEYR KKNKFPHFKC EKCNFKENAA YNAALNISNP KLKSTKEEP            529

SEQ ID NO: 81              moltype = AA   length = 529
FEATURE                    Location/Qualifiers
REGION                     1..529
                           note = Description of sequence: Modified CAS protein
source                     1..529
                           mol_type = protein
                           organism = synthetic construct
SEQUENCE: 81
MAKNTITKTL RLRIVRPYNS AEVEKIVADE KNNREKIALE KNKDKVKEAC SKHLKVAAYC  60
TTQVERNACL FCKARKLDDK FYQKLRGQFP DAVFWQEISE IFRQLQKQAA EIYNQSLIEL 120
YYEIFIKGKG IANASSVEHY LSDVCYTRAA ELFKNAAIAS GLRSKIKSNF RLKELKNMKS 180
GLPTTKSDNF PIPLVKQKGG QYTGFEISNH NSDFIIKIPF GRWQVKKEID KYRPWEKFDF 240
EQVQKSPKPI SLLLSTQRRK RNKGWSKDEG TEAEIKKVMN GDYQTSYIEV KRGSKICEKS 300
AWMLNLSIDV PKIDKGVDPS IIGGIAVGVK SPLVCAINNA FSRYSISDND LFHFNKKMFA 360
RRRILLKKNR HKRAGHGAKN KLKPITILTE KSERFRKKLI ERWACEIADF FIKNKVGTVQ 420
MENLESMKRK EDSYFNIRLR GFWPYAEMQN KIEFKLKQYG IEIRKVAPNN TSKTCSKCGH 480
LNNYFNFEYR KKNKFPHFKC EKCNFKENAA YNAALNISNP KLKSTKEEP            529

SEQ ID NO: 82              moltype = AA   length = 529
FEATURE                    Location/Qualifiers
REGION                     1..529
                           note = Description of sequence: Modified CAS protein
source                     1..529
```

```
                         mol_type = protein
                         organism = synthetic construct
SEQUENCE: 82
MAKNTITKTL KLRIVRPYNS AEVEKIVADE KNNREKIALE KNKDKVKEAC SKHLKVAAYC   60
TTQVERNACL FCRARKLDDK FYQKLRGQFP DAVFWQEISE IFRQLQKQAA EIYNQSLIEL  120
YYEIFIKGKG IANASSVEHY LSDVCYTRAA ELFKNAAIAS GLRSKIKSNF RLKELKNMKS  180
GLPTTKSDNF PIPLVKQKGG QYTGFEISNH NSDFIIKIPF GRWQVKKEID KYRPWEKFDF  240
EQVQKSPKPI SLLLSTQRRK RNKGWSKDEG TEAEIKKVMN GDYQTSYIEV KRGSKICEKS  300
AWMLNLSIDV PKIDKGVDPS IIGGIAVGVK SPLVCAINNA FSRYSISDND LFHFNKKMFA  360
RRRILLKKNR HKRAGHGAKN KLKPITILTE KSERFRKKLI ERWACEIADF FIKNKVGTVQ  420
MENLESMKRK EDSYFNIRLR GFWPYAEMQN KIEFKLKQYG IEIRKVAPNN TSKTCSKCGH  480
LNNYFNFEYR KKNKFPHFKC EKCNFKENAA YNAALNISNP KLKSTKEEP             529

SEQ ID NO: 83            moltype = AA  length = 529
FEATURE                  Location/Qualifiers
REGION                   1..529
                         note = Description of sequence: Modified CAS protein
source                   1..529
                         mol_type = protein
                         organism = synthetic construct
SEQUENCE: 83
MAKNTITKTL KLRIVRPYNS AEVEKIVADE KNNREKIALE KNKDKVKEAC SKHLKVAAYC   60
TTQVERNACL FCKARKLDDK FYQKLRGQFP DAVFWQEISE IFRQLQKRAA EIYNQSLIEL  120
YYEIFIKGKG IANASSVEHY LSDVCYTRAA ELFKNAAIAS GLRSKIKSNF RLKELKNMKS  180
GLPTTKSDNF PIPLVKQKGG QYTGFEISNH NSDFIIKIPF GRWQVKKEID KYRPWEKFDF  240
EQVQKSPKPI SLLLSTQRRK RNKGWSKDEG TEAEIKKVMN GDYQTSYIEV KRGSKICEKS  300
AWMLNLSIDV PKIDKGVDPS IIGGIAVGVK SPLVCAINNA FSRYSISDND LFHFNKKMFA  360
RRRILLKKNR HKRAGHGAKN KLKPITILTE KSERFRKKLI ERWACEIADF FIKNKVGTVQ  420
MENLESMKRK EDSYFNIRLR GFWPYAEMQN KIEFKLKQYG IEIRKVAPNN TSKTCSKCGH  480
LNNYFNFEYR KKNKFPHFKC EKCNFKENAA YNAALNISNP KLKSTKEEP             529

SEQ ID NO: 84            moltype = AA  length = 529
FEATURE                  Location/Qualifiers
REGION                   1..529
                         note = Description of sequence: Modified CAS protein
source                   1..529
                         mol_type = protein
                         organism = synthetic construct
SEQUENCE: 84
MAKNTITKTL KLRIVRPYNS AEVEKIVADE KNNREKIALE KNKDKVKEAC SKHLKVAAYC   60
TTQVERNACL FCKARKLDDK FYQKLRGQFP DAVFWQEISE IFRQLQKQAA EIYNQSLIEL  120
YYEIFIKGKG IANASSVEHY LSRVCYTRAA ELFKNAAIAS GLRSKIKSNF RLKELKNMKS  180
GLPTTKSDNF PIPLVKQKGG QYTGFEISNH NSDFIIKIPF GRWQVKKEID KYRPWEKFDF  240
EQVQKSPKPI SLLLSTQRRK RNKGWSKDEG TEAEIKKVMN GDYQTSYIEV KRGSKICEKS  300
AWMLNLSIDV PKIDKGVDPS IIGGIAVGVK SPLVCAINNA FSRYSISDND LFHFNKKMFA  360
RRRILLKKNR HKRAGHGAKN KLKPITILTE KSERFRKKLI ERWACEIADF FIKNKVGTVQ  420
MENLESMKRK EDSYFNIRLR GFWPYAEMQN KIEFKLKQYG IEIRKVAPNN TSKTCSKCGH  480
LNNYFNFEYR KKNKFPHFKC EKCNFKENAA YNAALNISNP KLKSTKEEP             529

SEQ ID NO: 85            moltype = AA  length = 529
FEATURE                  Location/Qualifiers
REGION                   1..529
                         note = Description of sequence: Modified CAS protein
source                   1..529
                         mol_type = protein
                         organism = synthetic construct
SEQUENCE: 85
MAKNTITKTL KLRIVRPYNS AEVEKIVADE KNNREKIALE KNKDKVKEAC SKHLKVAAYC   60
TTQVERNACL FCKARKLDDK FYQKLRGQFP DAVFWQEISE IFRQLQKQAA EIYNQSLIEL  120
YYEIFIKGKG IANASSVEHY LSDVCYRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF  240
EQVQKSPKPI SLLLSTQRRK RNKGWSKDEG TEAEIKKVMN GDYQTSYIEV KRGSKICEKS  300
AWMLNLSIDV PKIDKGVDPS IIGGIAVGVK SPLVCAINNA FSRYSISDND LFHFNKKMFA  360
RRRILLKKNR HKRAGHGAKN KLKPITILTE KSERFRKKLI ERWACEIADF FIKNKVGTVQ  420
MENLESMKRK EDSYFNIRLR GFWPYAEMQN KIEFKLKQYG IEIRKVAPNN TSKTCSKCGH  480
LNNYFNFEYR KKNKFPHFKC EKCNFKENAA YNAALNISNP KLKSTKEEP             529

SEQ ID NO: 86            moltype = AA  length = 529
FEATURE                  Location/Qualifiers
REGION                   1..529
                         note = Description of sequence: Modified CAS protein
source                   1..529
                         mol_type = protein
                         organism = synthetic construct
SEQUENCE: 86
MAKNTITKTL KLRIVRPYNS AEVEKIVADE KNNREKIALE KNKDKVKEAC SKHLKVAAYC   60
TTQVERNACL FCKARKLDDK FYQKLRGQFP DAVFWQEISE IFRQLQKQAA EIYNQSLIEL  120
YYEIFIKGKG IANASSVEHY LSDVCYTRAA RLFKNAAIAS GLRSKIKSNF RLKELKNMKS  180
GLPTTKSDNF PIPLVKQKGG QYTGFEISNH NSDFIIKIPF GRWQVKKEID KYRPWEKFDF  240
```

```
EQVQKSPKPI SLLLSTQRRK RNKGWSKDEG TEAEIKKVMN GDYQTSYIEV KRGSKICEKS  300
AWMLNLSIDV PKIDKGVDPS IIGGIAVGVK SPLVCAINNA FSRYSISDND LFHFNKKMFA  360
RRRILLKKNR HKRAGHGAKN KLKPITILTE KSERFRKKLI ERWACEIADF FIKNKVGTVQ  420
MENLESMKRK EDSYFNIRLR GFWPYAEMQN KIEFKLKQYG IEIRKVAPNN TSKTCSKCGH  480
LNNYFNFEYR KKNKFPHFKC EKCNFKENAA YNAALNISNP KLKSTKEEP             529

SEQ ID NO: 87              moltype = AA  length = 529
FEATURE                    Location/Qualifiers
REGION                     1..529
                           note = Description of sequence: Modified CAS protein
source                     1..529
                           mol_type = protein
                           organism = synthetic construct
SEQUENCE: 87
MAKNTITKTL KLRIVRPYNS AEVEKIVADE KNNREKIALE KNKDKVKEAC SKHLKVAAYC  60
TTQVERNACL FCKARKLDDK FYQKLRGQFP DAVFWQEISE IFRQLQKQAA EIYNQSLIEL  120
YYEIFIKGKG IANASSVEHY LSDVCYTRAA ELFRNAAIAS GLRSKIKSNF RLKELKNMKS  180
GLPTTKSDNF PIPLVKQKGG QYTGFEISNH NSDFIIKIPF GRWQVKKEID KYRPWEKFDF  240
EQVQKSPKPI SLLLSTQRRK RNKGWSKDEG TEAEIKKVMN GDYQTSYIEV KRGSKICEKS  300
AWMLNLSIDV PKIDKGVDPS IIGGIAVGVK SPLVCAINNA FSRYSISDND LFHFNKKMFA  360
RRRILLKKNR HKRAGHGAKN KLKPITILTE KSERFRKKLI ERWACEIADF FIKNKVGTVQ  420
MENLESMKRK EDSYFNIRLR GFWPYAEMQN KIEFKLKQYG IEIRKVAPNN TSKTCSKCGH  480
LNNYFNFEYR KKNKFPHFKC EKCNFKENAA YNAALNISNP KLKSTKEEP             529

SEQ ID NO: 88              moltype = AA  length = 529
FEATURE                    Location/Qualifiers
REGION                     1..529
                           note = Description of sequence: Modified CAS protein
source                     1..529
                           mol_type = protein
                           organism = synthetic construct
SEQUENCE: 88
MAKNTITKTL KLRIVRPYNS AEVEKIVADE KNNREKIALE KNKDKVKEAC SKHLKVAAYC  60
TTQVERNACL FCKARKLDDK FYQKLRGQFP DAVFWQEISE IFRQLQKQAA EIYNQSLIEL  120
YYEIFIKGKG IANASSVEHY LSDVCYTRAA ELFKRAAIAS GLRSKIKSNF RLKELKNMKS  180
GLPTTKSDNF PIPLVKQKGG QYTGFEISNH NSDFIIKIPF GRWQVKKEID KYRPWEKFDF  240
EQVQKSPKPI SLLLSTQRRK RNKGWSKDEG TEAEIKKVMN GDYQTSYIEV KRGSKICEKS  300
AWMLNLSIDV PKIDKGVDPS IIGGIAVGVK SPLVCAINNA FSRYSISDND LFHFNKKMFA  360
RRRILLKKNR HKRAGHGAKN KLKPITILTE KSERFRKKLI ERWACEIADF FIKNKVGTVQ  420
MENLESMKRK EDSYFNIRLR GFWPYAEMQN KIEFKLKQYG IEIRKVAPNN TSKTCSKCGH  480
LNNYFNFEYR KKNKFPHFKC EKCNFKENAA YNAALNISNP KLKSTKEEP             529

SEQ ID NO: 89              moltype = AA  length = 529
FEATURE                    Location/Qualifiers
REGION                     1..529
                           note = Description of sequence: Modified CAS protein
source                     1..529
                           mol_type = protein
                           organism = synthetic construct
SEQUENCE: 89
MAKNTITKTL KLRIVRPYNS AEVEKIVADE KNNREKIALE KNKDKVKEAC SKHLKVAAYC  60
TTQVERNACL FCKARKLDDK FYQKLRGQFP DAVFWQEISE IFRQLQKQAA EIYNQSLIEL  120
YYEIFIKGKG IANASSVEHY LSDVCYTRAA ELFKNAAIAS GLRSKIKSNF RLKELKNMKS  180
GLPTTKSDNF PIPLVRQKGG QYTGFEISNH NSDFIIKIPF GRWQVKKEID KYRPWEKFDF  240
EQVQKSPKPI SLLLSTQRRK RNKGWSKDEG TEAEIKKVMN GDYQTSYIEV KRGSKICEKS  300
AWMLNLSIDV PKIDKGVDPS IIGGIAVGVK SPLVCAINNA FSRYSISDND LFHFNKKMFA  360
RRRILLKKNR HKRAGHGAKN KLKPITILTE KSERFRKKLI ERWACEIADF FIKNKVGTVQ  420
MENLESMKRK EDSYFNIRLR GFWPYAEMQN KIEFKLKQYG IEIRKVAPNN TSKTCSKCGH  480
LNNYFNFEYR KKNKFPHFKC EKCNFKENAA YNAALNISNP KLKSTKEEP             529

SEQ ID NO: 90              moltype = AA  length = 529
FEATURE                    Location/Qualifiers
REGION                     1..529
                           note = Description of sequence: Modified CAS protein
source                     1..529
                           mol_type = protein
                           organism = synthetic construct
SEQUENCE: 90
MAKNTITKTL KLRIVRPYNS AEVEKIVADE KNNREKIALE KNKDKVKEAC SKHLKVAAYC  60
TTQVERNACL FCKARKLDDK FYQKLRGQFP DAVFWQEISE IFRQLQKQAA EIYNQSLIEL  120
YYEIFIKGKG IANASSVEHY LSDVCYTRAA ELFKNAAIAS GLRSKIKSNF RLKELKNMKS  180
GLPTTKSDNF PIPLVKQKGG QYTGFEISNH NSDFIIKIPF GRWQVKKEID KYRPWEKFDF  240
RQVQKSPKPI SLLLSTQRRK RNKGWSKDEG TEAEIKKVMN GDYQTSYIEV KRGSKICEKS  300
AWMLNLSIDV PKIDKGVDPS IIGGIAVGVK SPLVCAINNA FSRYSISDND LFHFNKKMFA  360
RRRILLKKNR HKRAGHGAKN KLKPITILTE KSERFRKKLI ERWACEIADF FIKNKVGTVQ  420
MENLESMKRK EDSYFNIRLR GFWPYAEMQN KIEFKLKQYG IEIRKVAPNN TSKTCSKCGH  480
LNNYFNFEYR KKNKFPHFKC EKCNFKENAA YNAALNISNP KLKSTKEEP             529

SEQ ID NO: 91              moltype = AA  length = 529
```

```
FEATURE                 Location/Qualifiers
REGION                  1..529
                        note = Description of sequence: Modified CAS protein
source                  1..529
                        mol_type = protein
                        organism = synthetic construct
SEQUENCE: 91
MAKNTITKTL KLRIVRPYNS AEVEKIVADE KNNREKIALE KNKDKVKEAC SKHLKVAAYC   60
TTQVERNACL FCKARKLDDK FYQKLRGQFP DAVFWQEISE IFRQLQKQAA EIYNQSLIEL  120
YYEIFIKGKG IANASSVEHY LSDVCYTRAA ELFKNAAIAS GLRSKIKSNF RLKELKNMKS  180
GLPTTKSDNF PIPLVKQKGG QYTGFEISNH NSDFIIKIPF GRWQVKKEID KYRPWEKFDF  240
EQVQKSPKPI SLLLSTQRRK RNKGWSKDEG TEAEIKKVMN GDYQTSYIRV KRGSKICEKS  300
AWMLNLSIDV PKIDKGVDPS IIGGIAVGVK SPLVCAINNA FSRYSISDND LFHFNKKMFA  360
RRRILLKKNR HKRAGHGAKN KLKPITILTE KSERFRKKLI ERWACEIADF FIKNKVGTVQ  420
MENLESMKRK EDSYFNIRLR GFWPYAEMQN KIEFKLKQYG IEIRKVAPNN TSKTCSKCGH  480
LNNYFNFEYR KKNKFPHFKC EKCNFKENAA YNAALNISNP KLKSTKEEP            529

SEQ ID NO: 92           moltype = AA  length = 529
FEATURE                 Location/Qualifiers
REGION                  1..529
                        note = Description of sequence: Modified CAS protein
source                  1..529
                        mol_type = protein
                        organism = synthetic construct
SEQUENCE: 92
MAKNTITKTL KLRIVRPYNS AEVEKIVADE KNNREKIALE KNKDKVKEAC SKHLKVAAYC   60
TTQVERNACL FCKARKLDDK FYQKLRGQFP DAVFWQEISE IFRQLQKQAA EIYNQSLIEL  120
YYEIFIKGKG IANASSVEHY LSDVCYTRAA ELFKNAAIAS GLRSKIKSNF RLKELKNMKS  180
GLPTTKSDNF PIPLVKQKGG QYTGFEISNH NSDFIIKIPF GRWQVKKEID KYRPWEKFDF  240
EQVQKSPKPI SLLLSTQRRK RNKGWSKDEG TEAEIKKVMN GDYQTSYIEV KRGSKICEKS  300
AWMLNLSIDV PKIDKGVRPS IIGGIAVGVK SPLVCAINNA FSRYSISDND LFHFNKKMFA  360
RRRILLKKNR HKRAGHGAKN KLKPITILTE KSERFRKKLI ERWACEIADF FIKNKVGTVQ  420
MENLESMKRK EDSYFNIRLR GFWPYAEMQN KIEFKLKQYG IEIRKVAPNN TSKTCSKCGH  480
LNNYFNFEYR KKNKFPHFKC EKCNFKENAA YNAALNISNP KLKSTKEEP            529

SEQ ID NO: 93           moltype = AA  length = 529
FEATURE                 Location/Qualifiers
REGION                  1..529
                        note = Description of sequence: Modified CAS protein
source                  1..529
                        mol_type = protein
                        organism = synthetic construct
SEQUENCE: 93
MAKNTITKTL KLRIVRPYNS AEVEKIVADE KNNREKIALE KNKDKVKEAC SKHLKVAAYC   60
TTQVERNACL FCKARKLDDK FYQKLRGQFP DAVFWQEISE IFRQLQKQAA EIYNQSLIEL  120
YYEIFIKGKG IANASSVEHY LSDVCYTRAA ELFKNAAIAS GLRSKIKSNF RLKELKNMKS  180
GLPTTKSDNF PIPLVKQKGG QYTGFEISNH NSDFIIKIPF GRWQVKKEID KYRPWEKFDF  240
EQVQKSPKPI SLLLSTQRRK RNKGWSKDEG TEAEIKKVMN GDYQTSYIEV KRGSKICEKS  300
AWMLNLSIDV PKIDKGVDPS IIGGIARGVK SPLVCAINNA FSRYSISDND LFHFNKKMFA  360
RRRILLKKNR HKRAGHGAKN KLKPITILTE KSERFRKKLI ERWACEIADF FIKNKVGTVQ  420
MENLESMKRK EDSYFNIRLR GFWPYAEMQN KIEFKLKQYG IEIRKVAPNN TSKTCSKCGH  480
LNNYFNFEYR KKNKFPHFKC EKCNFKENAA YNAALNISNP KLKSTKEEP            529

SEQ ID NO: 94           moltype = AA  length = 529
FEATURE                 Location/Qualifiers
REGION                  1..529
                        note = Description of sequence: Modified CAS protein
source                  1..529
                        mol_type = protein
                        organism = synthetic construct
SEQUENCE: 94
MAKNTITKTL KLRIVRPYNS AEVEKIVADE KNNREKIALE KNKDKVKEAC SKHLKVAAYC   60
TTQVERNACL FCKARKLDDK FYQKLRGQFP DAVFWQEISE IFRQLQKQAA EIYNQSLIEL  120
YYEIFIKGKG IANASSVEHY LSDVCYTRAA ELFKNAAIAS GLRSKIKSNF RLKELKNMKS  180
GLPTTKSDNF PIPLVKQKGG QYTGFEISNH NSDFIIKIPF GRWQVKKEID KYRPWEKFDF  240
EQVQKSPKPI SLLLSTQRRK RNKGWSKDEG TEAEIKKVMN GDYQTSYIEV KRGSKICEKS  300
AWMLNLSIDV PKIDKGVDPS IIGGIAVGVR SPLVCAINNA FSRYSISDND LFHFNKKMFA  360
RRRILLKKNR HKRAGHGAKN KLKPITILTE KSERFRKKLI ERWACEIADF FIKNKVGTVQ  420
MENLESMKRK EDSYFNIRLR GFWPYAEMQN KIEFKLKQYG IEIRKVAPNN TSKTCSKCGH  480
LNNYFNFEYR KKNKFPHFKC EKCNFKENAA YNAALNISNP KLKSTKEEP            529

SEQ ID NO: 95           moltype = AA  length = 529
FEATURE                 Location/Qualifiers
REGION                  1..529
                        note = Description of sequence: Modified CAS protein
source                  1..529
                        mol_type = protein
                        organism = synthetic construct
SEQUENCE: 95
```

```
MAKNTITKTL KLRIVRPYNS AEVEKIVADE KNNREKIALE KNKDKVKEAC SKHLKVAAYC   60
TTQVERNACL FCKARKLDDK FYQKLRGQFP DAVFWQEISE IFRQLQKQAA EIYNQSLIEL  120
YYEIFIKGKG IANASSVEHY LSDVCYTRAA ELFKNAAIAS GLRSKIKSNF RLKELKNMKS  180
GLPTTKSDNF PIPLVKQKGG QYTGFEISNH NSDFIIKIPF GRWQVKKEID KYRPWEKFDF  240
EQVQKSPKPI SLLLSTQRRK RNKGWSKDEG TEAEIKKVMN GDYQTSYIEV KRGSKICEKS  300
AWMLNLSIDV PKIDKGVDPS IIGGIAVGVK SPLVCAINNA FSRYSISDND LFHFNKKMFA  360
RRRILLKKNR HKRAGHGAKN KLKPITILTE KSERFRKKLI ERWACEIADF FIKNKVGTVQ  420
MENLNSMKRK EDSYFNIRLR GFWPYAEMQN KIEFKLKQYG IEIRKVAPNN TSKTCSKCGH  480
LNNYFNFEYR KKNKFPHFKC EKCNFKENAA YNAALNISNP KLKSTKEEP             529

SEQ ID NO: 96           moltype = AA  length = 529
FEATURE                 Location/Qualifiers
REGION                  1..529
                        note = Description of sequence: Modified CAS protein
source                  1..529
                        mol_type = protein
                        organism = synthetic construct
SEQUENCE: 96
MAKNTITKTL KLRIVRPYNS AEVEKIVADE KNNREKIALE KNKDKVKEAC SKHLKVAAYC   60
TTQVERNACL FCKARKLDDK FYQKLRGQFP DAVFWQEISE IFRQLQKQAA EIYNQSLIEL  120
YYEIFIKGKG IANASSVEHY LSDVCYTRAA ELFKNAAIAS GLRSKIKSNF RLKELKNMKS  180
GLPTTKSDNF PIPLVKQKGG QYTGFEISNH NSDFIIKIPF GRWQVKKEID KYRPWEKFDF  240
EQVQKSPKPI SLLLSTQRRK RNKGWSKDEG TEAEIKKVMN GDYQTSYIEV KRGSKICEKS  300
AWMLNLSIDV PKIDKGVDPS IIGGIAVGVK SPLVCAINNA FSRYSISDND LFHFNKKMFA  360
RRRILLKKNR HKRAGHGAKN KLKPITILTE KSERFRKKLI ERWACEIADF FIKNKVGTVQ  420
MENLESMKRK EDSYFNIRLR GFWPYAEMQN KIEFKLRQYG IEIRKVAPNN TSKTCSKCGH  480
LNNYFNFEYR KKNKFPHFKC EKCNFKENAA YNAALNISNP KLKSTKEEP             529

SEQ ID NO: 97           moltype = AA  length = 529
FEATURE                 Location/Qualifiers
REGION                  1..529
                        note = Description of sequence: Modified CAS protein
source                  1..529
                        mol_type = protein
                        organism = synthetic construct
SEQUENCE: 97
MAKNTITKTL KLRIVRPYNS AEVEKIVADE KNNREKIALE KNKDKVKEAC SKHLKVAAYC   60
TTQVERNACL FCKARKLDDK FYQKLRGQFP DAVFWQEISE IFRQLQKQAA EIYNQSLIEL  120
YYEIFIKGKG IANASSVEHY LSDVCYTRAA ELFKNAAIAS GLRSKIKSNF RLKELKNMKS  180
GLPTTKSDNF PIPLVKQKGG QYTGFEISNH NSDFIIKIPF GRWQVKKEID KYRPWEKFDF  240
EQVQKSPKPI SLLLSTQRRK RNKGWSKDEG TEAEIKKVMN GDYQTSYIEV KRGSKICEKS  300
AWMLNLSIDV PKIDKGVDPS IIGGIAVGVK SPLVCAINNA FSRYSISDND LFHFNKKMFA  360
RRRILLKKNR HKRAGHGAKN KLKPITILTE KSERFRKKLI ERWACEIADF FIKNKVGTVQ  420
MENLESMKRK EDSYFNIRLR GFWPYAEMQN KIEFKLKQYG IRIRKVAPNN TSKTCSKCGH  480
LNNYFNFEYR KKNKFPHFKC EKCNFKENAA YNAALNISNP KLKSTKEEP             529

SEQ ID NO: 98           moltype = AA  length = 529
FEATURE                 Location/Qualifiers
REGION                  1..529
                        note = Description of sequence: Modified CAS protein
source                  1..529
                        mol_type = protein
                        organism = synthetic construct
SEQUENCE: 98
MAKNTITKTL KLRIVRPYNS AEVEKIVADE KNNREKIALE KNKDKVKEAC SKHLKVAAYC   60
TTQVERNACL FCKARKLDDK FYQKLRGQFP DAVFWQEISE IFRQLQKQAA EIYNQSLIEL  120
YYEIFIKGKG IANASSVEHY LSDVCYTRAA ELFKNAAIAS GLRSKIKSNF RLKELKNMKS  180
GLPTTKSDNF PIPLVKQKGG QYTGFEISNH NSDFIIKIPF GRWQVKKEID KYRPWEKFDF  240
EQVQKSPKPI SLLLSTQRRK RNKGWSKDEG TEAEIKKVMN GDYQTSYIEV KRGSKICEKS  300
AWMLNLSIDV PKIDKGVDPS IIGGIAVGVK SPLVCAINNA FSRYSISDND LFHFNKKMFA  360
RRRILLKKNR HKRAGHGAKN KLKPITILTE KSERFRKKLI ERWACEIADF FIKNKVGTVQ  420
MENLESMKRK EDSYFNIRLR GFWPYAEMQN KIEFKLKQYG IEIRKVAPNN TSKTCSKCGH  480
LNNYFNFEYR KKNKFPHFKR EKCNFKENAA YNAALNISNP KLKSTKEEP             529

SEQ ID NO: 99           moltype = AA  length = 529
FEATURE                 Location/Qualifiers
REGION                  1..529
                        note = Description of sequence: Modified CAS protein
source                  1..529
                        mol_type = protein
                        organism = synthetic construct
SEQUENCE: 99
MAKNTITKTL KLRIVRPYNS AEVEKIVADE KNNREKIALE KNKDKVKEAC SKHLKVAAYC   60
TTQVERNACL FCKARKLDDK FYQKLRGQFP DAVFWQEISE IFRQLQKQAA EIYNQSLIEL  120
YYEIFIKGKG IANASSVEHY LSDVCYTRAA ELFKNAAIAS GLRSKIKSNF RLKELKNMKS  180
GLPTTKSDNF PIPLVKQKGG QYTGFEISNH NSDFIIKIPF GRWQVKKEID KYRPWEKFDF  240
EQVQKSPKPI SLLLSTQRRK RNKGWSKDEG TEAEIKKVMN GDYQTSYIEV KRGSKICEKS  300
AWMLNLSIDV PKIDKGVDPS IIGGIAVGVK SPLVCAINNA FSRYSISDND LFHFNKKMFA  360
RRRILLKKNR HKRAGHGAKN KLKPITILTE KSERFRKKLI ERWACEIADF FIKNKVGTVQ  420
```

```
MENLESMKRK EDSYFNIRLR GFWPYAEMQN KIEFKLKQYG IEIRKVAPNN TSKTCSKCGH  480
LNNYFNFEYR KKNKFPHFRR EKCNFKENAA YNAALNISNP KLKSTKEEP             529

SEQ ID NO: 100             moltype = AA  length = 529
FEATURE                    Location/Qualifiers
REGION                     1..529
                           note = Description of sequence: Modified CAS protein
source                     1..529
                           mol_type = protein
                           organism = synthetic construct
SEQUENCE: 100
MAKNTITKTL KLRIVRPYNS AEVEKIVADE KNNREKIALE KNKDKVKEAC SKHLKVAAYC  60
TTQVERNACL FCKARKLDDK FYQKLRGQFP DAVFWQEISE IFRQLQKQAA EIYNQSLIEL  120
YYEIFIKGKG IANASSVEHY LSDVCYTRAA ELFKNAAIAS GLRSKIKSNF RLKELKNMKS  180
GLPTTKSDNF PIPLVKQKGG QYTGFEISNH NSDFIIKIPF GRWQVKKEID KYRPWEKFDF  240
EQVQKSPKPI SLLLSTQRRK RNKGWSKDEG TEAEIKKVMN GDYQTSYIEV KRGSKICEKS  300
AWMLNLSIDV PKIDKGVDPS IIGGIAVGVK SPLVCAINNA FSRYSISDND LFHFNKKMFA  360
RRRILLKKNR HKRAGHGAKN KLKPITILTE KSERFRKKLI ERWACEIADF FIKNKVGTVQ  420
MENLESMKRK EDSYFNIRLR GFWPYAEMQN KIEFKLKQYG IEIRKVAPNN TSKTCSKCGH  480
LNNYFNFEYR KKNKFPHFKC RKCNFKENAA YNAALNISNP KLKSTKEEP             529

SEQ ID NO: 101             moltype = AA  length = 529
FEATURE                    Location/Qualifiers
REGION                     1..529
                           note = Description of sequence: Modified CAS protein
source                     1..529
                           mol_type = protein
                           organism = synthetic construct
SEQUENCE: 101
MAKNTITKTL KLRIVRPYNS AEVEKIVADE KNNREKIALE KNKDKVKEAC SKHLKVAAYC  60
TTQVERNACL FCKARKLDDK FYQKLRGQFP DAVFWQEISE IFRQLQKQAA EIYNQSLIEL  120
YYEIFIKGKG IANASSVEHY LSDVCYTRAA ELFKNAAIAS GLRSKIKSNF RLKELKNMKS  180
GLPTTKSDNF PIPLVKQKGG QYTGFEISNH NSDFIIKIPF GRWQVKKEID KYRPWEKFDF  240
EQVQKSPKPI SLLLSTQRRK RNKGWSKDEG TEAEIKKVMN GDYQTSYIEV KRGSKICEKS  300
AWMLNLSIDV PKIDKGVDPS IIGGIAVGVK SPLVCAINNA FSRYSISDND LFHFNKKMFA  360
RRRILLKKNR HKRAGHGAKN KLKPITILTE KSERFRKKLI ERWACEIADF FIKNKVGTVQ  420
MENLESMKRK EDSYFNIRLR GFWPYAEMQN KIEFKLKQYG IEIRKVAPNN TSKTCSKCGH  480
LNNYFNFEYR KKNKFPHFKC EKCRFKENAA YNAALNISNP KLKSTKEEP             529

SEQ ID NO: 102             moltype = AA  length = 529
FEATURE                    Location/Qualifiers
REGION                     1..529
                           note = Description of sequence: Modified CAS protein
source                     1..529
                           mol_type = protein
                           organism = synthetic construct
SEQUENCE: 102
MAKNTITKTL KLRIVRPYNS AEVEKIVADE KNNREKIALE KNKDKVKEAC SKHLKVAAYC  60
TTQVERNACL FCKARKLDDK FYQKLRGQFP DAVFWQEISE IFRQLQKQAA EIYNQSLIEL  120
YYEIFIKGKG IANASSVEHY LSDVCYTRAA ELFKNAAIAS GLRSKIKSNF RLKELKNMKS  180
GLPTTKSDNF PIPLVKQKGG QYTGFEISNH NSDFIIKIPF GRWQVKKEID KYRPWEKFDF  240
EQVQKSPKPI SLLLSTQRRK RNKGWSKDEG TEAEIKKVMN GDYQTSYIEV KRGSKICEKS  300
AWMLNLSIDV PKIDKGVDPS IIGGIAVGVK SPLVCAINNA FSRYSISDND LFHFNKKMFA  360
RRRILLKKNR HKRAGHGAKN KLKPITILTE KSERFRKKLI ERWACEIADF FIKNKVGTVQ  420
MENLESMKRK EDSYFNIRLR GFWPYAEMQN KIEFKLKQYG IEIRKVAPNN TSKTCSKCGH  480
LNNYFNFEYR KKNKFPHFKC EKCNFKRNAA YNAALNISNP KLKSTKEEP             529

SEQ ID NO: 103             moltype = AA  length = 529
FEATURE                    Location/Qualifiers
REGION                     1..529
                           note = Description of sequence: Modified CAS protein
source                     1..529
                           mol_type = protein
                           organism = synthetic construct
SEQUENCE: 103
MAKNTITKTL KLRIVRPYNS AEVEKIVADE KNNREKIALE KNKDKVKEAC SKHLKVAAYC  60
TTQVERNACL FCKARKLDDK FYQKLRGQFP DAVFWQEISE IFRQLQKQAA EIYNQSLIEL  120
YYEIFIKGKG IANASSVEHY LSDVCYTRAA ELFKNAAIAS GLRSKIKSNF RLKELKNMKS  180
GLPTTKSDNF PIPLVKQKGG QYTGFEISNH NSDFIIKIPF GRWQVKKEID KYRPWEKFDF  240
EQVQKSPKPI SLLLSTQRRK RNKGWSKDEG TEAEIKKVMN GDYQTSYIEV KRGSKICEKS  300
AWMLNLSIDV PKIDKGVDPS IIGGIAVGVK SPLVCAINNA FSRYSISDND LFHFNKKMFA  360
RRRILLKKNR HKRAGHGAKN KLKPITILTE KSERFRKKLI ERWACEIADF FIKNKVGTVQ  420
MENLESMKRK EDSYFNIRLR GFWPYAEMQN KIEFKLKQYG IEIRKVAPNN TSKTCSKCGH  480
LNNYFNFEYR KKNKFPHFKC EKCNFKEDAA YNAALNISNP KLKSTKEEP             529

SEQ ID NO: 104             moltype = AA  length = 529
FEATURE                    Location/Qualifiers
REGION                     1..529
                           note = Description of sequence: Modified CAS protein
```

-continued

```
source                  1..529
                        mol_type = protein
                        organism = synthetic construct
SEQUENCE: 104
MAKNTITKTL KLRIVRPYNS AEVEKIVADE KNNREKIALE KNKDKVKEAC SKHLKVAAYC   60
TTQVERNACL FCKARKLDDK FYQKLRGQFP DAVFWQEISE IFRQLQKQAA EIYNQSLIEL  120
YYEIFIKGKG IANASSVEHY LSDVCYTRAA ELFKNAAIAS GLRSKIKSNF RLKELKNMKS  180
GLPTTKSDNF PIPLVKQKGG QYTGFEISNH NSDFIIKIPF GRWQVKKEID KYRPWEKFDF  240
EQVQKSPKPI SLLLSTQRRK RNKGWSKDEG TEAEIKKVMN GDYQTSYIEV KRGSKICEKS  300
AWMLNLSIDV PKIDKGVDPS IIGGIAVGVK SPLVCAINNA FSRYSISDND LFHFNKKMFA  360
RRRILLKKNR HKRAGHGAKN KLKPITILTE KSERFRKKLI ERWACEIADF FIKNKVGTVQ  420
MENLESMKRK EDSYFNIRLR GFWPYAEMQN KIEFKLKQYG IEIRKVAPNN TSKTCSKCGH  480
LNNYFNFEYR KKNKFPHFKC EKCNFKENAA ANAALNISNP KLKSTKEEP            529

SEQ ID NO: 105          moltype = AA  length = 529
FEATURE                 Location/Qualifiers
REGION                  1..529
                        note = Description of sequence: Modified CAS protein
source                  1..529
                        mol_type = protein
                        organism = synthetic construct
SEQUENCE: 105
MAKNTITKTL KLRIVRPYNS AEVEKIVADE KNNREKIALE KNKDKVKEAC SKHLKVAAYC   60
TTQVERNACL FCKARKLDDK FYQKLRGQFP DAVFWQEISE IFRQLQKQAA EIYNQSLIEL  120
YYEIFIKGKG IANASSVEHY LSDVCYTRAA ELFKNAAIAS GLRSKIKSNF RLKELKNMKS  180
GLPTTKSDNF PIPLVKQKGG QYTGFEISNH NSDFIIKIPF GRWQVKKEID KYRPWEKFDF  240
EQVQKSPKPI SLLLSTQRRK RNKGWSKDEG TEAEIKKVMN GDYQTSYIEV KRGSKICEKS  300
AWMLNLSIDV PKIDKGVDPS IIGGIAVGVK SPLVCAINNA FSRYSISDND LFHFNKKMFA  360
RRRILLKKNR HKRAGHGAKN KLKPITILTE KSERFRKKLI ERWACEIADF FIKNKVGTVQ  420
MENLESMKRK EDSYFNIRLR GFWPYAEMQN KIEFKLKQYG IEIRKVAPNN TSKTCSKCGH  480
LNNYFNFEYR KKNKFPHFKC EKCNFKENAA YNAGLNISNP KLKSTKEEP            529

SEQ ID NO: 106          moltype = AA  length = 528
FEATURE                 Location/Qualifiers
REGION                  1..528
                        note = Description of sequence: Modified CAS protein
source                  1..528
                        mol_type = protein
                        organism = synthetic construct
SEQUENCE: 106
AKNTITKTLK LRIVRPYNSA EVEKIVADEK NNREKIALEK NKDKVKEACS KHLKVAAYCT   60
TQVERNACLF CKARKLDDKF YQKLRGQFPD AVFWQEISEI FRQLQKQAAE IYNQSLIELY  120
YEIFIKGKGI ANASSVEHYL SDVCYTRAAE LFKNAAIASG LRSKIKSNFR LKELKNMKSG  180
LPTTKSDNFP IPLVKQKGGQ YTGFEISNHN SDFIIKIPFG RWQVKKEIDK YRPWEKFDFE  240
QVQKSPKPIS LLLSTQRRKR NKGWSKDEGT EAEIKKVMNG DYQTSYIEVK RGSKICEKSA  300
WMLNLSIDVP KIDKGVDPSI IGGIAVGVKS PLVCAINNAF SRYSISDNDL FHFNKKMFAR  360
RRILLKKNRH KRAGHGAKNK LKPITILTEK SERFRKKLIE RWACEIADFF IKNKVGTVQM  420
ENLESMKRKE DSYFNIRLRG FWPYAEMQNK IEFKLKQYGI EIRKVAPNNT SKTCSKCGHL  480
NNYFNFEYRK KNKFPHFKCE KCNFKENAAY NAALRISNPK LKSTKEEP             528

SEQ ID NO: 107          moltype = AA  length = 529
FEATURE                 Location/Qualifiers
REGION                  1..529
                        note = Description of sequence: Modified CAS protein
source                  1..529
                        mol_type = protein
                        organism = synthetic construct
SEQUENCE: 107
MAKNTITKTL KLRIVRPYNS AEVEKIVADE KNNREKIALE KNKDKVKEAC SKHLKVAAYC   60
TTQVERNACL FCKARKLDDK FYQKLRGQFP DAVFWQEISE IFRQLQKQAA EIYNQSLIEL  120
YYEIFIKGKG IANASSVEHY LSDVCYTRAA ELFKNAAIAS GLRSKIKSNF RLKELKNMKS  180
GLPTTKSDNF PIPLVKQKGG QYTGFEISNH NSDFIIKIPF GRWQVKKEID KYRPWEKFDF  240
EQVQKSPKPI SLLLSTQRRK RNKGWSKDEG TEAEIKKVMN GDYQTSYIEV KRGSKICEKS  300
AWMLNLSIDV PKIDKGVDPS IIGGIAVGVK SPLVCAINNA FSRYSISDND LFHFNKKMFA  360
RRRILLKKNR HKRAGHGAKN KLKPITILTE KSERFRKKLI ERWACEIADF FIKNKVGTVQ  420
MENLESMKRK EDSYFNIRLR GFWPYAEMQN KIEFKLKQYG IEIRKVAPNN TSKTCSKCGH  480
LNNYFNFEYR KKNKFPHFKC EKCNFKENAA YNAALNISRP KLKSTKEEP            529

SEQ ID NO: 108          moltype = AA  length = 529
FEATURE                 Location/Qualifiers
REGION                  1..529
                        note = Description of sequence: Modified CAS protein
source                  1..529
                        mol_type = protein
                        organism = synthetic construct
SEQUENCE: 108
MAKNTITKTL KLRIVRPYNS AEVEKIVADE KNNREKIALE KNKDKVKEAC SKHLKVAAYC   60
TTQVERNACL FCKARKLDDK FYQKLRGQFP DAVFWQEISE IFRQLQKQAA EIYNQSLIEL  120
YYEIFIKGKG IANASSVEHY LSDVCYTRAA ELFKNAAIAS GLRSKIKSNF RLKELKNMKS  180
```

```
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIAVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAA YNAALNISNP KLKSTKREP              529

SEQ ID NO: 109           moltype = AA   length = 529
FEATURE                  Location/Qualifiers
REGION                   1..529
                         note = Description of sequence: Modified CAS protein
source                   1..529
                         mol_type = protein
                         organism = synthetic construct
SEQUENCE: 109
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSDVCYTRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIAVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAA YNAALNISNP KLKSTKERP              529

SEQ ID NO: 110           moltype = AA   length = 529
FEATURE                  Location/Qualifiers
REGION                   1..529
                         note = Description of sequence: Modified CAS protein
source                   1..529
                         mol_type = protein
                         organism = synthetic construct
SEQUENCE: 110
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSRVCYRRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIAVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAA YNAALNISNP KLKSTKEEP              529

SEQ ID NO: 111           moltype = AA   length = 529
FEATURE                  Location/Qualifiers
REGION                   1..529
                         note = Description of sequence: Modified CAS protein
source                   1..529
                         mol_type = protein
                         organism = synthetic construct
SEQUENCE: 111
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSRVCYTRAA RLFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIAVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAA YNAALNISNP KLKSTKEEP              529

SEQ ID NO: 112           moltype = AA   length = 529
FEATURE                  Location/Qualifiers
REGION                   1..529
                         note = Description of sequence: Modified CAS protein
source                   1..529
                         mol_type = protein
                         organism = synthetic construct
SEQUENCE: 112
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSRVCYTRAA ELFRNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIAVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAA YNAALNISNP KLKSTKEEP              529
```

```
SEQ ID NO: 113           moltype = AA  length = 529
FEATURE                  Location/Qualifiers
REGION                   1..529
                         note = Description of sequence: Modified CAS protein
source                   1..529
                         mol_type = protein
                         organism = synthetic construct
SEQUENCE: 113
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSRVCYTRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
RQVQKSPKPI SLLLSTQRRK RNKGWSKDEG TEAEIKKVMN GDYQTSYIEV KRGSKICEKS   300
AWMLNLSIDV PKIDKGVDPS IIGGIAVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAA YNAALNISNP KLKSTKEEP             529

SEQ ID NO: 114           moltype = AA  length = 529
FEATURE                  Location/Qualifiers
REGION                   1..529
                         note = Description of sequence: Modified CAS protein
source                   1..529
                         mol_type = protein
                         organism = synthetic construct
SEQUENCE: 114
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSRVCYTRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIAVGVR SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAA YNAALNISNP KLKSTKEEP             529

SEQ ID NO: 115           moltype = AA  length = 529
FEATURE                  Location/Qualifiers
REGION                   1..529
                         note = Description of sequence: Modified CAS protein
source                   1..529
                         mol_type = protein
                         organism = synthetic construct
SEQUENCE: 115
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSRVCYTRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIAVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLNSMKRK EDSYFNIRLR GFWPYAEMQN KIEFKLKQYG IEIRKVAPNN TSKTCSKCGH   480
LNNYFNFEYR KKNKFPHFKC EKCNFKENAA YNAALNISNP KLKSTKEEP             529

SEQ ID NO: 116           moltype = AA  length = 529
FEATURE                  Location/Qualifiers
REGION                   1..529
                         note = Description of sequence: Modified CAS protein
source                   1..529
                         mol_type = protein
                         organism = synthetic construct
SEQUENCE: 116
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSRVCYTRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIAVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKRNAA YNAALNISNP KLKSTKEEP             529

SEQ ID NO: 117           moltype = AA  length = 529
FEATURE                  Location/Qualifiers
REGION                   1..529
                         note = Description of sequence: Modified CAS protein
source                   1..529
                         mol_type = protein
                         organism = synthetic construct
```

```
SEQUENCE: 117
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKAA  EIYNQSLIEL   120
YYEIFIKGKG IANASSVEHY LSRVCYTRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIAVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAA YNAALRISNP KLKSTKEEP              529

SEQ ID NO: 118         moltype = AA  length = 529
FEATURE                Location/Qualifiers
REGION                 1..529
                       note = Description of sequence: Modified CAS protein
source                 1..529
                       mol_type = protein
                       organism = synthetic construct
SEQUENCE: 118
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKAA  EIYNQSLIEL   120
YYEIFIKGKG IANASSVEHY LSRVCYTRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIAVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAA YNAALNISRP KLKSTKEEP              529

SEQ ID NO: 119         moltype = AA  length = 529
FEATURE                Location/Qualifiers
REGION                 1..529
                       note = Description of sequence: Modified CAS protein
source                 1..529
                       mol_type = protein
                       organism = synthetic construct
SEQUENCE: 119
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKAA  EIYNQSLIEL   120
YYEIFIKGKG IANASSVEHY LSRVCYTRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIAVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAA YNAALNISNP KLKSTKREP              529

SEQ ID NO: 120         moltype = AA  length = 529
FEATURE                Location/Qualifiers
REGION                 1..529
                       note = Description of sequence: Modified CAS protein
source                 1..529
                       mol_type = protein
                       organism = synthetic construct
SEQUENCE: 120
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKAA  EIYNQSLIEL   120
YYEIFIKGKG IANASSVEHY LSRVCYTRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIAVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAA YNAALNISNP KLKSTKERP              529

SEQ ID NO: 121         moltype = AA  length = 529
FEATURE                Location/Qualifiers
REGION                 1..529
                       note = Description of sequence: Modified CAS protein
source                 1..529
                       mol_type = protein
                       organism = synthetic construct
SEQUENCE: 121
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKAA  EIYNQSLIEL   120
YYEIFIKGKG IANASSVEHY LSRVCYRRAA RLFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIAVGVK SPLVCAINNA FSRYSISDND LFHFNKKMFA   360
```

```
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAA YNAALNISNP KLKSTKEEP              529

SEQ ID NO: 122         moltype = AA   length = 529
FEATURE                Location/Qualifiers
REGION                 1..529
                       note = Description of sequence: Modified CAS protein
source                 1..529
                       mol_type = protein
                       organism = synthetic construct
SEQUENCE: 122
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSRVCYRRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIAVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAA YNAALNISNP KLKSTKEEP              529

SEQ ID NO: 123         moltype = AA   length = 529
FEATURE                Location/Qualifiers
REGION                 1..529
                       note = Description of sequence: Modified CAS protein
source                 1..529
                       mol_type = protein
                       organism = synthetic construct
SEQUENCE: 123
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSRVCYRRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
RQVQKSPKPI SLLLSTQRRK RNKGWSKDEG TEAEIKKVMN GDYQTSYIEV KRGSKICEKS   300
AWMLNLSIDV PKIDKGVDPS IIGGIAVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAA YNAALNISNP KLKSTKEEP              529

SEQ ID NO: 124         moltype = AA   length = 529
FEATURE                Location/Qualifiers
REGION                 1..529
                       note = Description of sequence: Modified CAS protein
source                 1..529
                       mol_type = protein
                       organism = synthetic construct
SEQUENCE: 124
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSRVCYRRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIAVGVR SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAA YNAALNISNP KLKSTKEEP              529

SEQ ID NO: 125         moltype = AA   length = 529
FEATURE                Location/Qualifiers
REGION                 1..529
                       note = Description of sequence: Modified CAS protein
source                 1..529
                       mol_type = protein
                       organism = synthetic construct
SEQUENCE: 125
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSRVCYRRAA ELFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIAVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLNSMKRK EDSYFNIRLR GFWPYAEMQN KIEFKLKQYG IEIRKVAPNN TSKTCSKCGH   480
LNNYFNFEYR KKNKFPHFKC EKCNFKENAA YNAALNISNP KLKSTKEEP              529

SEQ ID NO: 126         moltype = AA   length = 529
FEATURE                Location/Qualifiers
REGION                 1..529
```

```
                            note = Description of sequence: Modified CAS protein
source                      1..529
                            mol_type = protein
                            organism = synthetic construct
SEQUENCE: 126
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSRVCYRRAA ELFKNAAIAS GLRSKIKSNF RLKELKNMKS   180
GLPTTKSDNF PIPLVKQGG QYTGFEISNH NSDFIIKIPF GRWQVKKEID KYRPWEKFDF    240
EQVQKSPKPI SLLLSTQRRK RNKGWSKDEG TEAEIKKVMN GDYQTSYIEV KRGSKICEKS   300
AWMLNLSIDV PKIDKGVDPS IIGGIAVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKRNAA YNAALNISNP KLKSTKEEP              529

SEQ ID NO: 127              moltype = AA  length = 529
FEATURE                     Location/Qualifiers
REGION                      1..529
                            note = Description of sequence: Modified CAS protein
source                      1..529
                            mol_type = protein
                            organism = synthetic construct
SEQUENCE: 127
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSRVCYRRAA ELFKNAAIAS GLRSKIKSNF RLKELKNMKS   180
GLPTTKSDNF PIPLVKQGG QYTGFEISNH NSDFIIKIPF GRWQVKKEID KYRPWEKFDF    240
EQVQKSPKPI SLLLSTQRRK RNKGWSKDEG TEAEIKKVMN GDYQTSYIEV KRGSKICEKS   300
AWMLNLSIDV PKIDKGVDPS IIGGIAVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAA YNAALRISNP KLKSTKEEP              529

SEQ ID NO: 128              moltype = AA  length = 529
FEATURE                     Location/Qualifiers
REGION                      1..529
                            note = Description of sequence: Modified CAS protein
source                      1..529
                            mol_type = protein
                            organism = synthetic construct
SEQUENCE: 128
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSRVCYRRAA ELFKNAAIAS GLRSKIKSNF RLKELKNMKS   180
GLPTTKSDNF PIPLVKQGG QYTGFEISNH NSDFIIKIPF GRWQVKKEID KYRPWEKFDF    240
EQVQKSPKPI SLLLSTQRRK RNKGWSKDEG TEAEIKKVMN GDYQTSYIEV KRGSKICEKS   300
AWMLNLSIDV PKIDKGVDPS IIGGIAVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAA YNAALNISRP KLKSTKEEP              529

SEQ ID NO: 129              moltype = AA  length = 529
FEATURE                     Location/Qualifiers
REGION                      1..529
                            note = Description of sequence: Modified CAS protein
source                      1..529
                            mol_type = protein
                            organism = synthetic construct
SEQUENCE: 129
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSRVCYRRAA ELFKNAAIAS GLRSKIKSNF RLKELKNMKS   180
GLPTTKSDNF PIPLVKQGG QYTGFEISNH NSDFIIKIPF GRWQVKKEID KYRPWEKFDF    240
EQVQKSPKPI SLLLSTQRRK RNKGWSKDEG TEAEIKKVMN GDYQTSYIEV KRGSKICEKS   300
AWMLNLSIDV PKIDKGVDPS IIGGIAVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAA YNAALNISNP KLKSTKREP              529

SEQ ID NO: 130              moltype = AA  length = 529
FEATURE                     Location/Qualifiers
REGION                      1..529
                            note = Description of sequence: Modified CAS protein
source                      1..529
                            mol_type = protein
                            organism = synthetic construct
SEQUENCE: 130
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
```

```
YYEIFIKGKG IANASSVEHY LSRVCYRRAA ELFKNAAIAS GLRSKIKSNF RLKELKNMKS    180
GLPTTKSDNF PIPLVKQKGG QYTGFEISNH NSDFIIKIPF GRWQVKKEID KYRPWEKFDF    240
EQVQKSPKPI SLLLSTQRRK RNKGWSKDEG TEAEIKKVMN GDYQTSYIEV KRGSKICEKS    300
AWMLNLSIDV PKIDKGVDPS IIGGIAVGVK SPLVCAINNA FSRYSISDND LFHFNKKMFA    360
RRRILLKKNR HKRAGHGAKN KLKPITILTE KSERFRKKLI ERWACEIADF FIKNKVGTVQ    420
MENLESMKRK EDSYFNIRLR GFWPYAEMQN KIEFKLKQYG IEIRKVAPNN TSKTCSKCGH    480
LNNYFNFEYR KKNKFPHFKC EKCNFKENAA YNAALNISNP KLKSTKERP                529

SEQ ID NO: 131            moltype = AA   length = 529
FEATURE                   Location/Qualifiers
REGION                    1..529
                          note = Description of sequence: Modified CAS protein
source                    1..529
                          mol_type = protein
                          organism = synthetic construct
SEQUENCE: 131
MAKNTITKTL KLRIVRPYNS AEVEKIVADE KNNREKIALE KNKDKVKEAC SKHLKVAAYC     60
TTQVERNACL FCKARKLDDK FYQKLRGQFP DAVFWQEISE IFRQLQKQAA EIYNQSLIEL    120
YYEIFIKGKG IANASSVEHY LSRVCYRRAA SLFKNAAIAS GLRSKIKSNF RLKELKNMKS    180
GLPTTKSDNF PIPLVKQKGG QYTGFEISNH NSDFIIKIPF GRWQVKKEID KYRPWEKFDF    240
EQVQKSPKPI SLLLSTQRRK RNKGWSKDEG TEAEIKKVMN GDYQTSYIEV KRGSKICEKS    300
AWMLNLSIDV PKIDKGVDPS IIGGIAVGVK SPLVCAINNA FSRYSISDND LFHFNKKMFA    360
RRRILLKKNR HKRAGHGAKN KLKPITILTE KSERFRKKLI ERWACEIADF FIKNKVGTVQ    420
MENLESMKRK EDSYFNIRLR GFWPYAEMQN KIEFKLKQYG IEIRKVAPNN TSKTCSKCGH    480
LNNYFNFEYR KKNKFPHFKC EKCNFKENAA YNAALNISNP KLKSTKEEP                529

SEQ ID NO: 132            moltype = AA   length = 529
FEATURE                   Location/Qualifiers
REGION                    1..529
                          note = Description of sequence: Modified CAS protein
source                    1..529
                          mol_type = protein
                          organism = synthetic construct
SEQUENCE: 132
MAKNTITKTL KLRIVRPYNS AEVEKIVADE KNNREKIALE KNKDKVKEAC SKHLKVAAYC     60
TTQVERNACL FCKARKLDDK FYQKLRGQFP DAVFWQEISE IFRQLQKQAA EIYNQSLIEL    120
YYEIFIKGKG IANASSVEHY LSRVCYRRAA GLFKNAAIAS GLRSKIKSNF RLKELKNMKS    180
GLPTTKSDNF PIPLVKQKGG QYTGFEISNH NSDFIIKIPF GRWQVKKEID KYRPWEKFDF    240
EQVQKSPKPI SLLLSTQRRK RNKGWSKDEG TEAEIKKVMN GDYQTSYIEV KRGSKICEKS    300
AWMLNLSIDV PKIDKGVDPS IIGGIAVGVK SPLVCAINNA FSRYSISDND LFHFNKKMFA    360
RRRILLKKNR HKRAGHGAKN KLKPITILTE KSERFRKKLI ERWACEIADF FIKNKVGTVQ    420
MENLESMKRK EDSYFNIRLR GFWPYAEMQN KIEFKLKQYG IEIRKVAPNN TSKTCSKCGH    480
LNNYFNFEYR KKNKFPHFKC EKCNFKENAA YNAALNISNP KLKSTKEEP                529

SEQ ID NO: 133            moltype = AA   length = 529
FEATURE                   Location/Qualifiers
REGION                    1..529
                          note = Description of sequence: Modified CAS protein
source                    1..529
                          mol_type = protein
                          organism = synthetic construct
SEQUENCE: 133
MAKNTITKTL KLRIVRPYNS AEVEKIVADE KNNREKIALE KNKDKVKEAC SKHLKVAAYC     60
TTQVERNACL FCKARKLDDK FYQKLRGQFP DAVFWQEISE IFRQLQKQAA EIYNQSLIEL    120
YYEIFIKGKG IANASSVEHY LSRVCYRRAA ALFKNAAIAS GLRSKIKSNF RLKELKNMKS    180
GLPTTKSDNF PIPLVKQKGG QYTGFEISNH NSDFIIKIPF GRWQVKKEID KYRPWEKFDF    240
EQVQKSPKPI SLLLSTQRRK RNKGWSKDEG TEAEIKKVMN GDYQTSYIEV KRGSKICEKS    300
AWMLNLSIDV PKIDKGVDPS IIGGIAVGVK SPLVCAINNA FSRYSISDND LFHFNKKMFA    360
RRRILLKKNR HKRAGHGAKN KLKPITILTE KSERFRKKLI ERWACEIADF FIKNKVGTVQ    420
MENLESMKRK EDSYFNIRLR GFWPYAEMQN KIEFKLKQYG IEIRKVAPNN TSKTCSKCGH    480
LNNYFNFEYR KKNKFPHFKC EKCNFKENAA YNAALNISNP KLKSTKEEP                529

SEQ ID NO: 134            moltype = AA   length = 529
FEATURE                   Location/Qualifiers
REGION                    1..529
                          note = Description of sequence: Modified CAS protein
source                    1..529
                          mol_type = protein
                          organism = synthetic construct
SEQUENCE: 134
MAKNTITKTL KLRIVRPYNS AEVEKIVADE KNNREKIALE KNKDKVKEAC SKHLKVAAYC     60
TTQVERNACL FCKARKLDDK FYQKLRGQFP DAVFWQEISE IFRQLQKQAA EIYNQSLIEL    120
YYEIFIKGKG IANASSVEHY LSRVCYTRAA LLFKNAAIAS GLRSKIKSNF RLKELKNMKS    180
GLPTTKSDNF PIPLVKQKGG QYTGFEISNH NSDFIIKIPF GRWQVKKEID KYRPWEKFDF    240
EQVQKSPKPI SLLLSTQRRK RNKGWSKDEG TEAEIKKVMN GDYQTSYIEV KRGSKICEKS    300
AWMLNLSIDV PKIDKGVDPS IIGGIAVGVK SPLVCAINNA FSRYSISDND LFHFNKKMFA    360
RRRILLKKNR HKRAGHGAKN KLKPITILTE KSERFRKKLI ERWACEIADF FIKNKVGTVQ    420
MENLESMKRK EDSYFNIRLR GFWPYAEMQN KIEFKLKQYG IEIRKVAPNN TSKTCSKCGH    480
LNNYFNFEYR KKNKFPHFKC EKCNFKENAA YNAALNISNP KLKSTKEEP                529
```

```
SEQ ID NO: 135          moltype = AA  length = 529
FEATURE                 Location/Qualifiers
REGION                  1..529
                        note = Description of sequence: Modified CAS protein
source                  1..529
                        mol_type = protein
                        organism = synthetic construct
SEQUENCE: 135
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSRVCYTRAA SLFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIAVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAA YNAALNISNP KLKSTKEEP              529

SEQ ID NO: 136          moltype = AA  length = 529
FEATURE                 Location/Qualifiers
REGION                  1..529
                        note = Description of sequence: Modified CAS protein
source                  1..529
                        mol_type = protein
                        organism = synthetic construct
SEQUENCE: 136
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSRVCYTRAA TLFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIAVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAA YNAALNISNP KLKSTKEEP              529

SEQ ID NO: 137          moltype = AA  length = 529
FEATURE                 Location/Qualifiers
REGION                  1..529
                        note = Description of sequence: Modified CAS protein
source                  1..529
                        mol_type = protein
                        organism = synthetic construct
SEQUENCE: 137
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSRVCYTRAA WLFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIAVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAA YNAALNISNP KLKSTKEEP              529

SEQ ID NO: 138          moltype = AA  length = 529
FEATURE                 Location/Qualifiers
REGION                  1..529
                        note = Description of sequence: Modified CAS protein
source                  1..529
                        mol_type = protein
                        organism = synthetic construct
SEQUENCE: 138
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKQAA EIYNQSLIEL   120
YYEIFIKGKG IANASSVEHY LSRVCYTRAA FLFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIAVGVK SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAA YNAALNISNP KLKSTKEEP              529

SEQ ID NO: 139          moltype = AA  length = 529
FEATURE                 Location/Qualifiers
REGION                  1..529
                        note = Description of sequence: Modified CAS protein
source                  1..529
                        mol_type = protein
```

```
                        organism = synthetic construct
SEQUENCE: 139
MAKNTITKTL KLRIVRPYNS AEVEKIVADE KNNREKIALE KNKDKVKEAC SKHLKVAAYC   60
TTQVERNACL FCKARKLDDK FYQKLRGQFP DAVFWQEISE IFRQLQKQAA EIYNQSLIEL  120
YYEIFIKGKG IANASSVEHY LSRVCYTRAA CLFKNAAIAS GLRSKIKSNF RLKELKNMKS  180
GLPTTKSDNF PIPLVKQKGG QYTGFEISNH NSDFIIKIPF GRWQVKKEID KYRPWEKFDF  240
EQVQKSPKPI SLLLSTQRRK RNKGWSKDEG TEAEIKKVMN GDYQTSYIEV KRGSKICEKS  300
AWMLNLSIDV PKIDKGVDPS IIGGIAVGVK SPLVCAINNA FSRYSISDND LFHFNKKMFA  360
RRRILLKKNR HKRAGHGAKN KLKPITILTE KSERFRKKLI ERWACEIADF FIKNKVGTVQ  420
MENLESMKRK EDSYFNIRLR GFWPYAEMQN KIEFKLKQYG IEIRKVAPNN TSKTCSKCGH  480
LNNYFNFEYR KKNKFPHFKC EKCNFKENAA YNAALNISNP KLKSTKEEP             529

SEQ ID NO: 140          moltype = AA  length = 529
FEATURE                 Location/Qualifiers
REGION                  1..529
                        note = Description of sequence: Modified CAS protein
source                  1..529
                        mol_type = protein
                        organism = synthetic construct
SEQUENCE: 140
MAKNTITKTL KLRIVRPYNS AEVEKIVADE KNNREKIALE KNKDKVKEAC SKHLKVAAYC   60
TTQVERNACL FCKARKLDDK FYQKLRGQFP DAVFWQEISE IFRQLQKQAA EIYNQSLIEL  120
YYEIFIKGKG IANASSVEHY LSRVCYTRAA KLFKNAAIAS GLRSKIKSNF RLKELKNMKS  180
GLPTTKSDNF PIPLVKQKGG QYTGFEISNH NSDFIIKIPF GRWQVKKEID KYRPWEKFDF  240
EQVQKSPKPI SLLLSTQRRK RNKGWSKDEG TEAEIKKVMN GDYQTSYIEV KRGSKICEKS  300
AWMLNLSIDV PKIDKGVDPS IIGGIAVGVK SPLVCAINNA FSRYSISDND LFHFNKKMFA  360
RRRILLKKNR HKRAGHGAKN KLKPITILTE KSERFRKKLI ERWACEIADF FIKNKVGTVQ  420
MENLESMKRK EDSYFNIRLR GFWPYAEMQN KIEFKLKQYG IEIRKVAPNN TSKTCSKCGH  480
LNNYFNFEYR KKNKFPHFKC EKCNFKENAA YNAALNISNP KLKSTKEEP             529

SEQ ID NO: 141          moltype = AA  length = 529
FEATURE                 Location/Qualifiers
REGION                  1..529
                        note = Description of sequence: Modified CAS protein
source                  1..529
                        mol_type = protein
                        organism = synthetic construct
SEQUENCE: 141
MAKNTITKTL KLRIVRPYNS AEVEKIVADE KNNREKIALE KNKDKVKEAC SKHLKVAAYC   60
TTQVERNACL FCKARKLDDK FYQKLRGQFP DAVFWQEISE IFRQLQKQAA EIYNQSLIEL  120
YYEIFIKGKG IANASSVEHY LSRVCYTRAA GLFKNAAIAS GLRSKIKSNF RLKELKNMKS  180
GLPTTKSDNF PIPLVKQKGG QYTGFEISNH NSDFIIKIPF GRWQVKKEID KYRPWEKFDF  240
EQVQKSPKPI SLLLSTQRRK RNKGWSKDEG TEAEIKKVMN GDYQTSYIEV KRGSKICEKS  300
AWMLNLSIDV PKIDKGVDPS IIGGIAVGVK SPLVCAINNA FSRYSISDND LFHFNKKMFA  360
RRRILLKKNR HKRAGHGAKN KLKPITILTE KSERFRKKLI ERWACEIADF FIKNKVGTVQ  420
MENLESMKRK EDSYFNIRLR GFWPYAEMQN KIEFKLKQYG IEIRKVAPNN TSKTCSKCGH  480
LNNYFNFEYR KKNKFPHFKC EKCNFKENAA YNAALNISNP KLKSTKEEP             529

SEQ ID NO: 142          moltype = AA  length = 529
FEATURE                 Location/Qualifiers
REGION                  1..529
                        note = Description of sequence: Modified CAS protein
source                  1..529
                        mol_type = protein
                        organism = synthetic construct
SEQUENCE: 142
MAKNTITKTL KLRIVRPYNS AEVEKIVADE KNNREKIALE KNKDKVKEAC SKHLKVAAYC   60
TTQVERNACL FCKARKLDDK FYQKLRGQFP DAVFWQEISE IFRQLQKQAA EIYNQSLIEL  120
YYEIFIKGKG IANASSVEHY LSRVCYTRAA ILFKNAAIAS GLRSKIKSNF RLKELKNMKS  180
GLPTTKSDNF PIPLVKQKGG QYTGFEISNH NSDFIIKIPF GRWQVKKEID KYRPWEKFDF  240
EQVQKSPKPI SLLLSTQRRK RNKGWSKDEG TEAEIKKVMN GDYQTSYIEV KRGSKICEKS  300
AWMLNLSIDV PKIDKGVDPS IIGGIAVGVK SPLVCAINNA FSRYSISDND LFHFNKKMFA  360
RRRILLKKNR HKRAGHGAKN KLKPITILTE KSERFRKKLI ERWACEIADF FIKNKVGTVQ  420
MENLESMKRK EDSYFNIRLR GFWPYAEMQN KIEFKLKQYG IEIRKVAPNN TSKTCSKCGH  480
LNNYFNFEYR KKNKFPHFKC EKCNFKENAA YNAALNISNP KLKSTKEEP             529

SEQ ID NO: 143          moltype = AA  length = 529
FEATURE                 Location/Qualifiers
REGION                  1..529
                        note = Description of sequence: Modified CAS protein
source                  1..529
                        mol_type = protein
                        organism = synthetic construct
SEQUENCE: 143
MAKNTITKTL KLRIVRPYNS AEVEKIVADE KNNREKIALE KNKDKVKEAC SKHLKVAAYC   60
TTQVERNACL FCKARKLDDK FYQKLRGQFP DAVFWQEISE IFRQLQKQAA EIYNQSLIEL  120
YYEIFIKGKG IANASSVEHY LSRVCYTRAA PLFKNAAIAS GLRSKIKSNF RLKELKNMKS  180
GLPTTKSDNF PIPLVKQKGG QYTGFEISNH NSDFIIKIPF GRWQVKKEID KYRPWEKFDF  240
EQVQKSPKPI SLLLSTQRRK RNKGWSKDEG TEAEIKKVMN GDYQTSYIEV KRGSKICEKS  300
```

```
AWMLNLSIDV PKIDKGVDPS IIGGIAVGVK SPLVCAINNA FSRYSISDND LFHFNKKMFA    360
RRRILLKKNR HKRAGHGAKN KLKPITILTE KSERFRKKLI ERWACEIADF FIKNKVGTVQ    420
MENLESMKRK EDSYFNIRLR GFWPYAEMQN KIEFKLKQYG IEIRKVAPNN TSKTCSKCGH    480
LNNYFNFEYR KKNKFPHFKC EKCNFKENAA YNAALNISNP KLKSTKEEP               529

SEQ ID NO: 144          moltype = AA   length = 529
FEATURE                 Location/Qualifiers
REGION                  1..529
                        note = Description of sequence: Modified CAS protein
source                  1..529
                        mol_type = protein
                        organism = synthetic construct
SEQUENCE: 144
MAKNTITKTL KLRIVRPYNS AEVEKIVADE KNNREKIALE KNKDKVKEAC SKHLKVAAYC     60
TTQVERNACL FCKARKLDDK FYQKLRGQFP DAVFWQEISE IFRQLQKQAA EIYNQSLIEL    120
YYEIFIKGKG IANASSVEHY LSRVCYTRAA HLFKNAAIAS GLRSKIKSNF RLKELKNMKS    180
GLPTTKSDNF PIPLVKQKGG QYTGFEISNH NSDFIIKIPF GRWQVKKEID KYRPWEKFDF    240
EQVQKSPKPI SLLLSTQRRK RNKGWSKDEG TEAEIKKVMN GDYQTSYIEV KRGSKICEKS    300
AWMLNLSIDV PKIDKGVDPS IIGGIAVGVK SPLVCAINNA FSRYSISDND LFHFNKKMFA    360
RRRILLKKNR HKRAGHGAKN KLKPITILTE KSERFRKKLI ERWACEIADF FIKNKVGTVQ    420
MENLESMKRK EDSYFNIRLR GFWPYAEMQN KIEFKLKQYG IEIRKVAPNN TSKTCSKCGH    480
LNNYFNFEYR KKNKFPHFKC EKCNFKENAA YNAALNISNP KLKSTKEEP               529

SEQ ID NO: 145          moltype = AA   length = 529
FEATURE                 Location/Qualifiers
REGION                  1..529
                        note = Description of sequence: Modified CAS protein
source                  1..529
                        mol_type = protein
                        organism = synthetic construct
SEQUENCE: 145
MAKNTITKTL KLRIVRPYNS AEVEKIVADE KNNREKIALE KNKDKVKEAC SKHLKVAAYC     60
TTQVERNACL FCKARKLDDK FYQKLRGQFP DAVFWQEISE IFRQLQKQAA EIYNQSLIEL    120
YYEIFIKGKG IANASSVEHY LSRVCYTRAA ALFKNAAIAS GLRSKIKSNF RLKELKNMKS    180
GLPTTKSDNF PIPLVKQKGG QYTGFEISNH NSDFIIKIPF GRWQVKKEID KYRPWEKFDF    240
EQVQKSPKPI SLLLSTQRRK RNKGWSKDEG TEAEIKKVMN GDYQTSYIEV KRGSKICEKS    300
AWMLNLSIDV PKIDKGVDPS IIGGIAVGVK SPLVCAINNA FSRYSISDND LFHFNKKMFA    360
RRRILLKKNR HKRAGHGAKN KLKPITILTE KSERFRKKLI ERWACEIADF FIKNKVGTVQ    420
MENLESMKRK EDSYFNIRLR GFWPYAEMQN KIEFKLKQYG IEIRKVAPNN TSKTCSKCGH    480
LNNYFNFEYR KKNKFPHFKC EKCNFKENAA YNAALNISNP KLKSTKEEP               529

SEQ ID NO: 146          moltype = AA   length = 529
FEATURE                 Location/Qualifiers
REGION                  1..529
                        note = Description of sequence: Modified CAS protein
source                  1..529
                        mol_type = protein
                        organism = synthetic construct
SEQUENCE: 146
MAKNTITKTL KLRIVRPYNS AEVEKIVADE KNNREKIALE KNKDKVKEAC SKHLKVAAYC     60
TTQVERNACL FCKARKLDDK FYQKLRGQFP DAVFWQEISE IFRQLQKQAA EIYNQSLIEL    120
YYEIFIKGKG IANASSVEHY LSRVCYTRAA VLFKNAAIAS GLRSKIKSNF RLKELKNMKS    180
GLPTTKSDNF PIPLVKQKGG QYTGFEISNH NSDFIIKIPF GRWQVKKEID KYRPWEKFDF    240
EQVQKSPKPI SLLLSTQRRK RNKGWSKDEG TEAEIKKVMN GDYQTSYIEV KRGSKICEKS    300
AWMLNLSIDV PKIDKGVDPS IIGGIAVGVK SPLVCAINNA FSRYSISDND LFHFNKKMFA    360
RRRILLKKNR HKRAGHGAKN KLKPITILTE KSERFRKKLI ERWACEIADF FIKNKVGTVQ    420
MENLESMKRK EDSYFNIRLR GFWPYAEMQN KIEFKLKQYG IEIRKVAPNN TSKTCSKCGH    480
LNNYFNFEYR KKNKFPHFKC EKCNFKENAA YNAALNISNP KLKSTKEEP               529

SEQ ID NO: 147          moltype = AA   length = 529
FEATURE                 Location/Qualifiers
REGION                  1..529
                        note = Description of sequence: Modified CAS protein
source                  1..529
                        mol_type = protein
                        organism = synthetic construct
SEQUENCE: 147
MAKNTITKTL KLRIVRPYNS AEVEKIVADE KNNREKIALE KNKDKVKEAC SKHLKVAAYC     60
TTQVERNACL FCKARKLDDK FYQKLRGQFP DAVFWQEISE IFRQLQKQAA EIYNQSLIEL    120
YYEIFIKGKG IANASSVEHY LSRVCYTRAA QLFKNAAIAS GLRSKIKSNF RLKELKNMKS    180
GLPTTKSDNF PIPLVKQKGG QYTGFEISNH NSDFIIKIPF GRWQVKKEID KYRPWEKFDF    240
EQVQKSPKPI SLLLSTQRRK RNKGWSKDEG TEAEIKKVMN GDYQTSYIEV KRGSKICEKS    300
AWMLNLSIDV PKIDKGVDPS IIGGIAVGVK SPLVCAINNA FSRYSISDND LFHFNKKMFA    360
RRRILLKKNR HKRAGHGAKN KLKPITILTE KSERFRKKLI ERWACEIADF FIKNKVGTVQ    420
MENLESMKRK EDSYFNIRLR GFWPYAEMQN KIEFKLKQYG IEIRKVAPNN TSKTCSKCGH    480
LNNYFNFEYR KKNKFPHFKC EKCNFKENAA YNAALNISNP KLKSTKEEP               529

SEQ ID NO: 148          moltype = AA   length = 529
FEATURE                 Location/Qualifiers
```

-continued

```
REGION                    1..529
                          note = Description of sequence: Modified CAS protein
source                    1..529
                          mol_type = protein
                          organism = synthetic construct
SEQUENCE: 148
MAKNTITKTL KLRIVRPYNS AEVEKIVADE KNNREKIALE KNKDKVKEAC SKHLKVAAYC   60
TTQVERNACL FCKARKLDDK FYQKLRGQFP DAVFWQEISE IFRQLQKQAA EIYNQSLIEL  120
YYEIFIKGKG IANASSVEHY LSRVCYTRAA MLFKNAAIAS GLRSKIKSNF RLKELKNMKS  180
GLPTTKSDNF PIPLVKQKGG QYTGFEISNH NSDFIIKIPF GRWQVKKEID KYRPWEKFDF  240
EQVQKSPKPI SLLLSTQRRK RNKGWSKDEG TEAEIKKVMN GDYQTSYIEV KRGSKICEKS  300
AWMLNLSIDV PKIDKGVDPS IIGGIAVGVK SPLVCAINNA FSRYSISDND LFHFNKKMFA  360
RRRILLKKNR HKRAGHGAKN KLKPITILTE KSERFRKKLI ERWACEIADF FIKNKVGTVQ  420
MENLESMKRK EDSYFNIRLR GFWPYAEMQN KIEFKLKQYG IEIRKVAPNN TSKTCSKCGH  480
LNNYFNFEYR KKNKFPHFKC EKCNFKENAA YNAALNISNP KLKSTKEEP             529

SEQ ID NO: 149            moltype = AA  length = 529
FEATURE                   Location/Qualifiers
REGION                    1..529
                          note = Description of sequence: Modified CAS protein
source                    1..529
                          mol_type = protein
                          organism = synthetic construct
SEQUENCE: 149
MAKNTITKTL KLRIVRPYNS AEVEKIVADE KNNREKIALE KNKDKVKEAC SKHLKVAAYC   60
TTQVERNACL FCKARKLDDK FYQKLRGQFP DAVFWQEISE IFRQLQKQAA EIYNQSLIEL  120
YYEIFIKGKG IANASSVEHY LSRVCYTRAA DLFKNAAIAS GLRSKIKSNF RLKELKNMKS  180
GLPTTKSDNF PIPLVKQKGG QYTGFEISNH NSDFIIKIPF GRWQVKKEID KYRPWEKFDF  240
EQVQKSPKPI SLLLSTQRRK RNKGWSKDEG TEAEIKKVMN GDYQTSYIEV KRGSKICEKS  300
AWMLNLSIDV PKIDKGVDPS IIGGIAVGVK SPLVCAINNA FSRYSISDND LFHFNKKMFA  360
RRRILLKKNR HKRAGHGAKN KLKPITILTE KSERFRKKLI ERWACEIADF FIKNKVGTVQ  420
MENLESMKRK EDSYFNIRLR GFWPYAEMQN KIEFKLKQYG IEIRKVAPNN TSKTCSKCGH  480
LNNYFNFEYR KKNKFPHFKC EKCNFKENAA YNAALNISNP KLKSTKEEP             529

SEQ ID NO: 150            moltype = AA  length = 529
FEATURE                   Location/Qualifiers
REGION                    1..529
                          note = Description of sequence: Modified CAS protein
source                    1..529
                          mol_type = protein
                          organism = synthetic construct
SEQUENCE: 150
MAKNTITKTL KLRIVRPYNS AEVEKIVADE KNNREKIALE KNKDKVKEAC SKHLKVAAYC   60
TTQVERNACL FCKARKLDDK FYQKLRGQFP DAVFWQEISE IFRQLQKQAA EIYNQSLIEL  120
YYEIFIKGKG IANASSVEHY LSRVCYTRAA NLFKNAAIAS GLRSKIKSNF RLKELKNMKS  180
GLPTTKSDNF PIPLVKQKGG QYTGFEISNH NSDFIIKIPF GRWQVKKEID KYRPWEKFDF  240
EQVQKSPKPI SLLLSTQRRK RNKGWSKDEG TEAEIKKVMN GDYQTSYIEV KRGSKICEKS  300
AWMLNLSIDV PKIDKGVDPS IIGGIAVGVK SPLVCAINNA FSRYSISDND LFHFNKKMFA  360
RRRILLKKNR HKRAGHGAKN KLKPITILTE KSERFRKKLI ERWACEIADF FIKNKVGTVQ  420
MENLESMKRK EDSYFNIRLR GFWPYAEMQN KIEFKLKQYG IEIRKVAPNN TSKTCSKCGH  480
LNNYFNFEYR KKNKFPHFKC EKCNFKENAA YNAALNISNP KLKSTKEEP             529

SEQ ID NO: 151            moltype = AA  length = 529
FEATURE                   Location/Qualifiers
REGION                    1..529
                          note = Description of sequence: Modified CAS protein
source                    1..529
                          mol_type = protein
                          organism = synthetic construct
SEQUENCE: 151
MAKNTITKTL KLRIVRPYNS AEVEKIVADE KNNREKIALE KNKDKVKEAC SKHLKVAAYC   60
TTQVERNACL FCKARKLDDK FYQKLRGQFP DAVFWQEISE IFRQLQKQAA EIYNQSLIEL  120
YYEIFIKGKG IANASSVEHY LSRVCYRRAA YLFKNAAIAS GLRSKIKSNF RLKELKNMKS  180
GLPTTKSDNF PIPLVKQKGG QYTGFEISNH NSDFIIKIPF GRWQVKKEID KYRPWEKFDF  240
EQVQKSPKPI SLLLSTQRRK RNKGWSKDEG TEAEIKKVMN GDYQTSYIEV KRGSKICEKS  300
AWMLNLSIDV PKIDKGVDPS IIGGIAVGVK SPLVCAINNA FSRYSISDND LFHFNKKMFA  360
RRRILLKKNR HKRAGHGAKN KLKPITILTE KSERFRKKLI ERWACEIADF FIKNKVGTVQ  420
MENLESMKRK EDSYFNIRLR GFWPYAEMQN KIEFKLKQYG IEIRKVAPNN TSKTCSKCGH  480
LNNYFNFEYR KKNKFPHFKC EKCNFKENAA YNAALNISNP KLKSTKEEP             529

SEQ ID NO: 152            moltype = AA  length = 529
FEATURE                   Location/Qualifiers
REGION                    1..529
                          note = Description of sequence: Modified CAS protein
source                    1..529
                          mol_type = protein
                          organism = synthetic construct
SEQUENCE: 152
MAKNTITKTL KLRIVRPYNS AEVEKIVADE KNNREKIALE KNKDKVKEAC SKHLKVAAYC   60
```

```
TTQVERNACL FCKARKLDDK FYQKLRGQFP DAVFWQEISE IFRQLQKAA  EIYNQSLIEL   120
YYEIFIKGKG IANASSVEHY LSRVCYRRAA ALFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIAVGVR SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAA YNAALNISNP KLKSTKREP               529

SEQ ID NO: 153           moltype = AA  length = 529
FEATURE                  Location/Qualifiers
REGION                   1..529
                         note = Description of sequence: Modified CAS protein
source                   1..529
                         mol_type = protein
                         organism = synthetic construct
SEQUENCE: 153
MAKNTITKTL KLRIVRPYNS AEVEKIVADE KNNREKIALE KNKDKVKEAC SKHLKVAAYC    60
TTQVERNACL FCKARKLDDK FYQKLRGQFP DAVFWQEISE IFRQLQKAA  EIYNQSLIEL   120
YYEIFIKGKG IANASSVEHY LSRVCYRRAA ALFKNAAIAS GLRSKIKSNF RLKELKNMKS   180
GLPTTKSDNF PIPLVKQKGG QYTGFEISNH NSDFIIKIPF GRWQVKKEID KYRPWEKFDF   240
EQVQKSPKPI SLLLSTQRRK RNKGWSKDEG TEAEIKKVMN GDYQTSYIEV KRGSKICEKS   300
AWMLNLSIDV PKIDKGVDPS IIGGIAVGVR SPLVCAINNA FSRYSISDND LFHFNKKMFA   360
RRRILLKKNR HKRAGHGAKN KLKPITILTE KSERFRKKLI ERWACEIADF FIKNKVGTVQ   420
MENLESMKRK EDSYFNIRLR GFWPYAEMQN KIEFKLKQYG IEIRKVAPNN TSKTCSKCGH   480
LNNYFNFEYR KKNKFPHFKC EKCNFKENAA YNAALNISNP KLKSTKERP               529

SEQ ID NO: 154           moltype = AA  length = 1614
FEATURE                  Location/Qualifiers
REGION                   1..1614
                         note = Description of sequence: Modified CAS protein
source                   1..1614
                         mol_type = protein
                         organism = synthetic construct
SEQUENCE: 154
PKKKRKVGSG SSKLEKFTNC YSLSKTLRFK AIPVGKTQEN IDNKRLLVED EKRAEDYKGV    60
KKLLDRYYLS FINDVLHSIK LKNLNNYISL FRKKTRTEKE NKELENLEIN LRKEIAKAFK   120
GNEGYKSLFK KDIIETILPE FLDDKDEIAL VNSFNGFTTA FTGFFDNREN MFSEEAKSTS   180
IAFRCINENL TRYISNMDIF EKVDAIFDKH EVQOEIKEKIL NSDYDVEDFF EGEFFNFVLT   240
QEGIDVYNAI IGGFVTESGE KIKGLNEYIN LYNQKTKQKL PKFKPLYKQV LSDRESLSFY   300
GEGYTSDEEV LEVFRNTLNK NSEIFSSIKK LEKLFKNFDE YSSAGIFVKN GPAISTISKD   360
IFGEWNVIRD KWNAEYDDIH LKKKAVVTEK YEDDRRRSFK KIGSFSLEQL QEYADADLSV   420
VEKLKEIIIQ KVDEIYKVYG SSEKLFDADF VLEKSLKKND AVVAIMKDLL DSVKSFENYI   480
KAFFGEGKET NRDESFYGDF VLAYDILLKV DHIYDAIRNY VTQKPYSKDK FKLYFQNPQF   540
MGGWDKDKET DYRATILRYG SKYYLAIMDK KYAKCLQKID KDDVNGNYEK INYKLLPGPN   600
KMLPKVFFSK KWMAYYNPSE DIQKIYKNGT FKKGDMFNLN DCHKLIDFFK DSISRYPKWS   660
NAYDFNFSET EKYKDIAGFY REVEEQGYKV SFESASKKEV KDLVEEGKLY MFQIYNKDFS   720
DKSHGTPNLH TMYFKLLFDE NNHGQIRLSG GAELFMRRAS LKKEELVVHP ANSPIANKNP   780
DNPKKTTTLS YDVYKDKRFS EDQYELHIPI AINKCPKNIF KINTEVRVLL KHDDNPYVIG   840
IARGERNLLY IVVVDGKGNI VEQYSLNEII NNFNGIRIKT DYHSLLDKKE KERFEARQNW   900
TSIENIKELK AGYISQVVHK ICELVEKYDA VIALEDLNSG FKNSRVKVEK QVYQKFEKML   960
IDKLNYMVDK KSNPCATGGA LKGYQITNKF ESFKSMSTQN GFIFYIPAWL TSKIDPSTGF  1020
VNLLKTKYTS IADSKKFISS FDRIMYVPEE DLFEFALDYK NFSRTDADYI KKWKLYSYGN  1080
RIRIFRNPKK NNVFDWEEVC LTSAYKELFN KYGINYQQGD IRALLCEQSD KAFYSSFMAL  1140
MSLMLQMRNS ITGRTDVDFL ISPVKNSDGI FYDSRNYEAQ ENAILPKNAD ANGAYNIARK  1200
VLWAIGQFKK AEDEKLDKVK IAISNKEWLE YAQTSVKHGS YPYDVPDYAS LGSGDGIGSG  1260
SNGSSLMDAK SLTAWSRTLV TFKDVFVDFT REEWKLLDTA QQIVYRNVML ENYKNLVSLG  1320
YQLTKPDVIL RLEKGEEPHM GGGSGEDPAA KRVKLDMGSG ATNFSLLKQA GDVEENPGPV  1380
SKGEEDNMAI IKEFMRFKVH MEGSVNGHEF EIEGEGEGRP YEGTQTAKLK VTKGGPLPFA  1440
WDILSPQFMY GSKAYVKHPA DIPDYLKLSF PEGFKWERVM NFEDGGVVTV TQDSSLQDGE  1500
FIYKVKLRGT NFPSDGPVMQ KKTMGWEASS ERMYPEDGAL KGEIKQRLKL KDGGHYDAEV  1560
KTTYKAKKPV QLPGAYNVNI KLDITSHNED YTIVEQYERA EGRHSTGGMD ELYK        1614

SEQ ID NO: 155           moltype = AA  length = 1652
FEATURE                  Location/Qualifiers
REGION                   1..1652
                         note = Description of sequence: Modified CAS protein
source                   1..1652
                         mol_type = protein
                         organism = synthetic construct
SEQUENCE: 155
PKKKRKVGSG SSKLEKFTNC YSLSKTLRFK AIPVGKTQEN IDNKRLLVED EKRAEDYKGV    60
KKLLDRYYLS FINDVLHSIK LKNLNNYISL FRKKTRTEKE NKELENLEIN LRKEIAKAFK   120
GNEGYKSLFK KDIIETILPE FLDDKDEIAL VNSFNGFTTA FTGFFDNREN MFSEEAKSTS   180
IAFRCINENL TRYISNMDIF EKVDAIFDKH EVQOEIKEKIL NSDYDVEDFF EGEFFNFVLT   240
QEGIDVYNAI IGGFVTESGE KIKGLNEYIN LYNQKTKQKL PKFKPLYKQV LSDRESLSFY   300
GEGYTSDEEV LEVFRNTLNK NSEIFSSIKK LEKLFKNFDE YSSAGIFVKN GPAISTISKD   360
IFGEWNVIRD KWNAEYDDIH LKKKAVVTEK YEDDRRRSFK KIGSFSLEQL QEYADADLSV   420
VEKLKEIIIQ KVDEIYKVYG SSEKLFDADF VLEKSLKKND AVVAIMKDLL DSVKSFENYI   480
```

```
KAFFGEGKET NRDESFYGDF VLAYDILLKV DHIYDAIRNY VTQKPYSKDK FKLYFQNPQF    540
MGGWDKDKET DYRATILRYG SKYYLAIMDK KYAKCLQKID KDDVNGNYEK INYKLLPGPN    600
KMLPKVFFSK KWMAYYNPSE DIQKIYKNGT FKKGDMFNLN DCHKLIDFFK DSISRYPKWS    660
NAYDFNFSET EKYKDIAGFY REVEEQGYKV SFESASKKEV DKLVEEGKLY MFQIYNKDFS    720
DKSHGTPNLH TMYFKLLFDE NNHGQIRLSG GAELFMRRAS LKKEELVVHP ANSPIANKNP    780
DNPKKTTTLS YDVYKDKRFS EDQYELHIPI AINKCPKNIF KINTEVRVLL KHDDNPYVIG    840
IARGERNLLY IVVVDKGNI VEQYSLNEII NNFNGIRIKT DYHSLLDKKE KERFEARQNW     900
TSIENIKELK AGYISQVVHK ICELVEKYDA VIALEDLNSG FKNSRVKVEK QVYQKFEKML    960
IDKLNYMVDK KSNPCATGGA LKGYQITNKF ESFKSMSTQN GFIFYIPAWL TSKIDPSTGF   1020
VNLLKTKYTS IADSKKFISS FDRIMYVPEE DLFEFALDYK NFSRTDADYI KKWKLYSYGN   1080
RIRIFRNPKK NNVFDWEEVC LTSAYKELFN KYGINYQQGD IRALLCEQSD KAFYSSFMAL   1140
MSLMLQMRNS ITGRTDVDFL ISPVKNSDGI FYDSRNYEAQ ENAILPKNAD ANGAYNIARK   1200
VLWAIGQFKK AEDEKLDKVK IAISNKEWLE YAQTSVKHGS YPYDVPDYAS LGSGDGIGSG   1260
SNGSSLMNNS QGRVTFEDVT VNFTQGEWQR LNPEQRNLYR DVMLENYSNL VSVGQGETTK   1320
PDVILRLEQG KEPWLEEEEV LGSGRAEKNG DIGGQIWKPK DVKESLAREV PSINKEHMGG   1380
GSGEDPAAKR VKLDMGSGAT NFSLLKQAGD VEENPGPVSK GEEDNMAIIK EFMRFKVHME   1440
GSVNGHEFEI EGEGEGRPYE GTQTAKLKVT KGGPLPFAWD ILSPQFMYGS KAYVKHPADI   1500
PDYLKLSFPE GFKWERVMNF EDGGVVTVTQ DSSLQDGEFI YKVKLRGTNF PSDGPVMQKK   1560
TMGWEASSER MYPEDGALKG EIKQRLKLKD GGHYDAEVKT TYKAKKPVQL PGAYNVNIKL   1620
DITSHNEDYT IVEQYERAEG RHSTGGMDEL YK                                 1652

SEQ ID NO: 156        moltype = AA   length = 895
FEATURE               Location/Qualifiers
REGION                1..895
                      note = Description of sequence: Modified CAS protein
source                1..895
                      mol_type = protein
                      organism = synthetic construct
SEQUENCE: 156
PKKKRKVGSG SAKNTITKTL KLRIVRPYNS AEVEKIVADE KNNREKIALE KNKDKVKEAC    60
SKHLKVAAYC TTQVERNACL FCKARKLDDK FYQKLRGQFP DAVFWQEISE IFRQLQKQAA   120
EIYNQSLIEL YYEIFIKGKG IANASSVEHY LSDVCYTRAA ELFKNAAIAS GLRSKIKSNF   180
RLKELKNMKS GLPTTKSDNF PIPLVKQKGG QYTGFEISNH NSDFIIKPF GRWQVKKEID    240
KYRPWEKFDF EQVQKSPKPI SLLLSTQRRK RNKGWSKDEG TEAEIKKVMN GDYQTSYIEV   300
KRGSKICEKS AWMLNLSIDV PKIDKGVDPS IIGGIAVGVK SPLVCAINNA FSRYSISDND   360
LFHFNKKMFA RRRILLKKNR HKRAGHGAKN KLKPITILTE KSERFRKKLI ERWACEIADF   420
FIKNKVGTVQ MENLESMKRK EDSYFNIRLR GFWPYAEMQN KIEFKLKQYG IEIRKVAPNN   480
TSKTCSKCGH LNNYFNFEYR KKNKPPHFKC EKCNFKENAA YNAALNISNP KLKSTKEEPA   540
YPYDVPDYAS LGSGDGIGSG SNGSSLMDAK SLTAWSRTLV TFKDVFVDFT REEWKLLDTA   600
QQIVYRNVML ENYKNLVSLG YQLTKPDVIL RLEKGEEPHM GGGSGEDPAA KRVKLDMGSG   660
VSKGEEDNMA IIKEFMRFKV HMEGSVNGHE FEIEGEGEGR PYEGTQTAKL KVTKGGPLPF   720
AWDILSPQFM YGSKAYVKHP ADIPDYLKLS FPEGFKWERV MNFEDGGVVT VTQDSSLQDG   780
EFIYKVKLRG TNFPSDGPVM QKKTMGWEAS SERMYPEDGA LKGEIKQRLK LKDGGHYDAE   840
VKTTYKAKKP VQLPGAYNVN IKLDITSHNE DYTIVEQYER AEGRHSTGGM DELYK        895

SEQ ID NO: 157        moltype = AA   length = 933
FEATURE               Location/Qualifiers
REGION                1..933
                      note = Description of sequence: Modified CAS protein
source                1..933
                      mol_type = protein
                      organism = synthetic construct
SEQUENCE: 157
PKKKRKVGSG SAKNTITKTL KLRIVRPYNS AEVEKIVADE KNNREKIALE KNKDKVKEAC    60
SKHLKVAAYC TTQVERNACL FCKARKLDDK FYQKLRGQFP DAVFWQEISE IFRQLQKQAA   120
EIYNQSLIEL YYEIFIKGKG IANASSVEHY LSDVCYTRAA ELFKNAAIAS GLRSKIKSNF   180
RLKELKNMKS GLPTTKSDNF PIPLVKQKGG QYTGFEISNH NSDFIIKPF GRWQVKKEID    240
KYRPWEKFDF EQVQKSPKPI SLLLSTQRRK RNKGWSKDEG TEAEIKKVMN GDYQTSYIEV   300
KRGSKICEKS AWMLNLSIDV PKIDKGVDPS IIGGIAVGVK SPLVCAINNA FSRYSISDND   360
LFHFNKKMFA RRRILLKKNR HKRAGHGAKN KLKPITILTE KSERFRKKLI ERWACEIADF   420
FIKNKVGTVQ MENLESMKRK EDSYFNIRLR GFWPYAEMQN KIEFKLKQYG IEIRKVAPNN   480
TSKTCSKCGH LNNYFNFEYR KKNKPPHFKC ECNFKENAA YNAALNISNP KLKSTKEEPA    540
YPYDVPDYAS LGSGDGIGSG SNGSSLMNNS QGRVTFEDVT VNFTQGEWQR LNPEQRNLYR   600
DVMLENYSNL VSVGQGETTK PDVILRLEQG KEPWLEEEEV LGSGRAEKNG DIGGQIWKPK   660
DVKESLAREV PSINKEHMGG GSGEDPAAKR VKLDMGSGVS KGEEDNMAII KEFMRFKVHM   720
EGSVNGHEFE IEGEGEGRPY EGTQTAKLKV TKGGPLPFAW DILSPQFMYG SKAYVKHPAD   780
IPDYLKLSFP EGFKWERVMN FEDGGVVTVT QDSSLQDGEF IYKVKLRGTN FPSDGPVMQK   840
KTMGWEASSE RMYPEDGALK GEIKQRLKLK DGGHYDAEVK TTYKAKKPVQ LPGAYNVNIK   900
LDITSHNEDY TIVEQYERAE GRHSTGGMDE LYK                                933

SEQ ID NO: 158        moltype = AA   length = 895
FEATURE               Location/Qualifiers
REGION                1..895
                      note = Description of sequence: Modified CAS protein
source                1..895
                      mol_type = protein
                      organism = synthetic construct
SEQUENCE: 158
PKKKRKVGSG SAKNTITKTL KLRIVRPYNS AEVEKIVADE KNNREKIALE KNKDKVKEAC    60
```

```
SKHLKVAAYC TTQVERNACL FCKARKLDDK FYQKLRGQFP DAVFWQEISE IFRQLQKQAA  120
EIYNQSLIEL YYEIFIKGKG IANASSVEHY LSRVCYTRAA ELFKNAAIAS GLRSKIKSNF  180
RLKELKNMKS GLPTTKSDNF PIPLVKQKGG QYTGFEISNH NSDFIIKIPF GRWQVKKEID  240
KYRPWEKFDF EQVQKSPKPI SLLLSTQRRK RNKGWSKDEG TEAEIKKVMN GDYQTSYIEV  300
KRGSKICEKS AWMLNLSIDV PKIDKGVDPS IIGGIAVGVK SPLVCAINNA FSRYSISDND  360
LFHFNKKMFA RRRILLKKNR HKRAGHGAKN KLKPITILTE KSERFRKKLI ERWACEIADF  420
FIKNKVGTVQ MENLESMKRK EDSYFNIRLR GFWPYAEMQN KIEFKLKQYG IEIRKVAPNN  480
TSKTCSKCGH LNNYFNFEYR KKNKPPHFKC EKCNFKENAA YNAALNISNP KLKSTKEEPA  540
YPYDVPDYAS LGSGDGIGSG SNGSSLMDAK SLTAWSRTLV TFKDVFVDFT REEWKLLDTA  600
QQIVYRNVML ENYKNLVSLG YQLTKPDVIL RLEKGEEPHM GGGSGEDPAA KRVKLDMGSG  660
VSKGEEDNMA IIKEFMRFKV HMEGSVNGHE FEIEGEGEGR PYEGTQTAKL KVTKGGPLPF  720
AWDILSPQFM YGSKAYVKHP ADIPDYLKLS FPEGFKWERV MNFEDGGVVT VTQDSSLQDG  780
EFIYKVKLRG TNFPSDGPVM QKKTMGWEAS SERMYPEDGA LKGEIKQRLK LKDGGHYDAE  840
VKTTYKAKKP VQLPGAYNVN IKLDITSHNE DYTIVEQYER AEGRHSTGGM DELYK       895

SEQ ID NO: 159          moltype = AA   length = 933
FEATURE                 Location/Qualifiers
REGION                  1..933
                        note = Description of sequence: Modified CAS protein
source                  1..933
                        mol_type = protein
                        organism = synthetic construct
SEQUENCE: 159
PKKKRKVGSG SAKNTITKTL KLRIVRPYNS AEVEKIVADE KNNREKIALE KNKDKVKEAC   60
SKHLKVAAYC TTQVERNACL FCKARKLDDK FYQKLRGQFP DAVFWQEISE IFRQLQKQAA  120
EIYNQSLIEL YYEIFIKGKG IANASSVEHY LSRVCYTRAA ELFKNAAIAS GLRSKIKSNF  180
RLKELKNMKS GLPTTKSDNF PIPLVKQKGG QYTGFEISNH NSDFIIKIPF GRWQVKKEID  240
KYRPWEKFDF EQVQKSPKPI SLLLSTQRRK RNKGWSKDEG TEAEIKKVMN GDYQTSYIEV  300
KRGSKICEKS AWMLNLSIDV PKIDKGVDPS IIGGIAVGVK SPLVCAINNA FSRYSISDND  360
LFHFNKKMFA RRRILLKKNR HKRAGHGAKN KLKPITILTE KSERFRKKLI ERWACEIADF  420
FIKNKVGTVQ MENLESMKRK EDSYFNIRLR GFWPYAEMQN KIEFKLKQYG IEIRKVAPNN  480
TSKTCSKCGH LNNYFNFEYR KKNKPPHFKC EKCNFKENAA YNAALNISNP KLKSTKEEPA  540
YPYDVPDYAS LGSGDGIGSG SNGSSLMNNS QGRVTFEDVT VNFTQGEWQR LNPEQRNLYR  600
DVMLENYSNL VSVGQGETTK PDVILRLEQG KEPWLEEEEV LGSGRAEKNG DIGGQIWKPK  660
DVKESLAREV PSINKEHMGG GSGEDPAAKR VKLDMGSGVS KGEEDNMAII KEFMRFKVHM  720
EGSVNGHEFE IEGEGEGRPY EGTQTAKLKV TKGGPLPFAW DILSPQFMYG SKAYVKHPAD  780
IPDYLKLSFP EGFKWERVMN FEDGGVVTVT QDSSLQDGEF IYKVKLRGTN FPSDGPVMQK  840
KTMGWEASSE RMYPEDGALK GEIKQRLKLK DGGHYDAEVK TTYKAKKPVQ LPGAYNVNIK  900
LDITSHNEDY TIVEQYERAE GRHSTGGMDE LYK                              933

SEQ ID NO: 160          moltype = AA   length = 895
FEATURE                 Location/Qualifiers
REGION                  1..895
                        note = Description of sequence: Modified CAS protein
source                  1..895
                        mol_type = protein
                        organism = synthetic construct
SEQUENCE: 160
PKKKRKVGSG SAKNTITKTL KLRIVRPYNS AEVEKIVADE KNNREKIALE KNKDKVKEAC   60
SKHLKVAAYC TTQVERNACL FCKARKLDDK FYQKLRGQFP DAVFWQEISE IFRQLQKQAA  120
EIYNQSLIEL YYEIFIKGKG IANASSVEHY LSRVCYRRAA ELFKNAAIAS GLRSKIKSNF  180
RLKELKNMKS GLPTTKSDNF PIPLVKQKGG QYTGFEISNH NSDFIIKIPF GRWQVKKEID  240
KYRPWEKFDF EQVQKSPKPI SLLLSTQRRK RNKGWSKDEG TEAEIKKVMN GDYQTSYIEV  300
KRGSKICEKS AWMLNLSIDV PKIDKGVDPS IIGGIAVGVK SPLVCAINNA FSRYSISDND  360
LFHFNKKMFA RRRILLKKNR HKRAGHGAKN KLKPITILTE KSERFRKKLI ERWACEIADF  420
FIKNKVGTVQ MENLESMKRK EDSYFNIRLR GFWPYAEMQN KIEFKLKQYG IEIRKVAPNN  480
TSKTCSKCGH LNNYFNFEYR KKNKPPHFKC EKCNFKENAA YNAALNISNP KLKSTKEEPA  540
YPYDVPDYAS LGSGDGIGSG SNGSSLMDAK SLTAWSRTLV TFKDVFVDFT REEWKLLDTA  600
QQIVYRNVML ENYKNLVSLG YQLTKPDVIL RLEKGEEPHM GGGSGEDPAA KRVKLDMGSG  660
VSKGEEDNMA IIKEFMRFKV HMEGSVNGHE FEIEGEGEGR PYEGTQTAKL KVTKGGPLPF  720
AWDILSPQFM YGSKAYVKHP ADIPDYLKLS FPEGFKWERV MNFEDGGVVT VTQDSSLQDG  780
EFIYKVKLRG TNFPSDGPVM QKKTMGWEAS SERMYPEDGA LKGEIKQRLK LKDGGHYDAE  840
VKTTYKAKKP VQLPGAYNVN IKLDITSHNE DYTIVEQYER AEGRHSTGGM DELYK       895

SEQ ID NO: 161          moltype = AA   length = 933
FEATURE                 Location/Qualifiers
REGION                  1..933
                        note = Description of sequence: Modified CAS protein
source                  1..933
                        mol_type = protein
                        organism = synthetic construct
SEQUENCE: 161
PKKKRKVGSG SAKNTITKTL KLRIVRPYNS AEVEKIVADE KNNREKIALE KNKDKVKEAC   60
SKHLKVAAYC TTQVERNACL FCKARKLDDK FYQKLRGQFP DAVFWQEISE IFRQLQKQAA  120
EIYNQSLIEL YYEIFIKGKG IANASSVEHY LSRVCYRRAA ELFKNAAIAS GLRSKIKSNF  180
RLKELKNMKS GLPTTKSDNF PIPLVKQKGG QYTGFEISNH NSDFIIKIPF GRWQVKKEID  240
KYRPWEKFDF EQVQKSPKPI SLLLSTQRRK RNKGWSKDEG TEAEIKKVMN GDYQTSYIEV  300
KRGSKICEKS AWMLNLSIDV PKIDKGVDPS IIGGIAVGVK SPLVCAINNA FSRYSISDND  360
LFHFNKKMFA RRRILLKKNR HKRAGHGAKN KLKPITILTE KSERFRKKLI ERWACEIADF  420
```

```
FIKNKVGTVQ MENLESMKRK EDSYFNIRLR GFWPYAEMQN KIEFKLKQYG IEIRKVAPNN     480
TSKTCSKCGH LNNYFNFEYR KKNKFPHFKC EKCNFKENAA YNAALNISNP KLKSTKEEPA     540
YPYDVPDYAS LGSGDGIGSG SNGSSLMNNS QGRVTFEDVT VNFTQGEWQR LNPEQRNLYR     600
DVMLENYSNL VSVGQGETTK PDVILRLEQG KEPWLEEEEV LGSGRAEKNG DIGGQIWKPK     660
DVKESLAREV PSINKEHMGG GSGEDPAAKR VKLDMGSGVS KGEEDNMAII KEFMRFKVHM     720
EGSVNGHEFE IEGEGEGRPY EGTQTAKLKV TKGGPLPFAW DILSPQFMYG SKAYVKHPAD     780
IPDYLKLSFP EGFKWERVMN FEDGGVVTVT QDSSLQDGEF IYKVKLRGTN FPSDGPVMQK     840
KTMGWEASSE RMYPEDGALK GEIKQRLKLK DGGHYDAEVK TTYKAKKPVQ LPGAYNVNIK     900
LDITSHNEDY TIVEQYERAE GRHSTGGMDE LYK                                 933

SEQ ID NO: 162          moltype = DNA   length = 23
FEATURE                 Location/Qualifiers
misc_feature            1..23
                        note = Description of sequence: Synthetic oligonucleotide
source                  1..23
                        mol_type = other DNA
                        organism = synthetic construct
SEQUENCE: 162
gctcagcagg cacctgcctc agc                                              23

SEQ ID NO: 163          moltype = DNA   length = 23
FEATURE                 Location/Qualifiers
misc_feature            1..23
                        note = Description of sequence: Synthetic oligonucleotide
source                  1..23
                        mol_type = other DNA
                        organism = synthetic construct
SEQUENCE: 163
tttcccttca gctaaaataa agg                                              23

SEQ ID NO: 164          moltype = DNA   length = 23
FEATURE                 Location/Qualifiers
misc_feature            1..23
                        note = Description of sequence: Synthetic oligonucleotide
source                  1..23
                        mol_type = other DNA
                        organism = synthetic construct
SEQUENCE: 164
gctgaaggga aataaaagga aaa                                              23

SEQ ID NO: 165          moltype = DNA   length = 23
FEATURE                 Location/Qualifiers
misc_feature            1..23
                        note = Description of sequence: Synthetic oligonucleotide
source                  1..23
                        mol_type = other DNA
                        organism = synthetic construct
SEQUENCE: 165
acatgtcaat ctgtccgttc aca                                              23

SEQ ID NO: 166          moltype = DNA   length = 23
FEATURE                 Location/Qualifiers
misc_feature            1..23
                        note = Description of sequence: Synthetic oligonucleotide
source                  1..23
                        mol_type = other DNA
                        organism = synthetic construct
SEQUENCE: 166
ggaagtgtcc agggatgctt ccc                                              23

SEQ ID NO: 167          moltype = DNA   length = 23
FEATURE                 Location/Qualifiers
misc_feature            1..23
                        note = Description of sequence: Synthetic oligonucleotide
source                  1..23
                        mol_type = other DNA
                        organism = synthetic construct
SEQUENCE: 167
atgtctgcag gccagatgag ggc                                              23

SEQ ID NO: 168          moltype = DNA   length = 23
FEATURE                 Location/Qualifiers
misc_feature            1..23
                        note = Description of sequence: Synthetic oligonucleotide
source                  1..23
                        mol_type = other DNA
                        organism = synthetic construct
SEQUENCE: 168
ggactggagt tgcttcatgt aca                                              23
```

```
SEQ ID NO: 169          moltype = DNA  length = 23
FEATURE                 Location/Qualifiers
misc_feature            1..23
                        note = Description of sequence: Synthetic oligonucleotide
source                  1..23
                        mol_type = other DNA
                        organism = synthetic construct
SEQUENCE: 169
ggaggtcaga aatagggggt cca                                              23

SEQ ID NO: 170          moltype = DNA  length = 23
FEATURE                 Location/Qualifiers
misc_feature            1..23
                        note = Description of sequence: Synthetic oligonucleotide
source                  1..23
                        mol_type = other DNA
                        organism = synthetic construct
SEQUENCE: 170
ctcctggacc ccctatttct gac                                              23

SEQ ID NO: 171          moltype = DNA  length = 23
FEATURE                 Location/Qualifiers
misc_feature            1..23
                        note = Description of sequence: Synthetic oligonucleotide
source                  1..23
                        mol_type = other DNA
                        organism = synthetic construct
SEQUENCE: 171
gaaaggggt gggggagtt tgc                                                23

SEQ ID NO: 172          moltype = DNA  length = 23
FEATURE                 Location/Qualifiers
misc_feature            1..23
                        note = Description of sequence: Synthetic oligonucleotide
source                  1..23
                        mol_type = other DNA
                        organism = synthetic construct
SEQUENCE: 172
gccagagccg gggtgtgcag acg                                              23

SEQ ID NO: 173          moltype = RNA  length = 228
FEATURE                 Location/Qualifiers
misc_feature            1..228
                        note = Description of Unknown: sgRNA sequence
variation               206..228
                        note = n = a, c, u, g, unknown or other
source                  1..228
                        mol_type = other RNA
                        organism = unidentified
SEQUENCE: 173
gggcttcact gataaagtgg agaaccgctt caccaaaagc tgtcccttag gggattagaa      60
cttgagtgaa ggtgggctgc ttgcatcagc ctaatgtcga gaagtgcttt cttcggaaag    120
taaccctcga aacaaattca tttttcctct ccaattctgc acaagaaagt tgcagaaccc    180
gaatagacga atgaaggaat gcaacnnnnn nnnnnnnnnn nnnnnnnn                  228

SEQ ID NO: 174          moltype = RNA  length = 224
FEATURE                 Location/Qualifiers
misc_feature            1..224
                        note = Description of Artificial Sequence: Synthetic
                        polynucleotide
variation               206..224
                        note = n is a, c, u, g, unknown or other
source                  1..224
                        mol_type = other RNA
                        organism = synthetic construct
SEQUENCE: 174
gggcttcact gataaagtgg agaaccgctt caccaaaagc tgtcccttag gggattagaa      60
cttgagtgaa ggtgggctgc ttgcatcagc ctaatgtcga gaagtgcttt cttcggaaag    120
taaccctcga aacaaattca ttgttcctct ccaattctgc acaagaaagt tgcagaaccc    180
gaatagacta atgaaggaat gcaacnnnnn nnnnnnnnnn nnnn                      224

SEQ ID NO: 175          moltype = RNA  length = 179
FEATURE                 Location/Qualifiers
misc_feature            1..179
                        note = Description of Artificial Sequence: Synthetic
                        polynucleotide
variation               161..179
                        note = n is a, c, u, g, unknown or other
```

```
source                  1..179
                        mol_type = other RNA
                        organism = synthetic construct
SEQUENCE: 175
gggcttcact gataaagtgg agaaccgctt caccaaaagc tgtcccttag gggattagaa    60
cttgagtgaa ggtgggctgc ttgcatcagc ctaatgtcga gaagtgcttt cttcggaaag   120
taaccctcga aacaaattca tttgaatgaa ggaatgcaac nnnnnnnnnn nnnnnnnnn    179

SEQ ID NO: 176          moltype = RNA  length = 177
FEATURE                 Location/Qualifiers
misc_feature            1..177
                        note = Description of Artificial Sequence: Synthetic
                         polynucleotide
variation               159..177
                        note = n is a, c, u, g, unknown or other
source                  1..177
                        mol_type = other RNA
                        organism = synthetic construct
SEQUENCE: 176
gcttcactga taaagtggag aaccgcttca ccaaaagctg tcccttaggg gattagaact    60
tgagtgaagg tgggctgctt gcatcagcct aatgtcgaga agtgctttct tcggaaagta   120
accctcgaaa caaattcatt tgaatgaagg aatgcaacnn nnnnnnnnnn nnnnnnn      177

SEQ ID NO: 177          moltype = AA  length = 14
FEATURE                 Location/Qualifiers
REGION                  1..14
                        note = Description of Unknown: Cas14 sequence
source                  1..14
                        mol_type = protein
                        organism = unidentified
SEQUENCE: 177
GIDVGVKSPL VCAI                                                      14

SEQ ID NO: 178          moltype = AA  length = 14
FEATURE                 Location/Qualifiers
source                  1..14
                        mol_type = protein
                        organism = Acidaminococcus sp.
SEQUENCE: 178
GIDRGERNLI YITV                                                      14

SEQ ID NO: 179          moltype = AA  length = 14
FEATURE                 Location/Qualifiers
REGION                  1..14
                        note = Description of Unknown: Lachnospiraceae bacterium
                         sequence
source                  1..14
                        mol_type = protein
                        organism = unidentified
SEQUENCE: 179
GIDRGERNLL YIVV                                                      14

SEQ ID NO: 180          moltype = AA  length = 14
FEATURE                 Location/Qualifiers
source                  1..14
                        mol_type = protein
                        organism = Francisella tularensis
SEQUENCE: 180
SIDRGERHLA YYTL                                                      14

SEQ ID NO: 181          moltype = AA  length = 14
FEATURE                 Location/Qualifiers
source                  1..14
                        mol_type = protein
                        organism = Moraxella bovoculi
SEQUENCE: 181
GIDRGERHLL YLTV                                                      14

SEQ ID NO: 182          moltype = AA  length = 14
FEATURE                 Location/Qualifiers
source                  1..14
                        mol_type = protein
                        organism = Desulfurobacterium thermolithotrophum
SEQUENCE: 182
GVDLGLRNLA VVST                                                      14

SEQ ID NO: 183          moltype = AA  length = 13
FEATURE                 Location/Qualifiers
REGION                  1..13
```

```
                          note = Description of Unknown: Cas14 sequence
source                    1..13
                          mol_type = protein
                          organism = unidentified
SEQUENCE: 183
TVQMENLESM KRK                                                              13

SEQ ID NO: 184            moltype = AA  length = 13
FEATURE                   Location/Qualifiers
source                    1..13
                          mol_type = protein
                          organism = Acidaminococcus sp.
SEQUENCE: 184
VVVLENLNFG FKS                                                              13

SEQ ID NO: 185            moltype = AA  length = 13
FEATURE                   Location/Qualifiers
REGION                    1..13
                          note = Description of Unknown: Lachnospiraceae bacterium
                           sequence
source                    1..13
                          mol_type = protein
                          organism = unidentified
SEQUENCE: 185
VIALEDLNSG FKN                                                              13

SEQ ID NO: 186            moltype = AA  length = 13
FEATURE                   Location/Qualifiers
source                    1..13
                          mol_type = protein
                          organism = Francisella tularensis
SEQUENCE: 186
IVVFEDLNFG FKR                                                              13

SEQ ID NO: 187            moltype = AA  length = 13
FEATURE                   Location/Qualifiers
source                    1..13
                          mol_type = protein
                          organism = Moraxella bovoculi
SEQUENCE: 187
IVVLEDLNFG FKR                                                              13

SEQ ID NO: 188            moltype = AA  length = 13
FEATURE                   Location/Qualifiers
source                    1..13
                          mol_type = protein
                          organism = Desulfurobacterium thermolithotrophum
SEQUENCE: 188
VIVLEKLKGI RKR                                                              13

SEQ ID NO: 189            moltype = AA  length = 18
FEATURE                   Location/Qualifiers
REGION                    1..18
                          note = Description of Unknown: Cas14 sequence
source                    1..18
                          mol_type = protein
                          organism = unidentified
SEQUENCE: 189
NADYNAALNI SNPKLKST                                                         18

SEQ ID NO: 190            moltype = AA  length = 18
FEATURE                   Location/Qualifiers
source                    1..18
                          mol_type = protein
                          organism = Acidaminococcus sp.
SEQUENCE: 190
DADANGAYHI ALKGQLLL                                                         18

SEQ ID NO: 191            moltype = AA  length = 18
FEATURE                   Location/Qualifiers
REGION                    1..18
                          note = Description of Unknown: Lachnospiraceae bacterium
                           sequence
source                    1..18
                          mol_type = protein
                          organism = unidentified
SEQUENCE: 191
NADANGAYNI ARKVLWAI                                                         18
```

```
SEQ ID NO: 192            moltype = AA  length = 18
FEATURE                   Location/Qualifiers
source                    1..18
                          mol_type = protein
                          organism = Francisella tularensis
SEQUENCE: 192
DADANGAYHI GLKGLMLL                                                       18

SEQ ID NO: 193            moltype = AA  length = 18
FEATURE                   Location/Qualifiers
source                    1..18
                          mol_type = protein
                          organism = Moraxella bovoculi
SEQUENCE: 193
NADANGAYHI ALKGLWLL                                                       18

SEQ ID NO: 194            moltype = AA  length = 18
FEATURE                   Location/Qualifiers
source                    1..18
                          mol_type = protein
                          organism = Desulfurobacterium thermolithotrophum
SEQUENCE: 194
NADLNASRNI VKNYLASL                                                       18

SEQ ID NO: 195            moltype = AA  length = 24
FEATURE                   Location/Qualifiers
REGION                    1..24
                          note = Description of Unknown: Cas14 sequence
source                    1..24
                          mol_type = protein
                          organism = unidentified
SEQUENCE: 195
SVEHYLSDVC YTRAAELFKN AAIA                                                24

SEQ ID NO: 196            moltype = AA  length = 29
FEATURE                   Location/Qualifiers
source                    1..29
                          mol_type = protein
                          organism = Acidaminococcus sp.
SEQUENCE: 196
HENALLRSFD KFTTYFSGFY ENRKNVFSA                                           29

SEQ ID NO: 197            moltype = AA  length = 30
FEATURE                   Location/Qualifiers
REGION                    1..30
                          note = Description of Unknown: Lachnospiraceae bacterium
                           sequence
source                    1..30
                          mol_type = protein
                          organism = unidentified
SEQUENCE: 197
KDEIALVNSF NGFTTAFTGF FDNRENMFSE                                          30

SEQ ID NO: 198            moltype = AA  length = 30
FEATURE                   Location/Qualifiers
source                    1..30
                          mol_type = protein
                          organism = Francisella tularensis
SEQUENCE: 198
DEALEIIKSF KGWTTYFKGF HENRKNVYSS                                          30

SEQ ID NO: 199            moltype = AA  length = 30
FEATURE                   Location/Qualifiers
source                    1..30
                          mol_type = protein
                          organism = Moraxella bovoculi
SEQUENCE: 199
SPKLAHLAHF EKFSTYFTGF HDNRKNMYSD                                          30

SEQ ID NO: 200            moltype = AA  length = 30
FEATURE                   Location/Qualifiers
source                    1..30
                          mol_type = protein
                          organism = Butyrivibrio sp.
SEQUENCE: 200
EEDYNALESF RNFYTYFTSY NKVRENLYSD                                          30

SEQ ID NO: 201            moltype = AA  length = 30
FEATURE                   Location/Qualifiers
```

```
                              source          1..30
                                              mol_type = protein
                                              organism = Helcococcus kunzii
SEQUENCE: 201
EEDLEGLNLY SKFTTRLKNF WETRKNVFTD                                              30

SEQ ID NO: 202          moltype = AA  length = 30
FEATURE                 Location/Qualifiers
source                  1..30
                        mol_type = protein
                        organism = Lachnospira pectinoschiza
SEQUENCE: 202
EKALETIALF KGFTTYFTDY FNIRKNMFKE                                              30

SEQ ID NO: 203          moltype = AA  length = 30
FEATURE                 Location/Qualifiers
source                  1..30
                        mol_type = protein
                        organism = Pseudobutyrivibrio ruminis
SEQUENCE: 203
DTDYKALDSF SNFYTYFSSY NEVRKNLYSD                                              30

SEQ ID NO: 204          moltype = AA  length = 30
FEATURE                 Location/Qualifiers
source                  1..30
                        mol_type = protein
                        organism = Pseudobutyrivibrio xylanivorans
SEQUENCE: 204
DADNNALDSF SNFYTYFSSY NEVRKNLYSD                                              30

SEQ ID NO: 205          moltype = DNA  length = 30
FEATURE                 Location/Qualifiers
misc_feature            1..30
                        note = Description of sequence: Synthetic oligonucleotide
source                  1..30
                        mol_type = other DNA
                        organism = synthetic construct
SEQUENCE: 205
tttactccct atcagtgata gagaacgtat                                              30

SEQ ID NO: 206          moltype = DNA  length = 44
FEATURE                 Location/Qualifiers
source                  1..44
                        mol_type = genomic DNA
                        organism = Homo sapiens
SEQUENCE: 206
tgtttgggag gtcagaaata gggggtccag gagcaaactc cccc                              44

SEQ ID NO: 207          moltype = DNA  length = 44
FEATURE                 Location/Qualifiers
misc_feature            1..44
                        note = Description of sequence: Synthetic oligonucleotide
source                  1..44
                        mol_type = other DNA
                        organism = synthetic construct
SEQUENCE: 207
tgtttgggag gtcagaaata ggggtccag gagcaaactc cccc                               44

SEQ ID NO: 208          moltype = DNA  length = 43
FEATURE                 Location/Qualifiers
misc_feature            1..43
                        note = Description of sequence: Synthetic oligonucleotide
source                  1..43
                        mol_type = other DNA
                        organism = synthetic construct
SEQUENCE: 208
tgtttggagg tcagaaatag ggggtccagg agcaaactcc ccc                               43

SEQ ID NO: 209          moltype = DNA  length = 33
FEATURE                 Location/Qualifiers
misc_feature            1..33
                        note = Description of sequence: Synthetic oligonucleotide
source                  1..33
                        mol_type = other DNA
                        organism = synthetic construct
SEQUENCE: 209
tgtttgggag ggggtccagg agcaaactcc ccc                                          33

SEQ ID NO: 210          moltype = DNA  length = 41
```

```
FEATURE               Location/Qualifiers
misc_feature          1..41
                      note = Description of sequence: Synthetic oligonucleotide
source                1..41
                      mol_type = other DNA
                      organism = synthetic construct
SEQUENCE: 210
tgtttgggtc agaaataggg ggtccaggag caaactcccc c                              41

SEQ ID NO: 211        moltype = DNA  length = 42
FEATURE               Location/Qualifiers
misc_feature          1..42
                      note = Description of sequence: Synthetic oligonucleotide
source                1..42
                      mol_type = other DNA
                      organism = synthetic construct
SEQUENCE: 211
tgtttggggt cagaaatagg gggtccagga gcaaactccc cc                             42

SEQ ID NO: 212        moltype = DNA  length = 44
FEATURE               Location/Qualifiers
misc_feature          1..44
                      note = Description of sequence: Synthetic oligonucleotide
source                1..44
                      mol_type = other DNA
                      organism = synthetic construct
SEQUENCE: 212
tgtttgggag gtcagaaata ggtggtccag gagcaaactc cccc                           44

SEQ ID NO: 213        moltype = DNA  length = 44
FEATURE               Location/Qualifiers
misc_feature          1..44
                      note = Description of sequence: Synthetic oligonucleotide
source                1..44
                      mol_type = other DNA
                      organism = synthetic construct
SEQUENCE: 213
tgtttgggag gtaagaaata gggggtccag gagcaaactc cccc                           44

SEQ ID NO: 214        moltype = DNA  length = 40
FEATURE               Location/Qualifiers
misc_feature          1..40
                      note = Description of sequence: Synthetic oligonucleotide
source                1..40
                      mol_type = other DNA
                      organism = synthetic construct
SEQUENCE: 214
tgtttggtca gaaatagggg gtccaggagc aaactccccc                                40

SEQ ID NO: 215        moltype = DNA  length = 43
FEATURE               Location/Qualifiers
misc_feature          1..43
                      note = Description of sequence: Synthetic oligonucleotide
source                1..43
                      mol_type = other DNA
                      organism = synthetic construct
SEQUENCE: 215
tgtttggggg tcagaaatag ggggtccagg agcaaactcc ccc                            43

SEQ ID NO: 216        moltype = DNA  length = 35
FEATURE               Location/Qualifiers
misc_feature          1..35
                      note = Description of sequence: Synthetic oligonucleotide
source                1..35
                      mol_type = other DNA
                      organism = synthetic construct
SEQUENCE: 216
tgtttgggat aggggtcca ggagcaaact ccccc                                      35

SEQ ID NO: 217        moltype = DNA  length = 37
FEATURE               Location/Qualifiers
misc_feature          1..37
                      note = Description of sequence: Synthetic oligonucleotide
source                1..37
                      mol_type = other DNA
                      organism = synthetic construct
SEQUENCE: 217
tgtttgggaa atagggggtc caggagcaaa ctccccc                                   37
```

```
SEQ ID NO: 218            moltype = DNA   length = 44
FEATURE                   Location/Qualifiers
misc_feature              1..44
                          note = Description of sequence: Synthetic oligonucleotide
source                    1..44
                          mol_type = other DNA
                          organism = synthetic construct
SEQUENCE: 218
tgtttgggcg gtcagaaata gggggtccag gagcaaactc cccc                            44

SEQ ID NO: 219            moltype = DNA   length = 28
FEATURE                   Location/Qualifiers
source                    1..28
                          mol_type = genomic DNA
                          organism = Homo sapiens
SEQUENCE: 219
gtttgggagg tcagaaatag ggggtcca                                              28

SEQ ID NO: 220            moltype = DNA   length = 28
FEATURE                   Location/Qualifiers
misc_feature              1..28
                          note = Description of sequence: Synthetic oligonucleotide
source                    1..28
                          mol_type = other DNA
                          organism = synthetic construct
SEQUENCE: 220
gtttgggagg tcagaaatag ggggtcca                                              28

SEQ ID NO: 221            moltype = DNA   length = 28
FEATURE                   Location/Qualifiers
misc_feature              1..28
                          note = Description of sequence: Synthetic oligonucleotide
source                    1..28
                          mol_type = other DNA
                          organism = synthetic construct
SEQUENCE: 221
gtttgggggg tcagaaatag ggggtcca                                              28

SEQ ID NO: 222            moltype = DNA   length = 28
FEATURE                   Location/Qualifiers
misc_feature              1..28
                          note = Description of sequence: Synthetic oligonucleotide
source                    1..28
                          mol_type = other DNA
                          organism = synthetic construct
SEQUENCE: 222
gtttgggggg tcgaaaatag ggggtcca                                              28

SEQ ID NO: 223            moltype = DNA   length = 28
FEATURE                   Location/Qualifiers
misc_feature              1..28
                          note = Description of sequence: Synthetic oligonucleotide
source                    1..28
                          mol_type = other DNA
                          organism = synthetic construct
SEQUENCE: 223
gtttgggggg tcggaaatgg ggggtcca                                              28

SEQ ID NO: 224            moltype = DNA   length = 28
FEATURE                   Location/Qualifiers
misc_feature              1..28
                          note = Description of sequence: Synthetic oligonucleotide
source                    1..28
                          mol_type = other DNA
                          organism = synthetic construct
SEQUENCE: 224
gtttgggggg tcgggaatgg ggggtcca                                              28

SEQ ID NO: 225            moltype = DNA   length = 28
FEATURE                   Location/Qualifiers
misc_feature              1..28
                          note = Description of sequence: Synthetic oligonucleotide
source                    1..28
                          mol_type = other DNA
                          organism = synthetic construct
SEQUENCE: 225
gtttgggggg tcagaaatgg ggggtcca                                              28

SEQ ID NO: 226            moltype = DNA   length = 28
```

```
FEATURE                 Location/Qualifiers
misc_feature            1..28
                        note = Description of sequence: Synthetic oligonucleotide
source                  1..28
                        mol_type = other DNA
                        organism = synthetic construct
SEQUENCE: 226
gtttggagg tcacaaatag ggggtcca                                              28

SEQ ID NO: 227          moltype = DNA   length = 28
FEATURE                 Location/Qualifiers
misc_feature            1..28
                        note = Description of sequence: Synthetic oligonucleotide
source                  1..28
                        mol_type = other DNA
                        organism = synthetic construct
SEQUENCE: 227
gtttgggggg tcgggaatag ggggtcca                                             28

SEQ ID NO: 228          moltype = DNA   length = 28
FEATURE                 Location/Qualifiers
source                  1..28
                        mol_type = genomic DNA
                        organism = Homo sapiens
SEQUENCE: 228
gcaaactccc cccaccccct ttccaaag                                             28

SEQ ID NO: 229          moltype = DNA   length = 28
FEATURE                 Location/Qualifiers
misc_feature            1..28
                        note = Description of sequence: Synthetic oligonucleotide
source                  1..28
                        mol_type = other DNA
                        organism = synthetic construct
SEQUENCE: 229
gcaaactccc cccaccccct ttccaaag                                             28

SEQ ID NO: 230          moltype = DNA   length = 28
FEATURE                 Location/Qualifiers
misc_feature            1..28
                        note = Description of sequence: Synthetic oligonucleotide
source                  1..28
                        mol_type = other DNA
                        organism = synthetic construct
SEQUENCE: 230
gcaaactccc cccaccccct ctccaaag                                             28

SEQ ID NO: 231          moltype = DNA   length = 28
FEATURE                 Location/Qualifiers
misc_feature            1..28
                        note = Description of sequence: Synthetic oligonucleotide
source                  1..28
                        mol_type = other DNA
                        organism = synthetic construct
SEQUENCE: 231
gcaaactccc cccacccccc ttccaaag                                             28

SEQ ID NO: 232          moltype = DNA   length = 28
FEATURE                 Location/Qualifiers
misc_feature            1..28
                        note = Description of sequence: Synthetic oligonucleotide
source                  1..28
                        mol_type = other DNA
                        organism = synthetic construct
SEQUENCE: 232
gcaaactccc cccacccccc ctccaaag                                             28

SEQ ID NO: 233          moltype = DNA   length = 28
FEATURE                 Location/Qualifiers
misc_feature            1..28
                        note = Description of sequence: Synthetic oligonucleotide
source                  1..28
                        mol_type = other DNA
                        organism = synthetic construct
SEQUENCE: 233
gcaaactccc ctcaccccct ttccaaag                                             28

SEQ ID NO: 234          moltype = DNA   length = 28
FEATURE                 Location/Qualifiers
```

```
misc_feature          1..28
                      note = Description of sequence: Synthetic oligonucleotide
source                1..28
                      mol_type = other DNA
                      organism = synthetic construct
SEQUENCE: 234
gcaaactccc cccaccccccc ccccaaag                                               28

SEQ ID NO: 235        moltype = DNA   length = 54
FEATURE               Location/Qualifiers
source                1..54
                      mol_type = genomic DNA
                      organism = Homo sapiens
SEQUENCE: 235
gtagctgttt gggaggtcag aaatagggggg tccaggagca aactcccccc accc                  54

SEQ ID NO: 236        moltype = DNA   length = 54
FEATURE               Location/Qualifiers
misc_feature          1..54
                      note = Description of sequence: Synthetic oligonucleotide
source                1..54
                      mol_type = other DNA
                      organism = synthetic construct
SEQUENCE: 236
gtagctgttt gggaggtcag aaatagggggg tccaggagca aactcccccc accc                  54

SEQ ID NO: 237        moltype = DNA   length = 43
FEATURE               Location/Qualifiers
misc_feature          1..43
                      note = Description of sequence: Synthetic oligonucleotide
source                1..43
                      mol_type = other DNA
                      organism = synthetic construct
SEQUENCE: 237
gtagctgttt gggagggggt ccaggagcaa actcccccca ccc                               43

SEQ ID NO: 238        moltype = DNA   length = 47
FEATURE               Location/Qualifiers
misc_feature          1..47
                      note = Description of sequence: Synthetic oligonucleotide
source                1..47
                      mol_type = other DNA
                      organism = synthetic construct
SEQUENCE: 238
gtagctgttt gggaaatagg gggtccagga gcaaactccc cccaccc                           47

SEQ ID NO: 239        moltype = DNA   length = 40
FEATURE               Location/Qualifiers
misc_feature          1..40
                      note = Description of sequence: Synthetic oligonucleotide
source                1..40
                      mol_type = other DNA
                      organism = synthetic construct
SEQUENCE: 239
gtagctgttt gggggggtcca ggagcaaact ccccccaccc                                  40

SEQ ID NO: 240        moltype = DNA   length = 52
FEATURE               Location/Qualifiers
misc_feature          1..52
                      note = Description of sequence: Synthetic oligonucleotide
source                1..52
                      mol_type = other DNA
                      organism = synthetic construct
SEQUENCE: 240
gtagctgttt ggggtcagaa atagggggtc caggagcaaa ctcccccac cc                      52

SEQ ID NO: 241        moltype = DNA   length = 53
FEATURE               Location/Qualifiers
misc_feature          1..53
                      note = Description of sequence: Synthetic oligonucleotide
source                1..53
                      mol_type = other DNA
                      organism = synthetic construct
SEQUENCE: 241
gtagctgttt ggggggtcaga aatagggggt ccaggagcaa actccccccca ccc                  53

SEQ ID NO: 242        moltype = DNA   length = 51
FEATURE               Location/Qualifiers
misc_feature          1..51
```

```
                        note = Description of sequence: Synthetic oligonucleotide
source                  1..51
                        mol_type = other DNA
                        organism = synthetic construct
SEQUENCE: 242
gtagctgttt gggtcagaaa taggggtcc aggagcaaac tcccccacc c                51

SEQ ID NO: 243          moltype = DNA  length = 45
FEATURE                 Location/Qualifiers
misc_feature            1..45
                        note = Description of sequence: Synthetic oligonucleotide
source                  1..45
                        mol_type = other DNA
                        organism = synthetic construct
SEQUENCE: 243
gtagctgttt gggataggggg gtccaggagc aaactccccc caccc                    45

SEQ ID NO: 244          moltype = DNA  length = 53
FEATURE                 Location/Qualifiers
misc_feature            1..53
                        note = Description of sequence: Synthetic oligonucleotide
source                  1..53
                        mol_type = other DNA
                        organism = synthetic construct
SEQUENCE: 244
gtagctgttt ggaggtcaga aatagggggt ccaggagcaa actcccccca ccc            53

SEQ ID NO: 245          moltype = DNA  length = 46
FEATURE                 Location/Qualifiers
misc_feature            1..46
                        note = Description of sequence: Synthetic oligonucleotide
source                  1..46
                        mol_type = other DNA
                        organism = synthetic construct
SEQUENCE: 245
gtagctgttt gggaataggg ggtccaggag caaactcccc ccaccc                    46

SEQ ID NO: 246          moltype = DNA  length = 50
FEATURE                 Location/Qualifiers
misc_feature            1..50
                        note = Description of sequence: Synthetic oligonucleotide
source                  1..50
                        mol_type = other DNA
                        organism = synthetic construct
SEQUENCE: 246
gtagctgttt ggtcagaaat aggggtcca ggagcaaact cccccaccc                  50

SEQ ID NO: 247          moltype = DNA  length = 44
FEATURE                 Location/Qualifiers
misc_feature            1..44
                        note = Description of sequence: Synthetic oligonucleotide
source                  1..44
                        mol_type = other DNA
                        organism = synthetic construct
SEQUENCE: 247
gtagctgttt ggataggggg tccaggagca aactccccc accc                       44

SEQ ID NO: 248          moltype = DNA  length = 49
FEATURE                 Location/Qualifiers
misc_feature            1..49
                        note = Description of sequence: Synthetic oligonucleotide
source                  1..49
                        mol_type = other DNA
                        organism = synthetic construct
SEQUENCE: 248
gtagctgttt gggagaaata gggggtccag gagcaaactc ccccacccc                 49

SEQ ID NO: 249          moltype = DNA  length = 44
FEATURE                 Location/Qualifiers
misc_feature            1..44
                        note = Description of sequence: Synthetic oligonucleotide
source                  1..44
                        mol_type = other DNA
                        organism = synthetic construct
SEQUENCE: 249
gtagctgttt gggtagggggg tccaggagca aactcccccc accc                     44

SEQ ID NO: 250          moltype = DNA  length = 44
FEATURE                 Location/Qualifiers
```

```
SEQ ID NO: 250
FEATURE                 Location/Qualifiers
misc_feature            1..44
                        note = Description of sequence: Synthetic oligonucleotide
source                  1..44
                        mol_type = other DNA
                        organism = synthetic construct
SEQUENCE: 250
gtagctgttt gggagggggg tccaggagca aactcccccc accc          44

SEQ ID NO: 251          moltype = DNA  length = 39
FEATURE                 Location/Qualifiers
misc_feature            1..39
                        note = Description of sequence: Synthetic oligonucleotide
source                  1..39
                        mol_type = other DNA
                        organism = synthetic construct
SEQUENCE: 251
gtagctgttt gggggtccag gagcaaactc cccccaccc                39

SEQ ID NO: 252          moltype = RNA  length = 224
FEATURE                 Location/Qualifiers
misc_feature            1..224
                        note = Description of Unknown: tracrRNA sequence
variation               206..224
                        note = n is a, c, u, g, unknown or other
source                  1..224
                        mol_type = other RNA
                        organism = unidentified
SEQUENCE: 252
gggcttcact gataaagtgg agaaccgctt caccaaaagc tgtcccttag gggattagaa   60
cttgagtgaa ggtgggctgc ttgcatcagc ctaatgtcga gaagtgcttt cttcggaaag  120
taaccctcga aacaaattca tttttcctct ccaattctgc acaagaaagt tgcagaaccc  180
gaatagacga atgaaggaat gcaacnnnnn nnnnnnnnnn nnnn                   224

SEQ ID NO: 253          moltype = AA  length = 5
FEATURE                 Location/Qualifiers
REGION                  1..5
                        note = Description of sequence: Motif
VARIANT                 1
                        note = Position may also be glutamic acid, lysine or
                         asparagine
VARIANT                 2
                        note = X is any known amino acid
VARIANT                 3
                        note = Position may also arginine
VARIANT                 4
                        note = Position may also be lysine
source                  1..5
                        mol_type = protein
                        organism = synthetic construct
SEQUENCE: 253
DXFEN                                                              5
```

What is claimed is:

1. An engineered Clustered Regularly Interspaced Short Palindromic Repeat (CRISPR)-associated (Cas) protein that is capable of modulating a target nucleic acid in eukaryotic cells, with or without an effector domain attached thereto, the Cas protein comprising an amino acid sequence of a native amino acid sequence of SEQ ID NO: 1 with one or more substitutions thereto, wherein the amino acid sequence is at least 95% identical to SEQ ID NO: 1, and wherein
the one or more substitutions comprises at least one substitution at a position selected from the group consisting of: D143, K11, K73, T147, E151, K154, E241, D318, K330, K457, E425, E462, N504, N507, N516, N519, E527, and E528.

2. The engineered Cas protein of claim 1, wherein at least one of the one or more substitutions is to an amino acid selected from the group consisting of: arginine (R), alanine (A), serine(S), and glycine (G).

3. The engineered Cas protein of claim 1, wherein the at least one substitution is selected from the group consisting of: D143R, K11R, K73R, T147R, E151R, K154R, E241R, D318R, K330R, E425N, K457R, E462R, N504R, E507R, N516R, N519R, E527R, and E528R.

4. The engineered Cas protein of claim 3, wherein the at least one substitution is selected from the group consisting of: D143R, T147R, E151R, and E241R.

5. The engineered Cas protein of claim 1, wherein the one or more substitutions comprise at least two substitutions at positions selected from the group consisting of: D143, T147, E151, K154, E241, K330, E425, N504, E507, N516, N519, E527, and E528.

6. The engineered Cas protein of claim 5, wherein the at least two substitutions comprise a substitution at D143 and a substitution at a position selected from the group consisting of: T147, E151, K154, E241, K330, E425, N504, E507, N516, N519, E527, and E528.

7. The engineered Cas protein of claim 5, wherein the two substitutions are selected from the group consisting of: D143R, T147R, E151R, E151A, K154R, E241R, N504R, E507R, N516R, N519R, E527R, and E528R.

8. The engineered Cas protein of claim 6, wherein the at least two substitutions are selected from the group consisting of: D143R/T147R, D143R/E15IR, D143R/E241R, D143R/ E425N, D143R/E507R, D143R/N519R, D143R/E527R, D143R/E528R, D143R/E151S, D143R/E151G, and D143R/ E151A.

9. The engineered Cas protein of claim 5, wherein the one or more substitutions comprise at least three substitutions at positions selected from the group consisting of: D143, T147, E151, K154, E241, K330, E425, N504, E507, N516, N519, E527, and E528.

10. The engineered Cas protein of claim 9, wherein the at least three substitutions comprise substitutions at D143 and T147 and a substitution at a position selected from the group consisting of: E151, K154, E241, K330, E425, N504, E507, N516, N519, E527, and E528.

11. The engineered Cas protein of claim 9, wherein the at least three substitutions are selected from the group consisting of: D143R, T147R, E15IR, E151A, E151S, E151G, K154R, E241R, K330R, E425N, N504R, E507R, N516R, N519R, E527R, and E528R.

12. The engineered Cas protein of claim 11, wherein the at least three substitutions are selected from the group consisting of: D143R/T147R/K330R, D143R/T147R/ K154R, D143R/T147R/E241R, D143R/T147R/E507R, D143R/T147R/N519R, D143R/T147R/E527R, D143R/ T147R/E528R, D143R/T147R/E151S, D143R/T147R/ E151G, and D143R/T147R/E151A.

13. The engineered Cas protein of claim 5, wherein the one or more substitutions comprise at least four substitutions at positions selected from the group consisting of: D143, T147, E151, K154, E241, K330, E425, N504, E507, N516, N519, E527, and E528.

14. The engineered Cas protein of claim 13, wherein the at least four substitutions comprise substitutions at D143, T147, and K330 and a substitution at a position selected from the group consisting of: E151, K154, E241, E425, N504, E507, N516, N519, E527, and E528.

15. The engineered Cas protein of claim 13, wherein the at least four substitutions are selected from the group consisting of: D143R, T147R, E151R, E151A, E151S, E151G, K154R, E241R, K330R, E425N, N504R, E507R, N516R, N519R, E527R, and E528R.

16. The engineered Cas protein of claim 15, wherein the at least four substitutions are selected from the group consisting of: D143R/T147R/K330R/E528R, D143R/ T147R/K330R/E151A, and D143R/T147R/K330R/E527R.

17. The engineered Cas protein of claim 1, wherein the Cas protein is a fully or partially nuclease deactivated Cas (dCas) protein.

18. A system comprising:
the engineered Cas protein of claim 1; and
an sgRNA.

19. The engineered Cas protein of claim 1, wherein at least one of the one or more substitutions is at a position having an electrically charged amino acid in the native amino acid sequence.

20. The engineered Cas protein of claim 1, wherein the native amino acid sequence comprises a (D/E/K/N)X(R/F) (E/K)N (SEQ ID NO: 253) motif;
wherein the one or more substitutions comprises:
(a) no more than 4 substitutions within 30 amino acids upstream or downstream of the (D/E/K/N)X(R/F)(E/ K)N (SEQ ID NO: 253) motif;
(b) one substitution within 30 amino acids upstream or downstream of position 241 of the native amino acid sequence; and/or
(c) no more than 6 substitutions within 30 amino acids upstream or downstream of position 516 of the native amino acid sequence;
wherein the one or more substitutions comprises at least one substitution at a position selected from the group consisting of: D143, T147, E151, K154, E241, N504, E507, N516, N519, E527, and E528; and
wherein the Cas protein is a fully or partially nuclease deactivated Cas (dCas) protein.

21. The engineered Cas protein of claim 1, wherein the one or more substitutions comprise at least one substitution at a position selected from the group consisting of: D143, T147, K330, and E528.

22. The engineered Cas protein of claim 1, wherein the one or more substitutions comprise at least one of the following: D143R, T147R, K330R, or E528R.

23. The engineered Cas protein of claim 1, wherein the one or more substitutions comprise: D143R, T147R, K330R, and E528R.

24. A system comprising:
the Cas protein of claim 22; and
an sgRNA.

25. The engineered Cas protein of claim 24, wherein the one or more substitutions further comprise at least one substitution at D326 or D510.

26. The engineered Cas protein of claim 25, wherein the one or more substitutions further comprise D326A or D510A.

27. The engineered Cas protein of claim 1, wherein the one or more substitutions comprises:
(i) two or more substitutions comprising:
(A) at least one of the following:
(a) no more than six substitutions within or no more than 30 amino acids upstream or downstream of the (D/E/K/N)X(R/F)(E/K)N (SEQ ID NO: 253) motif;
(b) no more than six substitutions at or no more than 30 amino acids upstream or downstream of position 241 of the native amino acid sequence; and/or
(c) no more than six substitutions at or no more than 30 amino acids upstream or downstream of position 516 of the native amino acid sequence; and
(B) at least one substitution at a position selected from the group consisting of: D143, K11, K73, T147, E151, K154, E241, D318, K330, K457, E425, E462, N504, E507, N516, N519, E527, and E528; or
(ii) at least one of the following:
(a) no more than six substitutions within or no more than 30 amino acids upstream or downstream of the (D/E/K/N)X(R/F)(E/K)N (SEQ ID NO: 253) motif;
(b) no more than six substitutions at or no more than 30 amino acids upstream or downstream of position 241 of the native amino acid sequence; and/or
(c) no more than six substitutions at or no more than 30 amino acids upstream or downstream of position 516 of the native amino acid sequence,
wherein the one or more substitutions comprises at least one substitution at a position selected from the group consisting of: D143, T147, E151, K154, E241, N504, E507, N516, N519, E527, and E528.

28. An engineered Clustered Regularly Interspaced Short Palindromic Repeat (CRISPR)-associated (Cas) protein that is capable of modulating a target nucleic acid in eukaryotic cells, with or without an effector domain attached thereto, the Cas protein comprising an amino acid sequence of a native amino acid sequence of SEQ ID NO: 1 with one or more substitutions thereto, wherein the amino acid sequence is at least 95% identical to SEQ ID NO: 1, wherein:
- the native amino acid sequence comprises a (D/E/K/N)X(R/F)(E/K)N (SEQ ID NO: 253) motif;
- the one or more substitutions comprises at least one of the following:
  - (a) no more than six substitutions within or no more than 30 amino acids upstream or downstream of the (D/E/K/N)X(R/F)(E/K)N (SEQ ID NO: 253) motif;
  - (b) no more than six substitutions at or no more than 30 amino acids upstream or downstream of position 241 of the native amino acid sequence; and/or
  - (c) no more than six substitutions at or no more than 30 amino acids upstream or downstream of position 516 of the native amino acid sequence; and
- the one or more substitutions comprises at least one substitution at a position selected from the group consisting of: D143, T147, E151, K154, E241, N504, E507, N516, N519, E527, and E528.

29. The engineered Cas protein of claim 28, wherein the Cas protein is a fully or partially nuclease deactivated Cas (dCas) protein.

30. The engineered Cas protein of claim 28, wherein at least one of the one or more substitutions is at a position having an electrically charged amino acid in the native amino acid sequence.

31. A system comprising:
the Cas protein of claim 28; and
an sgRNA.

* * * * *